US012673052B2

(12) United States Patent
Schwab et al.

(10) Patent No.: US 12,673,052 B2
(45) Date of Patent: Jul. 7, 2026

(54) COMBINATIONS FOR THE TREATMENT OF CANCER

(71) Applicant: Exelixis, Inc., Alameda, CA (US)

(72) Inventors: Gisela Schwab, Hayward, CA (US); Christian Scheffold, Palo Alto, CA (US); Colin Chong, Fremont, CA (US); Ssucheng Jeff Hsu, Pinole, CA (US); Peter Lamb, Oakland, CA (US); Peiwen Yu, San Mateo, CA (US)

(73) Assignee: Exelixis, Inc., Alameda, CA (US)

( * ) Notice: Subject to any disclaimer, the term of this patent is extended or adjusted under 35 U.S.C. 154(b) by 676 days.

(21) Appl. No.: 18/018,805

(22) PCT Filed: Jul. 29, 2021

(86) PCT No.: PCT/US2021/043699

§ 371 (c)(1),
(2) Date: Jan. 30, 2023

(87) PCT Pub. No.: WO2022/026706

PCT Pub. Date: Feb. 3, 2022

(65) Prior Publication Data

US 2023/0301979 A1 Sep. 28, 2023

Related U.S. Application Data

(60) Provisional application No. 63/059,601, filed on Jul. 31, 2020, provisional application No. 63/113,556, filed on Nov. 13, 2020, provisional application No. 63/148,921, filed on Feb. 12, 2021.

(51) Int. Cl.

| | |
|---|---|
| ***A61K 31/47*** | (2006.01) |
| ***A61K 38/20*** | (2006.01) |
| ***A61K 45/06*** | (2006.01) |
| ***A61P 35/04*** | (2006.01) |
| ***C07K 16/28*** | (2006.01) |

(52) U.S. Cl.

CPC .......... *A61K 31/47* (2013.01); *A61K 38/2013* (2013.01); *A61K 45/06* (2013.01); *A61P 35/04* (2018.01); *C07K 16/2818* (2013.01); *C07K 16/2827* (2013.01); *C07B 2200/13* (2013.01)

(58) Field of Classification Search

CPC .... A61K 31/47; A61K 38/2013; A61K 45/06; A61P 35/04; C07K 16/2818; C07K 16/2827; C07B 2200/13

See application file for complete search history.

(56) References Cited

FOREIGN PATENT DOCUMENTS

| | | | | |
|---|---|---|---|---|
| WO | 2018064191 A1 | | 4/2018 | |
| WO | WO-2018136796 A1 | * | 7/2018 | .............. A61P 35/04 |
| WO | WO-2019148044 A1 | * | 8/2019 | ........... C07D 215/22 |
| WO | 2020123800 A1 | | 6/2020 | |

OTHER PUBLICATIONS

Bavencio (avelumab) prescribing information. Revised Jun. 2020. (Year: 2020).*

Markham, A. et al. Camrelizumab: First Global Approval. Drugs 2019, 79, 1355-1361. (Year: 2019).*

Checkpoint Therapeutics Announces Positive Interim Clinical Results of Anti-PD-L1 Antibody Cosibelimab. Checkpoint Therapeutics, Inc. Published May 1, 2019. (Year: 2019).*

Imfinzi (durvalumab) prescribing information. Revised Mar. 2020. (Year: 2020).*

Jemperli (dostarlimab) BLA Multi-disciplinary Review and Evaluation. Submitted Dec. 19, 2019. (Year: 2019).*

Keytruda (pembrolizumab) prescribing information. Revised Oct. 2016. (Year: 2016).*

Xu, J. et al. Phase I study of KN035, the first subcutaneously administered, novel fusion anti-PD-L1 antibody in patients with advanced solid tumors in China. American Society of Clinical Oncology (ASCO), Chicago, IL, May 31-Jun. 4, 2019, Poster #252. (Year: 2019).*

Libtayo (cemiplimab) prescribing information. Revised Mar. 2019. (Year: 2019).*

Opdivo (nivolumab) prescribing information. Revised Apr. 2019. (Year: 2019).*

Hoy, S. M. Sintilimab: First Global Approval. Drugs 2019, 79, 341-346. (Year: 2019).*

Wirth, L. J. et al. Phase I/II study of spartalizumab (PDR001), an anti-PD1 mAb, in patients with anaplastic thyroid cancer. Journal of Clinical Oncology, 2018, 36, abstract #6024. (Year: 2018).*

Tecentriq (atezolizumab) prescribing information. Revised Mar. 2019. (Year: 2019).*

Lee, A. Tislelizumab: First Approval. Drugs 2020, 80, 617-624. Published Mar. 18, 2020. (Year: 2020).*

Keam, S. J. Toripalimab: First Global Approval. Drugs 2019, 79, 573-578. (Year: 2019).*

Yervoy (ipilimumab) prescribing information. Revised May 2020. (Year: 2020).*

Anonymous: "ASCO 2020: Anti-Androgenic Cabozantinib Plus Nivolumab a Promising Combination in Endometrial Cancer: PracticeUpdate", Jun. 12, 2020 (Jun. 12, 2020), pp. 1-4, XP055855585, Retrieved from the Internet: URL: https://www.practiceupdate.com/content/asco-2020-anti-androgenic-cabozantinib-plus-nivolumab-a-promising-combination-in-endometrial-cancer/102124 [retrieved on Oct. 27, 2021] the whole document.

Derosa L. et al: "Efficacy of cabozantinib (C) after PD-1/PD-L1 checkpoint inhibitors in metastatic renal cell carcinoma (mRCC): The Gustave Roussy experience", Annals of Oncology, vol. 28, Sep. 1, 2917 (2017-99-91), p. v309, XP055860353, NL ISSN: 0923-7534, DOI: 10.1093/annonc/mdx371.030 the whole document.

(Continued)

*Primary Examiner* — Jeffrey H Murray
*Assistant Examiner* — Kristen W Romero
(74) *Attorney, Agent, or Firm* — Honigman LLP; Heidi Berven; Li Gao

(57) ABSTRACT

The present invention relates to combinations comprising a checkpoint inhibitor and a c-Met inhibitor, Compound 1. The invention also relates to crystalline forms of the free base of Compound 1, as well as crystalline forms of salts of Compound 1, in combination with a checkpoint inhibitor. The invention further relates to methods of treating cancer by administering Compound 1 as a single agent or a combination described herein.

18 Claims, 14 Drawing Sheets

(56) References Cited

OTHER PUBLICATIONS

Bergerot Paulo et al: “Cabozantinib in Combination with Immunotherapy for Advanced Renal Cell Carcinoma and Urothelial Carcinoma: Rationale and Clinical Evidence”, Molecular Cancer Therapeutics, vol. 18, No. 12 Dec. 1, 2019 (Dec. 1, 2019), pp. 2185-2193, XP055855574, ISSN: 1535-7163, DOI: 10.1158/1535-7163.MCT-18-1399 abstract p. 2187, right-hand column, paragraph 3-p. 2191, left-hand column, paragraph 2 conclusion; p. 2191, right-hand column.

* cited by examiner

Growth curve stops once a single tumor reaches the defined endpoint size (2000 $mm^3$)

LLOQ, lower limit of quantitation; PIB, powder in a bottle; tab, tablet. Note: Data below LLOQ (0.5 ng/mL) are shown as ½ LLOQ for illustration purposes only.

Compound 1 + Atezolizumab Combination Therapy Study Schema

COMBINATIONS FOR THE TREATMENT OF CANCER

CROSS-REFERENCE TO RELATED APPLICATIONS

This application claims the benefit of priority to U.S. Provisional Application Ser. No. 63/148,921, filed Feb. 12, 2021, U.S. Provisional Application Ser. No. 63/113,556, filed Nov. 13, 2020, and U.S. Provisional Application Ser. No. 63/059,601, filed Jul. 31, 2020, all of which are incorporated herein by reference in its entirety.

TECHNICAL FIELD OF THE INVENTION

The present invention relates to combinations comprising an immune checkpoint inhibitor (ICI) and Compound 1. The invention also relates to crystalline forms of the free base of Compound 1, as well as crystalline forms of salts of Compound 1, in combination with a checkpoint inhibitor. The invention also relates to pharmaceutical compositions of Compound 1 used in combination with a checkpoint inhibitor. The invention further relates to methods of treating cancer by administering Compound 1 as a single agent or a combination as described herein.

BACKGROUND OF THE INVENTION

Cancer is a significant cause of morbidity and mortality worldwide. While the standards of care for many different cancer types have greatly improved over the years, current standards of care still fail to meet the need for effective therapies to improve treatment of cancer. The clinical use of immuno-oncology agents targeting cytotoxic T-lymphocyte-associated protein 4 (CTLA-4) and the programmed cell death receptor-1 (PD-1) and its ligand PD-L1, have resulted in improvements over the standard of care in the treatment of many cancer types. While these checkpoint inhibitors have produced improved clinical responses in such certain cancers, durable clinical responses only occur in approximately 10-45% of patients. Moreover, a significant number of tumors are either resistant or become refractory.

In recent years, TAM tyrosine kinases, and in particular, AXL receptor tyrosine kinase, have emerged as a promising target for cancer therapeutics. AXL is a cell surface receptor tyrosine kinase, part of the TAM family of kinases including TYRO3 and MERTK. Several drugs classified as "AXL inhibitors" have entered clinical trials; however, many target multiple kinase receptors in addition to AXL.

Human Axl belongs to the Tyro3, Axl, and Mer (TAM) subfamily of receptor tyrosine kinases that includes Mer. TAM kinases are characterized by an extracellular ligand binding domain consisting of two immunoglobulin-like domains and two fibronectin type III domains. Axl is overexpressed in a number of tumor cell types and was initially cloned from patients with chronic myelogenous leukemia. When overexpressed, Axl exhibits transforming potential. Axl signaling is believed to cause tumor growth through activation of proliferative and anti-apoptotic signaling pathways. Axl has been associated with cancers such as lung cancer, myeloid leukemia, uterine cancer, ovarian cancer, gliomas, melanoma, thyroid cancer, renal cell carcinoma, osteosarcoma, gastric cancer, prostate cancer, and breast cancer. The over-expression of Axl results in a poor prognosis for patients with the indicated cancers.

Activation of Mer, like Axl, conveys downstream signaling pathways that cause tumor growth and activation. Mer binds ligands such as the soluble protein Gas-6. Gas-6 binding to Mer induces autophosphorylation of Mer on its intracellular domain, resulting in downstream signal activation. Over-expression of Mer in cancer cells leads to increased metastasis, most likely by generation of soluble Mer extracellular domain protein as a decoy receptor. Tumor cells secrete a soluble form of the extracellular Mer receptor which reduces the ability of soluble Gas-6 ligand to activate Mer on endothelial cells, leading to cancer progression.

Accordingly, there is a need in the art for new therapies, including, for example, combination therapies for the treatment of cancers. Provided herein are solutions to these and other problems in the art.

SUMMARY OF THE INVENTION

In one aspect, the invention includes a method for treating cancer in a subject, the method comprising:

(i) administering to the subject a dosage of from about 5 mg to about 100 mg of Compound 1 or a pharmaceutically acceptable salt thereof, wherein Compound 1 has the structure:

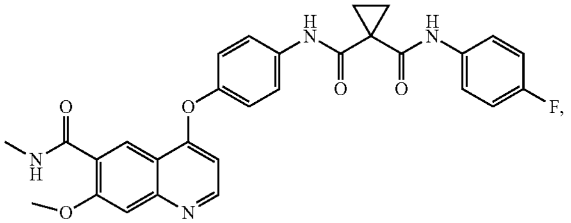 [SMILES: CNC(=O)c1cc2c(Oc3ccc(NC(=O)C4(C(=O)Nc5ccc(F)cc5)CC4)cc3)ccnc2cc1OC]

and (ii) administering to the subject a therapeutically effective amount of a checkpoint inhibitor.

In another aspect, the invention includes a method for treating cancer in a subject, the method comprising administering to the subject in need of such treatment a dosage of from about 5 mg to about 100 mg of Compound 1:

(1)

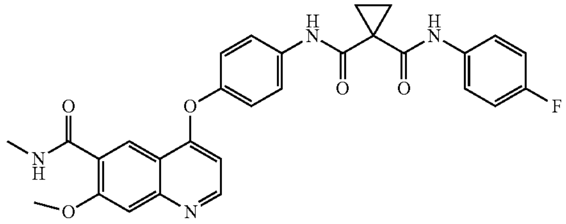

or a pharmaceutically acceptable salt thereof or a pharmaceutical composition comprising Compound 1 or the pharmaceutically acceptable salt thereof, and a pharmaceutically acceptable carrier or excipient, in combination with a therapeutically effective amount of a checkpoint inhibitor or a pharmaceutical composition comprising the checkpoint inhibitor.

In one aspect, the invention includes a method for treating urothelial carcinoma in a subject, the method comprising:

(i) administering to the subject a dosage of from about 5 mg to about 100 mg of Compound 1 or a pharmaceutically acceptable salt thereof, wherein Compound 1 has the structure:

(1)

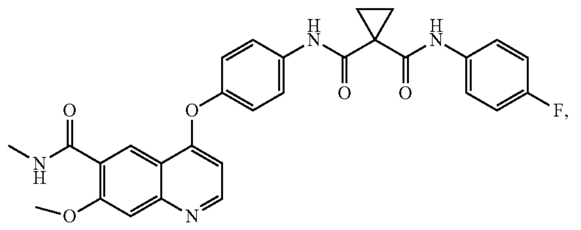 [SMILES: CNC(=O)c1cc2c(Oc3ccc(NC(=O)C4(C(=O)Nc5ccc(F)cc5)CC4)cc3)ccnc2cc1OC]

(ii) administering to the subject a therapeutically effective amount of a checkpoint inhibitor.

In another aspect, the invention includes a method for treating urothelial carcinoma in a subject, the method comprising administering to the subject in need of such treatment a dosage of from about 5 mg to about 100 mg of Compound 1:

(1)

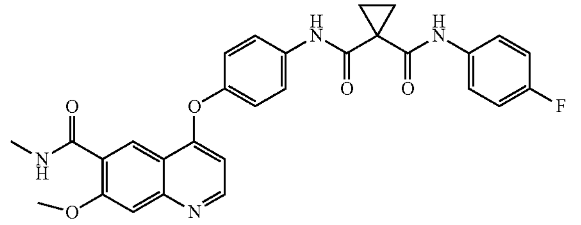

or a pharmaceutically acceptable salt thereof or a pharmaceutical composition comprising Compound 1 or the pharmaceutically acceptable salt thereof, and a pharmaceutically acceptable carrier or excipient, in combination with a therapeutically effective amount of a checkpoint inhibitor or a pharmaceutical composition comprising the checkpoint inhibitor.

In these and other aspects, the checkpoint inhibitor is selected from the group consisting of a PD-1 inhibitor, a PD-L1 inhibitor, and a CTLA-4 inhibitor. In these and other aspects and embodiments, the checkpoint inhibitor is selected from the group consisting of pembrolizumab, nivolumab, atezolizumab (TECENTRIQ®), durvalumab, avelumab (BAVENCIO®), cemiplimab, camrelizumab, sintilimab, tisleilizumab, toripalimab, spartalizumab, dostarlimab, KN035 (Jiangsu Alphamb Biopharmaceuticals Co.), Cosibelimab (formerly CK-301), CA-170 (Curis, Inc.), BMS-986189 (Bristol Myers Squibb Co.), and ipilimumab (Yervoy, Bristol Myers Squibb Co.).

In a further aspect, what is provided is a method of treating cancer in a subject, comprising:

(i) administering to the subject a dosage of from about 5 mg to about 100 mg of Compound 1 or a pharmaceutically acceptable salt thereof, wherein Compound 1 has the structure:

(1)

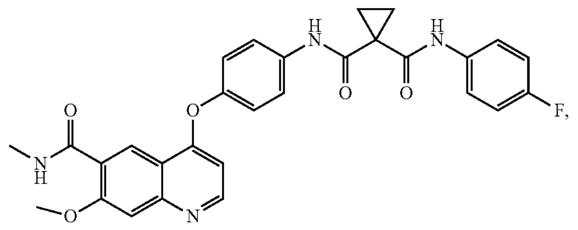 [SMILES: CNC(=O)c1cc2c(Oc3ccc(NC(=O)C4(C(=O)Nc5ccc(F)cc5)CC4)cc3)ccnc2cc1OC]

(ii) administering to the subject a therapeutically effective amount of nivolumab and at least one additional immunomodulating agent.

In one embodiment of this aspect, the immunomodulating agent is selected from the group consisting of a PD-1 inhibitor, a PD-L1 inhibitor, a CTLA-4 inhibitor, and an IL-2 targeting agent.

In these and other aspects, the subject is a human subject in need of treatment.

In these and other aspects, the checkpoint inhibitor is selected from the group consisting of a PD-1 inhibitor, a PD-L1 inhibitor, and a CTLA-4 inhibitor. In these and other aspects and embodiments, the checkpoint inhibitor is selected from the group consisting of pembrolizumab, nivolumab, atezolizumab (TECENTRIQ®), durvalumab, avelumab (BAVENCIO®), cemiplimab, camrelizumab, sintilimab, tisleilizumab, toripalimab, spartalizumab, dostarlimab, KN035 (Jiangsu Alphamb Biopharmaceuticals Co.), Cosibelimab (formerly CK-301), CA-170 (Curis, Inc.), BMS-986189 (Bristol Myers Squibb Co.), and ipilimumab (Yervoy, Bristol Myers Squibb Co.).

In these and other aspects, the IL-2 targeting agent is selected from the group consisting of a CD122-preferential IL-2 pathway agonist, a PEG-IL-2Rαβ-biased agonist, an IL-2Rβ-biased agonist, an IL-2Rβ$\gamma_c$-biased agonist, an IL-2v/IL-2a fusion protein, an anti-EDB mAb (L19)/IL-2v fused to L19/TNFv, an Anti-GD2 mAb/IL-2v, an anti-FAP mAb/IL-2v, an anti-CEA mAb/IL-2v, an anti-PD-1 mAb/IL-2v, a vaccine of patient derived tumor cells+HD-IL-2, adoptive cell therapy+IL-2 infusion, adoptive cell therapy+IL-2 infusion+anti-PD-1 mAb, orthogonal IL-2v/IL-2Rβ mutant pairs, an anti-IL-2RαmAb/PBD conjugate, a PEG-IL-2Rα-biased agonist, an IL-2v/human Fc fusion protein, a PEG-IL-2Rα-biased (N88D)/IgG1 fusion protein, an anti-IL-2 mAb/IL-2v, a recombinant plasmid encoding IL-2, PPI, TGF-1, and IL-10, and an IL-2Rβ antagonist.

In one embodiment, the IL-2 targeting agent is a CD122-preferential IL-2 pathway agonist. In one embodiment, CD122-preferential IL-2 pathway agonist is bempegaldesleukin (BEMPEG; NKTR-214; Bristol Myers Squibb Co.).

In one embodiment, the IL-2 targeting agent is a PEG-IL-2Rα-biased agonist. In one embodiment, the PEG-IL-2Rα-biased agonist is NKTR-358 (Bristol Myers Squibb Co.).

In a further aspect, the invention includes a method of treating cancer in a subject, the method comprising administering to the subject a dosage of from about 5 mg to about 100 mg of Compound 1 or a pharmaceutically acceptable salt thereof, or a pharmaceutical composition comprising Compound 1.

In these and other aspects, Compound 1 is administered as a free base crystalline solid or as a crystalline pharmaceutically acceptable salt. For avoidance of doubt, "Compound 1" means these crystalline free base forms as well as crystalline salt forms unless otherwise indicated.

In these and other aspects, Compound 1 is a crystalline solid form characterized as Form A, Form B, Form C, Form D, Form E, Form F, Form G, Form H, Form K, Form O, or Form Q.

In these and other aspects, Compound 1 is a crystalline HCl salt of Compound 1.

In these and other aspects, Compound 1 is a crystalline fumaric acid salt of Compound 1, or hydrate or solvate thereof.

In these and other aspects, Compound 1 is a crystalline phosphoric acid salt of Compound 1 or hydrate or solvate thereof.

DETAILED DESCRIPTION OF THE INVENTION

Analytical Techniques

Figure 1A:
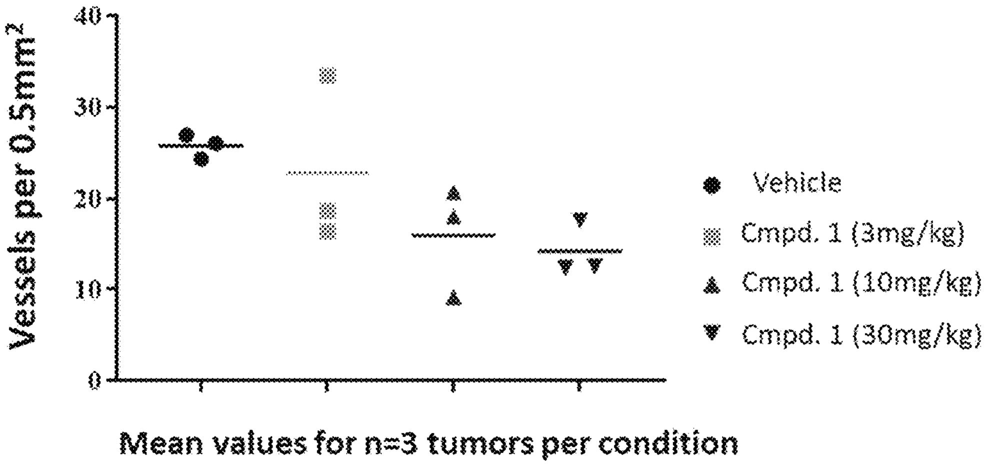
FIG. 1A shows the presence of tumor microvessels by CD31 staining after treatment with Compound 1. Horizontal bars represent mean values for n=3 tumors per condition.

| Analytical Techniques | |
|---|---|
| Abbreviations/Acronyms | Full Name/Description |
| DSC | Differential scanning calorimetry |
| DVS | Dynamic (water) vapor sorption |
| HSM | Hot stage microscopy |
| NMR | Nuclear magnetic resonance spectroscopy |
| OM | Optical microscopy |
| PLM | Polarized light microscopy |
| TGA | Thermogravimetry or Thermogravimetric analysis |
| XRPD | X-ray powder diffraction |

Experimental Techniques

| Experimental techniques | |
|---|---|
| Abbreviations/Acronyms | Full Name/Description |
| CC | Crash cooling |
| CP | Crash precipitation |
| FC | Fast cooling |
| FE | Fast evaporation |
| RC | Reaction crystallization |
| SC | Slow cooling |
| SE | Slow evaporation |
| VD | Vapor diffusion |
| VS | Vapor stress |

Miscellaneous

| Miscellaneous | |
|---|---|
| Abbreviations/Acronyms | Full Name/Description |
| ~ | About or approximately |
| API | Active pharmaceutical ingredient |
| B/E | Birefringence and extinction |
| Endo/endo | Endotherm or endothermic |
| eq | Equivalent |
| Exo/exo | Exotherm or exothermic |
| FB | Free base |
| FF | Free form |
| frz | Freezer |
| LIMS | Laboratory Information Management System |
| Max/max | Maximum or maxima |
| Obs | Observation |
| PO | Preferred orientation |
| ppt | Precipitate or precipitation |
| ref | Refrigerator |
| RH | Relative humidity |
| RT | Room temperature |
| Soln/soln | Solution |
| vac | Vacuum |
| wt % | Weight percent |

Solvents

| Solvents | |
|---|---|
| Abbreviations/Acronyms | Full Name/Description |
| ACN | Acetonitrile |
| AcOH | Acetic acid |
| DCM | Dichloromethane |
| DMSO | Dimethylsulfoxide |

-continued

| Solvents | |
|---|---|
| Abbreviations/Acronyms | Full Name/Description |
| EtOAc | Ethyl acetate |
| EtOH | Ethanol |
| HFIPA | Hexafluoroisopropanol |
| IPA | Isopropyl alcohol, 2-propanol |
| MEK | Methyl ethyl ketone |
| MeOH | Methanol |
| MTBE | Methyl-tertiary-butyl ether |
| TFE | 2,2,2-Trifluoroethanol |
| THF | Tetrahydrofuran |

As used herein, the following definitions shall apply unless otherwise indicated.

For purposes of this invention, the chemical elements are identified in accordance with the Periodic Table of the Elements, CAS version, Handbook of Chemistry and Physics, 95th Ed. Additionally, general principles of organic chemistry are described in "Organic Chemistry," $2^{nd}$ Ed., Thomas Sorrell, University Science Books, Sausalito: 2006, and "March's Advanced Organic Chemistry," 7th Ed., Ed.: Smith, M. B. and March, J., John Wiley & Sons, New York: 2013, the entire contents of which are hereby incorporated by reference.

As used herein, the term "Low/limited/significant hygroscopicity" refers to a material that exhibits <0.5/<2.0/≥2.0 wt % water uptake over a specified RH range.

As used herein, the term "stoichiometric hydrate" refers to crystalline material with a defined water content over an extended RH range. Typical stoichiometric hydrates are hemihydrates, monohydrates, sesquihydrates, dihydrates, and so on.

As used herein, the term "variable hydrate" refers to crystalline material with variable water content over an extended RH range, yet with no phase change.

As used herein, a chemical term designated as a "Form" refers to a chemical compound or salt thereof that consists of a single phase.

As used herein, the term "low/limited/intermediate/good/high solubility" refers to a material having a solubility of <1/1-20/20-100/100-200/>200 mg/mL.

As used herein, the term "crystalline" refers to a material that produces an XRPD pattern with sharp peaks (similar to instrumental peak widths) and weak diffuse scattering relative to the peaks.

As used herein, the term "disordered crystalline" refers to a material that produces XRPD pattern with broad peaks (relative to instrumental peak widths) and/or strong diffuse scattering relative to the peaks. Disordered materials may be:

1) microcrystalline,
2) crystalline with large defect density,
3) mixtures of crystalline and X-ray amorphous phases, or
4) a combination of the above.

As used herein, the term "insufficient signal" means that spectrographic analysis of a sample produced a spectrum or pattern (output) having insufficient signal above the expected background noise.

As used herein, the term "single crystalline phase" refers to an XRPD pattern that is judged to contain evidence of a single crystalline form due to the Bragg peaks being indexed with a single unit cell. Indexing is the process of assigning Miller index labels to each peak in a diffraction pattern. Also, the size and shape of the crystal unit cell is determined during the indexing process.

As used herein, the term "slurry" refers to a suspension prepared by adding enough solids to a given solvent at ambient conditions so that undissolved solids are present. A typical slurry includes agitation (typically by stirring or oscillation), an act that is also referred to as "slurrying," in a sealed vial at a given temperature for an extended period of time. Typically, the solids are recovered after a given period of time using a method described herein.

As used herein, the term "X-ray amorphous" or "amorphous" refers to a material having diffuse scatter present, but no evidence for Bragg peaks in the XRPD pattern.

As used herein, the term "crystalline" refers to compounds in a solid state having a periodic and repeating three-dimensional internal arrangement of atoms, ions or molecules characteristic of crystals, for example, arranged in fixed geometric patterns or lattices that have rigid long range order. The term crystalline does not necessarily mean that the compound exists as crystals, but that it has this crystal-like internal structural arrangement.

As used herein, the term "substantially crystalline" refers to a solid material that is predominately arranged in fixed geometric patterns or lattices that have rigid long range order. For example, substantially crystalline materials have more than about 85% crystallinity (e.g., more than about 90% crystallinity, more than about 95% crystallinity, or more than about 99% crystallinity). It is also noted that the term 'substantially crystalline' includes the descriptor 'crystalline,' which is defined in the previous paragraph.

"Patient" for the purposes of the present invention includes humans and any other animals, particularly mammals, and other organisms. Thus, the methods are applicable to both human therapy and veterinary applications. In a preferred embodiment, the patient is a mammal, and in a most preferred embodiment the patient is human. Examples of the preferred mammals include mice, rats, other rodents, rabbits, dogs, cats, swine, cattle, sheep, horses, and primates.

"Kinase-dependent diseases or conditions" refer to pathologic conditions that depend on the activity of one or more kinases. Kinases either directly or indirectly participate in the signal transduction pathways of a variety of cellular activities including proliferation, adhesion, migration, differentiation, and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

"Therapeutically effective amount" is an amount of a crystalline form or crystalline salt form of the present invention that, when administered to a patient, ameliorates a symptom of the disease. The amount of a crystalline form or crystalline salt form of the present invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit risk ratio.

As used herein, the phrase "pharmaceutically acceptable excipient" refers to a pharmaceutically-acceptable material, composition, or vehicle, such as a liquid or solid filler, diluent, solvent, or encapsulating material. Excipients are generally safe, non-toxic and neither biologically nor otherwise undesirable and include excipients that are acceptable for veterinary use as well as human pharmaceutical use. In one embodiment, each component is "pharmaceutically acceptable" as defined herein. See, e.g., Remington: The Science and Practice of Pharmacy, 21st ed.; Lippincott Williams & Wilkins: Philadelphia, Pa., 2005; Handbook of 'Pharmaceutical Excipients, 6th ed.; Rowe et al, Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Pref or mulation and Formulation, 2nd ed.; Gibson Ed.; CRC Press LLC: Boca Raton, Fla., 2009.

As used herein, the term "concurrently" means at the same time. For example, if two treatment regimens for a single patient are being conducted concurrently, then they are being conducted at the same time. It will be understood that two treatment regimens happening at the same time, does not necessarily mean that actual delivery of two drugs happens at the same time, as each regimen may call for a different dosing schedule and/or different delivery modes.

As used herein, and as provided by the National Cancer Institutes, "checkpoint inhibitor" refers to any agent that blocks, inhibits or modulates checkpoint proteins. Checkpoint inhibitors are made by some types of immune system cells, such as T cells, and some cancer cells. Examples of checkpoint proteins found on T cells or cancer cells include PD-1/PD-L1 and CTLA-4/B7-1/B7-2. Examples of checkpoint inhibitors include pembrolizumab, nivolumab, atezolizumab, durvalumab, avelumab, cemiplimab, camrelizumab, sintilimab, tisleilizumab, toripalimab, spartalizumab, dostarlimab, KN035 (Jiangsu Alphamb Biopharmaceuticals Co.), Cosibelimab (formerly CK-301), CA-170 (Curis, Inc.), and BMS-986189 (Bristol Myers Squibb Co.). Examples of FDA-approved checkpoint inhibitors include products pembrolizumab, nivolumab, atezolizumab, durvalumab, avelumab, cemiplimab. Dosing and other information for approved checkpoint inhibitors is available from the FDA, the EMEA, or other national medical regulating agencies.

"Cancer" refers to any physiological condition in mammals characterized by unregulated cell growth; in particular, cellular-proliferative disease states, including, but not limiting to: Cardiac: sarcoma (angiosarcoma, fibrosarcoma, rhabdomyosarcoma, liposarcoma), myxoma, rhabdomyoma, fibroma, lipoma and teratoma; Head and neck: squamous cell carcinomas of the head and neck, laryngeal and hypopharyngeal cancer, nasal cavity and paranasal sinus cancer, nasopharyngeal cancer, salivary gland cancer, oral and orppharyngeal cancer; Lung: bronchogenic carcinoma (squamous cell, undifferentiated small cell, undifferentiated large cell, adenocarcinoma, non-small cell lung cancer), alveolar (bronchiolar) carcinoma, alveolar sarcoma, alveolar soft part sarcoma, bronchial adenoma, sarcoma, lymphoma, chondromatous hamartoma, mesothelioma; Colon: colorectal cancer, adenocarcinoma, gastrointestinal stromal tumors, lymphoma, carcinoids, Turcot Syndrome; Gastrointestinal: gastric cancer, gastroesophageal junction adenocarcinoma, esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Breast: metastatic breast cancer, ductal carcinoma in situ, invasive ductal carcinoma, tubular carcinoma, medullary carcinoma, mucinous carcinoma, lobular carcinoma in situ, triple negative breast cancer; Genitourinary tract: kidney (adenocarcinoma, Wilm's tumor [nephroblastoma], lymphoma, leukemia, renal cell carcinoma, metastatic renal cell carcinoma), bladder and urethra (squamous cell carcinoma, transitional cell carcinoma, adenocarcinoma, urothelial carcinoma), prostate (adenocarcinoma, sarcoma, castrate resistant prostate cancer, bone metastases, bone metastases associated with castrate resistant prostate cancer), testis (seminoma, teratoma, embryonal carcinoma, teratocarcinoma, choriocarcinoma, sarcoma, interstitial cell carcinoma, fibroma, fibroadenoma, adenomatoid tumors, lipoma), clear cell carcinoma, papillary carcinoma, penile cancer, penile squamous cell carcinoma; Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma, and giant cell tumors; Thyroid: medullary thyroid cancer, differentiated thyroid cancer, papillary thyroid cancer, follicular thyroid cancer, hurthle cell cancer, and anaplastic thyroid cancer; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma), NF1, neurofibromatosis, plexiform neurofibromas; Gynecological: uterus (endometrial cancer), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), myelofibrosis, polycythemia vera, essential thrombocythemia, Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions. In some embodiments, a compound or combination as disclosed herein can be used for the treatment of diseases including HIV, sickle cell disease, graft-versus-host disease, acute graft-versus-host disease, chronic graft-versus-host disease, and sickle cell anemia.

As defined by the National Cancer Institute, the term "solid tumor" means an abnormal mass of tissue that usually does not contain cysts or liquid areas. Solid tumors may be benign (not cancer), or malignant (cancer). Different types of solid tumors are named for the type of cells that form them. Examples of solid tumors are sarcomas, carcinomas, and lymphomas. Leukemias (cancers of the blood) generally do not form solid tumors.

As defined by the National Cancer Institute, an "immunomodulating agent" is a substance that stimulates or suppresses the immune system.

The terms "treating" or "treatment" refer to any indicia of success or amelioration of the progression, severity, and/or duration of a disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; or improving a patient's physical or mental well-being.

The term "enhance" refers to an increase or improvement in the function or activity of a protein or cell after administration or contacting with a combination described herein compared to the protein or cell prior to such administration or contact.

The term "administering" refers to the act of delivering a combination or composition described herein into a subject by such routes as oral, mucosal, topical, suppository, intravenous, parenteral, intraperitoneal, intramuscular, intralesional, intrathecal, intranasal or subcutaneous administration. Parenteral administration includes intravenous, intramuscular, intra-arteriole, intradermal, subcutaneous, intraperitoneal, intraventricular, and intracranial administration. Administration generally occurs after the onset of the disease, disorder, or condition, or its symptoms but, in certain instances, can occur before the onset of the disease, disorder, or condition, or its symptoms (e.g., administration for patients prone to such a disease, disorder, or condition).

The term "coadministration" refers to administration of two or more agents (e.g., a combination described herein and another active agent such as an anti-cancer agent described herein). The timing of coadministration depends in part of the combination and compositions administered and can include administration at the same time, just prior to, or just after the administration of one or more additional therapies, for example cancer therapies such as chemotherapy, hormonal therapy, radiotherapy, or immunotherapy. The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g., to reduce metabolic degradation). The compounds described herein can be used in combination with one another, with other active agents known to be useful in treating cancer.

The term "anti-cancer agent" is used in accordance with its plain ordinary meaning and refers to a composition having anti-neoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

The term "chemotherapeutic" or "chemotherapeutic agent" is used in accordance with its plain ordinary meaning and refers to a chemical composition or compound having anti-neoplastic properties or the ability to inhibit the growth or proliferation of cells. "Chemotherapy" refers to a therapy or regimen that includes administration of a chemotherapeutic or anti-cancer agent described herein.

In general, the nomenclature used in this application is based on naming conventions adopted by the international union of pure and applied chemistry (IUPAC). Chemical structures shown herein were prepared using CHEMDRAW®. Any open valency appearing on a carbon, oxygen, or nitrogen atom in the structures herein indicates the presence of a hydrogen atom.

ASPECTS AND EMBODIMENTS

In one aspect, the invention includes a method for treating cancer in a subject, the method comprising administering to the subject in need of such treatment a therapeutically effective amount of Compound 1:

(1)

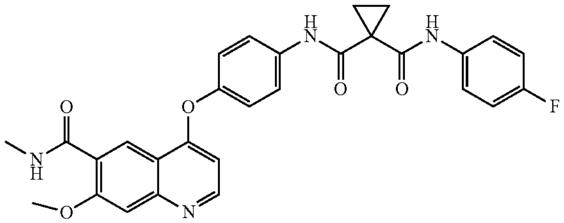

or a pharmaceutically acceptable salt thereof or a pharmaceutical composition comprising compound (I) or the pharmaceutically acceptable salt thereof, and a pharmaceutically acceptable carrier or excipient, in combination with a therapeutically effective amount of a checkpoint inhibitor or a pharmaceutical composition comprising the checkpoint inhibitor.

In one aspect, the invention includes a method for treating cancer in a subject, the method comprising administering to the subject in need of such treatment a dosage of from about 5 mg to about 100 mg of Compound 1:

(1)

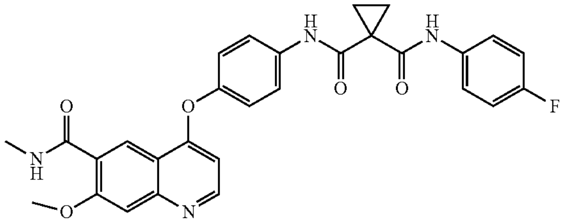

or a pharmaceutically acceptable salt thereof or a pharmaceutical composition comprising compound (I) or the pharmaceutically acceptable salt thereof, and a pharmaceutically acceptable carrier or excipient, in combination with a therapeutically effective amount of a checkpoint inhibitor or a pharmaceutical composition comprising the checkpoint inhibitor.

In another aspect, the invention includes a method for treating cancer in a subject, the method comprising:

(i) administering to the subject a therapeutically effective amount of Compound 1 or a pharmaceutically acceptable salt thereof, wherein Compound 1 has the structure:

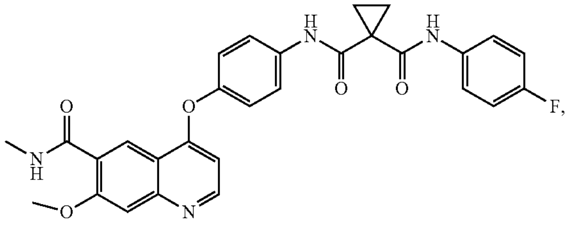

(ii) administering to the subject a therapeutically effective amount of a checkpoint inhibitor.

In another aspect, the invention includes a method for treating cancer in a subject, the method comprising:

(i) administering to the subject a dosage of from about 5 mg to about 100 mg of Compound 1 or a pharmaceutically acceptable salt thereof, wherein Compound 1 has the structure:

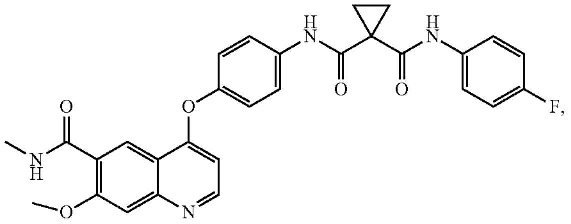

(ii) administering to the subject a therapeutically effective amount of a checkpoint inhibitor.

In another aspect, the invention includes a method for treating cancer in a subject, the method comprising administering to the subject in need of such treatment a therapeutically effective amount of Compound 1 or a pharmaceutically acceptable salt thereof or a pharmaceutical composition comprising compound (1) or the pharmaceutically acceptable salt thereof, and a pharmaceutically acceptable carrier or excipient.

In another aspect, the invention includes a method for treating cancer in a subject, the method comprising administering to the subject in need of such treatment a dosage of from about 5 mg to about 100 mg of Compound 1 or a pharmaceutically acceptable salt thereof or a pharmaceutical composition comprising compound (1) or the pharmaceutically acceptable salt thereof, and a pharmaceutically acceptable carrier or excipient.

In one aspect, the invention includes a method for treating urothelial carcinoma in a subject, the method comprising:

(i) administering to the subject a dosage of from about 5 mg to about 100 mg of Compound 1 or a pharmaceutically acceptable salt thereof wherein Compound 1 has the structure:

(1)

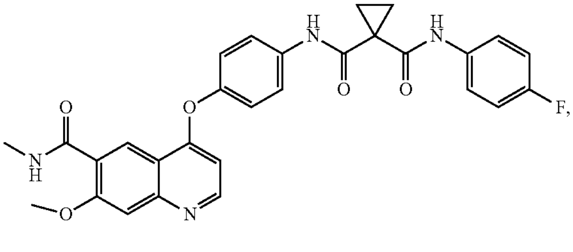

(ii) administering to the subject a therapeutically effective amount of a checkpoint inhibitor.

In another aspect, the invention includes a method for treating urothelial carcinoma in a subject, the method comprising administering to the subject in need of such treatment a dosage of from about 5 mg to about 100 mg of Compound 1:

(1)

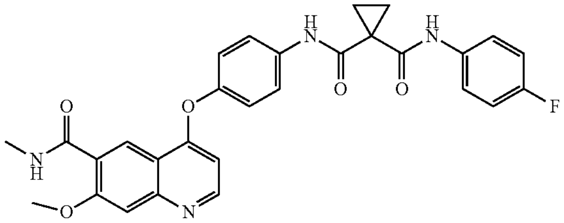

or a pharmaceutically acceptable salt thereof or a pharmaceutical composition comprising compound (1) or the pharmaceutically acceptable salt thereof, and a pharmaceutically acceptable carrier or excipient, in combination with a therapeutically effective amount of a checkpoint inhibitor or a pharmaceutical composition comprising the checkpoint inhibitor.

In one embodiment, the checkpoint inhibitor is selected from a PD-1 inhibitor, a PD-L1 inhibitor, and a CTLA-4 inhibitor.

In one embodiment, the checkpoint inhibitor is selected from an aPD-1 inhibitor, a PD-L1 inhibitor, and an aCTLA-4 inhibitor.

In another embodiment, the checkpoint inhibitor is selected from the group consisting of pembrolizumab, nivolumab, atezolizumab, durvalumab, avelumab, cemiplimab, camrelizumab, sintilimab, tisleilizumab, toripalimab, spartalizumab, dostarlimab, KN035 (Jiangsu Alphamb Biopharmaceuticals Co.), Cosibelimab (formerly CK-301), CA-170 (Curis, Inc.), BMS-986189 (Bristol Myers Squibb Co.), and ipilimumab.

In one embodiment, the checkpoint inhibitor is selected from the group consisting of atezolizumab, avelumab, and nivolumab.

In one embodiment, the checkpoint inhibitor is pembrolizumab.

In one embodiment, the checkpoint inhibitor is nivolumab.

In one embodiment, the checkpoint inhibitor is atezolizumab.

In one embodiment, the checkpoint inhibitor is avelumab.

In one embodiment, the checkpoint inhibitor is cemiplimab.

In one embodiment, the checkpoint inhibitor is camrelizumab.

In one embodiment, the checkpoint inhibitor is sintilimab.

In one embodiment, the checkpoint inhibitor is tisleilizumab.

In one embodiment, the checkpoint inhibitor is toripalimab.

In one embodiment, the checkpoint inhibitor is spartalizumab.

In one embodiment, the checkpoint inhibitor is dostarlimab.

In one embodiment, the checkpoint inhibitor is KN035.

In one embodiment, the checkpoint inhibitor is Cosibelimab.

In one embodiment, the checkpoint inhibitor is CA-170.

In one embodiment, the checkpoint inhibitor is BMS-986189.

In one embodiment, the checkpoint inhibitor is ipilimumab.

In one embodiment of the aforementioned aspects, Compound 1 or a pharmaceutically acceptable salt thereof is administered orally once per day (qd) or twice per day (bid). In one embodiment, Compound 1 or a pharmaceutically acceptable salt thereof is administered orally once per day (qd). In one embodiment, Compound 1 or a pharmaceutically acceptable salt thereof is administered orally twice per day (bid).

The dosage of Compound 1 herein is expressed as free base equivalents (FBE) unless stated otherwise.

In some embodiments, the therapeutically effective amount of Compound 1 is from about 1 mg to about 500 mg, from about 1 mg to about 300 mg, from about 1 mg to about 200 mg, from about 1 mg to about 150 mg, from about 5 mg to about 150 mg, or from about 5 mg to about 100 mg.

In one embodiment, the dosage of Compound 1 or a pharmaceutically acceptable salt thereof is from about 5 mg to about 80 mg. In one embodiment, the dosage of Compound 1 or a pharmaceutically acceptable salt thereof is from about 5 mg to about 50 mg.

In one embodiment, the dosage of Compound 1 or a pharmaceutically acceptable salt thereof, is from 8 mg to 12 mg. In one embodiment, the dosage of Compound 1 or a pharmaceutically acceptable salt thereof, is from 18 mg to 22 mg. In one embodiment, the dosage of Compound 1 or a pharmaceutically acceptable salt thereof, is from 38 mg to 40 mg. In one embodiment, the dosage of Compound 1 or a pharmaceutically acceptable salt thereof, is about 10 mg. In one embodiment, the dosage of Compound 1 or a pharmaceutically acceptable salt thereof, is about 20 mg. In one embodiment, the dosage of Compound 1 or a pharmaceutically acceptable salt thereof, is about 40 mg. In one embodiment, the dosage of Compound 1 or a pharmaceutically acceptable salt thereof, is about 60 mg. In one embodiment, the dosage of Compound 1 or a pharmaceutically acceptable salt thereof, is about 80 mg. In one embodiment, the dosage of Compound 1 or a pharmaceutically acceptable salt thereof, is about 100 mg. In one embodiment, the dosage of Compound 1 or a pharmaceutically acceptable salt thereof, is about 120 mg. In one embodiment, the dosage of Compound 1 or a pharmaceutically acceptable salt thereof, is about 140 mg. In one embodiment, the dosage of Compound 1 or a pharmaceutically acceptable salt thereof, is selected from about 10 mg, 20 mg, and 40 mg. In one embodiment, the dosage of Compound 1 or a pharmaceutically acceptable salt thereof, is selected from about 10 mg, 20 mg, 40 mg, 60 mg, and 80 mg. In one embodiment, the dosage of Compound 1 or a pharmaceutically acceptable salt thereof, is selected from about 10 mg, 20 mg, 40 mg, 60 mg, 80 mg, 100 mg, 120 mg, and 140 mg. In one embodiment, the dosage of Compound 1 or a pharmaceutically acceptable salt thereof, is selected from about 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, and 300 mg.

In a further embodiment:

- more than 0 mg and up to and including 100 mg of Compound 1 is administered;
- more than 0 mg and up to and including 95 mg of Compound 1 is administered;
- more than 0 mg and up to and including 90 mg of Compound 1 is administered;
- more than 0 mg and up to and including 85 mg of Compound 1 is administered;
- more than 0 mg and up to and including 80 mg of Compound 1 is administered;
- more than 0 mg and up to and including 75 mg of Compound 1 is administered;
- more than 0 mg and up to and including 70 mg of Compound 1 is administered;
- more than 0 mg and up to and including 65 mg of Compound 1 is administered;
- more than 0 mg and up to and including 60 mg of Compound 1 is administered;
- more than 0 mg and up to and including 55 mg of Compound 1 is administered;
- more than 0 mg and up to and including 50 mg of Compound 1 is administered;
- more than 0 mg and up to and including 45 mg of Compound 1 is administered;
- more than 0 mg and up to and including 40 mg of Compound 1 is administered;
- more than 0 mg and up to and including 35 mg of Compound 1 is administered;
- more than 0 mg and up to and including 30 mg of Compound 1 is administered;
- more than 0 mg and up to and including 25 mg of Compound 1 is administered;
- more than 0 mg and up to and including 20 mg of Compound 1 is administered;
- more than 0 mg and up to and including 15 mg of Compound 1 is administered;
- more than 0 mg and up to and including 10 mg of Compound 1 is administered; or
- more than 0 mg and up to and including 5 mg of Compound 1 is administered.

Compound One Solid Forms

In the aforementioned aspects and embodiments, Compound 1 may be administered as a crystalline (freebase) solid form or a crystalline salt.

Compound 1 Crystalline (Free Base) Solid

In one embodiment, Compound 1 is administered as a crystalline (freebase) solid. In one embodiment, the crystalline solid form of Compound 1 is characterized as Form A, Form B, Form C, Form D, Form E, Form F, Form G, Form H, Form I, Form J, Form K, Form L, Form M, Form N, Form O, Form P, or Form Q. In another embodiment, the crystalline solid form of Compound 1 is characterized as Form A, Form B, Form C, Form D, Form E, Form F, Form G, Form H, Form K, Form O, or Form Q. In another embodiment, the crystalline solid form of Compound 1 is characterized as Form I, Form J, Form L, Form M, Form N, or Form P. The crystalline solid form of Compound 1 characterized as Form A, Form B, Form C, Form D, Form E, Form F, Form G, Form H, Form I, Form J, Form K, Form L, Form M, Form N, Form O, Form P, or Form Q is disclosed in WO 2020/123800, the content of which is incorporated herein by reference in its entirety for all purposes.

In one embodiment, the crystalline solid is characterized as Compound 1 Form A.

In one embodiment, the crystalline solid is characterized as Compound 1 Form B.

In one embodiment, the crystalline solid is characterized as Compound 1 Form C.

In one embodiment, the crystalline solid is characterized as Compound 1 Form D.

In one embodiment, the crystalline solid is characterized as Compound 1 Form E.

In one embodiment, the crystalline solid is characterized as Compound 1 Form F.

In one embodiment, the crystalline solid is characterized as Compound 1 Form G.

In one embodiment, the crystalline solid is characterized as Compound 1 Form H.

In one embodiment, the crystalline solid is characterized as Compound 1 Form I.

In one embodiment, the crystalline solid is characterized as Compound 1 Form J.

In one embodiment, the crystalline solid is characterized as Compound 1 Form K.

In one embodiment, the crystalline solid is characterized as Compound 1 Form L.

In one embodiment, the crystalline solid is characterized as Compound 1 Form M.

In one embodiment, the crystalline solid is characterized as Compound 1 Form N.

In one embodiment, the crystalline solid is characterized as Compound 1 Form O.

In one embodiment, the crystalline solid is characterized as Compound 1 Form P.

In one embodiment, the crystalline solid is characterized as Compound 1 Form Q.

Compound 1 Crystalline Salts

In another embodiment, Compound 1 is administered as a crystalline salt or a hydrate or solvate thereof.

In one embodiment, the crystalline salt is characterized as Compound 1 HCl Form A, Compound 1 HCl Form B, Compound 1 HCl Form C, or Compound 1 HCl Form D. The crystalline salt form characterized as Compound 1 HCl Form A, Compound 1 HCl Form B, Compound 1 HCl Form C, or Compound 1 HCl Form D is disclosed in WO 2020/123800, the content of which is incorporated herein by reference in its entirety for all purposes.

In one embodiment, the crystalline salt is characterized as Compound 1 HCl Form A.

In one embodiment, the crystalline salt is characterized as Compound 1 HCl Form B.

In one embodiment, the crystalline salt is characterized as Compound 1 HCl Form C.

In one embodiment, the crystalline salt is characterized as Compound 1 HCl Form D.

In one embodiment, the pharmaceutical composition as disclosed herein comprises a crystalline fumaric acid salt of Compound 1, or hydrate or solvate thereof. In some embodiments, the crystalline fumaric acid salt of Compound 1 is characterized as Compound 1 fumarate Form A or Compound 1 hemifumarate Form B. The crystalline fumaric acid salt of Compound 1 characterized as Compound 1 fumarate Form A or Compound 1 hemifumarate Form B is disclosed in in WO 2020/123800, the content of which is incorporated herein by reference in its entirety for all purposes.

In one embodiment, the crystalline salt is characterized as Compound 1 Fumarate Form A.

In one embodiment, the crystalline fumaric acid salt is characterized as Compound 1 hemifumarate Form B.

Compound 1 Pharmaceutical Compositions

In the aforementioned aspects and embodiments, Compound 1 may be administered as a pharmaceutical composition. In one embodiment, the pharmaceutical composition comprises Compound 1 as a crystalline (freebase) solid form. In another embodiment, the pharmaceutical composition comprises Compound 1 as a crystalline salt.

In a further embodiment, the pharmaceutical composition is a tablet.

In a further embodiment, the tablet pharmaceutical composition comprises:

a. about 20 percent to about 40 percent by weight of Compound 1 as a crystalline solid or as a crystalline salt selected from the group consisting of Compound 1 HCl salt, Compound 1 fumaric Salt, and Compound 1 phosphoric acid salt;
b. about 35 percent to about 45 percent by weight of microcrystalline cellulose;
c. about 15 to about 25 percent by weight of lactose;
d. about 2 to about 8 percent by weight of hydroxypropyl cellulose;
e. about 4 to about 8 percent by weight of croscarmellose sodium;
f. about 0.1 to about 0.5 percent by weight of silicon dioxide; and
g. about 0.5 to about 3.5 percent by weight magnesium stearate; and optionally
h. a film coating.

In one embodiment, the tablet pharmaceutical composition comprises:

a. about 20 percent to about 40 percent by weight of Compound 1 as a crystalline solid or as a crystalline salt selected from the group consisting of Compound 1 HCl salt, Compound 1 fumaric Salt, and Compound 1 phosphoric acid salt;
b. about 35 percent to about 45 percent by weight of microcrystalline cellulose;
c. about 15 to about 25 percent by weight of anhydrous lactose;
d. about 2 to about 8 percent by weight of hydroxypropyl cellulose;
e. about 4 to about 8 percent by weight of croscarmellose sodium;
f. about 0.1 to about 0.5 percent by weight of colloidal silicon dioxide; and
g. about 0.5 to about 3.5 percent by weight magnesium stearate; and optionally
h. a film coating.

In one embodiment, the tablet pharmaceutical composition comprises:

a. about 25 percent to about 35 percent by weight of Compound 1 as a crystalline solid or as a crystalline salt selected from the group consisting of Compound 1 HCl salt, Compound 1 fumaric Salt, and Compound 1 phosphoric acid salt;
b. about 37 percent to about 43 percent by weight of microcrystalline cellulose;
c. about 18 to about 22 percent by weight of anhydrous lactose;
d. about 2 to about 6 percent by weight of hydroxypropyl cellulose;
e. about 5 to about 7 percent by weight of croscarmellose sodium;
f. about 0.2 to about 0.4 percent by weight of colloidal silicon dioxide; and
g. about 0.5 to about 3.5 percent by weight magnesium stearate; and optionally
h. a film coating.

Thus, in another embodiment, the tablet pharmaceutical composition comprises:

a. about 20 percent to about 40 percent by weight of Compound 1 as a crystalline solid or as a crystalline salt selected from the group consisting of Compound 1 HCl salt, Compound 1 fumaric Salt, and Compound 1 phosphoric acid salt;
b. about 35 percent to about 45 percent by weight of microcrystalline cellulose;
c. about 15 to about 25 percent by weight of lactose;
d. about 2 to about 8 percent by weight of hydroxypropyl cellulose;
e. about 2 to about 8 percent by weight of croscarmellose sodium;
f. about 0.1 to about 0.5 percent by weight of silicon dioxide; and
g. about 1 to about 5 percent by weight of stearic acid; and optionally
h. a film coating.

Thus, in another embodiment, the tablet pharmaceutical composition comprises:

a. about 20 percent to about 40 percent by weight of Compound 1 as a crystalline solid or as a crystalline salt selected from the group consisting of Compound 1 HCl salt, Compound 1 fumaric Salt, and Compound 1 phosphoric acid salt;
b. about 35 percent to about 45 percent by weight of microcrystalline cellulose;
c. about 15 to about 25 percent by weight of anhydrous lactose;
d. about 2 to about 8 percent by weight of hydroxypropyl cellulose;
e. about 2 to about 8 percent by weight of croscarmellose sodium;
f. about 0.1 to about 0.5 percent by weight of colloidal silicon dioxide; and
g. about 1 to about 5 percent by weight of stearic acid; and optionally
h. a film coating.

In one embodiment, the tablet pharmaceutical composition comprises:

a. about 25 percent to about 35 percent by weight of Compound 1 as a crystalline solid or as a crystalline salt selected from the group consisting of Compound 1 HCl salt, Compound 1 fumaric Salt, and Compound 1 phosphoric acid salt;
b. about 35 percent to about 40 percent by weight of microcrystalline cellulose;
c. about 16 to about 22 percent by weight of anhydrous lactose;
d. about 3 to about 7 percent by weight of hydroxypropyl cellulose;
e. about 3 to about 7 percent by weight of croscarmellose sodium
f. about 0.1 to about 0.5 percent by weight of colloidal silicon dioxide; and
g. about 0.5 to about 3.5 percent by weight stearic acid; and optionally
h. a film coating.

In one embodiment, the pharmaceutical compositions of this disclosure comprise Compound 1 as a crystalline (free-base) solid.

In one embodiment, the crystalline solid form of Compound 1 is characterized as Form A, Form B, Form C, Form D, Form E, Form F, Form G, Form H, Form I, Form J, Form K, Form L, Form M, Form N, Form O, Form P, or Form Q. In another embodiment, the crystalline solid form of Compound 1 is characterized as Form A, Form B, Form C, Form D, Form E, Form F, Form G, Form H, Form K, Form O, or Form Q. In another embodiment, the crystalline solid form of Compound 1 is characterized as Form I, Form J, Form L, Form M, Form N, or Form P. The crystalline solid form of Compound 1 characterized as Form A, Form B, Form C, Form D, Form E, Form F, Form G, Form H, Form I, Form J, Form K, Form L, Form M, Form N, Form O, Form P, or Form Q is disclosed in WO 2020/123800, the content of which is incorporated herein by reference in its entirety for all purposes.

In one embodiment, the crystalline solid is characterized as Compound 1 Form A.

In one embodiment, the crystalline solid is characterized as Compound 1 Form B.

In one embodiment, the crystalline solid is characterized as Compound 1 Form C.

In one embodiment, the crystalline solid is characterized as Compound 1 Form D.

In one embodiment, the crystalline solid is characterized as Compound 1 Form E.

In one embodiment, the crystalline solid is characterized as Compound 1 Form F.

In one embodiment, the crystalline solid is characterized as Compound 1 Form G.

In one embodiment, the crystalline solid is characterized as Compound 1 Form H.

In one embodiment, the crystalline solid is characterized as Compound 1 Form I.

In one embodiment, the crystalline solid is characterized as Compound 1 Form J.

In one embodiment, the crystalline solid is characterized as Compound 1 Form K.

In one embodiment, the crystalline solid is characterized as Compound 1 Form L.

In one embodiment, the crystalline solid is characterized as Compound 1 Form M.

In one embodiment, the crystalline solid is characterized as Compound 1 Form N.

In one embodiment, the crystalline solid is characterized as Compound 1 Form O.

In one embodiment, the crystalline solid is characterized as Compound 1 Form P.

In one embodiment, the crystalline solid is characterized as Compound 1 Form Q.

In another embodiment, the pharmaceutical compositions of this disclosure comprise Compound 1 as a crystalline salt or a hydrate or solvate thereof.

In one embodiment, the crystalline salt is characterized as Compound 1 HCl Form A, Compound 1 HCl Form B, Compound 1 HCl Form C, or Compound 1 HCl Form D. The crystalline salt form characterized as Compound 1 HCl Form A, Compound 1 HCl Form B, Compound 1 HCl Form C, or Compound 1 HCl Form D is disclosed in WO 2020/123800, the content of which is incorporated herein by reference in its entirety for all purposes.

In one embodiment, the crystalline salt is characterized as Compound 1 HCl Form A.

In one embodiment, the crystalline salt is characterized as Compound 1 HCl Form B.

In one embodiment, the crystalline salt is characterized as Compound 1 HCl Form C.

In one embodiment, the crystalline salt is characterized as Compound 1 HCl Form D.

In one embodiment, the pharmaceutical composition as disclosed herein comprises a crystalline fumaric acid salt of Compound 1, or hydrate or solvate thereof. In some embodiments, the crystalline fumaric acid salt of Compound 1 is characterized as Compound 1 fumarate Form A or Compound 1 hemifumarate Form B. The crystalline fumaric acid salt of Compound 1 characterized as Compound 1 fumarate Form A or Compound 1 hemifumarate Form B is disclosed in in WO 2020/123800, the content of which is incorporated herein by reference in its entirety for all purposes.

In one embodiment, the crystalline salt is characterized as Compound 1 Fumarate Form A.

In one embodiment, the crystalline fumaric acid salt is characterized as Compound 1 hemifumarate Form B.

In one embodiment, the pharmaceutical composition comprises a crystalline phosphoric acid salt of Compound 1 or hydrate or solvate thereof. In some embodiments, the crystalline phosphoric acid salt of Compound 1 is characterized as Compound 1 phosphate Form A. The crystalline phosphoric acid salt of Compound 1 characterized as Compound 1 phosphate Form A is disclosed in in WO 2020/123800, the content of which is incorporated herein by reference in its entirety for all purposes.

In one embodiment, the tablet pharmaceutical composition comprises:

a. about 25 percent to about 35 percent by weight of Compound 1 hemifumarate salt;
b. about 37 percent to about 43 percent by weight of microcrystalline cellulose;
c. about 18 to about 22 percent by weight of anhydrous lactose;
d. about 2 to about 6 percent by weight of hydroxypropyl cellulose;
e. about 5 to about 7 percent by weight of croscarmellose sodium;
f. about 0.2 to about 0.4 percent by weight of colloidal silicon dioxide; and
g. about 0.5 to about 3.5 percent by weight magnesium stearate; and optionally
h. a film coating.

In one embodiment, the tablet pharmaceutical composition comprises:

a. about 25 percent to about 35 percent by weight of Compound 1 hemifumarate salt Form B;
b. about 37 percent to about 43 percent by weight of microcrystalline cellulose;
c. about 18 to about 22 percent by weight of anhydrous lactose;
d. about 2 to about 6 percent by weight of hydroxypropyl cellulose;
e. about 5 to about 7 percent by weight of croscarmellose sodium;
f. about 0.2 to about 0.4 percent by weight of colloidal silicon dioxide; and
g. about 0.5 to about 3.5 percent by weight magnesium stearate; and optionally
h. a film coating.

In one embodiment, the tablet pharmaceutical composition comprises:

a. about 27.75 percent by weight of Compound 1 hemifumarate salt;
b. about 41.47 percent by weight of microcrystalline cellulose;
c. about 20.73 percent by weight of anhydrous lactose;
d. about 3 percent by weight of hydroxypropyl cellulose;
e. about 6 percent by weight of croscarmellose sodium;
f. about 0.3 percent by weight of colloidal silicon dioxide; and
g. about 0.75 percent by weight magnesium stearate; and optionally
h. a film coating.

In one embodiment, the tablet pharmaceutical composition comprises:

a. about 27.75 percent by weight of Compound 1 hemifumarate salt Form B;
b. about 41.47 percent by weight of microcrystalline cellulose;
c. about 20.73 percent by weight of anhydrous lactose;
d. about 3 percent by weight of hydroxypropyl cellulose;
e. about 6 percent by weight of croscarmellose sodium;
f. about 0.3 percent by weight of colloidal silicon dioxide; and
g. about 0.75 percent by weight magnesium stearate; and optionally
h. a film coating.

In one embodiment, the tablet pharmaceutical composition comprises:

a. 20 to 25 mg of Compound 1 hemifumarate salt;
b. 30 to 35 mg of microcrystalline cellulose;
c. 15 to 18 mg anhydrous lactose;
d. 1.5 to 4.5 mg hydroxypropyl cellulose;
e. 4 to 6 mg of croscarmellose sodium;
f. 0.1 to 0.3 mg colloidal silicon dioxide; and
g. 0.5 to 0.7 mg magnesium stearate; and optionally
h. 2 to 6 mg of a film coating.

In one embodiment, the tablet pharmaceutical composition comprises:

a. 20 to 25 mg of Compound 1 hemifumarate salt Form B;
b. 30 to 35 mg of microcrystalline cellulose;
c. 15 to 18 mg anhydrous lactose;
d. 1.5 to 4.5 mg hydroxypropyl cellulose;
e. 4 to 6 mg of croscarmellose sodium;
f. 0.1 to 0.3 mg colloidal silicon dioxide; and
g. 0.5 to 0.7 mg magnesium stearate; and optionally
h. 2 to 6 mg of a film coating.

In one embodiment, the tablet pharmaceutical composition comprises:

a. 22.20 mg of Compound 1 hemifumarate salt Form B;
b. 30 to 35 mg of microcrystalline cellulose;
c. 15 to 18 mg anhydrous lactose;
d. 1.5 to 4.5 mg hydroxypropyl cellulose;
e. 4 to 6 mg of croscarmellose sodium;
f. 0.1 to 0.3 mg colloidal silicon dioxide; and
g. 0.5 to 0.7 mg magnesium stearate; and optionally
h. 2 to 6 mg of a film coating.

In one embodiment, the tablet pharmaceutical composition comprises:

a. 22.20 mg of Compound 1 hemifumarate salt Form B;
b. 33.17 mg of microcrystalline cellulose;
c. 16.59 mg anhydrous lactose;
d. 2.4 mg hydroxypropyl cellulose;
e. 4.8 mg of croscarmellose sodium;
f. 0.24 mg colloidal silicon dioxide; and
g. 0.6 mg magnesium stearate; and optionally
h. 3.2 mg of a film coating.

In one embodiment, the tablet pharmaceutical composition comprises:

a. about 25 percent to about 35 percent by weight of Compound 1 hemifumarate salt;
b. about 35 percent to about 40 percent by weight of microcrystalline cellulose;
c. about 16 to about 22 percent by weight of anhydrous lactose;
d. about 3 to about 7 percent by weight of hydroxypropyl cellulose;

e. about 3 to about 7 percent by weight of croscarmellose sodium
f. about 0.1 to about 0.5 percent by weight of colloidal silicon dioxide; and
g. about 0.5 to about 3.5 percent by weight stearic acid; and optionally
h. a film coating.

In one embodiment, the tablet pharmaceutical composition comprises:

a. about 25 percent to about 35 percent by weight of Compound 1 hemifumarate salt Form B;
b. about 35 percent to about 40 percent by weight of microcrystalline cellulose;
c. about 16 to about 22 percent by weight of anhydrous lactose;
d. about 3 to about 7 percent by weight of hydroxypropyl cellulose;
e. about 3 to about 7 percent by weight of croscarmellose sodium
f. about 0.1 to about 0.5 percent by weight of colloidal silicon dioxide; and
g. about 0.5 to about 3.5 percent by weight stearic acid; and optionally
h. a film coating.

In one embodiment, the tablet pharmaceutical composition comprises:

a. about 27.75 percent by weight of Compound 1 hemifumarate salt;
b. about 38.63 percent by weight of microcrystalline cellulose;
c. about 19.32 percent by weight of anhydrous lactose;
d. about 5 percent by weight of hydroxypropyl cellulose;
e. about 6 percent by weight of croscarmellose sodium
f. about 0.3 percent by weight of colloidal silicon dioxide; and
g. about 3 percent by weight stearic acid; and optionally
h. a film coating.

In one embodiment, the tablet pharmaceutical composition comprises:

a. about 27.75 percent by weight of Compound 1 hemifumarate salt Form B;
b. about 38.63 percent by weight of microcrystalline cellulose;
c. about 19.32 percent by weight of anhydrous lactose;
d. about 5 percent by weight of hydroxypropyl cellulose;
e. about 6 percent by weight of croscarmellose sodium
f. about 0.3 percent by weight of colloidal silicon dioxide; and
g. about 3 percent by weight stearic acid; and optionally
h. a film coating.

In one embodiment, the tablet pharmaceutical composition comprises:

a. 20 to 25 mg of Compound 1 hemifumarate salt;
b. 30 to 40 mg of microcrystalline cellulose;
c. 15 to 20 mg anhydrous lactose;
d. 3 to 7 mg hydroxypropyl cellulose;
e. 3 to 7 mg of croscarmellose sodium;
f. 0.1 to 0.3 mg colloidal silicon dioxide; and
g. 2 to 4 mg stearic acid; and optionally
h. 2 to 5 mg of a film coating.

In one embodiment, the tablet pharmaceutical composition comprises:

a. 20 to 25 mg of Compound 1 hemifumarate salt Form B;
b. 30 to 40 mg of microcrystalline cellulose;
c. 15 to 20 mg anhydrous lactose;
d. 3 to 7 mg hydroxypropyl cellulose;
e. 3 to 7 mg of croscarmellose sodium;
f. 0.1 to 0.3 mg colloidal silicon dioxide; and
g. 2 to 4 mg stearic acid; and optionally
h. 2 to 5 mg of a film coating.

In one embodiment, the tablet pharmaceutical composition comprises:

a. 22.20 mg of Compound 1 hemifumarate salt Form B;
b. 30 to 40 mg of microcrystalline cellulose;
c. 15 to 20 mg anhydrous lactose;
d. 3 to 7 mg hydroxypropyl cellulose;
e. 3 to 7 mg of croscarmellose sodium;
f. 0.1 to 0.3 mg colloidal silicon dioxide; and
g. 2 to 4 mg stearic acid; and optionally
h. 2 to 5 mg of a film coating.

In one embodiment, the tablet pharmaceutical composition comprises:

a. 22.20 mg of Compound 1 hemifumarate salt Form B;
b. 30.9 mg of microcrystalline cellulose;
c. 15.46 mg anhydrous lactose;
d. 4 mg hydroxypropyl cellulose;
e. 4.8 mg of croscarmellose sodium;
f. 0.24 mg colloidal silicon dioxide; and
g. 2.4 mg stearic acid; and optionally
h. 3.2 mg of a film coating.

In one embodiment, the tablet pharmaceutical composition comprises:

a. 83 to 93 mg of Compound 1 hemifumarate salt;
b. 120 to 150 mg of microcrystalline cellulose;
c. 60 to 80 mg anhydrous lactose;
d. 12 to 30 mg hydroxypropyl cellulose;
e. 12 to 30 mg of croscarmellose sodium;
f. 0.5 to 1.5 mg colloidal silicon dioxide; and
g. 8 to 16 mg stearic acid; and optionally
h. 8 to 14 mg of a film coating.

In one embodiment, the tablet pharmaceutical composition comprises:

a. 83 to 93 mg of Compound 1 hemifumarate salt Form B;
b. 120 to 150 mg of microcrystalline cellulose;
c. 60 to 80 mg anhydrous lactose;
d. 12 to 30 mg hydroxypropyl cellulose;
e. 12 to 30 mg of croscarmellose sodium;
f. 0.5 to 1.5 mg colloidal silicon dioxide; and
g. 8 to 16 mg stearic acid; and optionally
h. 8 to 14 mg of a film coating.

In one embodiment, the tablet pharmaceutical composition comprises:

a. 88.78 mg of Compound 1 hemifumarate salt Form B;
b. 120 to 150 mg of microcrystalline cellulose;
c. 60 to 80 mg anhydrous lactose;
d. 12 to 30 mg hydroxypropyl cellulose;
e. 12 to 30 mg of croscarmellose sodium;
f. 0.5 to 1.5 mg colloidal silicon dioxide; and
g. 8 to 16 mg stearic acid; and optionally
h. 8 to 14 mg of a film coating.

In one embodiment, the tablet pharmaceutical composition comprises:

a. 88.78 mg of Compound 1 hemifumarate salt Form B;
b. 123.62 mg of microcrystalline cellulose;
c. 61.82 mg anhydrous lactose;
d. 16 mg hydroxypropyl cellulose;
e. 19.2 mg of croscarmellose sodium;
f. 0.96 mg colloidal silicon dioxide; and
g. 9.6 mg stearic acid; and optionally
h. 12.8 mg of a film coating.

In another embodiment, Compound 1 is administered as a tablet pharmaceutical composition as provided in the following table.

| Ingredient | Composition % w/w | Composition mg/unit dose |
|---|---|---|
| Compound 1 | 27.75 | 20[1] |
| Microcrystalline Cellulose, PH-102 | 41.47 | 33.17 |
| Lactose Anhydrous, 60M | 20.73 | 16.59 |
| Hydroxypropyl Cellulose, EXF | 3.00 | 2.40 |
| Croscarmellose Sodium | 6.00 | 4.80 |
| Colloidal Silicon Dioxide | 0.30 | 0.24 |
| Magnesium Stearate (Non-Bovine) | 0.75 | 0.60 |
| Total core tablet weight | | 80.00 |
| Opadry ® II Blue (85F105057) | 4.00 | 3.20 |
| Total coated tablet weight | | 83.20 |

[1]20 mg of Compound 1 free base is equivalent to 22.20 mg of Compound 1 hemifumarate salt.

In another embodiment, Compound 1 is administered as a tablet pharmaceutical composition as provided in the following table.

| Ingredient | Composition % w/w | Composition mg/unit dose 20 mg | Composition mg/unit dose 80 mg |
|---|---|---|---|
| Compound 1 | 27.75 | 20[1] | 80[2] |
| Microcrystalline Cellulose, PH-102 | 38.63 | 30.90 | 123.62 |
| Lactose Anhydrous, 60M | 19.32 | 15.46 | 61.82 |
| Hydroxypropyl Cellulose, EXF | 5.00 | 4.00 | 16.00 |
| Croscarmellose Sodium | 6.00 | 4.80 | 19.20 |
| Colloidal Silicon Dioxide | 0.30 | 0.24 | 0.96 |
| Stearic Acid 50 | 3.00 | 2.40 | 9.60 |
| Total core tablet weight | | 80.0 | 320.0 |
| Opadry ® II Blue (85F105057) | 4.00 | 3.20 | 12.80 |
| Total coated tablet weight | | 83.2 | 332.8 |

[1]20 mg of Compound 1 free base is equivalent to 22.20 mg of Compound 1 hemifumarate salt.
[2]80 mg of Compound 1 free base is equivalent to 88.78 mg of Compound 1 hemifumarate salt.

Any of the formulations provided above can be adjusted according to the dose of Compound 1 desired. Thus, the amount of each of the formulation ingredients can be proportionally adjusted to provide a tablet formulation containing various amounts of Compound 1 as provided in the previous paragraphs.

Treatment of Cancer

In the aforementioned aspects and embodiments, Compound 1 is administered along with a checkpoint inhibitor and optionally an additional immunomodulating agent to treat cancer.

In the aforementioned aspects and embodiments, Compound 1 is administered as a single agent to treat cancer.

In one embodiment, the cancer is selected from cardiac cancer, head and neck cancer, lung cancer, colon cancer, gastrointestinal cancer, breast cancer, genitourinary tract cancer, liver cancer, bone cancer, thyroid cancer, cancer of the nervous system, gynecological cancer, hematologic cancer, skin cancer, and cancer of the adrenal glands.

In a further embodiment, the cardiac cancer is selected from angiosarcoma, fibrosarcoma, rhabdomyosarcoma, liposarcoma, myxoma, rhabdomyoma, fibroma, lipoma, and teratoma.

In another further embodiment, the head and neck cancer is selected from squamous cell carcinomas of the head and neck, laryngeal and hypopharyngeal cancer, nasal cavity and paranasal sinus cancer, nasopharyngeal cancer, salivary gland cancer, oral and oropharyngeal cancer.

In another further embodiment, the lung cancer is selected from bronchogenic carcinomas selected from squamous cell, undifferentiated small cell, undifferentiated large cell, adenocarcinoma, and non-small cell lung cancer; alveolar (bronchiolar) carcinoma bronchial adenoma sarcoma lymphoma chondromatous hamartoma and mesothelioma.

In another further embodiment, the colon cancer is selected from colorectal cancer, adenocarcinoma, gastrointestinal stromal tumors, lymphoma, carcinoids, and Turcot Syndrome.

In another further embodiment, the gastrointestinal cancer is selected from gastric cancer, gastroesophageal junction adenocarcinoma, esophageal squamous cell carcinoma, esophageal adenocarcinoma, esophageal leiomyosarcoma, esophageal lymphoma, gastric carcinoma, gastric lymphoma, gastric leiomyosarcoma, pancreatic ductal adenocarcinoma, pancreatic insulinoma, pancreatic glucagonoma, pancreatic gastrinoma, pancreatic carcinoid tumors, vipoma, small intestinal adenocarcinoma, small intestinal lymphoma, small intestinal carcinoid tumors, small intestinal Karposi's sarcoma, small intestinal leiomyoma, small intestinal hemangioma, small intestinal lipoma, small intestinal neurofibroma, small intestinal fibroma, large intestinal adenocarcinoma, large intestinal tubular adenoma, large intestinal villous adenoma, large intestinal hamartoma, and large intestinal leiomyoma.

In another further embodiment, the breast cancer is selected from metastatic breast cancer, ductal carcinoma in situ, invasive ductal carcinoma, tubular carcinoma, medullary carcinoma, mucinous carcinoma, lobular carcinoma in situ, and triple negative breast cancer;

In another further embodiment, the genitourinary tract cancer is selected from renal adenocarcinoma, renal nephroblastoma, renal lymphoma, renal cell carcinoma, squamous cell carcinoma of the bladder or urethra, transitional cell carcinoma of the bladder or urethra, adenocarcinoma of the bladder or urethra, urothelial carcinoma of the bladder or urethra, prostate adenocarcinoma, prostate sarcoma, castrate resistant prostate cancer, seminoma, testicular teratoma, embryonal carcinoma, testicular teratocarcinoma, testicular choriocarcinoma, testicular sarcoma, testicular interstitial cell carcinoma, testicular fibroma, testicular fibroadenoma, testicular adenomatoid tumors, testicular lipoma, clear cell carcinoma, and papillary carcinoma.

In another further embodiment, the liver cancer is selected from hepatocellular carcinoma, cholangiocarcinoma, hepatoblastoma, angiosarcoma, hepatocellular adenoma, and hemangioma.

In another further embodiment, the bone cancer is selected from osteogenic sarcoma, fibrosarcoma, malignant fibrous histiocytoma, chondrosarcoma, Ewing's sarcoma, malignant lymphoma, reticulum cell sarcoma, multiple myeloma, malignant giant cell tumor chordoma, osteochrondroma, benign chondroma, chondroblastoma, chondromyxofibroma, osteoid osteoma, and giant cell tumors.

In another further embodiment, the thyroid cancer is selected from medullary thyroid cancer, differentiated thyroid cancer, papillary thyroid cancer, follicular thyroid cancer, hurthle cell cancer, and anaplastic thyroid cancer;

In another further embodiment, the nervous system cancer is selected from osteoma of the skull, hemangioma of the skull, granuloma of the skull, xanthoma of the skull, osteitis deformans of the skull, meningioma, meningiosarcoma, gliomatosis of the meninges, brain astrocytoma, medulloblastoma, glioma, brain ependymoma, germinoma [pinealoma], glioblastoma multiform, oligodendroglioma, schwannoma, retinoblastoma, congenital brain tumors, spinal cord neurofibroma, meningioma, and brain sarcoma.

In another further embodiment, the gynecological cancer is selected from endometrial cancer, cervical carcinoma, pre-tumor cervical dysplasia, ovarian carcinomas selected from serous cystadenocarcinoma, mucinous cystadenocarcinoma, and unclassified ovarian carcinoma, granulosa-thecal cell tumors, Sertoli-Leydig cell tumors, dysgerminoma, and malignant teratoma; squamous cell carcinoma of the vulva, intraepithelial carcinoma of the vulva, adenocarcinoma of the vulva, fibrosarcoma of the vulva, melanoma of the vulva, vaginal clear cell carcinoma, vaginal squamous cell carcinoma, embryonal rhabdomyosarcoma, and fallopian tube carcinoma.

In another further embodiment, the hematologic cancer is selected from myeloid leukemia [acute and chronic], acute lymphoblastic leukemia, chronic lymphocytic leukemia, myeloproliferative diseases, multiple myeloma, myelodysplastic syndrome), Hodgkin's disease, and non-Hodgkin's lymphoma [malignant lymphoma].

In another further embodiment, the skin cancer is selected from malignant melanoma, basal cell carcinoma, squamous cell carcinoma, Karposi's sarcoma, moles dysplastic nevi, lipoma, angioma, dermatofibroma, keloids, and psoriasis.

In one embodiment, the cancer is selected from cardiac cancer, head and neck cancer, lung cancer, non-small cell lung cancer, small cell lung cancer, non-clear cell renal cell carcinoma, advanced clear cell renal carcinoma, castration-resistant prostate cancer, hormone receptor-positive breast cancer, prostate cancer, colon cancer, gastrointestinal cancer, breast cancer, genitourinary tract cancer, liver cancer, bone cancer, thyroid cancer, cancer of the nervous system, gynecological cancer, hematologic cancer, skin cancer, and cancer of the adrenal glands.

In a further embodiment, the cancer is a solid tumor.

In a further embodiment, the cancer is a solid tumor that is inoperable, locally advanced, metastatic, or recurrent.

In a further embodiment, the solid tumor is unresectable or metastatic and life-prolonging therapies do not exist or currently available therapies are intolerable or no longer effective.

In another further embodiment, the cancer or the solid tumor is ICI-refractory.

In another further embodiment, the cancer or the solid tumor is platimum-refractory.

In a further embodiment, the solid tumor is a sarcoma, carcinoma, or lymphoma.

In a further embodiment, the cancer is advanced clear cell renal carcinoma, hormone receptor positive breast cancer, or castration resistant prostate cancer.

In one embodiment, the cancer is advanced clear cell renal carcinoma.

In one embodiment, the cancer is unresectable advanced or metastatic clear cell renal cell carcinoma.

In one embodiment, the cancer is non-clear cell renal cell carcinoma.

In one embodiment, the cancer is advanced non-clear cell renal cell carcinoma.

In one embodiment, the cancer is unresectable advanced or metastatic non-clear cell renal cell carcinoma.

In one embodiment, the unresectable advanced or metastatic non-clear cell renal cell carcinoma includes Papillary renal cell carcinoma, unclassified renal cell carcinoma, and sarcomatoid renal cell carcinoma.

In one embodiment, the cancer is hormone receptor positive breast cancer.

In one embodiment, the cancer is castration resistant prostate cancer.

In a further embodiment, the castration resistant prostate cancer is metastatic.

In another further embodiment, the adrenal gland cancer is neuroblastoma.

In another further embodiment, the cancer is urothelial carcinoma.

In another further embodiment, the urothelial carcinoma is locally advanced or metastatic transitional cell carcinoma of the urothelium.

In another further embodiment, the cancer is advanced urothelial carcinoma.

In another further embodiment, the cancer is metastatic urothelial carcinoma.

In another further embodiment, the cancer is ICI-refractory urothelial carcinoma.

In another further embodiment, the cancer is platinum-refractory urothelial carcinoma In another further embodiment, the cancer is urothelial carcinoma of the renal pelvis, ureter, bladder or urethra.

In another further embodiment, the cancer is urothelial carcinoma of the renal pelvis.

In another further embodiment, the cancer is urothelial carcinoma of ureter.

In another further embodiment, the cancer is urothelial carcinoma of the urethra.

In another further embodiment, the cancer is urothelial carcinoma of the bladder.

In another embodiment, the cancer is selected from endometrial cancer, sarcoma, neuroendocrine tumor, ovarian cancer, colorectal cancer, HCC, NSCLC, gastric cancer, and melanoma.

In another embodiment, the cancer is endometrial cancer.

In another embodiment, the cancer is sarcoma.

In another embodiment, the cancer is neuroendocrine tumor.

In another embodiment, the cancer is ovarian cancer.

In another embodiment, the cancer is colorectal cancer.

In another embodiment, the colorectal cancer is right-sided colorectal cancer (RCRC) or left-sided colorectal cancer (LCRC).

In another embodiment, the cancer is hepatocellular carcinoma.

In another embodiment, the cancer is non-small cell lung cancer.

In another embodiment, the cancer is gastric cancer.

In another embodiment, the cancer is melanoma.

In another embodiment, the cancer is a solid tumor. In a further embodiment, the cancer is an unresectable advanced or metastatic solid tumor. In a further embodiment, the solid tumor is a genitourinary cancer. In a further embodiment, the genitourinary cancer is selected from the group consisting of clear cell renal cell carcinoma (ccRCC), non-clear cell renal cell carcinoma (nccRCC), urothelial carcinoma (UC, ICI naïve, and experienced), and metastatic castration-resistant prostate cancer (mCRPC).

In one embodiment, the subject is human.

In one embodiment, Compound 1 or the pharmaceutically acceptable salt thereof, or the pharmaceutical composition comprising Compound 1, and the checkpoint inhibitor or pharmaceutical composition comprising the checkpoint inhibitor are administered concurrently, sequentially or separately.

In one embodiment, Compound 1 or the pharmaceutically acceptable salt thereof, or the pharmaceutical composition comprising Compound 1, and the checkpoint inhibitor or pharmaceutical composition comprising the immunomodulating agent are administered concurrently, sequentially or separately. In an embodiment, the immunomodulating agent is selected from the group consisting of a PD-1 inhibitor, a PD-L1 inhibitor, a CTLA-4 inhibitor, and an IL-2 targeting agent In one embodiment, the method further comprises assessing treatment with said combination therapy by determining one or more of: inhibition of disease progression, inhibition of tumor growth, reduction of primary tumor, relief of tumor-related symptoms, inhibition of tumor secreted factors, delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased overall response rate, increased Overall Survival (OS) or increased Duration of Response (DOR), changes in tumor markers from baseline.

In one embodiment, the method includes treatment of cancer that has not previously been treated with any other anticancer treatment. In another embodiment, the method includes treatment of cancer that has not previously been treated with a PD-1 inhibitor. In another embodiment, the method includes treatment of cancer that has previously been treated with a PD-1 inhibitor. In another embodiment, the method includes treatment of cancer that has previously been treated with pembrolizumab, nivolumab, atezolizumab, durvalumab, avelumab, cemiplimab, camrelizumab, sintilimab, tisleilizumab, toripalimab, spartalizumab, dostarlimab, KN035, Cosibelimab, CA-170 (Curis, Inc.), or BMS-986189. In another embodiment, the method includes treatment of cancer that has not previously been treated with pembrolizumab, nivolumab, atezolizumab, durvalumab, avelumab, cemiplimab, camrelizumab, sintilimab, tisleilizumab, toripalimab, spartalizumab, dostarlimab, KN035, Cosibelimab, CA-170 (Curis, Inc.), or BMS-986189.

In one embodiment, the method includes treatment of cancer that has previously been treated with a PD-1 inhibitor, wherein the treatment initially resulted in partial response, but later developed resistance to PD-1 with progression of disease.

In one embodiment, the method includes treatment of cancer that has previously been treated with a PD-1 inhibitor, wherein the treatment initially resulted in stable disease, but later developed resistance to PD-1 with progression of disease.

In one embodiment, the method includes treatment of cancer that has previously been treated with a PD-1 inhibitor, wherein the treatment initially resulted in a complete response, but later develops resistance to PD-1 with progression of disease.

In one embodiment, the method includes treatment of cancer that has previously been treated with a PD-1 inhibitor, wherein the treatment resulted in no response to treatment.

In one embodiment, the method includes treatment of cancer that has not previously been treated with a PD-1 inhibitor, wherein the treatment initially resulted in partial response, but later developed resistance to PD-1 with progression of disease.

In one embodiment, the method includes treatment of cancer that has not previously been treated with a PD-1 inhibitor, wherein the treatment initially resulted in stable disease, but later developed resistance to PD-1 with progression of disease.

In one embodiment, the method includes treatment of cancer that has not previously been treated with a PD-1 inhibitor, wherein the treatment initially resulted in a complete response, but later develops resistance to PD-1 with progression of disease.

In one embodiment, the method includes treatment of cancer that has not previously been treated with a PD-1 inhibitor, wherein the treatment resulted in no response to treatment.

In an embodiment of the disclosure, the checkpoint inhibitor or PD-1 inhibitor, in combination with a non-polymorphic form, crystalline form or crystalline salt form of Compound 1, is used to reduce or inhibit metastasis of a primary tumor or cancer to other sites, or the formation or establishment of metastatic tumors or cancers at other sites distal from the primary tumor or cancer thereby inhibiting or reducing tumor or cancer relapse or tumor or cancer progression.

In a further embodiment of the disclosure, provided herein is a combination therapy for treating cancer, which comprises a non-polymorphic form, crystalline form or crystalline salt form of Compound 1 and the checkpoint inhibitor or PD-1 inhibitor with the potential to elicit potent and durable immune responses with enhanced therapeutic benefit and more manageable toxicity.

In a further embodiment of the disclosure, provided herein is a combination therapy for treating cancer, which comprises a non-polymorphic form, crystalline form or crystalline salt form of Compound 1 and the checkpoint inhibitor or PD-1 inhibitor. In an embodiment of the disclosure provided herein is a method for treating cancer and/or preventing the establishment of metastases by employing a non-polymorphic form, crystalline form or crystalline salt form of Compound 1 of the present invention, which acts synergistically with a checkpoint inhibitor.

In further embodiments, the disclosure provides methods for one or more of the following: 1) reducing or inhibiting growth, proliferation, mobility or invasiveness of tumor or cancer cells that potentially or do develop metastases, 2) reducing or inhibiting formation or establishment of metastases arising from a primary tumor or cancer to one or more other sites, locations or regions distinct from the primary tumor or cancer; 3) reducing or inhibiting growth or proliferation of a metastasis at one or more other sites, locations or regions distinct from the primary tumor or cancer after a metastasis has formed or has been established, 4) reducing or inhibiting formation or establishment of additional metastasis after the metastasis has been formed or established, 5) prolonged overall survival, 6) prolonged progression free survival, or 7) disease stabilization. The methods include administering to a subject in need thereof a non-polymorphic form, crystalline form or crystalline salt form of Compound 1 of the present invention, in combination with a checkpoint inhibitor as described herein.

In an embodiment of the disclosure, administration of a non-polymorphic form, crystalline form or crystalline salt form of Compound 1 in combination with the checkpoint inhibitor or PD-1 inhibitor, provides a detectable or measurable improvement in a condition of a given subject, such as alleviating or ameliorating one or more adverse (physical) symptoms or consequences associated with the presence of a cell proliferative or cellular hyperproliferative disorder, neoplasia, tumor or cancer, or metastasis, i.e., a therapeutic benefit or a beneficial effect.

A therapeutic benefit or beneficial effect is any objective or subjective, transient, temporary, or long-term improvement in the condition or pathology, or a reduction in onset, severity, duration or frequency of adverse symptom associated with or caused by cell proliferation or a cellular hyperproliferative disorder such as a neoplasia, tumor or cancer, or metastasis. It may lead to improved survival. A satisfactory clinical endpoint of a treatment method in accordance with the disclosure is achieved, for example, when there is an incremental or a partial reduction in severity, duration or frequency of one or more associated pathologies, adverse symptoms or complications, or inhibition or reversal of one or more of the physiological, biochemical or cellular manifestations or characteristics of cell proliferation or a cellular hyperproliferative disorder such as a neoplasia, tumor or cancer, or metastasis. A therapeutic benefit or improvement therefore may be, but is not limited to destruction of target proliferating cells (e.g., neoplasia, tumor or cancer, or metastasis) or ablation of one or more, most or all pathologies, adverse symptoms or complications associated with or caused by cell proliferation or the cellular hyperproliferative disorder such as a neoplasia, tumor or cancer, or metastasis. However, a therapeutic benefit or improvement need not be a cure or complete destruction of all target proliferating cells (e.g., neoplasia, tumor or cancer, or metastasis) or ablation of all pathologies, adverse symptoms or complications associated with or caused by cell proliferation or the cellular hyperproliferative disorder such as a neoplasia, tumor or cancer, or metastasis. For example, partial destruction of a tumor or cancer cell mass, or a stabilization of the tumor or cancer mass, size or cell numbers by inhibiting progression or worsening of the tumor or cancer, can reduce mortality and prolong lifespan even if only for a few days, weeks or months, even though a portion or the bulk of the tumor or cancer mass, size or cells remain.

Specific non-limiting examples of therapeutic benefit include a reduction in neoplasia, tumor or cancer, or metastasis volume (size or cell mass) or numbers of cells; inhibiting or preventing an increase in neoplasia, tumor or cancer volume (e.g., stabilizing); slowing or inhibiting neoplasia, tumor or cancer progression, worsening or metastasis; or inhibiting neoplasia, tumor or cancer proliferation, growth or metastasis.

In an embodiment of the disclosure, administration of the checkpoint inhibitor or PD-1 inhibitor, in combination therapy with a non-polymorphic form, crystalline form or crystalline salt form of Compound 1, provides a detectable or measurable improvement or overall response according to the irRC (as derived from time-point response assessments and based on tumor burden), including one of more of the following: (i) irCR—complete disappearance of all lesions, whether measurable or not, and no new lesions (confirmation by a repeat, consecutive assessment no less than 4 weeks from the date first documented), (ii) irPR—decrease in tumor burden ≥50% relative to baseline (confirmed by a consecutive assessment at least 4 weeks after first documentation).

Optionally, any method described herein may not take effect immediately. For example, treatment may be followed by an increase in the neoplasia, tumor or cancer cell numbers or mass, but over time eventual stabilization or reduction in tumor cell mass, size or numbers of cells in a given subject may subsequently occur.

Additional adverse symptoms and complications associated with neoplasia, tumor, cancer and metastasis that can be inhibited, reduced, decreased, delayed or prevented include, for example, nausea, lack of appetite, lethargy, pain and discomfort. Thus, a partial or complete decrease or reduction in the severity, duration or frequency of adverse symptom or complication associated with or caused by a cellular hyperproliferative disorder, an improvement in the subject's quality of life and/or well-being, such as increased energy, appetite, psychological well-being, are all particular non-limiting examples of therapeutic benefit.

A therapeutic benefit or improvement therefore can also include a subjective improvement in the quality of life of a treated subject. In an additional embodiment, a method prolongs or extends lifespan (survival) of the subject. In a further embodiment, a method improves the quality of life of the subject.

In one embodiment, administration of the checkpoint inhibitor or PD-1 inhibitor, in combination therapy with a non-polymorphic form, crystalline form or crystalline salt form of Compound 1, results in a clinically relevant improvement in one or more markers of disease status and progression selected from one or more of the following: (i) overall survival, (ii) progression-free survival, (iii) overall response rate, (iv) reduction in metastatic disease, (v) circulating levels of tumor antigens such as carbohydrate antigen 19.9 (CA19.9) and carcinembryonic antigen (CEA) or others depending on tumor, (vii) nutritional status (weight, appetite, serum albumin), (viii) pain control or analgesic use, and (ix) CRP/albumin ratio.

Treatment with a non-polymorphic form, crystalline form or crystalline salt form of Compound 1 in combination with the checkpoint inhibitor or PD-1 inhibitor gives rise to more complex immunity including not only the development of innate immunity and type-1 immunity, but also immunoregulation which more efficiently restores appropriate immune functions.

Combination of Compound 1 with a Checkpoint Inhibitor

Combination of Compound 1 with Atezolizumab

In the aforementioned aspects and embodiments, Compound 1 is administered, along with a checkpoint inhibitor, and optionally an additional immunomodulating agent, to treat cancer.

In one embodiment, the checkpoint inhibitor is atezolizumab.

In one embodiment, the invention includes a method for treating cancer in a subject, the method comprising:

(i) administering to the subject a therapeutically effective amount of Compound 1 or a pharmaceutically acceptable salt or a pharmaceutical composition comprising Compound 1 thereof, and (ii) administering to the subject a therapeutically effective amount of atezolizumab.

In one embodiment, the invention includes a method for treating cancer in a subject, the method comprising:

(i) administering to the subject a dosage of from about 5 mg to about 100 mg of Compound 1 or a pharmaceutically acceptable salt or a pharmaceutical composition comprising Compound 1 thereof, and (ii) administering to the subject a therapeutically effective amount of atezolizumab.

In another embodiment, the invention includes a method for treating cancer in a subject, the method comprising administering to the subject in need of such treatment a therapeutically effective amount of Compound 1 or a pharmaceutically acceptable salt thereof or a pharmaceutical composition comprising compound (1) or the pharmaceutically acceptable salt thereof, and a pharmaceutically acceptable carrier or excipient, in combination with a therapeutically effective amount of atezolizumab or a pharmaceutical composition comprising atezolizumab.

In another embodiment, the invention includes a method for treating cancer in a subject, the method comprising administering to the subject in need of such treatment a dosage of from about 5 mg to about 100 mg of Compound 1 or a pharmaceutically acceptable salt thereof or a pharmaceutical composition comprising compound (1) or the pharmaceutically acceptable salt thereof, and a pharmaceutically acceptable carrier or excipient, in combination with a therapeutically effective amount of atezolizumab or a pharmaceutical composition comprising atezolizumab.

In one embodiment, Compound 1 or the pharmaceutically acceptable salt thereof, or the pharmaceutical composition comprising Compound 1, and atezolizumab or the pharmaceutical composition comprising atezolizumab are administered concurrently, sequentially or separately.

In one embodiment, the cancer is selected from cardiac cancer, head and neck cancer, lung cancer, non-small cell lung cancer, small cell lung cancer, non-clear cell renal cell carcinoma, advanced clear cell renal carcinoma, castration-resistant prostate cancer, hormone receptor-positive breast cancer, prostate cancer, colon cancer, gastrointestinal cancer, breast cancer, genitourinary tract cancer, liver cancer, bone cancer, thyroid cancer, cancer of the nervous system, gynecological cancer, hematologic cancer, skin cancer, urothelial carcinoma, and cancer of the adrenal glands.

In one embodiment, the amount of Compound 1, or a pharmaceutically acceptable salt thereof administered is from more than 0.0 mg and up to and including 100 mg of Compound 1; more than 0.0 mg and up to and including 95 mg of Compound 1; more than 0.0 mg and up to and including 90 mg of Compound 1; more than 0.0 mg and up to and including 85 mg of Compound 1; more than 0.0 mg and up to and including 80 mg of Compound 1; more than 0.0 mg and up to and including 75 mg of Compound 1; more than 0.0 mg and up to and including 70 mg of Compound 1; more than 0.0 mg and up to and including 65 mg of Compound 1; more than 0.0 mg and up to and including 60 mg of Compound 1; more than 0.0 mg and up to and including 55 mg of Compound 1; more than 0.0 mg and up to and including 50 mg of Compound 1; more than 0.0 mg and up to and including 45 mg of Compound 1; more than 0.0 mg and up to and including 40 mg of Compound 1; more than 0.0 mg and up to and including 35 mg of Compound 1; more than 0.0 mg and up to and including 30 mg of Compound 1; more than 0.0 mg and up to and including 25 mg of Compound 1; more than 0.0 mg and up to and including 20 mg of Compound 1; more than 0.0 mg and up to and including 15 mg of Compound 1; more than 0.0 mg and up to and including 10 mg of Compound 1; or up to and including 5 mg of Compound 1. In one embodiment, Compound 1 is administered once daily. In another embodiment, Compound 1 is administered twice daily.

In one embodiment, atezolizumab is administered intravenously (IV) to the subject. In another embodiment, the atezolizumab is administered by parenteral injection to the subject.

In one embodiment, atezolizumab is administered once every two weeks, once every three weeks, or once every four weeks for the duration of the treatment period. In a further embodiment, atezolizumab is administered once every two weeks for the duration of the treatment period. In another further embodiment, atezolizumab is administered once every three weeks for the duration of the treatment period. In another further embodiment, atezolizumab is administered once every four weeks for the duration of the treatment period.

In one embodiment, the dosage of atezolizumab is from about 800 mg to about 1700 mg.

In one embodiment, the dosage of atezolizumab is about 840 mg administered once every two weeks, about 1200 mg administered once every three weeks, or 1680 mg administered once every four weeks.

In one embodiment, atezolizumab is administered to a subject in an IV unit dosage form, wherein the dose form comprises 840 mg, 1200 mg, or 1680 mg of atezolizumab, water, glacial acetic acid, L-histidine, polysorbate 20, and sucrose.

In one embodiment, atezolizumab is administered to a subject in an IV unit dosage form, wherein the dose form is sold as Tecentriq®.

Combination of Compound 1 with Avelumab

In one embodiment, the checkpoint inhibitor is avelumab.

In one embodiment, the invention includes a method for treating cancer in a subject, the method comprising:

(i) administering to the subject a therapeutically effective amount of Compound 1 or a pharmaceutically acceptable salt or a pharmaceutical composition comprising Compound 1 thereof, and (ii) administering to the subject a therapeutically effective amount of avelumab.

In one embodiment, the invention includes a method for treating cancer in a subject, the method comprising:

(i) administering to the subject a dosage of from about 5 mg to about 100 mg of Compound 1 or a pharmaceutically acceptable salt or a pharmaceutical composition comprising Compound 1 thereof, and (ii) administering to the subject a therapeutically effective amount of avelumab.

In another embodiment, the invention includes a method for treating cancer in a subject, the method comprising administering to the subject in need of such treatment a therapeutically effective amount of Compound 1 or a pharmaceutically acceptable salt thereof or a pharmaceutical composition comprising Compound 1 or the pharmaceutically acceptable salt thereof, and a pharmaceutically acceptable carrier or excipient, in combination with a therapeutically effective amount of avelumab or a pharmaceutical composition comprising avelumab.

In another embodiment, the invention includes a method for treating cancer in a subject, the method comprising administering to the subject in need of such treatment a dosage of from about 5 mg to about 100 mg of Compound 1 or a pharmaceutically acceptable salt thereof or a pharmaceutical composition comprising Compound 1 or the pharmaceutically acceptable salt thereof, and a pharmaceutically acceptable carrier or excipient, in combination with a therapeutically effective amount of avelumab or a pharmaceutical composition comprising avelumab.

In one embodiment, the invention includes a method for treating urothelial carcinoma in a subject, the method comprising:

(i) administering to the subject a dosage of from about 5 mg to about 100 mg of Compound 1 or a pharmaceutically acceptable salt or a pharmaceutical composition comprising Compound 1 thereof, and (ii) administering to the subject a therapeutically effective amount of avelumab.

In another embodiment, the invention includes a method for treating urothelial carcinoma in a subject, the method comprising administering to the subject in need of such treatment a dosage of from about 5 mg to about 100 mg of Compound 1 or a pharmaceutically acceptable salt thereof, or a pharmaceutical composition comprising Compound 1 or the pharmaceutically acceptable salt thereof, and a pharmaceutically acceptable carrier or excipient, in combination with a therapeutically effective amount of avelumab or a pharmaceutical composition comprising avelumab.

In one embodiment, Compound 1 or the pharmaceutically acceptable salt thereof, or the pharmaceutical composition comprising Compound 1, and avelumab or the pharmaceutical composition comprising avelumab are administered concurrently, sequentially or separately.

In one embodiment, the cancer is selected from cardiac cancer, head and neck cancer, lung cancer, non-small cell lung cancer, small cell lung cancer, non-clear cell renal cell carcinoma, advanced clear cell renal carcinoma, castration-resistant prostate cancer, hormone receptor-positive breast cancer, prostate cancer, colon cancer, gastrointestinal cancer, breast cancer, genitourinary tract cancer, liver cancer, bone cancer, thyroid cancer, cancer of the nervous system, gynecological cancer, hematologic cancer, skin cancer, urothelial carcinoma, and cancer of the adrenal glands.

In one embodiment, the urothelial carcinoma is locally advanced or metastatic transitional cell carcinoma of the urothelium. In another embodiment, the urothelial carcinoma is advanced urothelial carcinoma. In another embodiment, the urothelial carcinoma is urothelial carcinoma of the renal pelvis, ureter, bladder or urethra.

In one embodiment, the amount of Compound 1, or a pharmaceutically acceptable salt thereof administered is from more than 0.0 mg and up to and including 100 mg of Compound 1; more than 0.0 mg and up to and including 95 mg of Compound 1; more than 0.0 mg and up to and including 90 mg of Compound 1; more than 0.0 mg and up to and including 85 mg of Compound 1; more than 0.0 mg and up to and including 80 mg of Compound 1; more than 0.0 mg and up to and including 75 mg of Compound 1; more than 0.0 mg and up to and including 70 mg of Compound 1; more than 0.0 mg and up to and including 65 mg of Compound 1; more than 0.0 mg and up to and including 60 mg of Compound 1; more than 0.0 mg and up to and including 55 mg of Compound 1; more than 0.0 mg and up to and including 50 mg of Compound 1; more than 0.0 mg and up to and including 45 mg of Compound 1; more than 0.0 mg and up to and including 40 mg of Compound 1; more than 0.0 mg and up to and including 35 mg of Compound 1; more than 0.0 mg and up to and including 30 mg of Compound 1; more than 0.0 mg and up to and including 25 mg of Compound 1; more than 0.0 mg and up to and including 20 mg of Compound 1; more than 0.0 mg and up to and including 15 mg of Compound 1; more than 0.0 mg and up to and including 10 mg of Compound 1; or up to and including 5 mg of Compound 1. In one embodiment, Compound 1 is administered once daily. In another embodiment, Compound 1 is administered twice daily.

In one embodiment, avelumab is administered intravenously (IV) to the subject. In another embodiment, avelumab is administered by intravenous infusion to the subject.

In one embodiment, avelumab is administered once every two weeks, once every three weeks, or once every four weeks for the duration of the treatment period. In a further embodiment, avelumab is administered once every two weeks for the duration of the treatment period. In another further embodiment, avelumab is administered once every three weeks for the duration of the treatment period. In another further embodiment, avelumab is administered once every four weeks for the duration of the treatment period.

In one embodiment, the dosage of avelumab is from about 500 mg to about 1700 mg.

In one embodiment, the dosage of avelumab is about 800 mg administered once every two weeks, about 1200 mg administered once every three weeks, or 1600 mg administered once every four weeks.

In one embodiment, the dosage of avelumab is about 800 mg administered once every two weeks.

In one embodiment, avelumab is administered to a subject in an IV unit dosage form, wherein the dose form is sold as Bavencio®.

In one embodiment, the subject is human.

In one embodiment, the subject with advanced urothelial carcinoma has stage IV disease per AJCC TNM staging criteria (8th edition, 1 Jan. 2018).

In one embodiment, Compound 1 or the pharmaceutically acceptable salt thereof, or the pharmaceutical composition comprising Compound 1, and avelumab or pharmaceutical composition comprising avelumab are administered concurrently, sequentially or separately.

In one embodiment, the combination of Compound 1 or the pharmaceutically acceptable salt thereof, or the pharmaceutical composition comprising Compound 1, and avelumab or pharmaceutical composition comprising avelumab is administered as a maintenance therapy in a subject with advanced urothelial carcinoma.

In one embodiment, the subject with advanced urothelial carcinoma received first-line platinum-based doublet chemotherapy before the maintenance therapy.

In one embodiment, the first-line platinum-based doublet chemotherapy includes gemcitabine+cisplatin and/or gemcitabine+carboplatin.

In one embodiment, the combination of Compound 1 or the pharmaceutically acceptable salt thereof, or the pharmaceutical composition comprising Compound 1, and avelumab or pharmaceutical composition comprising avelumab is administered as a Second-line or Third-line therapy in a subject with advanced urothelial carcinoma.

In one embodiment, the subject with advanced urothelial carcinoma received first-line platinum-based doublet chemotherapy before the Second-line or Third-line therapy.

In one embodiment, the first-line platinum-based doublet chemotherapy includes gemcitabine+cisplatin and/or gemcitabine+carboplatin.

In one embodiment, the subject with advanced urothelial carcinoma received first-line platinum-based doublet chemotherapy for at least 4 cycles but not more than 6 cycles.

In one embodiment, the subject has progressed after the first-line platinum-based doublet chemotherapy.

In one embodiment, the method includes treatment of cancer that has not previously been treated with prior immunotherapy with IL-2, IFN-α or any anti-PD-1, anti-PD-L1, anti-PD-L2, anti-CD137, or CTLA-4 antibody (including ipilimumab), or any other antibody or drug specifically targeting T-cell co-stimulation or immune checkpoint. In another embodiment, the method includes treatment of cancer that has not previously been treated with a PD-1 or PD-L1 inhibitor.

Combination of Compound 1 with Nivolumab

In one embodiment, the invention includes a method for treating cancer in a subject, the method comprising:

(i) administering to the subject a therapeutically effective amount of Compound 1 or a pharmaceutically acceptable salt or a pharmaceutical composition comprising Compound 1 thereof, and (ii) administering to the subject a therapeutically effective amount of nivolumab.

In one embodiment, the invention includes a method for treating cancer in a subject, the method comprising:

(i) administering to the subject a dosage of from about 5 mg to about 100 mg of Compound 1 or a pharmaceutically acceptable salt or a pharmaceutical composition comprising Compound 1 thereof, and (ii) administering to the subject a therapeutically effective amount of nivolumab.

In another embodiment, the invention includes a method for treating cancer in a subject, the method comprising administering to the subject in need of such treatment a therapeutically effective amount of Compound 1 or a pharmaceutically acceptable salt thereof or a pharmaceutical composition comprising Compound 1 or the pharmaceutically acceptable salt thereof, and a pharmaceutically acceptable carrier or excipient, in combination with a therapeutically effective amount of nivolumab or a pharmaceutical composition comprising nivolumab.

In another embodiment, the invention includes a method for treating cancer in a subject, the method comprising administering to the subject in need of such treatment a dosage of from about 5 mg to about 100 mg of Compound 1 or a pharmaceutically acceptable salt thereof or a pharmaceutical composition comprising Compound 1 or the pharmaceutically acceptable salt thereof, and a pharmaceutically acceptable carrier or excipient, in combination with a therapeutically effective amount of nivolumab or a pharmaceutical composition comprising nivolumab.

In one embodiment, Compound 1 or the pharmaceutically acceptable salt thereof, or the pharmaceutical composition comprising Compound 1, and nivolumab or the pharmaceutical composition comprising nivolumab are administered concurrently, sequentially or separately.

In these and other embodiments, nivoluamb is administered at about 360 mg every three weeks.

In one embodiment, the cancer is selected from melanoma, cardiac cancer, head and neck cancer, lung cancer, non-small cell lung cancer, small cell lung cancer, non-clear cell renal cell carcinoma, advanced clear cell renal carcinoma, castration-resistant prostate cancer, hormone receptor-positive breast cancer, prostate cancer, colon cancer, gastrointestinal cancer, breast cancer, genitourinary tract cancer, liver cancer, bone cancer, thyroid cancer, cancer of the nervous system, gynecological cancer, hematologic cancer, skin cancer, and cancer of the adrenal glands. In another embodiment, the cancer is selected from melanoma, non-small cell lung cancer, small cell lung cancer, renal cell carcinoma, classical Hodgkin lymphoma, head and neck squamous cell carcinoma, urothelial carcinoma, microsatellite instability-high colorectal cancer, and hepatocellular carcinoma.

In one embodiment, the cancer is a solid tumor. In another embodiment, the solid tumor is selected from the group consisting of sarcomas, carcinomas, and lymphomas. In a further embodiment, the solid tumor is a genitourinary cancer. In a further embodiment, the genitourinary cancer is selected from the group consisting of clear cell renal cell carcinoma (ccRCC), non-clear cell renal cell carcinoma (nccRCC), urothelial carcinoma (UC, ICI naïve, and experienced), and metastatic castration-resistant prostate cancer (mCRPC)

The amount of Compound 1, or a pharmaceutically acceptable salt thereof administered is from more than 0.0 mg and up to and including 100 mg of Compound 1; more than 0.0 mg and up to and including 95 mg of Compound 1; more than 0.0 mg and up to and including 90 mg of Compound 1; more than 0.0 mg and up to and including 85 mg of Compound 1; more than 0.0 mg and up to and including 80 mg of Compound 1; more than 0.0 mg and up to and including 75 mg of Compound 1; more than 0.0 mg and up to and including 70 mg of Compound 1; more than 0.0 mg and up to and including 65 mg of Compound 1; more than 0.0 mg and up to and including 60 mg of Compound 1; more than 0.0 mg and up to and including 55 mg of Compound 1; more than 0.0 mg and up to and including 50 mg of Compound 1; more than 0.0 mg and up to and including 45 mg of Compound 1; more than 0.0 mg and up to and including 40 mg of Compound 1; more than 0.0 mg and up to and including 35 mg of Compound 1; more than 0.0 mg and up to and including 30 mg of Compound 1; more than 0.0 mg and up to and including 25 mg of Compound 1; more than 0.0 mg and up to and including 20 mg of Compound 1; more than 0.0 mg and up to and including 15 mg of Compound 1; more than 0.0 mg and up to and including 10 mg of Compound 1; or up to and including 5 mg of Compound 1. In one embodiment, Compound 1 is administered once daily. In another embodiment, Compound 1 is administered twice daily.

In one embodiment, nivolumab is administered intravenously (IV) to the subject. In another embodiment, nivolumab is administered by intravenous infusion to the subject.

In one embodiment, nivolumab is administered once every two weeks, once every three weeks, or once every four weeks for the duration of the treatment period. In a further embodiment, nivolumab is administered once every two weeks for the duration of the treatment period. In another further embodiment, nivolumab is administered once every three weeks for the duration of the treatment period. In another further embodiment, nivolumab is administered once every four weeks for the duration of the treatment period.

In one embodiment, the dosage of nivolumab is from about 50 mg to about 500 mg.

In one embodiment, nivolumab is administered to a subject in an IV unit dosage form, wherein the dose form is sold as OPDIVO®.

Combination of Compound 1 with Other Checkpoint Inhibitors

In one embodiment, the checkpoint inhibitor is pembrolizumab.

In one embodiment, the invention includes a method for treating cancer in a subject, the method comprising:

(i) administering to the subject a dosage of from about 5 mg to about 100 mg of Compound 1 or a pharmaceutically acceptable salt or a pharmaceutical composition comprising Compound 1 thereof, and (ii) administering to the subject a therapeutically effective amount of pembrolizumab.

In another embodiment, the invention includes a method for treating cancer in a subject, the method comprising administering to the subject in need of such treatment a dosage of from about 5 mg to about 100 mg of Compound 1 or a pharmaceutically acceptable salt thereof or a pharmaceutical composition comprising Compound 1 or the pharmaceutically acceptable salt thereof, and a pharmaceutically acceptable carrier or excipient, in combination with a therapeutically effective amount of pembrolizumab or a pharmaceutical composition comprising pembrolizumab.

In one embodiment, Compound 1 or the pharmaceutically acceptable salt thereof, or the pharmaceutical composition comprising Compound 1, and pembrolizumab or the pharmaceutical composition comprising pembrolizumab are administered concurrently, sequentially or separately.

In one embodiment, the cancer is selected from melanoma, cardiac cancer, head and neck cancer, lung cancer, non-small cell lung cancer, small cell lung cancer, non-clear cell renal cell carcinoma, advanced clear cell renal carcinoma, castration-resistant prostate cancer, hormone receptor-positive breast cancer, prostate cancer, colon cancer, gastrointestinal cancer, breast cancer, genitourinary tract cancer, liver cancer, bone cancer, thyroid cancer, cancer of the nervous system, gynecological cancer, hematologic cancer, skin cancer, and cancer of the adrenal glands. In another embodiment, the cancer is selected from melanoma, non-small cell lung cancer, small cell lung cancer, head and neck squamous cell cancer, classical Hodgkin lymphoma, primary mediastinallarge B-cell lymphoma, microsatellite instability-high cancer, gastric cancer, esophageal cancer, cervical cancer, hepatocellular carcinoma, Merkel cell carcinoma, renal cell carcinoma, urothelial carcinoma, or endometrial cancer, The amount of Compound 1, or a pharmaceutically acceptable salt thereof administered is from more than 0.0 mg and up to and including 100 mg of Compound 1; more than 0.0 mg and up to and including 95 mg of Compound 1; more than 0.0 mg and up to and including 90 mg of Compound 1; more than 0.0 mg and up to and including 85 mg of Compound 1; more than 0.0 mg and up to and including 80 mg of Compound 1; more than 0.0 mg and up to and including 75 mg of Compound 1; more than 0.0 mg and up to and including 70 mg of Compound 1; more than 0.0 mg and up to and including 65 mg of Compound 1; more than 0.0 mg and up to and including 60 mg of Compound 1; more than 0.0 mg and up to and including 55 mg of Compound 1; more than 0.0 mg and up to and including 50 mg of Compound 1; more than 0.0 mg and up to and including 45 mg of Compound 1; more than 0.0 mg and up to and including 40 mg of Compound 1; more than 0.0 mg and up to and including 35 mg of Compound 1; more than 0.0 mg and up to and including 30 mg of Compound 1; more than 0.0 mg and up to and including 25 mg of Compound 1; more than 0.0 mg and up to and including 20 mg of Compound 1; more than 0.0 mg and up to and including 15 mg of Compound 1; more than 0.0 mg and up to and including 10 mg of Compound 1; or up to and including 5 mg of Compound 1.

In one embodiment, Compound 1 is administered once daily. In another embodiment, Compound 1 is administered twice daily.

In one embodiment, pembrolizumab is administered intravenously (IV) to the subject. In another embodiment, pembrolizumab is administered by intravenous infusion to the subject.

In one embodiment, pembrolizumab is administered once every two weeks, once every three weeks, or once every four weeks for the duration of the treatment period. In a further embodiment, pembrolizumab is administered once every two weeks for the duration of the treatment period. In another further embodiment, pembrolizumab is administered once every three weeks for the duration of the treatment period. In another further embodiment, pembrolizumab is administered once every four weeks for the duration of the treatment period.

In one embodiment, the dosage of pembrolizumab is from about 50 mg to about 250 mg.

In one embodiment, pembrolizumab is administered to a subject in an IV unit dosage form, wherein the dose form is sold as KETRUDA®.

In one embodiment, the checkpoint inhibitor is durvalumab.

In one embodiment, the invention includes a method for treating cancer in a subject, the method comprising:

(i) administering to the subject a dosage of from about 5 mg to about 100 mg of Compound 1 or a pharmaceutically acceptable salt or a pharmaceutical composition comprising Compound 1 thereof, and (ii) administering to the subject a therapeutically effective amount of durvalumab.

In another embodiment, the invention includes a method for treating cancer in a subject, the method comprising administering to the subject in need of such treatment a dosage of from about 5 mg to about 100 mg of Compound 1 or a pharmaceutically acceptable salt thereof or a pharmaceutical composition comprising Compound 1 or the pharmaceutically acceptable salt thereof, and a pharmaceutically acceptable carrier or excipient, in combination with a therapeutically effective amount of durvalumab or a pharmaceutical composition comprising durvalumab.

In one embodiment, Compound 1 or the pharmaceutically acceptable salt thereof, or the pharmaceutical composition comprising Compound 1, and durvaluamb or the pharmaceutical composition comprising durvalumab are administered concurrently, sequentially or separately.

In one embodiment, the cancer is selected from melanoma, cardiac cancer, head and neck cancer, lung cancer, non-small cell lung cancer, small cell lung cancer, non-clear cell renal cell carcinoma, advanced clear cell renal carcinoma, castration-resistant prostate cancer, hormone receptor-positive breast cancer, prostate cancer, colon cancer, gastrointestinal cancer, breast cancer, genitourinary tract cancer, liver cancer, bone cancer, thyroid cancer, cancer of the nervous system, gynecological cancer, hematologic cancer, skin cancer, urothelial carcinoma, and cancer of the adrenal glands. In another embodiment, the cancer is selected from the group consisting of urothelial carcinoma and non-small cell lung cancer.

The amount of Compound 1, or a pharmaceutically acceptable salt thereof administered is from more than 0.0 mg and up to and including 100 mg of Compound 1; more than 0.0 mg and up to and including 95 mg of Compound 1; more than 0.0 mg and up to and including 90 mg of Compound 1; more than 0.0 mg and up to and including 85 mg of Compound 1; more than 0.0 mg and up to and including 80 mg of Compound 1; more than 0.0 mg and up to and including 75 mg of Compound 1; more than 0.0 mg and up to and including 70 mg of Compound 1; more than 0.0 mg and up to and including 65 mg of Compound 1; more than 0.0 mg and up to and including 60 mg of Compound 1; more than 0.0 mg and up to and including 55 mg of Compound 1; more than 0.0 mg and up to and including 50 mg of Compound 1; more than 0.0 mg and up to and including 45 mg of Compound 1; more than 0.0 mg and up to and including 40 mg of Compound 1; more than 0.0 mg and up to and including 35 mg of Compound 1; more than 0.0 mg and up to and including 30 mg of Compound 1; more than 0.0 mg and up to and including 25 mg of Compound 1;

more than 0.0 mg and up to and including 20 mg of Compound 1; more than 0.0 mg and up to and including 15 mg of Compound 1; more than 0.0 mg and up to and including 10 mg of Compound 1; or up to and including 5 mg of Compound 1. In one embodiment, Compound 1 is administered once daily. In another embodiment, Compound 1 is administered twice daily.

In one embodiment, durvalumab is administered intravenously (IV) to the subject. In another embodiment, durvalumab is administered by parenteral injection to the subject.

In one embodiment, durvalumab is administered once every two weeks, once every three weeks, or once every four weeks for the duration of the treatment period. In a further embodiment, durvalumab is administered once every two weeks for the duration of the treatment period. In another further embodiment, durvalumab is administered once every three weeks for the duration of the treatment period. In another further embodiment, durvalumab is administered once every four weeks for the duration of the treatment period.

In one embodiment, the dosage of durvalumab is about 10 mg/kg every two weeks.

In one embodiment, durvalumab is administered to a subject in an IV unit dosage form, wherein the dose form is sold as IMFINZI®.

In one embodiment, the checkpoint inhibitor is cemiplimab.

In one embodiment, the invention includes a method for treating cancer in a subject, the method comprising:

(i) administering to the subject a dosage of from about 5 mg to about 100 mg of Compound 1 or a pharmaceutically acceptable salt or a pharmaceutical composition comprising Compound 1 thereof, and (ii) administering to the subject a therapeutically effective amount of cemiplimab or a pharmaceutically acceptable salt or prodrug thereof.

In another embodiment, the invention includes a method for treating cancer in a subject, the method comprising administering to the subject in need of such treatment a dosage of from about 5 mg to about 100 mg of Compound 1 or a pharmaceutically acceptable salt thereof or a pharmaceutical composition comprising Compound 1 or the pharmaceutically acceptable salt thereof, and a pharmaceutically acceptable carrier or excipient, in combination with a therapeutically effective amount of cemiplimab or a pharmaceutical composition comprising cemiplimab.

In one embodiment, Compound 1 or the pharmaceutically acceptable salt thereof, or the pharmaceutical composition comprising Compound 1, and cemiplimab or the pharmaceutical composition comprising cemiplimab are administered concurrently, sequentially or separately.

In one embodiment, the cancer is selected from melanoma, cardiac cancer, head and neck cancer, lung cancer, non-small cell lung cancer, small cell lung cancer, non-clear cell renal cell carcinoma, advanced clear cell renal carcinoma, castration-resistant prostate cancer, hormone receptor-positive breast cancer, prostate cancer, colon cancer, gastrointestinal cancer, breast cancer, genitourinary tract cancer, liver cancer, bone cancer, thyroid cancer, cancer of the nervous system, gynecological cancer, hematologic cancer, skin cancer, urothelial carcinoma, and cancer of the adrenal glands. In another embodiment, the cancer is cutaneous squamous cell carcinoma.

The amount of Compound 1, or a pharmaceutically acceptable salt thereof administered is from more than 0.0 mg and up to and including 100 mg of Compound 1; more than 0.0 mg and up to and including 95 mg of Compound 1; more than 0.0 mg and up to and including 90 mg of Compound 1; more than 0.0 mg and up to and including 85 mg of Compound 1; more than 0.0 mg and up to and including 80 mg of Compound 1; more than 0.0 mg and up to and including 75 mg of Compound 1; more than 0.0 mg and up to and including 70 mg of Compound 1; more than 0.0 mg and up to and including 65 mg of Compound 1; more than 0.0 mg and up to and including 60 mg of Compound 1; more than 0.0 mg and up to and including 55 mg of Compound 1; more than 0.0 mg and up to and including 50 mg of Compound 1; more than 0.0 mg and up to and including 45 mg of Compound 1; more than 0.0 mg and up to and including 40 mg of Compound 1; more than 0.0 mg and up to and including 35 mg of Compound 1; more than 0.0 mg and up to and including 30 mg of Compound 1; more than 0.0 mg and up to and including 25 mg of Compound 1; more than 0.0 mg and up to and including 20 mg of Compound 1; more than 0.0 mg and up to and including 15 mg of Compound 1; more than 0.0 mg and up to and including 10 mg of Compound 1; or up to and including 5 mg of Compound 1. In one embodiment, Compound 1 is administered once daily. In another embodiment, Compound 1 is administered twice daily.

In one embodiment, cemiplimab is administered intravenously (IV) to the subject. In another embodiment, cemiplimab is administered by parenteral injection to the subject.

In one embodiment, cemiplimab is administered once every two weeks, once every three weeks, or once every four weeks for the duration of the treatment period. In a further embodiment, cemiplimab is administered once every two weeks for the duration of the treatment period. In another further embodiment, cemiplimab is administered once every three weeks for the duration of the treatment period. In another further embodiment, cemiplimab is administered once every four weeks for the duration of the treatment period.

In one embodiment, the dosage of cemiplimab is about 350 mg/7 mL every three weeks.

In one embodiment, cemiplimab is administered to a subject in an IV unit dosage form, wherein the dose form is sold as LIBTAYO®.

Combination of Compound 1 with a Checkpoint Inhibitor and an Additional Immunomodulating Agent In the aforementioned aspects and embodiments, Compound 1 is administered, along with a checkpoint inhibitor, and optionally an additional immunomodulating agent to treat cancer. In one embodiment, the checkpoint inhibitor is selected from the group consisting of a PD-1 inhibitor, a PD-L1 inhibitor, and a CTLA-4 inhibitor. In these and other aspects and embodiments, the checkpoint inhibitor is selected from the group consisting of pembrolizumab, nivolumab, atezolizumab (TECENTRIQ®), durvalumab, avelumab (BAVENCIO®), cemiplimab, camrelizumab, sintilimab, tisleilizumab, toripalimab, spartalizumab, dostarlimab, KN035 (Jiangsu Alphamb Biopharmaceuticals Co.), Cosibelimab (formerly CK-301), CA-170 (Curis, Inc.), BMS-986189 (Bristol Myers Squibb Co.), and ipilimumab (Yervoy, Bristol Myers Squibb Co.).

In one embodiment, the checkpoint inhibitor is nivolumab.

In one embodiment, the additional immunomodulating agent is ipilimumab.

In another embodiment, the additional immunomodulating agent is an IL-2 targeting agent. In a further embodiment, the IL-2 targeting agent is selected from the group consisting of a CD122-preferential IL-2 pathway agonist, a PEG-IL-2Rαβ-biased agonist, an IL-2Rβ-biased agonist, an IL-2Rβ$\gamma_c$-biased agonist, an IL-2v/IL-2a fusion protein, an anti-EDB mAb (L19)/IL-2v fused to L19/TNFv, an Anti-GD2 mAb/IL-2v, an anti-FAP mAb/IL-2v, an anti-CEA mAb/IL-2v, an anti-PD-1 mAb/IL-2v, a vaccine of patient derived tumor cells+HD-IL-2, adoptive cell therapy+IL-2 infusion, adoptive cell therapy+IL-2 infusion+anti-PD-1 mAb, orthogonal IL-2v/IL-2Rβ mutant pairs, an anti-IL-2RαmAb/PBD conjugate, a PEG-IL-2Rα-biased agonist, an IL-2v/human Fc fusion protein, a PEG-IL-2Rα-biased (N88D)/IgG1 fusion proten, an anti-IL-2 mAb/IL-2v, a recombinant plasmid encoding IL-2, PPI, TGF-β1, and IL-10, and an IL-2Rβ antagonist.

In one embodiment, the IL-2 targeting agent is a CD122-preferential IL-2 pathway agonist.

In one embodiment, the IL-2 targeting agent is Bempegaldesleukin (BEMPEG; NKTR-214; Bristol Myers Squibb Co.).

In one embodiment, the IL-2 targeting agent is a PEG-IL-2Rαβ-biased agonist.

In one embodiment, the IL-2 targeting agent is THOR-707 (Sanofi).

In one embodiment, the IL-2 targeting agent is TransCon IL-2 β/γ (Ascendis Pharma).

In one embodiment, the IL-2 targeting agent is an IL-2Rβ-biased agonist.

In one embodiment, the IL-2 targeting agent is MDNA-19 (Medicenna)

In one embodiment, the IL-2 targeting agent is an IL-2Rβ 7$T_c$-biased agonist.

In one embodiment, the IL-2 targeting agent is Neo-2/15 (Neoleukin).

In one embodiment, the IL-2 targeting agent is an IL-2v/IL-2Rαfusion protein.

In one embodiment, the IL-2 targeting agent is an anti-EDB mAb (L19)/IL-2v fused to L19/TNFv.

In one embodiment, the IL-2 targeting agent is daromum (Philogen).

In one embodiment, the IL-2 targeting agent is an anti-EDB mAb (L19)/IL-2v.

In one embodiment, the IL-2 targeting agent is darleukin (Philogen).

In one embodiment, the IL-2 targeting agent is an anti-GD2 mAb/IL-2v.

In one embodiment, the IL-2 targeting agent is APN-301 (APerion).

In one embodiment, the IL-2 targeting agent is RG-7461 (Roche).

In one embodiment, the IL-2 targeting agent is anti-CEA mAb/IL-2v.

In one embodiment, the IL-2 targeting agent is cergutuzumab amanaleukin (Roche).

In one embodiment, the IL-2 targeting agent is an anti-PD-1 mAb/IL-2v. In one embodiment, the IL-2 targeting agent is PD1-IL2v (Roche).

In one embodiment, the IL-2 targeting agent is a vaccine of patient-derived tumor cells plus HD-IL-2.

In one embodiment, the IL-2 targeting agent is the Oncoquest-L-vaccine (Xemebiopharma.com).

In one embodiment, the IL-2 targeting agent is adoptive cell therapy plus IL_2 infusion.

In one embodiment, the IL-2 targeting agent is lifileucel (Iovance).

In one embodiment, the IL-2 targeting agent is adoptive cell therapy+IL-2 infusion+anti-PD-1 mAb.

In one embodiment, the IL-2 targeting agent is lifileucel plus pembrolizumab.

In one embodiment, the IL-2 targeting agent is orthogonal IL-2v/IL-2Rβ mutant pairs.

In one embodiment, the IL-2 targeting agent is an anti-IL-2RαmAb·PBD conjugate.

In one embodiment, the IL-2 targeting agent is camidanlumab tesirine (ADC Therapeutics).

In one embodiment, the IL-2 targeting agent is a PEG-IL2-Ra-biased agonist.

In one embodiment, the IL-2 targeting agent is NKTR-358 (Bristol Myers Squibb).

In one embodiment, the IL-2 targeting agent is THOR-809 (Sanofi).

In one embodiment, the IL-2 targeting agent is an IL-2v/human fusion protein.

In one embodiment, the IL-2 targeting agent is efavaleukin alfa (AMG592) (Amgen).

In one embodiment, the IL-2 targeting agent is an IL-2Rα-biased (N88D)/IgG1 fusion protein.

In one embodiment, the IL-2 targeting agent is RG-7835 (R07049665) (Roche).

In one embodiment, the IL-2 targeting agent is and an IL-2 mutein/Fc fusion protein.

In one embodiment, the IL-2 targeting agent is CC-92252 (Bristol Myers Squibb).

In one embodiment, the IL-2 targeting agent is an Anit-IL-2 mAb/IL-2v,

In one embodiment, the IL-2 targeting agent is F5111.2 (Creative Biolabs).

In one embodiment, the IL-2 targeting agent is a recombinant plasmid encoding IL-2, PPI, TGF-β1, and IL-10.

In one embodiment, the IL-2 targeting agent is NNC0361-0041 (NIDDK).

In one embodiment, the IL-2 targeting agent is an IL-2Rβ antagonist.

In one embodiment, the IL-2 targeting agent is MDNA-209 (Medicenna).

In one embodiment, the invention includes a method for treating cancer in a subject, the method comprising:

(i) administering to the subject a therapeutically effective amount of Compound 1 or a pharmaceutically acceptable salt or a pharmaceutical composition comprising Compound 1 thereof;

(ii) administering to the subject a therapeutically effective amount of nivolumab or a pharmaceutical composition comprising nivolumab; and (iii) administering to the subject a therapeutically effective amount of an immunomodulating agent or a pharmaceutical composition comprising a therapeutically effective amount of the immunomodulating agent.

In one embodiment, the invention includes a method for treating cancer in a subject, the method comprising:

(i) administering to the subject a dosage of from about 5 mg to about 100 mg of Compound 1 or a pharmaceutically acceptable salt or a pharmaceutical composition comprising Compound 1 thereof, (ii) administering to the subject a therapeutically effective amount of nivolumab or a pharmaceutical composition comprising nivolumab; and (iii) administering to the subject a therapeutically effective amount of an immunomodulating agent or a pharmaceutical composition comprising a therapeutically effective amount of the immunomodulating agent.

In one embodiment, the invention includes a method for treating cancer in a subject, the method comprising:

(i) administering to the subject a therapeutically effective amount of Compound 1 or a pharmaceutically acceptable salt or a pharmaceutical composition comprising Compound 1 thereof;

(ii) administering to the subject a therapeutically effective amount of nivolumab or a pharmaceutical composition comprising nivolumab; and (iii) administering to the subject a therapeutically effective amount of an ipilimumab or a pharmaceutical composition comprising a therapeutically effective amount of ipilimumab.

In one embodiment, the invention includes a method for treating cancer in a subject, the method comprising:

(i) administering to the subject a dosage of from about 5 mg to about 100 mg of Compound 1 or a pharmaceutically acceptable salt or a pharmaceutical composition comprising Compound 1 thereof, (ii) administering to the subject a therapeutically effective amount of nivolumab or a pharmaceutical composition comprising nivolumab; and (iii) administering to the subject a therapeutically effective amount of an ipilimumab or a pharmaceutical composition comprising a therapeutically effective amount of ipilimumab.

In one embodiment, the invention includes a method for treating cancer in a subject, the method comprising:

(i) administering to the subject a therapeutically effective amount of Compound 1 or a pharmaceutically acceptable salt or a pharmaceutical composition comprising Compound 1 thereof;

(ii) administering to the subject a therapeutically effective amount of nivolumab or a pharmaceutical composition comprising nivolumab; and (iii) administering to the subject a therapeutically effective amount of an BEMPEG or a pharmaceutical composition comprising a therapeutically effective amount of BEMPEG.

In one embodiment, the invention includes a method for treating cancer in a subject, the method comprising:

(i) administering to the subject a dosage of from about 5 mg to about 100 mg of Compound 1 or a pharmaceutically acceptable salt or a pharmaceutical composition comprising Compound 1 thereof, (ii) administering to the subject a therapeutically effective amount of nivolumab or a pharmaceutical composition comprising nivolumab; and (iii) administering to the subject a therapeutically effective amount of an BEMPEG or a pharmaceutical composition comprising a therapeutically effective amount of BEMPEG.

In one embodiment, Compound 1 or the pharmaceutically acceptable salt thereof, or the pharmaceutical composition comprising Compound 1, nivolumab or the pharmaceutical composition comprising nivolumab, and ipilimumab or the pharmaceutical composition comprising ipilimumab are administered concurrently, sequentially or separately.

In one embodiment, Compound 1 or the pharmaceutically acceptable salt thereof, or the pharmaceutical composition comprising Compound 1, nivolumab or the pharmaceutical composition comprising nivolumab, and BEMPEG or the pharmaceutical composition comprising BEMPEG are administered concurrently, sequentially or separately.

In these and other embodiments, nivolumab is administered at about 360 mg IV every three weeks or about 240 mg IV every two weeks.

In these and other embodiments, ipilimumab is administered as four IV doses at about 1 mg/kg IV every three weeks.

In these and other embodiments, BEMPEG is administered at about 0.003 mg/kg IV every two weeks, about 0.006 mg/kg IV every three weeks, or about 0.009 mg/kg IV every three weeks.

In one embodiment, the cancer is selected from melanoma, cardiac cancer, head and neck cancer, lung cancer, non-small cell lung cancer, small cell lung cancer, non-clear cell renal cell carcinoma, advanced clear cell renal carcinoma, castration-resistant prostate cancer, hormone receptor-positive breast cancer, prostate cancer, colon cancer, gastrointestinal cancer, breast cancer, genitourinary tract cancer, liver cancer, bone cancer, thyroid cancer, cancer of the nervous system, gynecological cancer, hematologic cancer, skin cancer, and cancer of the adrenal glands. In another embodiment, the cancer is selected from melanoma, non-small cell lung cancer, small cell lung cancer, renal cell carcinoma, classical Hodgkin lymphoma, head and neck squamous cell carcinoma, urothelial carcinoma, microsatellite instability-high colorectal cancer, and hepatocellular carcinoma.

In one embodiment, wherein the cancer is selected from cardiac cancer, head and neck cancer, lung cancer, non-small cell lung cancer, small cell lung cancer, non-clear cell renal cell carcinoma, advanced or metastatic clear cell renal cell carcinoma, castration-resistant prostate cancer, hormone receptor-positive breast cancer, prostate cancer, colon cancer, gastrointestinal cancer, breast cancer, genitourinary tract cancer, liver cancer, bone cancer, thyroid cancer, cancer of the nervous system, gynecological cancer, hematologic cancer, skin cancer, urothelial carcinoma, cancer of the adrenal glands, endometrial cancer, sarcoma, neuroendocrine tumor, ovarian cancer, hepatocellular carcinoma, gastric cancer, colorectal cancer, and melanoma.

In one embodiment, the cancer is selected from endometrial cancer, sarcoma, neuroendocrine tumor, ovarian cancer, colorectal cancer, HCC, NSCLC, gastric cancer, and melanoma In one embodiment, the cancer is a solid tumor. In another embodiment, the solid tumor is selected from the group consisting of sarcomas, carcinomas, and lymphomas. In a further embodiment, the solid tumor is a genitourinary cancer. In a further embodiment, the genitourinary cancer is selected from the group consisting of clear cell renal cell carcinoma (ccRCC), non-clear cell renal cell carcinoma (nccRCC), urothelial carcinoma (UC, ICI naïve, and experienced), and metastatic castration-resistant prostate cancer (mCRPC)

The amount of Compound 1, or a pharmaceutically acceptable salt thereof administered is from more than 0.0 mg and up to and including 100 mg of Compound 1; more than 0.0 mg and up to and including 95 mg of Compound 1; more than 0.0 mg and up to and including 90 mg of Compound 1; more than 0.0 mg and up to and including 85 mg of Compound 1; more than 0.0 mg and up to and including 80 mg of Compound 1; more than 0.0 mg and up to and including 75 mg of Compound 1; more than 0.0 mg and up to and including 70 mg of Compound 1; more than 0.0 mg and up to and including 65 mg of Compound 1; more than 0.0 mg and up to and including 60 mg of Compound 1; more than 0.0 mg and up to and including 55 mg of Compound 1; more than 0.0 mg and up to and including 50 mg of Compound 1; more than 0.0 mg and up to and including 45 mg of Compound 1; more than 0.0 mg and up to and including 40 mg of Compound 1; more than 0.0 mg and up to and including 35 mg of Compound 1; more than 0.0 mg and up to and including 30 mg of Compound 1; more than 0.0 mg and up to and including 25 mg of Compound 1; more than 0.0 mg and up to and including 20 mg of Compound 1; more than 0.0 mg and up to and including 15 mg of Compound 1; more than 0.0 mg and up to and including 10 mg of Compound 1; or up to and including 5 mg of Compound 1. In one embodiment, Compound 1 is administered once daily. In another embodiment, Compound 1 is administered twice daily.

In one embodiment, nivolumab is administered intravenously (IV) to the subject. In another embodiment, nivolumab is administered by intravenous infusion to the subject.

In one embodiment, nivolumab is administered once every two weeks, once every three weeks, or once every four weeks for the duration of the treatment period. In a further embodiment, nivolumab is administered once every two weeks for the duration of the treatment period. In another further embodiment, nivolumab is administered once every three weeks for the duration of the treatment period. In another further embodiment, nivolumab is administered once every four weeks for the duration of the treatment period.

In one embodiment, the dosage of nivolumab is from about 50 mg to about 500 mg.

In one embodiment, nivolumab is administered to a subject in an IV unit dosage form, wherein the dose form is sold as OPDIVO®.

In these and other embodiments, nivolumab is administered at about 3 mg/kg IV every two weeks.

In these and other embodiments, ipilimumab is administered as four IV doses at about 3 mg/kg IV mg every three weeks.

In some embodiments, nivolumab is administered at about 1 mg/kg IV every three weeks, and ipilimumab is administered at about 3 mg/kg IV on the same day for maximum of 4 doses.

In some embodiments, nivolumab is administered at about 3 mg/kg IV every three weeks, and ipilimumab is administered at about 1 mg/kg IV on the same day for 4 doses.

In some embodiments, nivolumab is administered at about 3 mg/kg IV every three weeks for 4 doses and then 480 mg every four weeks, and ipilimumab is administered at about 1 mg/kg IV every three weeks for 4 doses.

In some embodiments, nivolumab is administered at about 3 mg/kg IV every two weeks, and ipilimumab is administered at about 1 mg/kg IV every 6 weeks.

In some embodiments, nivolumab is administered at about 360 mg every three weeks, and ipilimumab is administered at about 1 mg/kg IV on the same day for 4 doses.

In some embodiments, nivolumab is administered at about 240 mg every two weeks, and BEMPEG is administered at about 0.006 mg/kg every three weeks.

In some embodiments, nivolumab is administered at about 240 mg every two weeks, and BEMPEG is administered at about 0.003 mg/kg every two weeks.

In some embodiments, nivolumab is administered at about 240 mg every two weeks, and BEMPEG is administered at about 0.006 mg/kg every two weeks.

In some embodiments, nivolumab is administered at about 360 mg every three weeks, and BEMPEG is administered at about 0.006 mg/kg every three weeks.

In some embodiments, nivolumab is administered at about 360 mg every three weeks, and BEMPEG is administered at about 0.009 mg/kg every three weeks.

Additional Combinations of Compound 1 and Other Immunomodulating Agents

A non-polymorphic form, crystalline form or crystalline salt form of Compound 1 as disclosed herein is administered concurrently with a checkpoint inhibitor or PD-1 inhibitor. Hereinafter this is referred to as "the Combination". The Combination can be administered with one or more additional therapies for the treatment of a disease or disorder, for instance a disease or disorder associated with hyper-proliferation such as cancer. The one or more additional therapies include: (i) surgery; (ii) radiotherapy (for example, gamma radiation, neutron beam radiotherapy, electron beam radiotherapy, proton therapy, brachytherapy, and systemic radioactive isotopes); (iii) endocrine therapy; (iv) adjuvant therapy, immunotherapy, CAR T-cell therapy; and (v) other chemotherapeutic agents.

The term "co-administered" ("co-administering") refers to either simultaneous administration, or any manner of separate sequential administration, of the Combination as disclosed herein, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Typically, any agent that has activity against a disease or condition being treated may be co-administered. Examples of such agents for cancer treatment can be found, for instance, at https://www.cancer.gov/about-cancer/treatment/drugs (last visited Jan. 22, 2019) and in publically available sources such as Cancer Principles and Practice of Oncology by V. T. Devita and S. Hellman (editors), $11^{th}$ edition (2018), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of the Combination and at one or more additional therapies including immunotherapy. Immunotherapy (also called biological response modifier therapy, biologic therapy, biotherapy, immune therapy, or biological therapy) is a treatment that uses parts of the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include, but are not limited to vaccines including cancer vaccines, tumor cell vaccines (autologous or allogeneic), dendritic cell vaccines, antigen vaccines, anti-idiotype vaccines, DNA vaccines, viral vaccines, or Tumor-Infiltrating Lymphocyte (TIL) Vaccine with Interleukin-2 (IL-2) or Lymphokine-Activated Killer (LAK) Cell Therapy.

Examples of passive immunotherapies include but are not limited to monoclonal antibodies and targeted therapies containing toxins. Monoclonal antibodies include naked antibodies and conjugated monoclonal antibodies (also called tagged, labeled, or loaded antibodies). Naked monoclonal antibodies do not have a drug or radioactive material attached whereas conjugated monoclonal antibodies are joined to, for example, a chemotherapy drug (chemolabeled), a radioactive particle (radiolabeled), or a toxin (immunotoxin). Examples of these naked monoclonal antibody drugs include, but are not limited to Rituximab (Rituxan), an antibody against the CD20 antigen used to treat, for example, B cell non-Hodgkin lymphoma; Trastuzumab (Herceptin), an antibody against the HER2 protein used to treat, for example, advanced breast cancer; Alemtuzumab (Campath), an antibody against the CD52 antigen used to treat, for example, B cell chronic lymphocytic leukemia (B-CLL); Cetuximab (Erbitux), an antibody against the EGFR protein used, for example, in combination with irinotecan to treat, for example, advanced colorectal cancer and head and neck cancers; and Bevacizumab (Avastin) which is an antiangiogenesis therapy that works against the VEGF protein and is used, for example, in combination with chemotherapy to treat, for example, metastatic colorectal cancer. Examples of the conjugated monoclonal antibodies include, but are not limited to Radiolabeled antibody Ibritumomab tiuxetan (Zevalin) which delivers radioactivity directly to cancerous B lymphocytes and is used to treat, for example, B cell non-Hodgkin lymphoma; radiolabeled antibody Tositumomab (Bexxar) which is used to treat, for example, certain types of non-Hodgkin lymphoma; and immunotoxin Gemtuzumab ozogamicin (Mylotarg) which contains calicheamicin and is used to treat, for example, acute myelogenous leukemia (AMIL). BL22 is a conjugated monoclonal antibody for treating, for example, hairy cell leukemia, immunotoxins for treating, for example, leukemias, lymphomas, and brain tumors, and radiolabeled antibodies such as OncoScint for example, for colorectal and ovarian cancers and ProstaScint for example, for prostate cancers.

Further examples of therapeutic antibodies that can be used include, but are not limited to, HERCEPTIN™ (Trastuzumab) (Genentech, Calif.) which is a humanized anti-HER2 monoclonal antibody for the treatment of patients with metastatic breast cancer; REOPRO®. (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3epitope) IgG antibody (ImClone System); IMC-C225 which is a chimeric anti-EGFR IgG antibody (ImClone System); VITAXIN™ which is a humanized anti-alpha V beta 3 integrin antibody (Applied Molecular Evolution/Medlmmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-alpha antibody (CAT/BASF); CDP870 is a humanized anti-TNF-alpha. Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptdavidin (+biotin-yttrium 90; NeoRx); CDP571 is a humanized anti-TNF-alpha. IgG4 antibody (Celltech); LDP-02 is a humanized anti-alpha4 beta7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-$beta_2$ antibody (Cambridge Ab Tech). Others are provided in later paragraphs.

The one or more additional therapies also includes adjuvant immunotherapies. Examples include cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and an IL-27), tumor necrosis factors (including TNF-alpha), and interferons (including IFN-alpha, IFN-beta, and IFN-gamma); aluminum hydroxide (alum); Bacille Calmette-Guerin (BCG); Keyhole limpet hemocyanin (KLH); Incomplete Freund's adjuvant (IFA); QS-21; DETOX; Levamisole; and Dinitrophenyl (DNP), and combinations thereof, such as combinations of interleukins, for example IL-2 with other cytokines, such as IFN-alpha.

In various embodiments, the one or more additional therapies can include, one or more of the following: an adoptive cell transfer, an angiogenesis inhibitor, *Bacillus* Calmette-Guerin therapy, biochemotherapy, a cancer vaccine, a chimeric antigen receptor (CAR) T-cell therapy, a cytokine therapy, gene therapy, an immune checkpoint modulator, an immunoconjugate, a radioconjugate, an oncolytic virus therapy, or a targeted drug therapy. The immunological therapy or immunological therapeutic agent, is collectively referred to herein as an "immunotherapeutic agent".

The present disclosure provides a method for preventing, treating, reducing, inhibiting or controlling a neoplasia, a tumor or a cancer in a subject in need thereof, involving administering a therapeutically effective amount of the Combination and one or more additional therapies. In various embodiments, treatment with the Combination and one or more additional therapies provides a cooperative effect, an additive effect, or a synergistic effect in reducing the number of cancer cells when treated with the combination as compared to each treatment alone. In some embodiments, treatment with the Combination and one or more additional therapies, results in synergistic anti-tumor activity and/or antitumor activity that is more potent than the additive effect of administration of a non-polymorphic form, crystalline form or crystalline salt form of Compound 1 or immunotherapeutic agent alone.

Human cancers harbor numerous genetic and epigenetic alterations, generating neoantigens potentially recognizable by the immune system (Sjoblom et al. (2006) Science 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

In various embodiments, the one or more additional therapies include: an adoptive cell transfer, an angiogenesis inhibitor, *Bacillus* Calmette-Guerin therapy, biochemotherapy, a cancer vaccine, a chimeric antigen receptor (CAR) T-cell therapy, a cytokine therapy, gene therapy, an immune checkpoint modulator, for example an immune checkpoint inhibitor, an immunoconjugate, a radioconjugate, an oncolytic virus therapy, or a targeted drug therapy.

In certain embodiments of each of the aforementioned aspects, as well as other aspects and embodiments described elsewhere herein, the one or more additional therapies enhances the activity of the combination.

In certain embodiments of each of the aforementioned aspects, as well as other aspects and embodiments described elsewhere herein, the one or more additional therapies is an immune cell (e.g. T-cell, dendritic cell, a natural killer cell and the like) modulator chosen from an agonist or an activator of a costimulatory molecule, wherein the modulator is a monoclonal antibody, a bispecific antibody comprising one or more immune checkpoint antigen binding moieties, a trispecific antibody, or an immune cell-engaging multivalent antibody/fusion protein/construct known in the art. In some embodiments, the immunotherapeutic agent can be an antibody that modulates a costimulatory molecule, bind to an antigen on the surface of an immune cell, or a cancer cell. In each of these different embodiments, the antibody modulator can be a monoclonal antibody, a polyclonal antibody, a bispecific antibody, a trispecific or multispecific format antibody, a fusion protein, or a fragment thereof, for example, a Diabody, a Single-chain (sc)-diabody (scFv)2, a Miniantibody, a Minibody, a Barnase-barstar, a scFv-Fc, a sc(Fab)2, a Trimeric antibody construct, a Triabody antibody construct, a Trimerbody antibody construct, a Tribody antibody construct, a Collabody antibody construct, a (scFv-TNFa)3, or a F(ab)3/DNL antibody construct.

In certain embodiments of each of the aforementioned aspects, as well as other aspects and embodiments described elsewhere herein, the one or more additional therapies is immunotherapeutic agent that modulates immune responses, for example, a checkpoint inhibitor or a checkpoint agonist. In some embodiments, the one or more additional therapies is an immunotherapeutic agent that enhances anti-tumor immune responses. In some embodiments, the one or more additional therapies is an immunotherapeutic agent that increases cell-mediated immunity. In some embodiments, the one or more additional therapies is an immunotherapeutic agent that increases T-cell activity. In some embodiments, the one or more additional therapies is an immunotherapeutic agent that increases cytolytic T-cell (CTL) activity.

In some embodiments, the one or more additional therapies can include a molecule, for example, a binding agent, for example, an antibody or functional fragment thereof that modulates (activates or inhibits) a checkpoint protein in the concurrent administration with atezolizumab. A checkpoint inhibitor can be any molecule, agent, treatment and/or method of inhibiting an immune checkpoint, and/or promoting an inhibitor of an immune checkpoint, e.g., by promoting an intrinsic immune checkpoint inhibitor; inhibiting a transcription factor involved in the expression of an immune checkpoint; and/or by acting in concert with some additional extrinsic factor. For example, a checkpoint inhibitor could include a treatment that inhibits transcription factors involved in the expression of immune checkpoint genes, or promotes the expression of transcription factors for tumor-suppressor genes, e.g., BACH2 (Luan et al., (2016). Transcription Factors and Checkpoint Inhibitor Expression with Age: Markers of Immunosenescence. Blood, 128(22), 5983). Moreover, a checkpoint inhibitor can inhibit the transcription of immune checkpoint genes; the modification and/or processing of immune checkpoint mRNA; the translation of immune checkpoint proteins; and/or molecules involved in immunity or the immune checkpoint pathway, e.g., PD-1 transcription factors such as HIF-1, STAT3, NF-κB, and AP-1, or the activation of common oncogenic pathways such as JAK/STAT, RAS/ERK, or PI3K/AKT/mTOR (Zerdes et al., Genetic, transcriptional and post-translational regulation of the programmed death protein ligand 1 in cancer: biology and clinical correlations, Oncogene volume 37, pages 4639-4661 (2018), the disclosure of which is incorporated herein by reference in its entirety).

Checkpoint inhibitors can include treatments, molecules, agents, and/or methods that regulate immune checkpoints at the transcriptional level, e.g., using the RNA-interference pathway co-suppression, and/or post-transcriptional gene silencing (PTGS) (e.g., microRNAs, miRNA; silencing-RNA, small-interfering-RNA, or short-interfering-RNA (siRNA). Transcriptional regulation of checkpoint molecules has been shown to involve mir-16, which has been shown to target the 3'UTR of the checkpoint mRNAs CD80, CD274 (PD-L1) and CD40 (Leibowitz et al., Post-transcriptional regulation of immune checkpoint genes by mir-16 in melanoma, Annals of Oncology (2017) 28; v428-v448). Mir-33a has also been shown to be involved in regulating the expression of PD-1 in cases of lung adenocarcinoma (Boldini et al., Role of microRNA-33a in regulating the expression of PD-1 in lung adenocarcinoma, Cancer Cell Int. 2017; 17: 105, the disclosure of which is incorporated herein by reference in its entirety).

T-cell-specific aptamer-siRNA chimeras have been suggested as a highly specific method of inhibiting molecules in the immune checkpoint pathway (Hossain et al., The aptamer-siRNA conjugates: reprogramming T cells for cancer therapy, Ther. Deliv. 2015 January; 6(1): 1-4, the disclosure of which is incorporated herein by reference in its entirety).

Alternatively, members of the immune checkpoint pathway can be inhibited using treatments that affect associated pathways, e.g., metabolism. For example, oversupplying the glycolytic intermediate pyruvate in mitochondria from CAD macrophages promoted expression of PD-L1 via induction of the bone morphogenetic protein 4/phosphorylated SMAD1/5/IFN regulatory factor 1 (BMP4/p-SMAD1/5/IRF1) signaling pathway. Accordingly, implementing treatments that modulate the metabolic pathway can result in subsequent modulation of the immunoinhibitory PD-1/PD-L1 checkpoint pathway (Watanabe et al., Pyruvate controls the checkpoint inhibitor PD-L1 and suppresses T cell immunity, J Clin Invest. 2017 Jun. 30; 127(7): 2725-2738).

Checkpoint immunity can be regulated via oncolytic viruses that selectively replicate within tumor cells and induce acute immune responses in the tumor-micro-environment, i.e., by acting as genetic vectors that carry specific agents (e.g., antibodies, miRNA, siRNA, and the like) to cancer cells and effecting their oncolysis and secretion of cytokines and chemokines to synergize with immune checkpoint inhibition (Shi et al., Cancer Immunotherapy: A Focus on the Regulation of Immune Checkpoints, Int J Mol Sci. 2018 May; 19(5): 1389). Currently, there are clinical trials underway that utilize the following viruses as checkpoint inhibitors: poliovirus, measles virus, adenoviruses, poxviruses, herpes simplex virus (HSV), coxsackieviruses, reovirus, Newcastle disease virus (NDV), T-VEC (a herpes virus encoded with GM-CSF (granulocyte-macrophage colony stimulating factor)), and H101 (Shi et al., supra).

Checkpoint inhibitors can operate at the translational level of checkpoint immunity. The translation of mRNA into protein represents a key event in the regulation of gene expression, thus inhibition of immune checkpoint translation is a method in which the immune checkpoint pathway can be inhibited.

Inhibition of the immune checkpoint pathway can occur at any stage of the immune checkpoint translational process. For example, drugs, molecules, agents, treatments, and/or methods can inhibit the initiation process (whereby the 40S ribosomal subunit is recruited to the 5' end of the mRNA and scans the 5'UTR of the mRNA toward its 3' end. Inhibition can occur by targeting the anticodon of the initiator methionyl-transfer RNA (tRNA) (Met-tRNAi), its base-pairing with the start codon, or the recruitment of the 60S subunit to begin elongation and sequential addition of amino acids in the translation of immune-checkpoint-specific genes. Alternatively, a checkpoint inhibitor can inhibit checkpoints at the translational level by preventing the formation of the ternary complex (TC), i.e., eukaryotic initiation factor (eIF)2 (or one or more of its $\alpha$, $\beta$, and $\gamma$ subunits); GTP; and Met-tRNAi.

Checkpoint inhibition can occur via destabilization of eIF2a by precluding its phosphorylation via protein kinase R (PKR), PERK, GCN2, or HRI, or by precluding TCs from associating with the 40S ribosome and/or other initiation factors, thus preventing the preinitiation complex (PIC) from forming; inhibiting the eIF4F complex and/or its cap-binding protein eIF4E, the scaffolding protein eIF4G, or eIF4A helicase. Methods discussing the translational control of cancer are discussed in Truitt et al., New frontiers in translational control of the cancer genome, Nat Rev Cancer. 2016 Apr. 26; 16(5): 288-304, the disclosure of which is incorporated herein by reference in its entirety.

Checkpoint inhibitors can also include treatments, molecules, agents, and/or methods that regulate immune checkpoints at the cellular and/or protein level, e.g., by inhibiting an immune checkpoint receptor. Inhibition of checkpoints can occur via the use of antibodies, antibody fragments, antigen-binding fragments, small-molecules, and/or other drugs, agents, treatments, and/or methods.

Immune checkpoints refer to inhibitory pathways in the immune system that are responsible for maintaining self-tolerance and modulating the degree of immune system response to minimize peripheral tissue damage. However, tumor cells can also activate immune system checkpoints to decrease the effectiveness of immune response ('block' the immune response) against tumor tissues. In contrast to the majority of anti-cancer agents, checkpoint inhibitors do not target tumor cells directly, but rather target lymphocyte receptors or their ligands in order to enhance the endogenous antitumor activity of the immune system. (Pardoll, 2012, Nature Reviews Cancer 12:252-264).

In some embodiments, the one or more additional therapies is a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, an modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a cytokine, a chemokine, an interferon, an interleukin, a lymphokine, a member of the tumor necrosis factor (TNF) family, or an immunostimulatory oligonucleotide. In some embodiments, the immune checkpoint modulator, i.e. is an inhibitor or antagonist, or is an activator or agonist, for example, a CD28 modulator, a 4-1BB modulator, an OX40 modulator, a CD27 modulator, a CD80 modulator, a CD86 modulator, a CD40 modulator, or a GITR modulator, a Lag-3 modulator, a 41BB modulator, a LIGHT modulator, a CD40 modulator, a GITR modulator, a TGF-beta modulator, a TIM-3 modulator, a SIRP-alpha modulator, a TIGIT modulator, a VSIG8 modulator, a BTLA modulator, a SIGLEC7 modulator, a SIGLEC9 modulator, a ICOS modulator, a B7H3 modulator, a B7H4 modulator, a FAS modulator, and/or a BTNL2 modulator. In some embodiments, the immunotherapeutic agent is an immune checkpoint modulator as described above (e.g., an immune checkpoint modulator antibody, which can be in the form of a monoclonal antibody, a bispecific antibody comprising one or more immune checkpoint antigen binding moieties, a trispecific antibody, or an immune cell-engaging multivalent antibody/fusion protein/construct known in the art).

In some embodiments, the one or more additional therapies is an agent that inhibits the activity of PD-1. In some embodiments, the one or more additional therapies is an agent that inhibits the activity of PD-L1 and/or PD-L2. In some embodiments, the one or more additional therapies is an agent that inhibits the activity of CTLA-4. In some embodiments, the one or more additional therapies is an agent that inhibits the activity of CD80 and/or CD86. In some embodiments, the one or more additional therapies is an agent that inhibits the activity of TIGIT. In some embodiments, the one or more additional therapies is an agent that inhibits the activity of KIR. In some embodiments, the one or more additional therapies is an agent that enhances or stimulates the activity of activating immune checkpoint receptors.

PD-1 (also known as Programmed Death 1, CD279, PDCD1) is a cell surface receptor with a critical role in regulating the balance between stimulatory and inhibitory signals in the immune system and maintaining peripheral tolerance (Ishida, Y et al. 1992 EMBO J. 11 3887; Kier, Mary E et al. 2008 Annu Rev Immunol 26 677-704; Okazaki, Taku et al. 2007 International Immunology 19 813-824). PD-1 is an inhibitory member of the immunoglobulin super-family with homology to CD28. The structure of PD-1 is a monomeric type 1 transmembrane protein, consisting of one immunoglobulin variable-like extracellular domain and a cytoplasmic domain containing an immunoreceptor tyrosine-based inhibitory motif (ITIM) and an immunoreceptor tyrosine-based switch motif (ITSM). Expression of PD-1 is inducible on T cells, B cells, natural killer (NK) cells and monocytes, for example upon lymphocyte activation via T cell receptor (TCR) or B cell receptor (BCR) signalling (Kier, Mary E et al. 2008 Annu Rev Immunol 26 677-704; Agata, Y et al 1996 Int Immunol 8 765-72). PD-1 is a receptor for the ligands CD80, CD86, PD-L1 (B7-H1, CD274) and PD-L2 (B7-DC, CD273), which are cell surface expressed members of the B7 family (Freeman, Gordon et al. 2000 J Exp Med 192 1027; Latchman, Y et al. 2001 Nat Immunol 2: 261). Upon ligand engagement, PD-1 recruits phosphatases such as SHP-1 and SHP-2 to its intracellular tyrosine motifs which subsequently dephosphorylate effector molecules activated by TCR or BCR signalling (Chemnitz, J et al. 2004 J Immunol 173: 945-954; Riley, James L 2009 Immunological Reviews 229: 114-125) In this way, PD-1 transduces inhibitory signals into T and B cells only when it is engaged simultaneously with the TCR or BCR.

PD-1 has been demonstrated to down-regulate effector T cell responses via both cell-intrinsic and cell-extrinsic functional mechanisms. Inhibitory signaling through PD-1 induces a state of unresponsiveness in T cells, resulting in the cells being unable to clonally expand or produce optimal levels of effector cytokines. PD-1 may also induce apoptosis in T cells via its ability to inhibit survival signals from co-stimulation, which leads to reduced expression of key anti-apoptotic molecules such as Bcl-XL (Kier, Mary E et al. 2008 Annu Rev Immunol 26: 677-704). In addition to these direct effects, recent publications have implicated PD-1 as being involved in the suppression of effector cells by promoting the induction and maintenance of regulatory T cells (TREG). For example, PD-L1 expressed on dendritic cells was shown to act in synergy with TGF-β to promote the induction of CD4+ FoxP3+TREG with enhanced suppressor function (Francisco, Loise M et al. 2009 J Exp Med 206: 3015-3029).

TIM-3 (also known as T-cell immunoglobulin and mucin-domain containing-3, TIM-3, Hepatitis A virus cellular receptor 2, HAVCR2, HAVcr-2, KIM-3, TIMD-3, TIMD3, Tim-3, and CD366) is a ~33.4-kDa single-pass type I membrane protein involved in immune responses (Sanchez-Fueyo et al., Tim-3 inhibits T helper type 1-mediated auto- and alloimmune responses and promotes immunological tolerance, Nat. Immunol. 4: 1093-1101(2003)).

TIM-3 is selectively expressed on Th1-cells, and phagocytic cells (e.g., macrophages and dendritic cells). The use of siRNA or a blocking antibody to reduce the expression of human TIM-3 resulted in increased secretion of interferon γ (IFN-7) from CD4 positive T-cells, implicating the inhibitory role of TIM-3 in human T cells. Analysis of clinical samples from autoimmune disease patients showed no expression of TIM-3 in CD4 positive cells. In particular, expression level of TIM-3 is lower and secretion of IFN-7 is higher in T cell clones derived from the cerebrospinal fluid of patients with multiple sclerosis than those in clones derived from normal healthy persons (Koguchi K et al., J Exp Med. 203: 1413-8. (2006)).

TIM-3 is the receptor for the ligand Galectin-9, which is a member of galectin family, molecules ubiquitously expressed on a variety of cell types and which binds β-galactoside; Phospatidyl serine (PtdSer) (DeKryff et al., T cell/transmembrane, Ig, and mucin-3 allelic variants differentially recognize phosphatidylserine and mediate phagocytosis of apoptotic cells, J Immunol. 2010 Feb. 15; 184(4): 1918-30); High Mobility Group Protein 1 (also known as HMGB1, HMG1, HMG3, SBP-1, HMG-1, and high mobility group box 1) Chiba et al., Tumor-infiltrating DCs suppress nucleic acid-mediated innate immune responses through interactions between the receptor TIM-3 and the alarmin HMGB1, Nat Immunol. 2012 September; 13(9): 832-42); and Carcinoembryonic Antigen Related Cell Adhesion Molecule 1 (also known as CEACAMI, BGP, BGP1, BGPI, carcinoembryonic antigen related cell adhesion molecule 1) (Huang et al., CEACAMI regulates TIM-3-mediated tolerance and exhaustion, Nature. 2015 Jan. 15; 517 (7534): 386-90).

BTLA (also known as B- and T-lymphocyte attenuator, BTLA1, CD272, and B and T lymphocyte associated) is a ~27.3-kDa single-pass type I membrane protein involved in lymphocyte inhibition during immune response. BTLA is constitutively expressed in both B and T cells. BTLA interacts with HVEM (herpes virus-entry mediator), a member of the tumor-necrosis factor receptor (TNFR) family (Gonzalez et al., Proc. Natl. Acad. Sci. USA, 2005, 102: 1116-21). The interaction of BTLA, which belongs to the CD28 family of the immunoglobulin superfamily, and HVEM, a costimulatory tumor-necrosis factor (TNF) receptor (TNFR), is unique in that it defines a cross talk between these two families of receptors. BTLA contains a membrane proximal immunoreceptor tyrosine-based inhibitory motif (ITIM) and membrane distal immunoreceptor tyrosine-based switch motif (ITSM). Disruption of either the ITIM or ITSM abrogated the ability of BTLA to recruit either SHP1 or SHP2, suggesting that BTLA recruits SHP1 and SHP2 in a manner distinct from PD-1 and both tyrosine motifs are required to block T cell activation. The BTLA cytoplasmic tail also contains a third conserved tyrosine-containing motif within the cytoplasmic domain, similar in sequence to a Grb-2 recruitment site (YXN). Also, a phosphorylated peptide containing this BTLA N-terminal tyrosine motif can interact with GRB2 and the p85 subunit of PI3K in vitro, although the functional effects of this interaction remain unexplored in vivo (Gavrieli et al., Biochem. Biophysi Res Commun, 2003, 312, 1236-43). BTLA is the receptor for the ligands PTPN6/SHP-1; PTPN11/SHP-2; TNFRSF14/HVEM; and B7H4.

VISTA (also known as V-domain Ig suppressor of T cell activation VSIR, B7-H5, B7H5, GI24, PP2135, SISP1, DD1alpha, VISTA, C10orf54, chromosome 10 open reading frame 54, PD-1H, and V-set immunoregulatory receptor) is a ~33.9-kDa single-pass type I membrane protein involved in T-cell inhibitory response, embryonic stem cells differentiation via BMP4 signaling inhibition, and MMP14-mediated MMP2 activation (Yoon et al., Control of signaling-mediated clearance of apoptotic cells by the tumor suppressor p53, Science. 2015 Jul. 31; 349(6247): 1261669). VISTA interacts with the ligand VSIG-3 (Wang et al., VSIG-3 as a ligand of VISTA inhibits human T-cell function, Immunology. 2019 January; 156(1): 74-85)

LAG-3 (also known as Lymphocyte-activation gene 3, LAG3, CD223, and lymphocyte activating 3) is a ~57.4-kDa single-pass type I membrane protein involved in lymphocyte activation that also binds to HLA class-II antigens. LAG-3 is a member of the immunoglobulin supergene family, and is expressed on activated T cells (Huard et al., 1994, Immunogenetics 39: 213), NK cells (Triebel et al., 1990, J. Exp. Med. 171: 1393-1405), regulatory T cells (Huang et al., 2004, Immunity 21: 503-513; Camisaschi et al., 2010, J Immunol. 184: 6545-6551; Gagliani et al., 2013, Nat Med 19: 739-746), and plasmacytoid dendritic cells (DCs) (Workman et al., 2009, J Immunol 182: 1885-1891). LAG-3 is a membrane protein encoded by a gene located on chromosome 12, and is structurally and genetically related to CD4. Similar to CD4, LAG-3 can interact with MHC class II molecules on the cell surface (Baixeras et al., 1992, J. Exp. Med. 176: 327-337; Huard et al., 1996, Eur. J. Immunol. 26: 1180-1186). It has been suggested that the direct binding of LAG-3 to MHC class II plays a role in down-regulating antigen-dependent stimulation of CD4+T lymphocytes (Huard et al., 1994, Eur. J. Immunol. 24: 3216-3221) and LAG-3 blockade has also been shown to reinvigorate CD8+ lymphocytes in both tumor or self-antigen (Gross et al., 2007, J Clin Invest. 117: 3383-3392) and viral models (Blackburn et al., 2009, Nat. Immunol. 10: 29-37). Further, the intra-cytoplasmic region of LAG-3 can interact with LAP (LAG-3-associated protein), which is a signal transduction molecule involved in the downregulation of the CD3/TCR activation pathway (Iouzalen et al., 2001, Eur. J. Immunol. 31: 2885-2891). Moreover, CD4+CD25+ regulatory T cells (Treg) have been shown to express LAG-3 upon activation, which contributes to the suppressor activity of Treg cells (Huang, C. et al., 2004, Immunity 21: 503-513). LAG-3 can also negatively regulate T cell homeostasis by Treg cells in both T cell-dependent and independent mechanisms (Workman, C. J. and Vignali, D. A., 2005, J. Immunol. 174: 688-695).

LAG-3 has been shown to interact with MHC class II molecules (Huard et al., CD4/major histocompatibility complex class II interaction analyzed with CD4–and lymphocyte activation gene-3 (LAG-3)-Ig fusion proteins, Eur J Immunol. 1995 September; 25(9): 2718-21).

Additionally, several kinases are known to be checkpoint inhibitors. For example, CHEK-1, CHEK-2, and A2aR.

CHEK-1 (also known as CHK 1 kinase, CHK1, and checkpoint kinase 1) is a ~54.4-kDa serine/threonine-protein kinase that is involved with checkpoint-mediated cell cycle arrest, and the activation of DNA repair in response to the DNA damage and/or unreplicated DNA.

CHEK-2 (also known as CHK2 kinase, CDS1, CHK2, HuCdsl, LFS2, PP1425, RAD53, hCdsl, and checkpoint kinase 2) is a ~60.9-kDa. serine/threonine-protein kinase involved in checkpoint-mediated cell cycle arrest, DNA-repair activation, and double-strand break-mediated apoptosis.

A2aR (also known as adenosine A2A receptor, ADORA2A, adenosine A2a receptor, A2aR, ADORA2, and RDC8) is a ~44.7-kDa multi-pass membrane receptor for adenosine and other ligands.

In some embodiments, illustrative immunotherapeutic agents can include one or more antibody modulators that target PD-1, PD-L1, PD-L2, CEACAM (e.g., CEACAM-1, -3 and/or -5), CTLA-4, TIM-3, LAG-3, VISTA, BTLA, TIGIT, LAIR1, CD160, 2B4, TGF beta, OX40, 41BB, LIGHT, CD40, GITR, TGF-beta, TIM-3, SIRP-alpha, VSIG8, BTLA, SIGLEC7, SIGLEC9, ICOS, B7H3, B7H4, FAS, and/or BTNL2 among others known in the art,. In some embodiments, the immunotherapeutic agent is an agent that increases natural killer (NK) cell activity. In some embodiments, the one or more additional therapies is an agent that inhibits suppression of an immune response. In some embodiments, the one or more additional therapies is an agent that inhibits suppressor cells or suppressor cell activity. In some embodiments, the one or more additional therapies is an agent or therapy that inhibits Treg activity. In some embodiments, the one or more additional therapies is an agent that inhibits the activity of inhibitory immune checkpoint receptors.

In some embodiments, the one or more additional therapies includes a T cell modulator chosen from an agonist or an activator of a costimulatory molecule in the concurrent administration with a checkpoint inhibitor. In one embodiment, the agonist of the costimulatory molecule is chosen from an agonist (e.g., an agonistic antibody or antigen-binding fragment thereof, or a soluble fusion) of GITR, OX40, SLAM (e.g., SLAMF7), HVEM, LIGHT, CD2, CD27, CD28, CDS, ICAM-1, LFA-1 (CD11a/CD18), ICOS (CD278), 4-1BB (CD137), CD30, CD40, BAFFR, CD7, NKG2C, NKp80, CD160, B7-H3, or CD83 ligand. In other embodiments, the effector cell combination includes a bispecific T cell engager (e.g., a bispecific antibody molecule that binds to CD3 and a tumor antigen (e.g., EGFR, PSCA, PSMA, EpCAM, HER2 among others).

In some embodiments, the one or more additional therapies is a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, an modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a modulator of SIRP-alpha activity, a modulator of TIGIT activity, a modulator of VSIG8 activity, a modulator of BTLA activity, a modulator of SIGLEC7 activity, a modulator of SIGLEC9 activity, a modulator of ICOS activity, a modulator of B7H3 activity, a modulator of B7H4 activity, a modulator of FAS activity, a modulator of BTNL2 activity, a cytokine, a chemokine, an interferon, an interleukin, a lymphokine, a member of the tumor necrosis factor (TNF) family, or an immunostimulatory oligonucleotide.

In some embodiments, the one or more additional therapies is an immune checkpoint modulator (e.g., an immune checkpoint inhibitor e.g. an inhibitor of PD-1 activity, a modulator of PD-L1 activity, a modulator of PD-L2 activity, a modulator of CTLA-4, or a CD40 agonist (e.g., an anti-CD40 antibody molecule), (xi) an OX40 agonist (e.g., an anti-OX40 antibody molecule), or (xii) a CD27 agonist (e.g., an anti-CD27 antibody molecule). In one embodiment, the immunotherapeutic agent is an inhibitor of: PD-1, PD-L1, PD-L2, CTLA-4, TIM-3, LAG-3, CEACAM (e.g., CEACAM-1, -3 and/or -5), VISTA, BTLA, TIGIT, LAIR1, CD160, 2B4 and/or TGF beta, Galectin 9, CD69, Galectin-1, CD113, GPR56, CD48, GARP, PD1H, LAIR1, TIM-1, and TIM-4. In one embodiment, the inhibitor of an immune checkpoint molecule inhibits PD-1, PD-L1, LAG-3, TIM-3, CEACAM (e.g., CEACAM-1, -3 and/or -5), CTLA-4, or any combination thereof.

In one embodiment, the immunotherapeutic agent is an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, the one or more additional therapies is an activator or agonist of a costimulatory molecule. In one embodiment, the agonist of the costimulatory molecule is chosen from an agonist (e.g., an agonistic antibody or antigen-binding fragment thereof, or a soluble fusion) of CD2, CD28, CDS, ICAM-1, LFA-1 (CD11a/CD18), ICOS (CD278), 4-1BB (CD137), GITR, CD30, BAFFR, HVEM, CD7, LIGHT, NKG2C, SLAMF7, NKp80, CD160, B7-H3, or CD83 ligand.

Inhibition of an inhibitory molecule can be performed at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand (e.g., PD-1-Ig or CTLA-4 Ig), or an antibody or antigen-binding fragment thereof, for example, a monoclonal antibody, a bispecific antibody comprising one or more immune checkpoint antigen binding moieties, a trispecific antibody, or an immune cell-engaging multivalent antibody/fusion protein/construct known in the art that binds to the inhibitory molecule; e.g., an antibody or fragment thereof (also referred to herein as "an antibody molecule") that binds to PD-1, PD-L1, PD-L2, CTLA-4, TIM-3, LAG-3, CEACAM (e.g., CEACAM-1, -3 and/or -5), VISTA, BTLA, TIGIT, LAIR1, CD160, 2B4 and/or TGF beta, Galectin 9, CD69, Galectin-1, CD113, GPR56, CD48, GARP, PD1H, LAIR1, TIM-1, TIM-4, or a combination thereof.

In some embodiments, the one or more additional therapies is a monoclonal antibody or a bispecific antibody in the concurrent administration with a checkpoint inhibitor. For example, the monoclonal or bispecific antibody may specifically bind a member of the c-Met pathway and/or an immune checkpoint modulator (e.g., the bispecific antibody binds to both a hepatocyte growth factor receptor (HGFR) and an immune checkpoint modulator described herein, such as an antibody that binds PD-1, PD-L1, PD-L2, or CTLA-4, LAG-3, OX40, 41BB, LIGHT, CD40, GITR, TGF-beta, TIM-3, SIRP-alpha, TIGIT, VSIG8, BTLA, SIGLEC7, SIGLEC9, ICOS, B7H3, B7H4, FAS, BTNL2 or CD27). In particular embodiments, the bispecific antibody specifically binds a human HGFR protein and one of PD-1, PD-L1, and CTLA-4.

In some of the embodiments of the methods described herein, the one or more additional therapies is a PD-1 antagonist, a PD-L1 antagonist, a PD-L2 antagonist, a CTLA-4 antagonist, a CD80 antagonist, a CD86 antagonist, a KIR antagonist, a Tim-3 antagonist, a LAG3 antagonist, a TIGIT antagonist, a CD20 antagonist, a CD96 antagonist, or an IDO1 antagonist.

In some embodiments, the PD-1 antagonist is an antibody that specifically binds PD-1. In some embodiments, the antibody that binds PD-1 is pembrolizumab (KEYTRUDA®, MK-3475; Merck), pidilizumab (CT-011; Curetech Ltd.), nivolumab (OPDIVO®, BMS-936558, MDX-1106; Bristol Myer Squibb), MEDIO680 (AMP-514; AstraZenenca/MedImmune), REGN2810 (Regeneron Pharmaceuticals), BGB-A317 (BeiGene Ltd.), PDR-001 (Novartis), or STI-A1110 (Sorrento Therapeutics). In some embodiments, the antibody that binds PD-1 is described in PCT Publication WO 2014/179664, for example, an antibody identified as APE2058, APE1922, APE1923, APE1924, APE 1950, or APE1963 (Anaptysbio), or an antibody containing the CDR regions of any of these antibodies. In other embodiments, the PD-1 antagonist is a fusion protein that includes the extracellular domain of PD-L1 or PD-L2, for example, AMP-224 (AstraZeneca/MedImmune). In other embodiments, the PD-1 antagonist is a peptide inhibitor, for example, AUNP-12 (Aurigene).

In some embodiments, the PD-L1 antagonist is an antibody that specifically binds PD-L1. In some embodiments, the antibody that binds PD-L1 is MEDI4736 (AstraZeneca/MedImmune), BMS-936559 (MDX-1105; Bristol Myers Squibb), avelumab (MSB0010718C; Merck KGaA), KD033 (Kadmon), the antibody portion of KD033, or STI-A1014 (Sorrento Therapeutics). In some embodiments, the antibody that binds PD-L1 is described in PCT Publication WO 2014/055897, for example, Ab-14, Ab-16, Ab-30, Ab-31, Ab-42, Ab-50, Ab-52, or Ab-55, or an antibody that contains the CDR regions of any of these antibodies, the disclosure of which is incorporated herein by reference in its entirety.

In some embodiments, the CTLA-4 antagonist is an antibody that specifically binds CTLA-4. In some embodiments, the antibody that binds CTLA-4 is ipilimumab (YERVOY®; Bristol Myer Squibb) or tremelimumab (CP-675, 206; Pfizer). In some embodiments, the CTLA-4 antagonist a CTLA-4 fusion protein or soluble CTLA-4 receptor, for example, KARR-102 (Kahr Medical Ltd.).

In some embodiments, the LAG3 antagonist is an antibody that specifically binds LAG3. In some embodiments, the antibody that binds LAG3 is IMP701 (Prima BioMed), IMP731 (Prima BioMed/GlaxoSmithKline), BMS-986016 (Bristol Myer Squibb), LAG525 (Novartis), and GSK2831781 (GlaxoSmithKline). In some embodiments, the LAG3 antagonist includes a soluble LAG3 receptor, for example, IMP321 (Prima BioMed).

In some embodiments, the KIR antagonist is an antibody that specifically binds KIR. In some embodiments, the antibody that binds KIR is lirilumab (Bristol Myer Squibb/Innate Pharma).

In some embodiments, the immunotherapeutic agent is a cytokine, for example, a chemokine, an interferon, an interleukin, lymphokine, or a member of the tumor necrosis factor family. In some embodiments, the cytokine is IL-2, IL15, or interferon-gamma.

In some embodiments of any of the above aspects or those described elsewhere herein, the cancer is selected from the group consisting of lung cancer (e.g., a non-small cell lung cancer (NSCLC)), a kidney cancer (e.g., a kidney urothelial carcinoma), a bladder cancer (e.g., a bladder urothelial (transitional cell) carcinoma), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycoses fungoides, a merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, adrenal cortex carcinoma, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, an Ewing's tumor, a squamous cell carcinoma, a basal cell carcinoma, an adenocarcinoma, a sweat gland carcinoma, a sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, an epithelial carcinoma, a glioma, anaplastic astrocytoma, an astrocytoma, a medulloblastoma, a craniopharyngioma, an ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familiar hypereosinophilia, a neuroendocrine cancer, or a carcinoid tumor.

In some embodiments of any of the above aspects or those described elsewhere herein, the subject's cancer or tumor does not respond to immune checkpoint inhibition (e.g., to any immune checkpoint inhibitor described herein, such as a PD-1 antagonist or PD-L1 antagonist) or the subject's cancer or tumor has progressed following an initial response to immune checkpoint inhibition (e.g., to any immune checkpoint inhibitor described herein, such as a PD-1 antagonist or PD-L1 antagonist).

In various embodiments, the one or more additional therapies can comprise an antibody or an antigen binding fragment thereof. Within this definition, immune checkpoint inhibitors include bispecific antibodies and immune cell-engaging multivalent antibody/fusion protein/constructs known in the art. In some embodiments, the one or more additional therapies which comprise bispecific antibodies may include bispecific antibodies that are bivalent and bind either the same epitope of the immune checkpoint molecule, two different epitopes of the same immune checkpoint molecule or different epitopes of two different immune checkpoints.

Persons of ordinary skill in the art can implement several bispecific antibody formats known in the field to target one or more of CTLA4, PD1, PD-L1 TIM-3, LAG-3, various B-7 ligands, B7H3, B7H4, CHK 1 and CHK2 kinases, BTLA, A2aR, OX40, 41BB, LIGHT, CD40, GITR, TGF-beta, SIRP-alpha, TIGIT, VSIG8, SIGLEC7, SIGLEC9, ICOS, FAS, BTNL2 and other for use in the combination described herein.

In various embodiments, the one or more additional therapies can include an immune cell-engaging multivalent antibody/fusion protein/construct.

In some embodiments of the present disclosure, the one or more additional therapies is a population of immune cells, which can be administered in combination with a non-polymorphic form, crystalline form or crystalline salt form of Compound 1 to treat a subject with cancer in the concurrent administration with a checkpoint inhibitor. In some embodiments, the immunotherapeutic agent is a population of immune cells, such as leukocytes (nucleated white blood cells), comprising (e.g., expressing) a receptor that binds to an antigen of interest. A leukocyte of the present disclosure may be, for example, a neutrophil, eosinophil, basophil, lymphocyte or a monocyte. In some embodiments, a leukocyte is a lymphocyte. Examples of lymphocytes include T cells, B cells, Natural Killer (NK) cells or NKT cells. In some embodiments, a T-cell is a CD4+Th (T helper) cell, a CD8+ cytotoxic T cell, a 76T cell or a regulatory (suppressor) T cell. In some embodiments, an immune cell is a dendritic cell.

Immune cells of the present disclosure, in some embodiments, are genetically engineered to express an antigen-binding receptor. A cell is considered "engineered" if it contains an engineered (exogenous) nucleic acid. Engineered nucleic acids of the present disclosure may be introduced into a cell by any known (e.g., conventional) method. For example, an engineered nucleic acid may be introduced into a cell by electroporation (see, e.g., Heiser W. C. Transcription Factor Protocols: Methods in Molecular Biology™. 2000; 130: 117-134), chemical (e.g., calcium phosphate or lipid), transfection (see, e.g., Lewis W. H., et al., Somatic Cell Genet. 1980 May; 6(3): 333-47; Chen C., et al., Mol Cell Biol. 1987 August; 7(8): 2745-2752), fusion with bacterial protoplasts containing recombinant plasmids (see, e.g., Schaffner W. Proc Natl Acad Sci USA. 1980 April; 77(4): 2163-7), microinjection of purified DNA directly into the nucleus of the cell (see, e.g., Capecchi M. R. Cell. 1980 November; 22(2 Pt 2): 479-88), or retrovirus transduction.

Some aspects of the present disclosure including one or more additional therapies provide an "adoptive cell" approach, which involves isolating immune cells (e.g., T-cells) from a subject with cancer, genetically engineering the immune cells (e.g., to express an antigen-binding receptor, such as a chimeric antigen receptor), expanding the cells ex vivo, and then re-introducing the immune cells into the subject. This method results in a greater number of engineered immune cells in the subject relative to what could be achieved by conventional gene delivery and vaccination methods. In some embodiments, immune cells are isolated from a subject, expanded ex vivo without genetic modification, and then re-introduced into the subject.

Immune cells of the present disclosure comprise receptors that bind to antigens, such as an antigen encoded by an exogenously delivered nucleic acid, as provided herein. In some embodiments, a leukocyte is modified (e.g., genetically modified) to express a receptor that binds to an antigen. The receptor may be, in some embodiments, a naturally-occurring antigen receptor (normally expressed on the immune cell), recombinant antigen receptor (not normally expressed on the immune cell) or a chimeric antigen receptor (CAR). Naturally-occurring and recombinant antigen receptors encompassed by the present disclosure include T cell receptors, B cell receptors, NK cell receptors, NKT cell receptors and dendritic cell receptors. A "chimeric antigen receptor" refers to an artificial immune cell receptor that is engineered to recognize and bind to an antigen expressed by tumor cells. Generally, a CAR is designed for a T cell and is a chimera of a signaling domain of the T-cell receptor (TcR) complex and an antigen-recognizing domain (e.g., a single chain fragment (scFv) of an antibody) (Enblad et al., Human Gene Therapy. 2015; 26(8): 498-505), the disclosure of which is incorporated herein by reference in its entirety.

In some embodiments, an antigen binding receptor is a chimeric antigen receptor (CAR). A T cell that expresses a CAR is referred to as a "CAR T cell." A CAR T cell receptor, in some embodiments, comprises a signaling domain of the T-cell receptor (TcR) complex and an antigen-recognizing domain (e.g., a single chain fragment (scFv) of an antibody) (Enblad et al., Human Gene Therapy. 2015; 26(8): 498-505) the disclosure of which is incorporated herein by reference in its entirety.

There are four generations of CARs, each of which contains different components. First generation CARs join an antibody-derived scFv to the CD3zeta (zeta. or z) intracellular signaling domain of the T-cell receptor through hinge and transmembrane domains. Second generation CARs incorporate an additional domain, e.g., CD28, 4-1BB (41BB), or ICOS, to supply a costimulatory signal. Third-generation CARs contain two costimulatory domains fused with the TcR CD3-zeta chain. Third-generation costimulatory domains may include, e.g., a combination of CD3z, CD27, CD28, 4-1BB, ICOS, or OX40. CARs, in some embodiments, contain an ectodomain (e.g., CD3), commonly derived from a single chain variable fragment (scFv), a hinge, a transmembrane domain, and an endodomain with one (first generation), two (second generation), or three (third generation) signaling domains derived from CD3Z and/or co-stimulatory molecules (Maude et al., Blood. 2015; 125(26): 4017-4023; Kakarla and Gottschalk, Cancer J. 2014; 20(2): 151-155) the disclosure of which is incorporated herein by reference in its entirety.

In some embodiments, the chimeric antigen receptor (CAR) is a T-cell redirected for universal cytokine killing (TRUCK), also known as a fourth generation CAR. TRUCKs are CAR-redirected T-cells used as vehicles to produce and release a transgenic cytokine that accumulates in the targeted tissue, e.g., a targeted tumor tissue. The transgenic cytokine is released upon CAR engagement of the target. TRUCK cells may deposit a variety of therapeutic cytokines in the target. This may result in therapeutic concentrations at the targeted site and avoid systemic toxicity.

CARs typically differ in their functional properties. The CD3zeta signaling domain of the T-cell receptor, when engaged, will activate and induce proliferation of T-cells but can lead to anergy (a lack of reaction by the body's defense mechanisms, resulting in direct induction of peripheral lymphocyte tolerance). Lymphocytes are considered anergic when they fail to respond to a specific antigen. The addition of a costimulatory domain in second-generation CARs improved replicative capacity and persistence of modified T-cells. Similar antitumor effects are observed in vitro with CD28 or 4-1BB CARs, but preclinical in vivo studies suggest that 4-1BB CARs may produce superior proliferation and/or persistence. Clinical trials suggest that both of these second-generation CARs are capable of inducing substantial T-cell proliferation in vivo, but CARs containing the 4-1BB costimulatory domain appear to persist longer. Third generation CARs combine multiple signaling domains (costimulatory) to augment potency. Fourth generation CARs are additionally modified with a constitutive or inducible expression cassette for a transgenic cytokine, which is released by the CAR T-cell to modulate the T-cell response. See, for example, Enblad et al., Human Gene Therapy. 2015; 26(8): 498-505; Chmielewski and Hinrich, Expert Opinion on Biological Therapy. 2015; 15(8): 1145-1154 the disclosures of which are incorporated herein by reference in their entireties.

In some embodiments, the one or more additional therapies is a first generation chimeric antigen receptor CAR. In some embodiments, a chimeric antigen receptor is a second generation CAR. In some embodiments, a chimeric antigen receptor is a third generation CAR. In some embodiments, the chimeric antigen receptor is a fourth generation CAR or a T-cell redirected for universal cytokine killing (TRUCK).

In some embodiments, a chimeric antigen receptor (CAR) comprises an extracellular domain comprising an antigen binding domain, a transmembrane domain, and a cytoplasmic domain. In some embodiments, a CAR is fully human. In some embodiments, the antigen binding domain of a CAR is specific for one or more antigens. In some embodiments, a "spacer" domain or "hinge" domain is located between an extracellular domain (comprising the antigen binding domain) and a transmembrane domain of a CAR, or between a cytoplasmic domain and a transmembrane domain of the CAR. A "spacer domain" refers to any oligopeptide or polypeptide that functions to link the transmembrane domain to the extracellular domain and/or the cytoplasmic domain in the polypeptide chain. A "hinge domain" refers to any oligopeptide or polypeptide that functions to provide flexibility to the CAR, or domains thereof, or to prevent steric hindrance of the CAR, or domains thereof. In some embodiments, a spacer domain or hinge domain may comprise up to 300 amino acids (e.g., 10 to 100 amino acids, or 5 to 20 amino acids). In some embodiments, one or more spacer domain(s) may be included in other regions of a CAR.

In some embodiments, a CAR of the disclosure comprises an antigen binding domain, such as a single chain Fv (scFv) specific for a tumor antigen. The choice of binding domain depends upon the type and number of ligands that define the surface of a target cell. For example, the antigen binding domain may be chosen to recognize a ligand that acts as a cell surface marker on target cells associated with a particular disease state, such as cancer or an autoimmune disease. Thus, examples of cell surface markers that may act as ligands for the antigen binding domain in the CAR of the present disclosure include those associated with cancer cells and/or other forms of diseased cells. In some embodiments, a CAR is engineered to target a tumor antigen of interest by way of engineering a desired antigen binding domain that specifically binds to an antigen on a tumor cell encoded by an engineered nucleic acid, as provided herein.

An antigen binding domain (e.g., an scFv) that "specifically binds" to a target or an epitope is a term understood in the art, and methods to determine such specific binding are also known in the art. A molecule is said to exhibit "specific binding" if it reacts or associates more frequently, more rapidly, with greater duration and/or with greater affinity with a particular target antigen than it does with alternative targets. An antigen binding domain (e.g., an scFv) that specifically binds to a first target antigen may or may not specifically bind to a second target antigen. As such, "specific binding" does not necessarily require (although it can include) exclusive binding.

In some embodiments, immune cells expressing a CAR are genetically modified to recognize multiple targets or antigens, which permits the recognition of unique target or antigen expression patterns on tumor cells. Examples of CARs that can bind multiple targets include: "split signal CARs," which limit complete immune cell activation to tumors expressing multiple antigens; "tandem CARs" (TanCARs), which contain ectodomains having two scFvs; and "universal ectodomain CARs," which incorporate avidin or a fluorescein isothiocyanate (FITC)-specific scFv to recognize tumor cells that have been incubated with tagged monoclonal antibodies (Mabs).

A CAR is considered "bispecific" if it recognizes two distinct antigens (has two distinct antigen recognition domains). In some embodiments, a bispecific CAR is comprised of two distinct antigen recognition domains present in tandem on a single transgenic receptor (referred to as a TanCAR; see, e.g., Grada Z et al. Molecular Therapy Nucleic Acids 2013; 2: e105, incorporated herein by reference in its entirety). Thus, methods, in some embodiments, comprise delivering to a tumor a combination comprising a non-polymorphic form, crystalline form or crystalline salt form of Compound 1 and an immunotherapeutic agent in the concurrent administration with a checkpoint inhibitor, wherein the immunotherapeutic agent is an engineered nucleic acid that encodes an antigen, or delivering to a tumor an engineered nucleic acid that induces expression of a self-antigen, and delivering to the tumor an immune cell expressing a bispecific CAR that binds to two antigens, one of which is encoded by the engineered nucleic acid.

In some embodiments, a CAR is an antigen-specific inhibitory CAR (iCAR), which may be used, for example, to avoid off-tumor toxicity (Fedorov, V D et al. Sci. Transl. Med. published online Dec. 11, 2013, incorporated herein by reference in its entirety). iCARs contain an antigen-specific inhibitory receptor, for example, to block nonspecific immunosuppression, which may result from extra tumor target expression. iCARs may be based, for example, on inhibitory molecules CTLA-4 or PD-1. In some embodiments, these iCARs block T cell responses from T cells activated by either their endogenous T cell receptor or an activating CAR. In some embodiments, this inhibiting effect is temporary.

In some embodiments, CARs may be used in adoptive cell transfer, wherein immune cells are removed from a subject and modified so that they express receptors specific to an antigen, e.g., a tumor-specific antigen. The modified immune cells, which may then recognize and kill the cancer cells, are reintroduced into the subject (Pule, et al., Cytotherapy. 2003; 5(3): 211-226; Maude et al., Blood. 2015; 125(26): 4017-4023, each of which is incorporated herein by reference in their entireties).

According to other aspects of the disclosure, the tumor antigenic component in the vaccine of the invention is any natural or synthetic tumor-associated protein or peptide or combination of tumor-associated proteins and/or peptides or glycoproteins or glycopeptides. In still yet other aspects, the antigenic component can be patient-specific or common to many or most patients with a particular type of cancer. According to one aspect, the antigenic component consists of a cell lysate derived from tumor tissue removed from the patient being treated. In another aspect, the lysate can be engineered or synthesized from exosomes derived from tumor tissue. In yet another aspect, the antigenic component consists of a cell lysate derived from tumor tissue extracted from one or more unrelated individuals or from tumor-cell lines.

In various embodiments, the tumor-associated antigen component of the vaccine may be manufactured by any of a variety of well-known techniques. For individual protein components, the antigenic protein is isolated from tumor tissue or a tumor-cell line by standard chromatographic means such as high-pressure liquid chromatography or affinity chromatography or, alternatively, it is synthesized by standard recombinant DNA technology in a suitable expression system, such as *E. coli*, yeast or plants. The tumor-associated antigenic protein is then purified from the expression system by standard chromatographic means. In the case of peptide antigenic components, these are generally prepared by standard automated synthesis. Proteins and peptides can be modified by addition of amino acids, lipids and other agents to improve their incorporation into the delivery system of the vaccine (such as a multilamellar liposome). For a tumor-associated antigenic component derived from the patient's own tumor, or tumors from other individuals, or cell lines, the tumor tissue, or a single cell suspension derived from the tumor tissue, is typically homogenized in a suitable buffer. The homogenate can also be fractionated, such as by centrifugation, to isolate particular cellular components such as cell membranes or soluble material. The tumor material can be used directly or tumor-associated antigens can be extracted for incorporation in the vaccine using a buffer containing a low concentration of a suitable agent such as a detergent. An example of a suitable detergent for extracting antigenic proteins from tumor tissue, tumor cells, and tumor-cell membranes is diheptanoyl phosphatidylcholine. Exosomes derived from tumor tissue or tumor cells, whether autologous or heterologous to the patient, can be used for the antigenic component for incorporation in the vaccine or as a starting material for extraction of tumor-associated antigens.

In some embodiments of the present disclosure, the one or more additional therapies is a cancer vaccine immunotherapeutic agent in the concurrent administration with a checkpoint inhibitor. In various examples, the cancer vaccine includes at least one tumor-associated antigen, at least one immunostimulant, and optionally, at least one cell-based immunotherapeutic agent. In some embodiments, the immunostimulant component in the cancer vaccine of the disclosure is any Biological Response Modifier (BRM) with the ability to enhance the therapeutic cancer vaccine's effectiveness to induce humoral and cellular immune responses against cancer cells in a patient. According to one aspect, the immunostimulant is a cytokine or combination of cytokines. Examples of such cytokines include the interferons, such as IFN-gamma, the interleukins, such as IL-2, IL-15 and an IL-23, the colony stimulating factors, such as M-CSF and GM-CSF, and tumor necrosis factor. According to another aspect, the immunostimulant component of the disclosed cancer vaccine includes one or more adjuvant-type immunostimulatory agents such as APC Toll-like Receptor agonists or costimulatory/cell adhesion membrane proteins, with or without immunostimulatory cytokines. Examples of Toll-like Receptor agonists include lipid A and CpG, and costimulatory/adhesion proteins such as CD80, CD86, and ICAM-1.

In some embodiments, the one or more additional therapies is an immunostimulant selected from the group consisting of IFN-gamma (IFN-7), IL-2, IL-15, IL-23, M-CSF, GM-CSF, tumor necrosis factor, lipid A, CpG, CD80, CD86, and ICAM-1, or combinations thereof. According to other aspects, the cell-based immunotherapeutic agent is selected from the group consisting of dendritic cells, tumor-infiltrating T lymphocytes, chimeric antigen receptor-modified T effector cells directed to the patient's tumor type, B lymphocytes, natural killer cells, bone marrow cells, and any other cell of a patient's immune system, or combinations thereof. In one aspect, the cancer vaccine immunostimulant includes one or more cytokines, such as interleukin 2 (IL-2), GM-CSF, M-CSF, and interferon-gamma (IFN-7), one or more Toll-like Receptor agonists and/or adjuvants, such as monophosphoryl lipid A, lipid A, muramyl dipeptide (MDP) lipid conjugate and double stranded RNA, or one or more costimulatory membrane proteins and/or cell adhesion proteins, such CD80, CD86 and ICAM-1, or any combination of the above. In one aspect, the cancer vaccine includes an immunostimulant that is a cytokine selected from the group consisting of interleukin 2 (IL-2), GM-CSF, M-CSF, and interferon-gamma (IFN-7). In another aspect, the cancer vaccine includes an immunostimulant that is a Toll-like Receptor agonist and/or adjuvant selected from the group consisting of monophosphoryl lipid A, lipid A, and muramyl dipeptide (MDP) lipid conjugate and double stranded RNA. In yet another aspect, the cancer vaccine includes an immunostimulant that is a costimulatory membrane protein and/or cell adhesion protein selected from the group consisting of CD80, CD86, and ICAM-1.

In various embodiments, one or more additional therapies can include a cancer vaccine, wherein the cancer vaccine incorporates any tumor antigen that can be potentially used to construct a fusion protein according to the invention and particularly the following: (a) cancer-testis antigens including NY-ESO-1, SSX2, SCP1 as well as RAGE, BAGE, GAGE and MAGE family polypeptides, for example, GAGE-1, GAGE-2, MAGE-1 MAGE-2, MAGE-3, MAGE-4, MAGE-5, MAGE-6, and MAGE-12, which can be used, for example, to address melanoma, lung, head and neck, NSCLC, breast, gastrointestinal, and bladder tumors; (b) mutated antigens, including p53, associated with various solid tumors, e.g., colorectal, lung, head and neck cancer; p21/Ras associated with, e.g., melanoma, pancreatic cancer and colorectal cancer; CDK4, associated with, e.g., melanoma; MUM1 associated with, e.g., melanoma; caspase-8 associated with, e.g., head and neck cancer; CIA 0205 associated with, e.g., bladder cancer; HLA-A2-R1701, beta catenin associated with, e.g., melanoma; TCR associated with, e.g., T-cell non-Hodgkin lymphoma; BCR-abl associated with, e.g., chronic myelogenous leukemia; triosephosphate isomerase; KIA 0205; CDC-27, and LDLR-FUT; (c) over-expressed antigens, including, Galectin 4 associated with, e.g., colorectal cancer; Galectin 9 associated with, e.g., Hodgkin's disease; proteinase 3 associated with, e.g., chronic myelogenous leukemia; WT 1 associated with, e.g., various leukemias; carbonic anhydrase associated with, e.g., renal cancer; aldolase A associated with, e.g., lung cancer; PRAME associated with, e.g., melanoma; HER-2/neu associated with, e.g., breast, colon, lung and ovarian cancer; mammaglobin, alpha-fetoprotein associated with, e.g., hepatoma; KSA associated with, e.g., colorectal cancer; gastrin associated with, e.g., pancreatic and gastric cancer; telomerase catalytic protein, MUC-1 associated with, e.g., breast and ovarian cancer; G-250 associated with, e.g., renal cell carcinoma; p53 associated with, e.g., breast, colon cancer; and carcinoembryonic antigen associated with, e.g., breast cancer, lung cancer, and cancers of the gastrointestinal tract such as colorectal cancer; (d) shared antigens, including melanoma-melanocyte differentiation antigens such as MART-1/Melan A; gp100; MC1R; melanocyte-stimulating hormone receptor; tyrosinase; tyrosinase related protein-1/TRP1 and tyrosinase related protein-2/TRP2 associated with, e.g., melanoma; (e) prostate associated antigens including PAP, PSA, PSMA, PSH-P1, PSM-P1, PSM-P2, associated with e.g., prostate cancer; (f) immunoglobulin idiotypes associated with myeloma and B cell lymphomas. In certain embodiments, the one or more TAA can be selected from pi 5, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, pl85erbB2, pl 80erbB-3, c-met, mn-23H1, TAG-72-4, CA 19-9, CA 72-4, CAM 17.1, NuMa, K-ras, pi 6, TAGE, PSCA, CT7, 43-9F, 5T4, 791 Tgp72, beta-HCG, BCA225, BTAA, CA 125, CA 15-3 (CA 27.29BCAA), CA 195, CA 242, CA-50, CAM43, CD68KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS or any combinations thereof.

In some embodiments, the one or more additional therapies can include a tumor antigen comprising the entire amino acid sequence, a portion of it, or specific immunogenic epitopes of a human protein.

In various embodiments, the one or more additional therapies may include an mRNA operable to encode any one or more of the aforementioned cancer antigens useful for synthesizing a cancer vaccine. In some illustrative embodiments, the mRNA based cancer vaccine may have one or more of the following properties: a) the mRNA encoding each cancer antigen is interspersed by cleavage sensitive sites; b) the mRNA encoding each cancer antigen is linked directly to one another without a linker; c) the mRNA encoding each cancer antigen is linked to one another with a single nucleotide linker; d) each cancer antigen comprises a 20-40 amino acids and includes a centrally located SNP mutation; e) at least 40% of the cancer antigens have a highest affinity for class I MHC molecules from the subject; f) at least 40% of the cancer antigens have a highest affinity for class II MHC molecules from the subject; g) at least 40% of the cancer antigens have a predicted binding affinity of IC>500 nM for HLA-A, HLA-B and/or DRB1; h) the mRNA encodes 1 to 15 cancer antigens; i) 10-60% of the cancer antigens have a binding affinity for class I MHC and 10-60% of the cancer antigens have a binding affinity for class II MHC; and/or j) the mRNA encoding the cancer antigens is arranged such that the cancer antigens are ordered to minimize pseudo-epitopes.

In various embodiments, the one or more additional therapies is an RNA vaccine comprising at least one RNA polynucleotide having an open reading frame encoding at least one antigenic polypeptide or an immunogenic fragment thereof, thereby inducing in the subject an immune response specific to the antigenic polypeptide or an immunogenic fragment thereof, in combination with administering a non-polymorphic form, crystalline form or crystalline salt form of Compound 1 either in the same composition or a separate composition, administered at the same time, or sequentially dosed, wherein the anti-antigenic polypeptide antibody titer in the subject is increased following vaccination relative to anti-antigenic polypeptide antibody titer in a subject vaccinated with a prophylactically effective dose of a traditional vaccine against the cancer. An "anti-antigenic polypeptide antibody" is a serum antibody the binds specifically to the antigenic polypeptide.

A prophylactically effective dose is a therapeutically effective dose that prevents advancement of cancer at a clinically acceptable level. In some embodiments the therapeutically effective dose is a dose listed in a package insert for the vaccine. A traditional vaccine, as used herein, refers to a vaccine other than the mRNA vaccines of the invention. For instance, a traditional vaccine includes but is not limited to live microorganism vaccines, killed microorganism vaccines, subunit vaccines, protein antigen vaccines, DNA vaccines, and the like. In exemplary embodiments, a traditional vaccine is a vaccine that has achieved regulatory approval and/or is registered by a national drug regulatory body, for example the Food and Drug Administration (FDA) in the United States or the European Medicines Agency (EMA.)

In some embodiments the anti-antigenic polypeptide antibody titer in the subject is increased 1 log to 10 log following vaccination relative to anti-antigenic polypeptide antibody titer in a subject vaccinated with a prophylactically effective dose of a traditional vaccine against the cancer. In some embodiments the anti-antigenic polypeptide antibody titer in the subject is increased 1 log following vaccination relative to anti-antigenic polypeptide antibody titer in a subject vaccinated with a prophylactically effective dose of a traditional vaccine against the cancer. In some embodiments the anti-antigenic polypeptide antibody titer in the subject is increased 2 log following vaccination relative to anti-antigenic polypeptide antibody titer in a subject vaccinated with a prophylactically effective dose of a traditional vaccine against the cancer.

Aspects of the invention provide nucleic acid vaccines comprising one or more RNA polynucleotides having an open reading frame encoding a first antigenic polypeptide, wherein the RNA polynucleotide is present in the formulation for in vivo administration to a host, which confers an antibody titer superior to the criterion for sero-protection for the first antigen for an acceptable percentage of human subjects. In some embodiments, the antibody titer produced by the mRNA vaccines of the invention is a neutralizing antibody titer. In some embodiments the neutralizing antibody titer is greater than a protein vaccine. In other embodiments the neutralizing antibody titer produced by the mRNA vaccines of the invention is greater than an adjuvanted protein vaccine. In yet other embodiments the neutralizing antibody titer produced by the mRNA vaccines of the invention is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

In preferred aspects, RNA vaccine immunotherapeutic agents of the present disclosure (e.g., mRNA vaccines) produce prophylactically- and/or therapeutically-efficacious levels, concentrations and/or titers of antigen-specific antibodies in the blood or serum of a vaccinated subject. As defined herein, the term antibody titer refers to the amount of antigen-specific antibody produced in a subject, e.g., a human subject. In exemplary embodiments, antibody titer is expressed as the inverse of the greatest dilution (in a serial dilution) that still gives a positive result. In exemplary embodiments, antibody titer is determined or measured by enzyme-linked immunosorbent assay (ELISA). In exemplary embodiments, antibody titer is determined or measured by neutralization assay, e.g., by microneutralization assay. In certain aspects, antibody titer measurement is expressed as a ratio, such as 1:40, 1:100, and the like.

In exemplary embodiments of the invention, an efficacious vaccine produces an antibody titer of greater than 1:40, greater that 1:100, greater than 1:400, greater than 1:1000, greater than 1:2000, greater than 1:3000, greater than 1:4000, greater than 1:500, greater than 1:6000, greater than 1:7500, greater than 1:10000. In exemplary embodiments, the antibody titer is produced or reached by 10 days following vaccination, by 20 days following vaccination, by 30 days following vaccination, by 40 days following vaccination, or by 50 or more days following vaccination. In exemplary embodiments, the titer is produced or reached following a single dose of vaccine administered to the subject. In other embodiments, the titer is produced or reached following multiple doses, e.g., following a first and a second dose (e.g., a booster dose.) In exemplary aspects of the invention, antigen-specific antibodies are measured in units of g/ml or are measured in units of IU/L (International Units per liter) or mIU/ml (milli International Units per ml). In exemplary embodiments of the invention, an efficacious vaccine produces >0.5 μg/mL, >0.1 μg/mL, >0.2 μg/mL, >0.35 μg/mL, >0.5 μg/mL, >1 μg/mL, >2 μg/mL, >5 μg/mL or >10 μg/mL. In exemplary embodiments of the invention, an efficacious vaccine produces >10 mIU/mL, >20 mIU/mL, >50 mIU/mL, >100 mIU/mL, >200 mIU/mL, >500 mIU/ml or >1000 mIU/ml. In exemplary embodiments, the antibody level or concentration is produced or reached by 10 days following vaccination, by 20 days following vaccination, by 30 days following vaccination, by 40 days following vaccination, or by 50 or more days following vaccination. In exemplary embodiments, the level or concentration is produced or reached following a single dose of vaccine administered to the subject. In other embodiments, the level or concentration is produced or reached following multiple doses, e.g., following a first and a second dose (e.g., a booster dose.) In exemplary embodiments, antibody level or concentration is determined or measured by enzyme-linked immunosorbent assay (ELISA). In exemplary embodiments, antibody level or concentration is determined or measured by neutralization assay, e.g., by microneutralization assay. Also provided are nucleic acid vaccines comprising one or more RNA polynucleotides having an open reading frame encoding a first antigenic polypeptide or a concatemeric polypeptide, wherein the RNA polynucleotide is present in a formulation for in vivo administration to a host for eliciting a longer lasting high antibody titer than an antibody titer elicited by an mRNA vaccine having a stabilizing element or formulated with an adjuvant and encoding the first antigenic polypeptide. In some embodiments, the RNA polynucleotide is formulated to produce neutralizing antibodies within one week of a single administration. In some embodiments, the adjuvant is selected from a cationic peptide and an immunostimulatory nucleic acid. In some embodiments, the cationic peptide is protamine.

Immunotherapeutic agents comprising a nucleic acid vaccine comprising one or more RNA polynucleotides having an open reading frame comprising at least one chemical modification or optionally no nucleotide modification, the open reading frame encoding a first antigenic polypeptide or a concatemeric polypeptide, wherein the RNA polynucleotide is present in the formulation for in vivo administration to a host such that the level of antigen expression in the host significantly exceeds a level of antigen expression produced by an mRNA vaccine having a stabilizing element or formulated with an adjuvant and encoding the first antigenic polypeptide.

Other aspects provide nucleic acid vaccines comprising one or more RNA polynucleotides having an open reading frame comprising at least one chemical modification or optionally no nucleotide modification, the open reading frame encoding a first antigenic polypeptide or a concatemeric polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Aspects of the invention also provide a unit of use vaccine, comprising between 10 μg and 400 μg of one or more RNA polynucleotides having an open reading frame comprising at least one chemical modification or optionally no nucleotide modification, the open reading frame encoding a first antigenic polypeptide or a concatemeric polypeptide, and a pharmaceutically acceptable excipient, formulated for delivery to a human subject. In some embodiments, the vaccine further comprises a cationic lipid nanoparticle.

Aspects of the invention provide methods of creating, maintaining or restoring antigenic memory to a tumor in an individual or population of individuals comprising administering to said individual or population an antigenic memory booster nucleic acid vaccine comprising (a) at least one RNA polynucleotide, said polynucleotide comprising at least one chemical modification or optionally no nucleotide modification and two or more codon-optimized open reading frames, said open reading frames encoding a set of reference antigenic polypeptides, and (b) optionally a pharmaceutically acceptable excipient. In some embodiments, the vaccine is administered to the individual via a route selected from the group consisting of intramuscular administration, intradermal administration and subcutaneous administration. In some embodiments, the administering step comprises contacting a muscle tissue of the subject with a device suitable for injection of the composition. In some embodiments, the administering step comprises contacting a muscle tissue of the subject with a device suitable for injection of the composition in combination with electroporation.

Aspects of the invention provide methods of vaccinating a subject comprising administering to the subject a single dosage of between 25 μg/kg and 400 μg/kg of a nucleic acid vaccine comprising one or more RNA polynucleotides having an open reading frame encoding a first antigenic polypeptide or a concatemeric polypeptide in an effective amount to vaccinate the subject.

Other aspects provide nucleic acid vaccines comprising one or more RNA polynucleotides having an open reading frame comprising at least one chemical modification, the open reading frame encoding a first antigenic polypeptide or a concatemeric polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

In some embodiments, the one or more additional therapies a non-polymorphic form, crystalline form or crystalline salt form of Compound 1 can be a bispecific antibody immunotherapeutic agent. The bispecific antibody can include a protein construct having a first antigen binding moiety and a second antigen binding site that binds to a cytotoxic immune cell. The first antigen binding site can bind to a tumor antigen that is specifically being treated with the combination of the present invention. For example, the first antigen binding moiety may bind to a non-limiting example of tumor antigens selected from: EGFR, HGFR, Her2, Ep-CAM, CD20, CD30, CD33, CD47, CD52, CD133, CEA, gpA33, Mucins, TAG-72, CIX, PSMA, folate-binding protein, GD2, GD3, GM2, VEGF. VEGFR, Integrin aVP3, Integrin $\alpha 5\beta 1$, MUC1, ERBB2, ERBB3, MET, IGF1R, EPHA3, TRAILR1, TRAILR2, RANKL, FAP and Tenascin among others. In some embodiments, the first antigen binding moiety has specificity to a protein or a peptide that is overexpressed on a tumor cell as compared to a corresponding non-tumor cell. In some embodiments, the first antigen binding moiety has specificity to a protein that is overexpressed on a tumor cell as compared to a corresponding non-tumor cell. A "corresponding non-tumor cell" as used here, refers to a non-tumor cell that is of the same cell type as the origin of the tumor cell. It is noted that such proteins are not necessarily different from tumor antigens. Non-limiting examples include carcinoembryonic antigen (CEA), which is overexpressed in most colon, rectum, breast, lung, pancreas and gastrointestinal tract carcinomas; heregulin receptors (HER-2, neu or c-erbB-2), which is frequently overexpressed in breast, ovarian, colon, lung, prostate and cervical cancers; epidermal growth factor receptor (EGFR), which is highly expressed in a range of solid tumors including those of the breast, head and neck, non-small cell lung and prostate; asialoglycoprotein receptor; transferrin receptor; serpin enzyme complex receptor, which is expressed on hepatocytes; fibroblast growth factor receptor (FGFR), which is overexpressed on pancreatic ductal adenocarcinoma cells; vascular endothelial growth factor receptor (VEGFR), for anti-angiogenesis gene therapy; folate receptor, which is selectively overexpressed in 90% of nonmucinous ovarian carcinomas; cell surface glycocalyx; carbohydrate receptors; and polymeric immunoglobulin receptor.

The second antigen-binding moiety is any molecule that specifically binds to an antigen or protein or polypeptide expressed on the surface of a cytotoxic immune cell (a CIK cell). Exemplary non-limiting antigens expressed on the surface of the cytotoxic immune cells suitable for use with the present disclosure may include CD2, CD3, CD4, CD5, CD8, CD11a, CD11 b, CD14, CD16a, CD27, CD28, CD45, CD45RA, CD56, CD62L, the Fc receptor, LFA, LFA-1, TCRap, CCR7, macrophage inflammatory protein 1a, perforin, PD-1, PD-L1, PD-L2, or CTLA-4, LAG-3, OX40, 41BB, LIGHT, CD40, GITR, TGF-beta, TIM-3, SIRP-alpha, TIGIT, VSIG8, BTLA, SIGLEC7, SIGLEC9, ICOS, B7H3, B7H4, FAS, BTNL2, CD27 and Fas ligand. In some embodiments, the second antigen binding moiety binds to CD3 of the cytotoxic immune cell, e.g., CIK cell. In some embodiments, the second antigen binding moiety binds to CD56 of the cytotoxic immune cell. In some embodiments, the second antigen binding moiety binds to the Fc receptor of the cytotoxic immune cell. In some embodiments, the Fc region of the bispecific antibody binds to the Fc receptor of the cytotoxic immune cell. In some embodiments, a second antigen-binding moiety is any molecule that specifically binds to an antigen expressed on the surface of a cytotoxic immune cell (e.g., a CIK cell). The second antigen binding moiety is specific for an antigen on a cytotoxic immune cell. Exemplary cytotoxic immune cells include, but are not limited to CIK cells, T-cells, CD8+ T cells, activated T-cells, monocytes, natural killer (NK) cells, NK T cells, lymphokine-activated killer (LAK) cells, macrophages, and dendritic cells. The second antigen binding moiety specifically binds to an antigen expressed on the surface of a cytotoxic immune cell. Exemplary non-limiting antigens expressed on the surface of the cytotoxic immune cells suitable for modulation with the present disclosure may include CD2, CD3, CD4, CD5, CD8, CD11a, CD11 b, CD14, CD16a, CD27, CD28, CD45, CD45RA, CD56, CD62L, the Fc receptor, LFA, LFA-1, TCRap, CCR7, macrophage inflammatory protein 1a, perforin, PD-1, PD-L1, PD-L2, or CTLA-4, LAG-3, OX40, 41BB, LIGHT, CD40, GITR, TGF-beta, TIM-3, SIRP-alpha, TIGIT, VSIG8, BTLA, SIGLEC7, SIGLEC9, ICOS, B7H3, B7H4, FAS, BTNL2, CD27 and Fas ligand. In other embodiments, the bispecific antibody modulator is an activator of a costimulatory molecule (e.g., an OX40 agonist). In one embodiment, the OX40 agonist is a bispecific antibody molecule to OX40 and another tumor antigen or a costimulatory antigen. The OX40 agonist can be administered alone, or in combination with other immunomodulators, e.g., in combination with an inhibitor (for example an antibody construct) of PD-1, PD-L1, CTLA-4, CEACAM (e.g., CEACAM-1, -3 and/or -5), TIM-3 or LAG-3. In some embodiments, the anti-OX40 antibody molecule is a bispecific antibody that binds to GITR and PD-1, PD-L1, CTLA-4, CEACAM (e.g., CEACAM-1, -3 and/or -5), TIM-3 or LAG-3. In one exemplary embodiment, an OX40 antibody molecule is administered in combination with an anti-PD-1 antibody molecule (e.g., an anti-PD-1 molecule as described herein). The OX40 antibody molecule and the anti-PD-1 antibody molecule may be in the form of separate antibody composition, or as a bispecific antibody molecule. In other embodiments, the OX40 agonist can be administered in combination with other costimulatory molecule, e.g., an agonist of GITR, CD2, CD27, CD28, CDS, ICAM-1, LFA-1 (CD11a/CD18), ICOS (CD278), 4-1BB (CD137), CD30, CD40, BAFFR, HVEM, CD7, LIGHT, NKG2C, SLAMF7, NKp80, CD160, B7-H3, or CD83 ligand. In some embodiments, the second antigen binding moiety binds to the Fc receptor on the cytotoxic immune cell, e.g., CIK cell.

In some embodiments, the bispecific antibody immunotherapeutic agent has specificities for a tumor antigen and a CIK cell, which brings the tumor antigen expressing tumor cell in close proximity of the CIK cell, leading to the elimination of the tumor cell through anti-tumor cytotoxicity of CIK cell. In some embodiments, the bispecific antibody has specificity for a tumor antigen but does not have specificity for a CIK cell, however, the Fc region of the bispecific antibody can bind to the Fc receptor of the CIK cell, which in turn brings the tumor cell in close proximity of the CIK cell, leading to the elimination of the tumor cell through anti-tumor cytotoxicity of CIK cell. In some embodiments, the bispecific antibody has specificity for a CIK cell but does not have specificity for tumor cell, however, the Fc region of the bispecific antibody can bind to the Fc receptor of the tumor cell, which in turn brings the tumor cell in close proximity of the CIK cell, leading to the elimination of the tumor cell through anti-tumor cytotoxicity of CIK cell.

In some embodiments, the one or more additional therapies is an immune cell-engaging multivalent antibody/fusion protein/construct immunotherapeutic agent in the concurrent administration with a checkpoint inhibitor. In various embodiments, the one or more additional therapies can include immune cell-engaging multivalent antibody/fusion protein/construct which may comprise a recombinant structure, for example, all engineered antibodies that do not imitate the original IgG structure. Here, different strategies to multimerize antibody fragments are utilized. For example, shortening the peptide linker between the V domains forces the scFv to self-associate into a dimer (diabody; 55 kDa). Bispecific diabodies are formed by the noncovalent association of two VHA-VLB and VHB-VLA fragments expressed in the same cell. This leads to the formation of heterodimers with two different binding sites. Single-chain diabodies (sc-diabodies) are bispecific molecules where the VHA-VLB and VHB-VLA fragments are linked together by an additional third linker. Tandem-diabodies (Tandabs) are tetravalent bispecific antibodies generated by two scDiabodies.

Also included are the di-diabodies known in the art. This 130-kDa molecule is formed by the fusion of a diabody to the N-terminus of the CH3 domain of an IgG, resulting in an IgG-like structure. Further diabody derivatives are the triabody and the tetra-body, which fold into trimeric and tetrameric fragments by shortening the linker to <5 or 0-2 residues. Also exemplified are $(scFv)_2$ constructs known as 'bispecific T cell engager' (BITE). BITEs are bispecific single-chain antibodies consisting of two scFv antibody fragments, joined via a flexible linker, that are directed against a surface antigen on target cells and CD3 on T cells. Also exemplified are bivalent (Fab)2 and trivalent (Fab)3 antibody formats. Also exemplified are minibodies and trimerbodies generated from scFvs. Exemplary constructs useful to target tumor antigens as can include one or more of. Diabody, Single-chain (sc)-diabody (scFv)2, Minianti-body, Minibody, Barnase-barstar, scFv-Fc, sc(Fab)2, Trimeric antibody constructs, Triabody antibody constructs, Trimerbody antibody constructs, Tribody antibody constructs, Collabody antibody constructs, (scFv-TNFa)3, F(ab) 3/DNL. Exemplary cytotoxic immune cells include, but are not limited to CIK cells, T-cells, CD8+ T cells, activated T-cells, monocytes, natural killer (NK) cells, NK T cells, lymphokine-activated killer (LAK) cells, macrophages, and dendritic cells.

In some embodiments, the one or more additional therapies is a radioconjugate.

In various embodiments, a radioconjugate is a small molecule or large molecule (herein referred to as a "cell targeting agent"), for example and polypeptide, an antibody or an antibody fragment thereof, that is coupled to or otherwise affixed to a radionuclide, or a plurality of radionuclides, such that the binding of the radioconjugate to its target (a protein or molecule on or in a cancer cell), will lead to the death or morbidity of said cancer cell. In various embodiments, the radioconjugate can be a cell targeting agent labelled with a radionuclide, or the cell targeting agent may be coupled or otherwise affixed to a particle, or microparticle, or nanoparticle containing a plurality of radionuclides, wherein the radionuclides are the same or different. Methods for synthesizing radioconjugates are known in the art, and may include the class of immunoglobulin or antigen binding parts thereof, that are conjugated to a toxic radionuclide.

In some embodiments, the one or more additional therapies can be a molecule that binds to the cancer cell can be known as a "cell targeting agent". As used herein, an exemplary cell targeting agent can allow the drug-containing nanoparticles or radionuclide to target the specific types of cells of interest. Examples of cell targeting agents include, but are not limited to, small molecules (e.g., folate, adenosine, purine) and large molecule (e.g., peptide or antibody) that bind to or target a tumor associated antigen. Examples of tumor associated antigens include, but are not limited to, adenosine receptors, alpha v beta 3, aminopeptidase P, alpha fetoprotein, cancer antigen 125, carcinoembryonic antigen, cCaveolin-1, chemokine receptors, clusterin, oncofetal antigens, CD20, epithelial tumor antigen, melanoma associated antigen, Ras, p53, Her2/Neu, ErbB2, ErbB3, ErbB4, folate receptor, prostate-specific membrane antigen, prostate specific antigen, purine receptors, radiation-induced cell surface receptor, serpin B3, serpin B4, squamous cell carcinoma antigens, thrombospondin, tumor antigen 4, tumor-associated glycoprotein 72, tyosinase, and tyrosine kinases. In some embodiments, the cell targeting agent is folate or a folate derivative that binds specifically to folate receptors (FRs). In some embodiments, the cell targeting agent is an antibody, a bispecific antibody, a trispecific antibody or an antigen binding construct thereof, that specifically binds to a cancer antigen selected from: EGFR, HGFR, Her2, Ep-CAM, CD20, CD30, CD33, CD47, CD52, CD133, CEA, gpA33, Mucins, TAG-72, CIX, PSMA, folate-binding protein, GD2, GD3, GM2, VEGF. VEGFR, Integrin $\alpha V\beta 3$, Integrin $\alpha 5\beta 1$, MUC1, ERBB2, ERBB3, MET, IGF1R, EPHA3, TRAILR1, TRAILR2, RANKL, FAP and Tenascin among others.

The use of folate as a targeting agent in the radioconjugate also allow both tumor cells and regulatory T (Treg) cells to be targeted for destruction. It is well accepted that high numbers of Treg cells suppress tumor immunity. Specifically, Treg cells suppress (foreign and self) reactive T cells without killing them through contact-dependent or cytokine (e.g., IL-10, TGF-beta., and the like) secretion. FR4 is selectively upregulated on Treg cells. It has been shown that antibody blockade of FR4 depleted Treg cells and provoked tumor immunity in tumor-bearing mice. Thus, folate-coated PBM nanoparticles carrying a cytotoxic agent would take FR-expressing cells for their destruction, which would both directly (i.e., BrCa cell) and indirectly (i.e., breast tumor associated and peripheral Treg cells) inhibit tumor progression.

In another further embodiment, the targeting agent is an antibody or peptide, or immune cell-engaging multivalent antibody/fusion protein/constructs capable of binding tumor associated antigens consisting of but not limited to: adenosine receptors, alpha v beta 3, aminopeptidase P, alpha fetoprotein, cancer antigen 125, carcinoembryonic antigen, caveolin-1, chemokine receptors, clusterin, oncofetal antigens, CD20, Human Growth Factor Receptor (HGFR), epithelial tumor antigen, melanoma associated antigen, MUC1, Ras, p53, Her2/Neu, ErbB2, ErbB3, ErbB4, folate receptor, prostate-specific membrane antigen, prostate specific antigen, purine receptors, radiation-induced cell surface receptor, serpin B3, serpin B4, squamous cell carcinoma antigens, thrombospondin, tumor antigen 4, tumor-associated glycoprotein 72, tyrosinase, tyrosine kinases, and the like.

In some embodiments, one or more additional therapies is a vaccination protocol. In some embodiments, the vaccines can include those used to stimulate the immune response to cancer antigens.

The amount of both the non-polymorphic form, crystalline form or crystalline salt form of Compound 1 as disclosed herein and the additional one or more additional therapeutic agents (in those compositions which comprise an additional therapeutic agent as described above) that may be combined with excipient materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-10,000 g/kg body weight/day of the additional therapeutic agent can be administered.

In some embodiments, the one or more additional therapies is a kinase inhibitor selected from the following: Akt1, Akt2, Akt3, TGF-βR, PKA, PKG, PKC, CaM-kinase, phosphorylase kinase, MEKK, ERK, MAPK, mTOR, EGFR, HER2, HER3, HER4, 1NS-R, IGF-1R, IR-R, PDGFαR, PDGFβ/R, CSFIR, KIT, FLK-II, KDR/FLK-1, FLK-4, fit-1, FGFR1, FGFR2, FGFR3, FGFR4, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYR, FRK, JAK, ABL, ALK, CDK7, CDK12, CDK13, KRAS, and B-Raf. In some embodiments, the one or more additional therapies is an inhibitor of CD47 and MALT1 proteins.

In some embodiments, the one or more additional therapies is a Poly ADP ribose polymerase (PARP) inhibitor. Exemplary PARP inhibitors include, but are not limited to, olaparib (Lynparza®), rucaprib (Rubraca®) niraparib (Zejula®), talzoparib (Talzenna®) and TPST-1120.

In some embodiments, the one or more additional therapies is a kinase inhibitor. Exemplary kinase inhibitors include imatinib, baricitinib gefitinib, erlotinib, sorafenib, dasatinib, sunitinib, lapatinib, nilotinib, pirfenidone, zanubrutinib, updacitinib, fedratinib, entrectinib, alpelisib, pazopanib, crizotinib, vemurafenib, vandetanib, ruxolitinib, axitinib, bosutinib, regorafenib, tofacitinib, cabozantinib, ponatinib, trametinib, dabrafenib, afatinib, ibrutinib, ceritinib, idelalisib, nintedanib, palbociclib, lenvatinib, cobimetinib, abemaciclib, acalabrutinib, alectinib, binimetinib, brigatinib, encorafenib, erdafitinib, everolimus, fostamatinib, gilter, larotrectinib, lorlatinib, netarsudil, osimertinib, pexidartinib, ribociclib, temsirolimus, XL-147, XL-765, XL-499, and XL-880. In some embodiments, the kinase inhibitor is a HSP90 inhibitor (e.g., XL888), liver X receptor (LXR) modulators, retinoid-related orphan receptor gamma (RORy) modulators, a CK1 inhibitor, a CK1-a inhibitor, a Wnt pathway inhibitor (e.g., SST-215), or a mineralocorticoid receptor inhibitor, (e.g., esaxerenone or XL-550) for the treatment of a disease disclosed herein such as cancer.

In some embodiments, the one or more additional therapies is polatuzumab vedotin.

Pharmaceutical compositions containing a non-polymorphic form, crystalline form or crystalline salt form of Compound 1 according to the present disclosure will comprise an effective amount of a non-polymorphic form, crystalline form or crystalline salt form of Compound 1, an immunotherapeutic agent, and/or both, typically dispersed in a pharmaceutically acceptable excipient. The phrases "pharmaceutically or pharmacologically acceptable" refers to molecular entities and compositions that do not produce adverse, allergic or other untoward reaction when administered to animal, such as, for example, a human, as appropriate. The preparation of an pharmaceutical composition that contains a non-polymorphic form, crystalline form or crystalline salt form of Compound 1 will be known to those of skill in the art in light of the present disclosure, as exemplified by Remington's Pharmaceutical Sciences, 21$^{st}$ Ed., (Lippincott, Williams and Wilkins Philadelphia, PA, 2006). Moreover, for animal (e.g., human) administration, it will be understood that preparations should meet sterility, pyrogenicity, general safety and purity standards. A specific example of a pharmacologically acceptable excipient for a combination composition, containing a non-polymorphic form, crystalline form or crystalline salt form of Compound 1 in admixture with an immunotherapeutic agent as described herein is borate buffer or sterile saline solution (0.9% NaCl).

Formulations of the an immunotherapeutic agent, for example an immune checkpoint modulator antibody used in accordance with the present disclosure can be prepared for storage by mixing an antibody having the desired degree of purity with optional pharmaceutically acceptable excipients or stabilizers as amply described and illustrated in Remington's Pharmaceutical Sciences 21$^{st}$ Ed., (Lippincott, Williams and Wilkins Philadelphia, PA, 2006), in the form of lyophilized formulations or aqueous solutions and/or suspensions. Acceptable excipients, buffers or stabilizers are nontoxic to recipients at the dosages and concentrations employed, and include suitable aqueous and/or non-aqueous excipients that may be employed in the pharmaceutical compositions of the disclosure, for example, water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants, buffers such as phosphate, citrate, and other organic acids. Antioxidants may be included, for example, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like; preservatives (such as octade-cyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues). Other exemplary pharmaceutically acceptable excipients may include polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In one illustrative embodiment, the pharmaceutical compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. In some embodiments, the checkpoint inhibitor antibodies or antigen-binding fragments thereof of the present disclosure are formulated for and can be lyophilized for storage and reconstituted in a suitable excipient prior to use according to art-known lyophilization and reconstitution techniques. In one exemplary pharmaceutical composition containing one or more checkpoint inhibitor antibodies or antigen-binding fragment thereof, the composition is formulated as a sterile, preservative-free solution of one or more checkpoint inhibitor antibodies or antigen-binding fragment thereof for intravenous or subcutaneous administration. The formulation can be supplied as either a single-use, prefilled pen, as a single-use, for example containing about 1 mL prefilled glass syringe, or as a single-use institutional use vial. Preferably, the pharmaceutical composition containing the checkpoint inhibitor antibody or antigen-binding fragment thereof is clear and colorless, with a pH of about 6.9-5.0, preferably a pH of 6.5-5.0, and even more preferably a pH ranging from about 6.0 to about 5.0. In various embodiments, the formulations comprising the pharmaceutical compositions can contain from about 500 mg to about 10 mg, or from about 400 mg to about 20 mg, or from about 300 mg to about 30 mg or from about 200 mg to about 50 mg of the checkpoint inhibitor antibody or antigen-binding fragment thereof per mL of solution when reconstituted and administered to the subject. Exemplary injection or infusion excipients can include mannitol, citric acid monohydrate, dibasic sodium phosphate dihydrate, monobasic sodium phosphate dihydrate, polysorbate 80, sodium chloride, sodium citrate and water for parenteral administration, for example, intravenously, intramuscularly, intraperitoneally, or subcutaneous administration.

In another exemplary embodiment, one or more immunotherapeutic agents, or an antigen-binding fragment thereof is formulated for intravenous or subcutaneous administration as a sterile aqueous solution containing 1-75 mg/mL, or more preferably, about 5-60 mg/mL, or yet more preferably, about 10-50 mg/mL, or even more preferably, about 10-40 mg/mL of antibody, with sodium acetate, polysorbate 80, and sodium chloride at a pH ranging from about 5 to 6. Preferably, the intravenous or subcutaneous formulation is a sterile aqueous solution containing 5, 10, 15, 20, 25, 30, 35, 40, 45, or 50 mg/mL of the immunotherapeutic agent, for example, an immune checkpoint inhibitor antibody or an antigen-binding fragment thereof, with 20 mM sodium acetate, 0.2 mg/mL polysorbate 80, and 140 mM sodium chloride at pH 5.5. Further, a solution comprising a checkpoint inhibitor antibody or an antigen-binding fragment thereof, can comprise, among many other compounds, histidine, mannitol, sucrose, trehalose, glycine, poly(ethylene) glycol, EDTA, methionine, and any combination thereof, and many other compounds known in the relevant art.

In one embodiment, a pharmaceutical composition of the present disclosure comprises the following components: 5-500 mg of an immunotherapeutic agent or antigen-binding fragment thereof of the present disclosure, 10 mM histidine, 5% sucrose, and 0.01% polysorbate 80 at pH 5.8, with a non-polymorphic form, crystalline form or crystalline salt form of Compound 1. This composition may be provided as a lyophilized powder. When the powder is reconstituted at full volume, the composition retains the same formulation. Alternatively, the powder may be reconstituted at half volume, in which case the composition comprises 10-500 mg of an immunotherapeutic agent or antigen-binding fragment thereof of the present disclosure, 20 mM histidine, 10% sucrose, and 0.02% polysorbate 80 at pH 5.8.

In one embodiment, part of the dose is administered by an intravenous bolus and the rest by infusion of the immunotherapeutic agent formulation. For example, from about 0.001 to about 200 mg/kg, for example, from about 0.001 mg/kg to about 100 mg/kg, or from about 0.001 mg/kg to about 50 mg/kg, or from about 0.001 mg/kg to about 10 mg/kg intravenous injection of the immunotherapeutic agent, or antigen-binding fragment thereof, may be given as a bolus, and the rest of the antibody dose may be administered by intravenous injection. A predetermined dose of the immunotherapeutic agent, or antigen-binding fragment thereof, may be administered, for example, over a period of an hour to two hours to five hours.

In a further embodiment, part of the dose is administered by a subcutaneous injection and/or infusion in the form of a bolus and the rest by infusion of the immunotherapeutic agent formulation. In some exemplary doses, the immunotherapeutic agent formulation can be administered subcutaneously in a dose ranging from about 0.001 to about 200 mg/kg, for example, from about 0.001 mg/kg to about 100 mg/kg, or from about 0.001 mg/kg to about 50 mg/kg, or from about 0.001 mg/kg to about 10 mg/kg intravenous injection of the immunotherapeutic agent, or antigen-binding fragment thereof. In some embodiments the dose may be given as a bolus, and the rest of the immunotherapeutic agent dose may be administered by subcutaneous or intravenous injection. A predetermined dose of the immunotherapeutic agent, or antigen-binding fragment thereof, may be administered, for example, over a period of an hour to two hours to five hours.

The formulation herein may also contain more than one active compound as necessary for the particular indication being treated, preferably those with complementary activities that do not adversely affect each other. For example, it may be desirable to provide one or more immunotherapeutic agents with other specificities. Alternatively, or in addition, the composition may comprise an anti-inflammatory agent, a chemotherapeutic agent, a cytotoxic agent, a cytokine, a growth inhibitory agent and/or a small molecule antagonist. Such molecules are suitably present in combination in amounts that are effective for the purpose intended.

The formulations to be used for in vivo administration should be sterile, or nearly so. This is readily accomplished by filtration through sterile filtration membranes.

In various embodiments, illustrative formulations of the pharmaceutical compositions described herein can be prepared using methods widely known in the field of pharmaceutical formulations. In general, such preparatory methods can include the step of bringing the active ingredient into association with a excipient or one or more other accessory ingredients, and then, if desirable, packaging the product into a desired single- or multi-dose unit.

In some embodiments, the composition comprising a non-polymorphic form, crystalline form or crystalline salt form of Compound 1 can be also delivered in a vesicle, and the immunotherapeutic agent can be delivered in the same liposome formulation, or in a separate formulation that is compatible with the liposomal formulation containing the non-polymorphic form, crystalline form or crystalline salt form of Compound 1. In some illustrative examples, a liposome containing one or more liposomal surface moieties for example, polyethylene glycol, antibodies and antibody fragments thereof that target a desired tumor surface antigen, receptor, growth factor, glycoprotein, glycolipid or neoantigen, which are selectively transported into specific cells or organs, thus enhance targeted drug delivery.

In another embodiment, a non-polymorphic form, crystalline form or crystalline salt form of Compound 1 can be delivered in a vesicle, in particular a liposome (see Langer, Science 249: 1527-1533 (1990); Treat et al., in LIPOSOMES IN THE THERAPY OF INFECTIOUS DISEASE AND CANCER, Lopez-Berestein and Fidler (eds.), Liss, N.Y., pp. 353-365 (1989); Lopez-Berestein, ibid., pp. 317-327; see generally ibid.).

In yet another embodiment, a non-polymorphic form, crystalline form or crystalline salt form of Compound 1, or the composition containing the combination, or a composition containing the immunotherapeutic agent, can be delivered in a controlled release system. In one embodiment, a pump can be used (see Langer, supra; Sefton, CRC Crit. Ref. Biomed. Eng. 14: 201 (1987); Buchwald et al., Surgery 88: 507 (1980); Saudek et al., N. Engl. J. Med. 321: 574 (1989)). In another embodiment, controlled release of the non-polymorphic form, crystalline form or crystalline salt form of Compound 1 can comprise polymeric materials to provide sustained, intermediate, pulsatile, or alternate release (see MEDICAL APPLICATIONS OF CONTROLLED RELEASE, Langer and Wise (eds.), CRC Pres., Boca Raton, Fla. (1974); CONTROLLED DRUG BIOAVAILABILITY, DRUG PRODUCT DESIGN AND PERFORMANCE, Smolen and Ball (eds.), Wiley, New York (1984); Ranger and Peppas, J. Macromol. Sci. Rev. Macromol. Chem. 23: 61 (1983); see also Levy et al., Science 228: 190 (1985); During et al., Ann. Neurol. 25: 351(1989); Howard et al., J. Neurosurg. 71: 105 (1989)). Other controlled-release systems discussed in the review by Langer (Science 249: 1527-1533 (1990)) can be used.

The optimum concentration of the active ingredient(s) in the chosen medium can be determined empirically, according to procedures well known to the skilled artisan, and will depend on the ultimate pharmaceutical formulation desired and the use to be employed.

The present disclosure also provides a pharmaceutical pack or kit comprising one or more containers filled with one or more of the ingredients of the pharmaceutical compositions of the disclosure, which at minimum will include a non-polymorphic form, crystalline form or crystalline salt form of Compound 1 and one or more checkpoint inhibitor antibodies or antigen-binding fragment thereof as described herein. In other embodiments, the kit may contain one or more further containers providing a pharmaceutically acceptable excipient, for example a diluent. In one embodiment a kit may comprise at least one container, wherein the container can include a non-polymorphic form, crystalline form or crystalline salt form of Compound 1, a checkpoint inhibitor antibody or an antigen-binding fragment thereof of the present disclosure. The kit may also include a set of instructions for preparing and administering the final pharmaceutical composition to the subject in need thereof, for the treatment of a checkpoint molecule-mediated disease or disorder.

Labeled Compounds and Assay Methods

Another aspect relates to labeled non-polymorphic forms, crystalline forms or crystalline salt forms of the present invention (radio-labeled, fluorescent-labeled, etc.) that would be useful not only in imaging techniques but also in assays, both in vitro and in vivo, for localizing and quantitating TAM kinases in tissue samples, including human, and for identifying TAM kinase ligands by inhibition binding of a labeled compound. Accordingly, the present invention includes TAM kinase assays that contain such labeled compounds.

The present invention further includes isotopically-labeled non-polymorphic forms, crystalline forms or crystalline salt forms of the present invention. An “isotopically” or “radio-labeled” compound is a crystalline form or crystalline salt form of the present invention where one or more atoms are replaced or substituted by an atom having an atomic mass or mass number different from the atomic mass or mass number typically found in nature (i.e., naturally occurring). Suitable radionuclides that may be incorporated in non-polymorphic forms, crystalline forms or crystalline salt forms of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$. The radionuclide that is incorporated in the instant radio-labeled compounds will depend on the specific application of that radio-labeled compound. For example, for in vitro metalloprotease labeling and competition assays, compounds that incorporate $^{3}H$, $^{14}C$, $^{82}Br$, $^{125}I$, $^{131}I$, or $^{35}S$ will generally be most useful. For radio-imaging applications $^{11}C$, $^{18}F$, $^{125}I$, $^{123}I$, $^{124}I$, $^{131}I$, $^{75}Br$, $^{76}Br$, or $^{77}Br$ will generally be most useful. In some embodiments, the non-polymorphic forms, crystalline forms or crystalline salt forms described herein in which one or more hydrogens is/are replaced by deuterium, such as hydrogen bonded to a carbon atom. Such compounds exhibit increased resistance to metabolism and are thus useful for increasing the half-life of any compound when administered to a mammal, particularly a human.

It is understood that a “radio-labeled” or “labeled compound” is a compound that has incorporated at least one radionuclide. In some embodiments, the radionuclide is selected from the group consisting of $^{3}H$, $^{14}C$, $^{125}I$, $^{35}S$, and $^{82}Br$.

The present invention can further include synthetic methods for incorporating radio-isotopes into non-polymorphic forms, crystalline forms or crystalline salt forms of the present invention. Synthetic methods for incorporating radio-isotopes into organic compounds are well known in the art, and a person of ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a TAM by monitoring its concentration variation when contacting with the TAM kinases, through tracking of the labeling. For example, a test compound (labeled) can be evaluated for its ability to reduce binding of another compound which is known to bind to a TAM kinase (i.e., standard compound). Accordingly, the ability of a test compound to compete with the standard compound for binding to the TAM kinase directly correlates to its binding affinity. Conversely, in some other screening assays, the standard compound is labeled, and test compounds are unlabeled. Accordingly, the concentration of the labeled standard compound is monitored in order to evaluate the competition between the standard compound and the test compound, and the relative binding affinity of the test compound is thus ascertained.

PREPARATIONS AND EXAMPLES

General Experimental Techniques

Aqueous Slurry Experiments: Salts of Compound 1 that were determined to have aqueous solubility less than 1 mg/mL were slurried in 20 mL of water at ambient temperature for 1 day. Solids were then collected by vacuum filtration and analyzed by XRPD.

Crash Cooling (CC): Concentrated solutions of Compound 1 and various counterions were prepared in MeOH at elevated temperature with stirring. Capped vials containing hot solutions were transferred to the freezer (~-20° C.) and rapidly cooled. Solids that were formed were collected. If no solids were present, additional crystallization techniques were employed.

Crash Precipitation (CP): Clear solutions of Compound 1 and coformer were prepared in various solvents at RT. Aliquots of various anti-solvents were added to the solution, slowly, with gentle stirring until solids crashed out of solution. Mixtures were allowed to stir for a specified period of time. Solids that formed were collected by positive-pressure filtration.

Fast Cooling (FC): Concentrated solutions of Compound 1 and various counterions were prepared in acetone or MeOH at elevated temperature with stirring. Capped vials containing hot solutions were transferred to the bench top at ambient temperature. Solids that were formed were collected. If no solids were present, additional crystallization techniques were employed.

Fast Evaporation (FE): Clear solutions of Compound 1 and coformer were prepared in various solvents. Vials were left uncapped and solvent evaporated at ambient conditions.

Interconversion Slurry: A slurry of Compound 1 Form A was prepared by adding enough solids to a given solvent system at ambient conditions so that undissolved solids were present. The mixture was then agitated for an extended period of time to ensure saturation. Solids of the forms of interest were then added to an aliquot of the saturated solution (filtered through a 0.2-am nylon filter) so that undissolved solids were present. The mixture was then agitated at ambient temperature for an extended period of time, and the solids were isolated.

Isolation Techniques: In general, isolation was done quickly after removing non-ambient samples from their respective temperature control devices to minimize equilibration to ambient temperature prior to isolation of the solids.

Decanting LiquidPhase: Some of the solids isolated from solution-based crystallization techniques were collected by centrifuging the suspension (if needed) and discarding the liquid phase, leaving behind damp solids. Solids were dried briefly (e.g., air dried or dried under nitrogen) unless specified as "analyzed damp" herein.

Positive-Pressure Filtration: Solids were collected on 0.2-am nylon or PTFE filters by pressing a slurry through a syringe and Swinnex filter holder assembly. In general, solids were dried briefly by blowing a 20-mL syringe of air over the filter. If designated as "analyzed damp" herein, solids were left damp with mother liquor. Some samples were additionally dried briefly under a gentle stream of nitrogen gas prior to analysis.

Vacuum Filtration: Solids were collected on paper or nylon filters by vacuum filtration and air dried on the filters under reduced pressure briefly before transferring to a vial.

Reaction Crystallization (RC): A mixture of Compound 1 and various coformers were combined in an elevated temperature, acetone slurry, such that the molarity of coformer was 2-fold greater than the API. The solution stirred for a given period of time. Additional crystallization techniques were employed when clear solutions were observed.

Stability Testing: Various Compound 1 salts were placed in open vials within a 75% RH chamber (saturated sodium chloride solutiona). The RH chamber was placed in a 40° C. oven for 15-16 days. Samples were analyzed by PLM and XRPD upon the end of the duration.

Slow Cooling (SC): Concentrated solutions of Compound 1 and various coformers were prepared in a variety of solvents at elevated temperatures with stirring. Vials were capped in the heated sample block and the hot plate was turned off, allowing the vials to gradually cool to ambient temperature in the heated vial block. Clear solutions, upon cooling to ambient, were further cooled in the refrigerator (5 to 7° C.) and/or the freezer (~-20° C.). If no solids were present, additional crystallization techniques were employed.

Slow Evaporation: Solutions were prepared in various solvents with agitation and, typically, filtered through a 0.2-μm nylon or PTFE filter. Each solution was allowed to evaporate from a covered vial (such as loosely capped or covered with perforated aluminum foil) at ambient conditions, unless otherwise stated. Solutions were allowed to evaporate to dryness unless designated as partial evaporations (solid present with a small amount of solvent remaining), in which case solids were isolated as described herein.

Solubility Estimation: Aliquots of various solvents were added to measured amounts of Compound 1 with agitation (typically sonication) at stated temperatures until complete dissolution was achieved, as judged by visual observation. If dissolution occurred after the addition of the first aliquot, values are reported as ">." If dissolution did not occur, values are reported as "<."

Aqueous Solubility Estimation: Aliquots of water were added to measured amounts of various Compound 1 salts with sonication.

Slurry Experiments: Saturated solutions of Compound 1 and various coformers were prepared in a variety of solvents and solvent mixtures. Mixtures were stirred at ambient and elevated temperatures for the noted duration of time. Solids were collected by the stated technique and additional crystallization techniques were employed where appropriate.

Vacuum Oven Desolvation: Salts of Compound 1 that were determined to be solvates by various analytical methods underwent an attempted desolvation. Samples were placed in a vacuum oven at temperatures ranging from ambient to 80° C. for a given period of time. Samples were analyzed by XRPD and/or TGA for determination of desolvation success.

Vapor Diffusion: Concentrated solutions were prepared in various solvents and, typically, filtered through a 0.2-am nylon or PTFE filter. The filtered solution was dispensed into a small vial, which was then placed inside a larger vial containing anti-solvent. The small vial was left uncapped and the larger vial was capped to allow vapor diffusion to occur. Any solids present were isolated as described herein.

Vapor Stressing: Select solids were transferred to a small vial, which was then placed inside a larger vial containing solvent. The small vial was left uncapped and the larger vial was capped to allow vapor stressing to occur at the stated temperature.

Coformer means one or more pharmaceutically acceptable bases and/or pharmaceutically acceptable acids disclosed herein in association with Compound 1. Exemplary coformers as used herein include fumaric acid, HCl, and phosphoric acid.

Instrumental Techniques

Differential Scanning Calorimetry (DSC): DSC was performed using a Mettler-Toledo DSC3+ differential scanning calorimeter. Temperature calibration was performed using adamantane, phenyl salicylate, indium, tin, and zinc. The sample was placed into a hermetically sealed or an open aluminum DSC pan, and the weight was accurately recorded. A weighed aluminum pan configured as the sample pan was placed on the reference side of the cell. The samples were analyzed from −30 to 250° C. at a ramp rate of 10° C./min. Although thermograms are plotted by reference temperature (x-axis), results are reported according to sample temperatures.

Dynamic Vapor Sorption (DVS)

a. VTI: Automated vapor sorption (VS) data were collected on a VTI SGA-100 Vapor Sorption Analyzer. NaCl and PVP were used as calibration standards. Samples were dried prior to analysis. Sorption and desorption data were collected over a range from 5% to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

b. Intrinsic: Automated vapor sorption (VS) data were collected on a Surface Measurement System DVS Intrinsic instrument. Samples were not dried prior to analysis. Sorption and desorption data were collected over a range from 5% to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

Hot stage Microscopy (HSM): Hot stage microscopy was performed using a Linkam hot stage (FTIR 600) mounted on a Leica DM LP microscope equipped with a SPOT Insight™ color digital camera. Temperature calibrations were performed using USP melting point standards. Samples were placed on a cover glass, and a second cover glass was placed on top of the sample. As the stage was heated, each sample was visually observed using a 20× objective with crossed polarizers and a first order red compensator. Images were captured using SPOT software (v. 4.5.9).

Optical Microscopy: Samples were observed under a Motic or Wolfe optical microscope with crossed polarizers or under a Leica stereomicroscope with a first order red compensator with crossed polarizers.

pKa and logP Determination: pKa and logP determination were performed by Pion Inc./Sirius Analytical Instruments Ltd. in East Sussex, United Kingdom.

Solution Proton Nuclear Magnetic Resonance Spectroscopy (HNMR): The solution $^1$H NMR spectra were acquired by Spectral Data Services of Champaign, IL. The samples were prepared by dissolving approximately 5-10 mg of sample in DMSO-$d_6$.

Thermogravimetric Analysis (TGA): Thermogravimetric analyses were performed using a Mettler Toledo TGA/DSC3+ analyzer. Temperature calibration was performed using phenyl salicylate, indium, tin, and zinc. The sample was placed in an aluminum pan. The open pan was inserted into the TG furnace. The furnace was heated under nitrogen. Each sample was heated from ambient temperature to 350° C., at ramp rates of 2, 5, or 10° C./min. Although thermograms are plotted by reference temperature (x-axis), results are reported according to sample temperatures.

X-ray Powder Diffraction (XRPD)

a. Reflection: XRPD patterns were collected with a PANalytical X'Pert PRO MPD diffractometer using an incident beam of Cu Kα radiation produced using a long, fine-focus source and a nickel filter at room temperature (298 Kelvin). The diffractometer was configured using the symmetric Bragg-Brentano geometry. Prior to the analysis, a silicon specimen (NIST SRM 640e) was analyzed to verify the observed position of the Si 111 peak is consistent with the NIST-certified position. A specimen of the sample was packed in a well. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b.

b. Transmission: XRPD patterns were collected with a PANalytical X'Pert PRO MPD diffractometer using an incident beam of Cu radiation produced using an Optix long, fine-focus source at room temperature (298 Kelvin). An elliptically graded multilayer mirror was used to focus Cu Kα X-rays through the specimen and onto the detector. Prior to the analysis, a silicon specimen (NIST SRM 640e) was analyzed to verify the observed position of the Si 111 peak is consistent with the NIST-certified position. A specimen of the sample was sandwiched between 3-μm-thick films and analyzed in transmission geometry. A beam-stop, short antiscatter extension, antiscatter knife edge, were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

XRPD Indexing

Indexing and structure refinement are computational studies. Within the figure referenced for a given indexed XRPD pattern, agreement between the allowed peak positions, marked with bars, and the observed peaks indicates a consistent unit cell determination. Successful indexing of a pattern indicates that the sample is composed primarily of a single crystalline phase unless otherwise stated. Space groups consistent with the assigned extinction symbol, unit cell parameters, and derived quantities are tabulated.

PD-1 Antibody

The PD-1 antibodies used in the examples were purchased from BioXcell cat #BE0146, clone RPMI-14, lot 780120J3.

EXAMPLES

Preparative Example 1: Synthesis of Compound 1

Step 1: N-(4-Fluorophenyl)-N-(4-hydroxyphenyl) cyclopropane-1,1-dicarboxamide

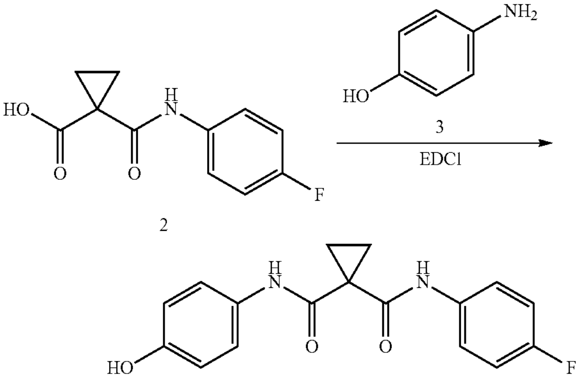

2

4

To a solution of Compound 2 (10 g, 44.80 mmol, 1 eq.) and Compound 3 (5.87 g, 53.8 mmol, 1.2 eq.) in dimethyl acetamide (DMA) (60 mL) was added 3-(ethyliminomethyleneamino)-N,N-dimethyl-propan-1-amine hydrochloride (EDCI) (10.31 g, 53.8 mmol, 1.2 eq.). The mixture was stirred vigorously at 20° C. until the reaction was complete. The mixture was poured into aqueous (aq) saturated $NaHCO_3$ (400 mL) and extracted with EtOAc (4×100 mL). The combined organic phases were washed with aqueous saturated NaCl (100 mL), dried over anhydrous (anhyd) $Na_2SO_4$, and concentrated. Compound 4 (21 g, crude) (50% purity) was obtained. $^1H$ NMR (400 MHz, DMSO-$d_6$) δ 10.16 (br s, 1H), 9.72 (br s, 1H), 7.61 (dd, 2H), 7.34 (d, 2H), 7.13 (t, 2H) 6.68 (d, 2H), 1.42 (s, 4H); MS (EI) for $C_{17}H_{15}FN_2O_3$, found 314.9 (MH+).

Step 2: Methyl 4-[4-[[1-[(4-fluorophenyl)carbamoyl]cyclopropane-carbonyl]amino]phenoxyl]-7-methoxyquinoline-6-carboxylate (6)

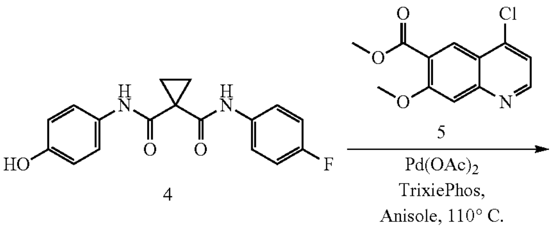

4

5

-continued

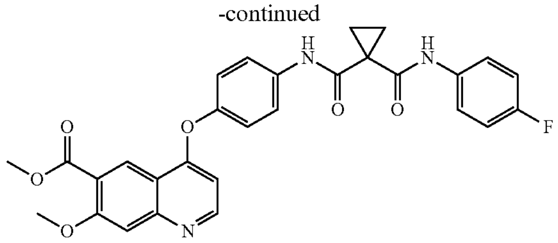

6

A mixture of Compound 4 (5.99 g, 9.5 mmol, 1.2 eq.), Compound 5 (2 g, 8.0 mmol, 1.0 eq.), $Pd(OAc)_2$ (89 mg, 397.4 mol, 0.05 eq.), rac-2-(Di-tert-butylphosphino)-1,1'-binaphthyl (TrixiePhos, 316.71 mg, 794.7 mol, 0.1 eq.) and $K_3PO_4$ (2.53 g, 11.9 mmol, 1.5 eq.) in anisole (50 mL) was stirred at 110° C. for 2 hours (h) under an atmosphere of nitrogen. The mixture was filtered, and the filtrate was concentrated. The residue was purified by flash silica gel chromatography (1:1 petroleum ether:EtOAc to 20:1 EtOAc:MeOH). Compound 6 was obtained (2.6 g, 61.8% yield). $^1H$ NMR (400 MHz, $CDCl_3$) δ 9.38 (s, 1H), 8.80 (s, 1H), 8.63 (d, 2H), 7.64 (d, 2H), 7.54-7.41 (m, 3H), 7.18 (d, 2H), 7.09-7.01 (m, 2H), 6.43 (d, 1H), 4.05 (s, 3H), 3.97 (s, 3H), 1.78-1.72 (m, 2H), 1.69-1.63 (m, 2H); MS (EI) for $C_{29}H_{24}FN_3O_6$, found 530.0 (MH+).

Step 3: 4-[4-[[1-[(4-Fluorophenvl)carbamoyl]cyclopropane-carbonyl]amino]phenoxyl]-7-methoxyquinoline-6-carboxylic acid (7)

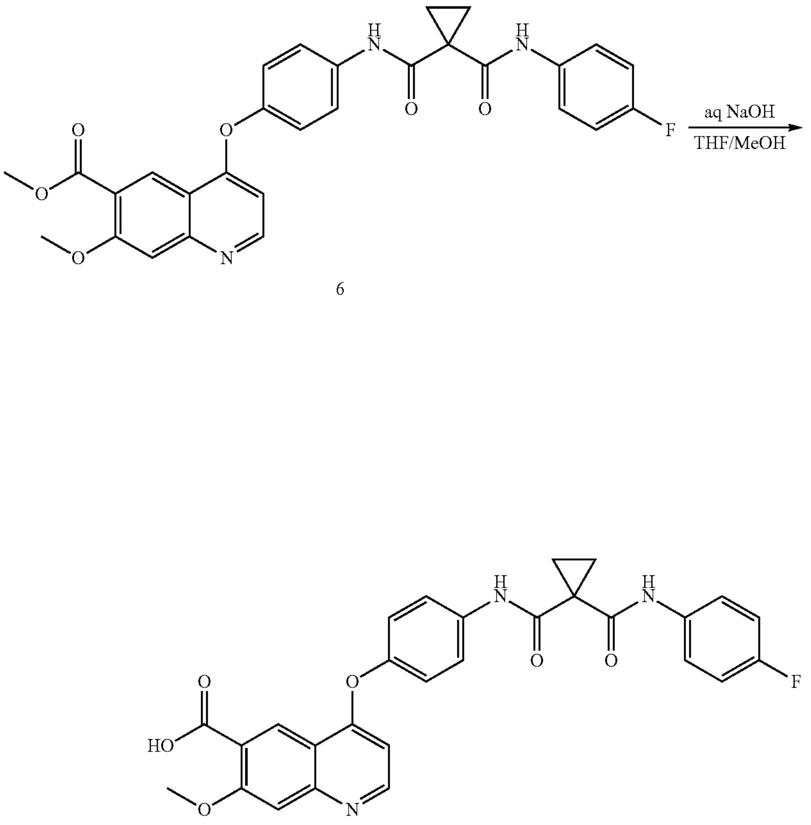

6

7

To a solution of Compound 6 (1.8 g, 3.4 mmol, 1 eq.) in tetrahydrofuran (THF) (15 mL) and MeOH (15 mL) was added 2 M aqueous NaOH (7 mL, 4.1 eq.). The mixture was stirred at 6-13° C. for 4 hours. The mixture was adjusted to a pH of approximately 8 with 1 M aqueous HCl and concentrated to remove solvent. Water (50 mL) was added, and the mixture was adjusted to a pH of approximately 6 with 1 M aqueous HCl. The resulting precipitate was filtered, washed with water (2×10 mL), and dried under vacuum. Compound 7 was obtained (1.7 g, 97.0% yield). $^1$H NMR (400 MHz, DMSO-$d_6$) δ 10.22 (s, 1H), 10.08 (s, 1H), 8.65 (d, 1H), 8.48 (s, 1H), 7.77 (d, 2H), 7.64 (dd, 2H) 7.47 (s, 1H), 7.25 (d, 2H), 7.15 (t, 2H), 6.45 (d, 1H), 3.96 (s, 3H), 1.47 (s, 4H); MS (EI) for $C_{28}H_{22}FN_3O_6$, found 516.1 (MH+).

Step 4: 1-N'-(4-Fluorophenvl)-1-N-[4-[7-methoxy-6-(methylcarbamovl)quinolin-4-yl]oxyphenyl]cyclo-propane-1,1-dicarboxamide (1)

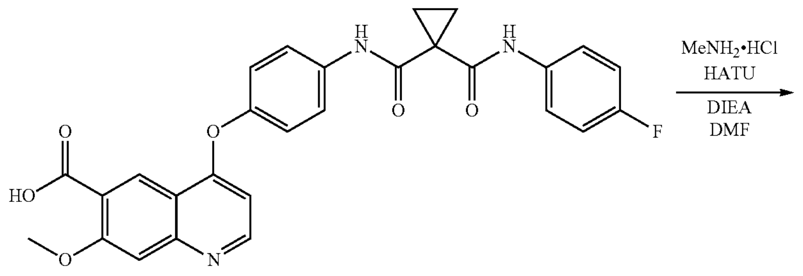

7

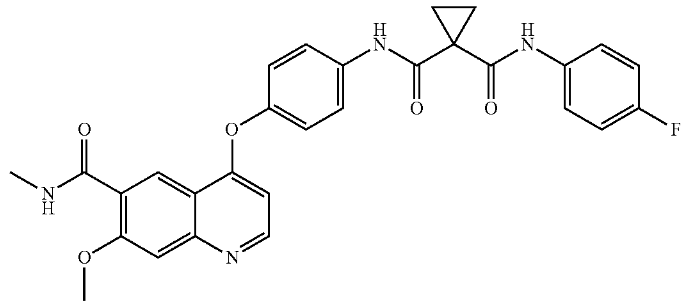

1

A solution of Compound 7 (300 mg, 582.0 mol, 1 eq.), HATU (332 mg, 873.2 mol, 1.5 eq.), and DIEA (301 mg, 2.3 mmol, 406 L, 4 eq.) in DMF (10 mL) was stirred at 6-10° C. for 1 hour. Methanamine hydrochloride (79 mg, 1.2 mmol, 2.0 eq.) was added, and the mixture was stirred at 6-10° C. for 17 hours. The mixture was filtered, and the resulting filtrate purified by prep HPLC (Column: Waters Xbridge 150 mm*25 mm*5 m, gradient: 33-63% of acetonitrile in 10 mM aqueous $NH_4HCO_3$, flow rate: 25 mL/min). Compound 1 was obtained (105.4 mg, 34.3% yield). $^1$H NMR (400 MHz, DMSO-$d_6$) δ 10.20 (s, 1H), 10.06 (s, 1H), 8.65 (d, 1H), 8.61 (s, 1H), 8.42-8.33 (m, 1H), 7.77 (d, 2H), 7.68-7.61 (m, 2H), 7.51 (s, 1H), 7.25 (d, 2H), 7.19-7.11 (m, 2H), 6.46 (d, 1H), 4.02 (s, 3H), 2.84 (d, 3H) 1.47 (s, 4H); MS (EI) for $C_{29}H_{25}FN_405$, found 529.1 (MH+).

Example 1: Preparation of Compound 1 Fumarate Form A

Fumaric acid (1 eq.) in acetone was added to the free base of Compound 1 (1 eq.) and the resulting reddish slurry was stirred at about 50° C. for 4 days. The slurry was then SC to RT and stirred for an addition 1 day to provide a pink slurry. The solids were then removed by positive pressure filtration to provide a mixture of Fumarate Form A and free base Form A.

Example 2: Preparation of Compound 1 Hemifumarate Form B

Fumaric acid (2 eq.) in acetone was added to the free base of Compound 1 (1 eq.) and the resulting reddish slurry was stirred at about 50° C. for 6 days to provide a resulting off-white slurry. The solids were then removed by positive pressure filtration of the hot solution to provide Hemifumarate Form B.

Example 3: Preparation of Compound 1 HCl Form A 1 eq. of HCl was added to the free base of Compound 1 in THF and the resulting dark reddish slurry was stirred at RT for 3 days to provide a resulting thick off-white slurry. The solids were then removed by positive pressure filtration to provide HCl Form A.

Example 4: Preparation of Compound 1 HCl Form B 1 eq. of HCl was added to the free base of Compound 1 in chloroform and the resulting reddish slurry was stirred at about 50° C. for 3 days to provide a resulting pale pink slurry. The solids were then removed by positive pressure filtration to provide HCl Form B.

Example 5: Preparation of Compound 1 HCl Form C 1 eq. of HCl was added to the free base of Compound 1 in methanol at a temperature of about 60° C. resulting in a yellowish slurry. The solution was then CC to about −20° C. and kept cold for about 2 days to provide a clear orange solution. Partial FE provided a clear red solution and then four volumes of the anti-solvent MTBE was added and the solution was stirred for 1 day at RT to provide off-white solid Compound 1 HCl Form C that was separated by positive pressure filtration.

Example 6: Preparation of Compound 1 HCl Form D 2 eq. HCl was added to the free base of Compound 1 at about 50° C., and the resulting pink slurry was stirred at 50° C. for 5 days. The solid Compound 1 HCl Form D was separated by positive pressure filtration.

Example 7: Preparation of Compound 1 Form A

Compound 1 Form A is likely the most thermodynamically stable crystalline form of the free base of Compound 1. Accordingly, multiple procedures lead to the formation of this form. A list of some of the possible procedures to obtain Compound 1 Form A are listed in the table below. This list is not meant to be exclusive, indeed there are likely many more procedures that will produce this form.

Selected procedures for producing Compound 1 Form A

Selected procedures for producing Compound 1 Form A

| Solvent | Conditions |
|---|---|
| ACN/water 80:20 | 1) Slurry at 2-8° C. for 14 d; or<br>2) Slurry at room temperature for 14 d |
| Chloroform | Slurry at 57° C. for 2 days |
| DCM | Slurry at room temperature for 14 days |
| Ethyl Acetate | Slurry at 76° C. for 3 days |
| Ethanol | 1) Slurry at room temperature for 14 days; or<br>2) Slurry at 76° C. for 3 days |
| Ethanol/water 90:10 | Slurry at room temperature for 14 days |
| Isopropyl alcohol | 1) Slurry at room temperature for 14 days; or<br>2) Slurry at 76° C. for 3 days |
| Methanol | 1) Slurry at room temperature for 14 days;<br>2) Slurry at 57-58° C. for 4 days; or<br>3) Fast evaporation |
| Methanol/Ethyl Acetate 3:2 | Slurry at room temperature for 14 days |
| 2,2,2-Trifluoroethanol | 1) Slow evaporation;<br>2) Fast evaporation; or<br>3) Crash precipitation using diethyl ether as the anti-solvent, then slurry for 1 day. |
| Tetrahydrofuran | 1) Slurry at room temperature for 14 days; or<br>2) Slurry at 57-58° C. for 4 days |
| Tetrahydrofuran/water 50:50 | Slurry at room temperature for 14 days |

Example 8: Preparation of Compound 1 Form B

Compound 1 was dissolved in AcOH, and crystallized by VD with diethyl ether as the anti-solvent.

Example 9: Preparation of Compound 1 Form C

Compound 1 was dissolved in HFIPA, and crystallized by CP with MTBE as the anti-solvent.

Example 10: Preparation of Compound 1 Form D

Compound 1 was dissolved in methanol, and crystallized by CC. The mixture was then slurried at 2-8° C. to provide Form D.

Example 11: Preparation of Compound 1 Form E

Method A: Compound 1 was dissolved in THF, and crystallized by CC.

Method B: Compound 1 was dissolved in 90:10 THF: Water, and precipitated by CP.

Example 12: Preparation of Compound 1 Form F

Method A: Compound 1 was dissolved in chloroform, and crystallized by SE.

Method B: Compound 1 was slurried in chloroform.

Example 13: Preparation of Compound 1 Form G

Compound 1 was dissolved in chloroform, and crystallized by placing the mixture in the freezer.

Example 14: Preparation of Compound 1 Form H

Form H was obtained by VS of Amorphous Compound 1 with DCM.

Example 15: Preparation of Compound 1 Form K

Compound 1 Form K was made by desolvation of Form F or Form G, which are chloroform solvates.

Example 16: Preparation of Compound 1 Form O

Compound 1 Form O was discovered during salt attempts with various counterions in TFE-containing solvent systems, and is likely a TFE solvate.

Example 17: Preparation of Compound 1 Phosphate Form A 1 molar equivalent of phosphoric acid was added to a slurry of Compound 1 in chloroform, and then the resulting mixture was slurried for 3 days at about ~50° C. The product was isolated by positive pressure filtration.

Example 18: Preparation of Compound 1 Form I

Compound 1 in a 90:10 THF/water mixture was crash precipitated with heptane and then stirred at freezing temperatures for 7 days.

Example 19: Preparation of Compound 1 Form J

Compound 1 was slurried in acetone for 14 days.

Example 20: Preparation of Compound 1 Form L

Compound 1 was slurried in chloroform for 14 days.

Example 21: Preparation of Compound 1 Form M

Dehydration of Compound 1 Form E in a vacuum oven at ~77° C. for 1 day.

Example 22: Preparation of Compound 1 Form N

Compound 1 was slurried in a 70:30 mixture of TFE/MTBE for 7 days at room temperature.

Example 23: In Vivo Study of the Effect of Compound 1 on Tumor Angiogenesis

Figure 1B:
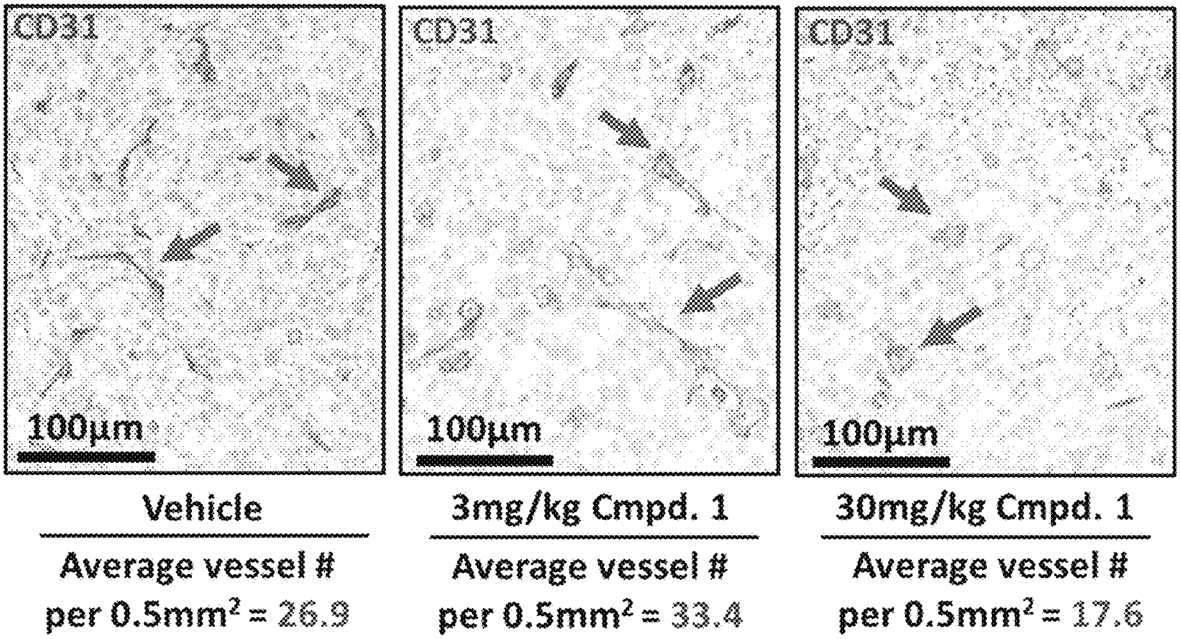
FIG. 1B shows the presence of tumor microvessels by CD31 staining after treatment with Compound 1. Paraffin-embedded tumor tissue was stained with the blood vessel marker CD31 and scored for the density of blood vessels across conditions.

MC38 tumor-bearing animals were treated with a range of Compound 1 doses (PO, qd; 3 mg/kg, 10 mg/kg, 30 mg/kg Compound 1) for 5 days. Tumors were analyzed for the presence of tumor microvessels by CD31 staining. FIG. 1A and FIG. 1B compare the tumor microvessels after administration of different doses of Compared 1 with vehicle. The results show that Compound 1 inhibits in vivo angiogenesis. There is a significant decrease in the average vessel number after treatment with 30 mg/kg Compound 1 compared to vehicle (26.9 v. 17.6). Dose-dependent decreases in the presence of tumor microvessels were also observed.

Example 24: Effect of Compound 1 Combination Therapy on Immune Cells

MC38 tumor-bearing animals were treated with Compound 1 (PO, qd; 10 mg/kg) and anti-PD-1 antibody (IP, Days 1, 2, 4, 6; 5 mg/kg) for 7 days, and tumors were analyzed for the presence of cytotoxic T-cells by CD8 staining. The results show that the combination of Compound 1 and aPD-1 increased national killer (NK) and NK-T cells within the tumor. Elevated levels of T cells and B cells in the blood were observed. There were decreased total macrophages and dendritic cells, but increases in g/mMDSCs and M2 macrophages. Decreased g/mMDSC macrophages and dendritic cells but increased M2 macrophages in blood were also observed.

Figure 2A:
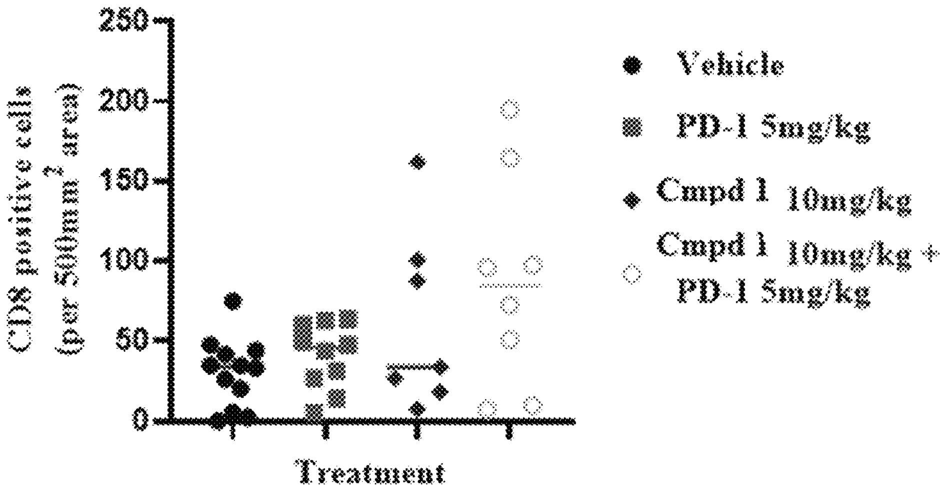
FIG. 2A shows the presence of cytotoxic T-cells by CD8 staining after treatment with Compound 1, aPD-1, and combination of Compound 1+aPD-1. Horizontal bars represent median values for n=8-12 tumors per condition.
Figure 2B:
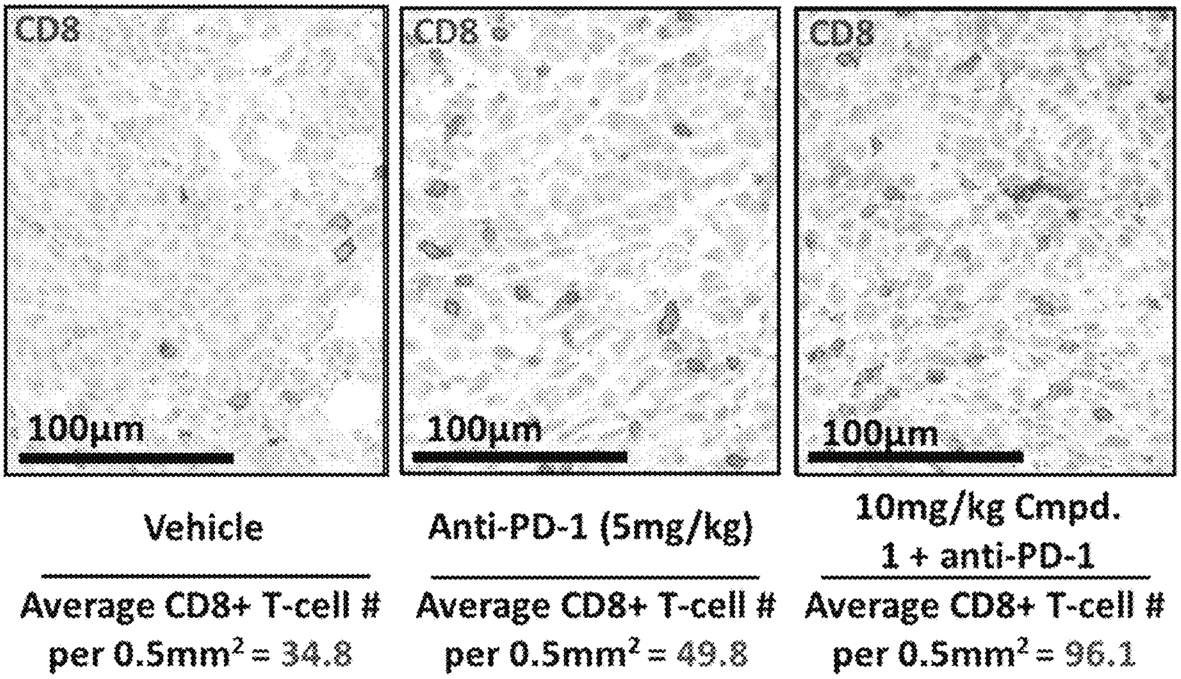
FIG. 2B shows presence of cytotoxic T-cells by CD8 staining after treatment with aPD-1 and combination of Compound 1+aPD-1. Paraffin-embedded tumor tissue was stained with the blood vessel marker CD8 and scored for the density of blood vessels across conditions.

FIG. 2A and FIG. 2B compare the numbers of CD8+ cells after treatment of aPD-1, Compound 1+aPD-1, and vehicle. There is a significant increase in the average CD8+ T-cell number after treatment with 10 mg/kg Compound 1+aPD-1 (96.1 per 0.5 $mm^2$) compared to vehicle (34.8 per 0.5 $mm^2$) and aPD-1 treatment (49.8 per 0.5 $mm^2$).

Figure 3A:
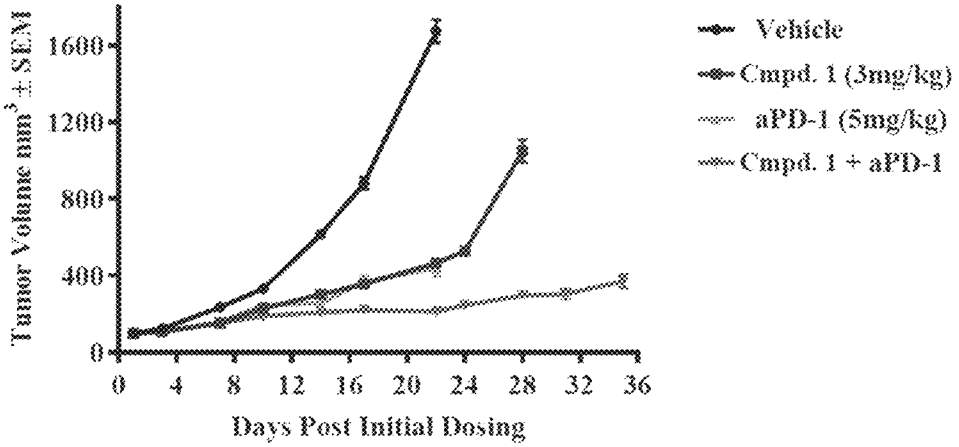
FIGS. 3A-3C show the tumor volume after the treatment with combination therapies Compound 1+aPD-1, Compound 1+aPD-L1, and Compound 1+aCTLA-4.
Figure 3B:
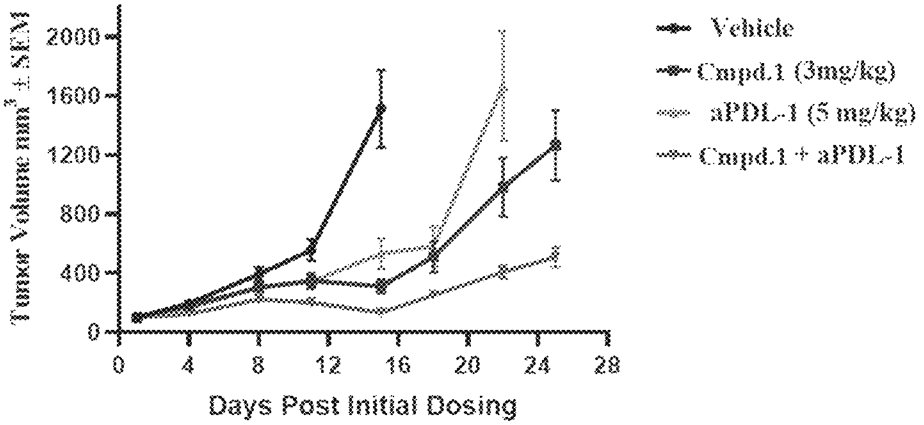
Figure 3C:
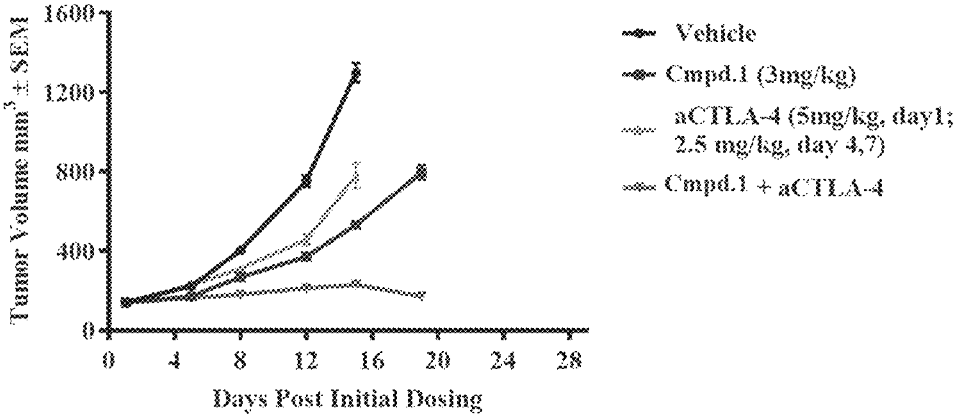

Example 25: Effect of Compound 1 Combination Therapy on Tumor Growth in MC38 Model MC38 tumor-bearing animals were treated with Compound 1 (3 mg/kg)+aPD-1 (5 mg/kg), Compound 1 (3 mg/kg)+aPD-L1 (5 mg/kg), and Compound 1 (3 mg/kg)+aCTLA-4 (5 mg/kg), and tumor volume was analyzed. FIGS. 3A-3C show the tumor volume after the treatment with the combination therapies. Compared to Compound 1, aPD-1, aPD-L1, and aCTLA-4, the combination therapies significantly lowered the tumor volume and significantly slowed tumor growth or stopped tumor growth.

Example 26: An In Vivo Assessment of the Efficacy of Compound 1 Following Oral Dose Administration to CT26 Tumor Bearing Female Balb/c Mice During cancer progression, expression of TAM (TYRO3, AXL, MER) receptor tyrosine kinases (RTKs) on multiple cell types affects a range of extrinsic cellular characteristics in the tumor microenvironment (TME). Activation of these receptors on tumor cells leads to increasedtumor growth, survival and metastatic potential, whereas their activation on immune cell subtypes can lead to immunosuppression and resistance to chemotherapeutic regimens.

Compound 1 has shown potent in vitro against MET, VEGFR2 and the TAM RTK receptors, AXL and MER. Aside from its effects on tumor cells, Compound 1 could also affect the TAM RTK signaling of tumor-associated macrophages, where it inhibited efferocytosis and polarized macrophages toward an immunopermissive M1 phenotype. Treatment with Compound 1 also resulted in decreased angiogenic capacity in the TME, as evidenced by decreased blood vessel formation and VEGFR2 inhibition. Collectively, these effects were shown to result in significant improvements in tumor growth inhibition (TGI) when combined with an anti-PD-1 antibody.

In this study, the inhibitory effects of Compound 1 as a single agent and in combination with an anti-PD-1 inhibitor in Balb/c mice grafted with CT26 colon carcinoma cells were studied. CT26 cells inoculated into syngeneic mice are highly tumorigenic (Brattain et al. 1980) and share molecular features with undifferentiated, invasive human colorectal carcinoma cells (Castle et al. 2014). Therefore, the CT26 cell line can serve as a valid cellular model for the metastatic and poorly differentiated human colorectal cancer. Moreover, this model has been reported to express significant levels of RTKs, indicating a potential reliance on these signaling pathway for the maintenance of a tumorigenic phenotype in vivo (Pryzybyszewska et al. 2017).

Methods

Cell Line Culture and Maintenance

CT26 colon carcinoma cells (ATCC, CRL-2638) were thawed from the Exelixis pharmacology cell bank into T-75 flasks (Corning, 43064U) using fresh culture medium, ie, RPMI-1640 containing 10% fetal bovine serum (GIBCO, A384002). Cells were incubated at 37° C. in a humidified incubator with 5% CO2, and grown until 80-90% confluency until implantation.

Implantation

Mice were anesthetized with isoflurane during implantation. One hundred sixty Balb/C mice were implanted subcutaneously (sc) with 1 million CT26 cells in 0.1 ml serum-free culture medium with an equal volume of Matrigel (Corning, 354235, protein concentration 11.0 mg/ml, endotoxin level <1.5 units/ml) at the right hind flank using a 25 G needle attached to a 1 ml syringe. Cells were prepared in 50 ml tubes, kept on ice and mixed before loading each syringe.

Randomization

One hundred twenty mice were selected after randomization to match an average size of 180 mm3using Studylog software. Mice were sorted by treatment group with five mice per cage; two cages per group.

Dose Administration

Oral doses were administered via a -20 ga, 1.5" stainless steel needle with silicone tip (VWR, 20068-666). Mice were dosed daily according to body weight. Survival was monitored for a maximum of 40 days. Compound 1 (EXEL-04621820), lot 11 from the Exelixis compound repository was used to dose as a single agent or in combination with anti-PD-1 (BioXcell cat #BE0146, clone RPMI-14, lot 780120J3).

Observations

All animals were measured twice a week for tumor volume and body weight using Studylog software.

Statistical Methods

Significance values represent differences in comparison to vehicle or anti-PD-1 treatment groups and were determined using a nonparametric Mann-Whitney U-test. Depicted significance levels are: *: $p<0.05$, : $p<0.01$, *: $p<0.001$, ****: $p<0.0001$

RESULTS

Figure 4:
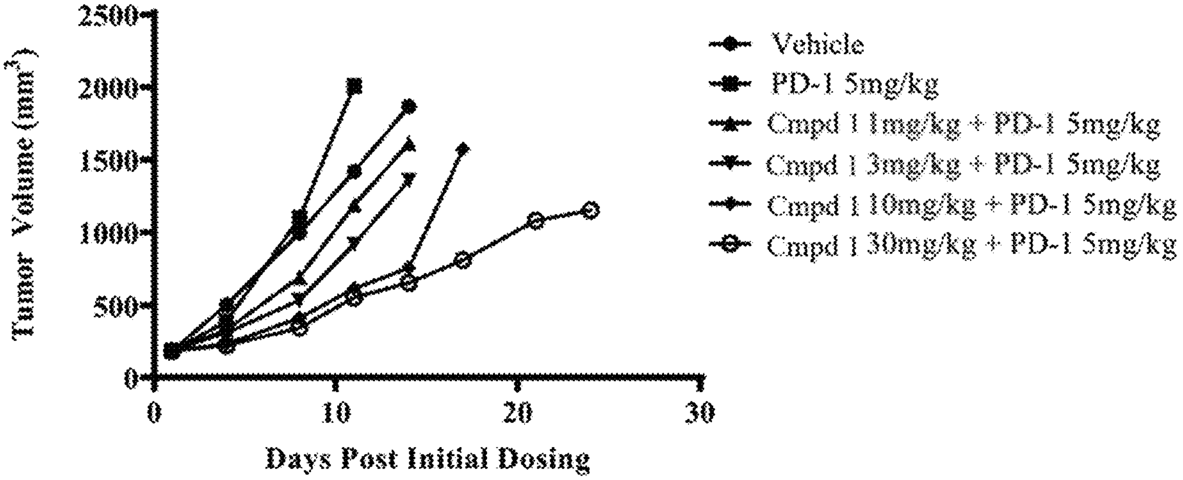
FIG. 4 shows the growth curve of subcutaneously grafted CT26 colon cells in mice treated with Compound 1 as a single agent or in combination with an anti-PD-1 inhibitor (40-day dosing period).
Figure 5:
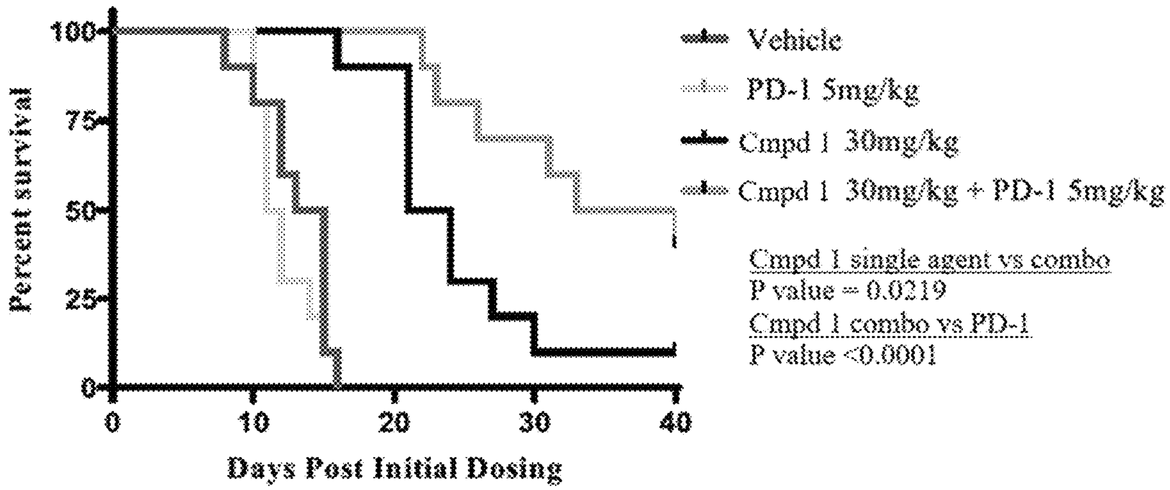
FIG. 5 shows the Kaplan Meier survival curve of CT26 colon tumor-bearing mice treated with Compound 1, an anti-PD-1 inhibitor and combination of Compound 1+anti-PD-1 inhibitor (40-day dosing period).

Treatment of xenografted mice with Compound 1 at doses of 1, 3, 10, and 30 mg/kg/day for 40 days resulted in tumor growth delay. Further tumor growth delay was observed when Compound 1 treatment was combined with 5 mg/kg anti-PD-1 (FIG. 4). Survival benefit and dose response was observed in Compound 1 single agent and in combination with aPD-1. Statistical significance (P value<0.0001) was observed between Compound 1 and Vehicle. Statistical significance (P value<0.0001) was also observed between Compound 1+aPD-1 Combiantion and aPD-1 alone. Compound 1+aPD-1 vs Compound 1 also showed statistical significance (P value<0.05). These results are shown in FIG. 5.

Figure 6A:
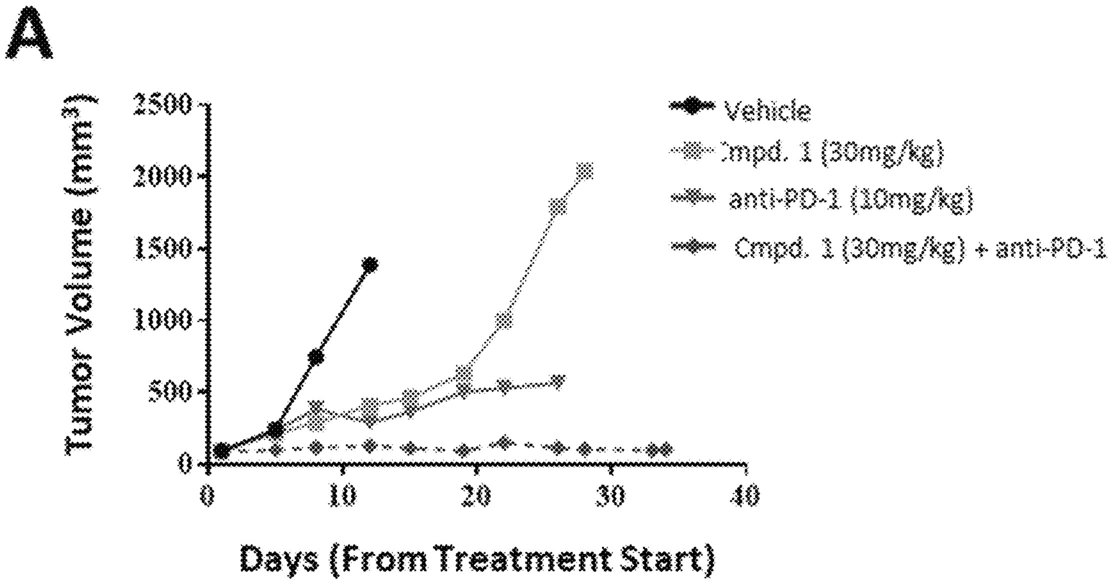
FIG. 6A compares the tumor growth following treatment with either vehicle, 30 mg/kg Compound 1, 10 mg/kg anti-PD-1 or both. Symbols represent median tumor volumes.
Figure 6B:
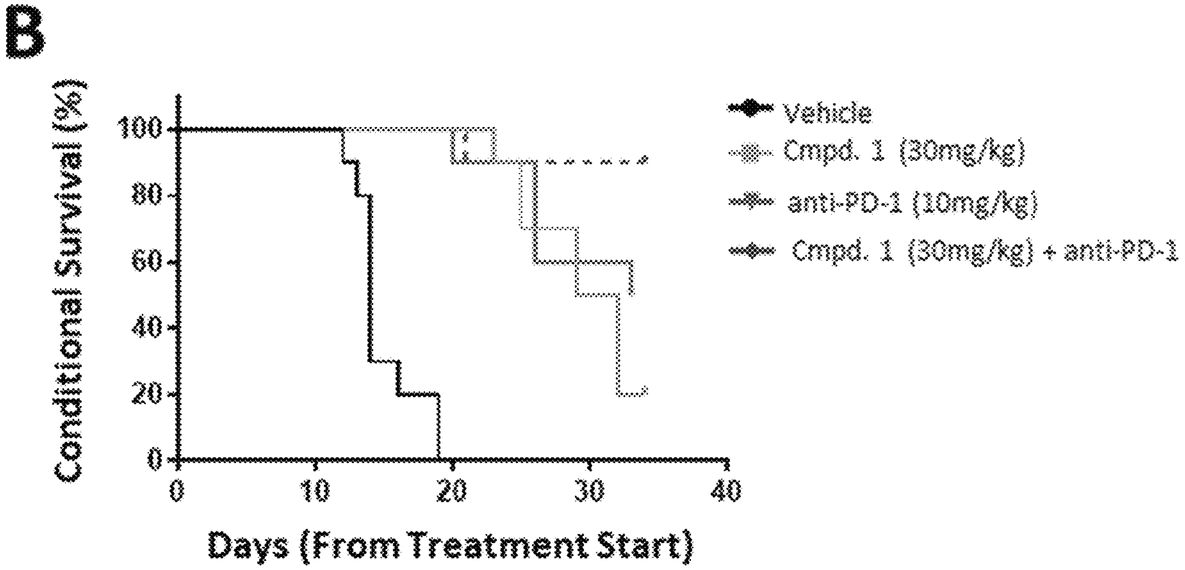
FIG. 6B shows the Kaplan-Meier plot showing conditional survival for CT26 tumor-bearing mice following treatment. For conditional survival, treatment groups were removed from study when 40% of associated animals reached the tumor size threshold.

Compound 1 in combination with aPD-1 treatment also improved conditional survival in CT26 xenograft compared to single agent Compound 1 or anti-PD-1 treatment. FIG. 6A compares the tumor growth following treatment with either vehicle, 30 mg/kg Compound 1, 10 mg/kg anti-PD-1 or both. FIG. 6B shows the Kaplan-Meier plot showing conditional survival for CT26 tumor-bearing mice following treatment.

Example 27: Effects of Compound 1 on Inhibition of Receptor Tyrosine Kinases In Vitro Compound 1 inhibitory activity was evaluated in multiple kinase catalytic activity assays using a radioactive assay platform. Compound 1 inhibits MET and VEGFR2 with $IC_{50}$ values of 3.0 nM and 15 nM, respectively. Compound 1 also exhibits high potency against AXL and MER with $IC_{50}$ values of 5.8 nM and 0.6 nM, respectively. All in vitro biochemical assays were performed at 10 μM ATP concentrations.

Example 28: Effects of Compound 1 on Inhibition of RTK Autophosphorylation in Human Cell Lines In Vitro The activity of Compound 1 was evaluated in cell-based assays that assessed the mechanistic effects of the compound in tumor and normal cells. Consistent with the biochemical data, Compound 1 is a potent inhibitor of cellular RTKs as assessed by analysis of receptor autophosphorylation as measured by enzyme-linked immunosorbent assay. Assays were performed using cell lines (PC-3, HUVEC, and A-172) stimulated with ligands to their respective receptors to induce autophosphorylation (MET, VEGFR2, and AXL) or a cell line (293A) transfected with an expression vector encoding the receptor of interest (MER). Inhibition of endogenous phosphorylated MET by Compound 1 in Hs 746T gastric carcinoma cells was also investigated due to the presence of the skip-splice mutation of exon 14 in the MET gene. This MET exon 14 alteration leads to increased MET stability and oncogenic activation, including constitutive MET phosphorylation. Also this mutation is known to occur in 3% of lung adenocarcinoma patients and to be sensitive to MET-targeted therapies (Frampton et al 2015). Compound 1 shows potent inhibition of MET autophosphorylation in Hs 746T cells with $IC_{50}$ value of 26 nM and would therefore be a strong therapeutic candidate for this subset of patients. A summary of the cellular $IC_{50}$ values is shown in Table 1.

TABLE 1

Inhibition of RTK Autophosphorylation by Compound 1

| Assay | Ligand | Cellular $IC_{50}$ (nM) |
|---|---|---|
| MET (PC-3) | HGF | 15 |
| MET (Hs 746T) | — | 26 |
| VEGFR2 | VEGF165 | 1.5 |
| AXL | Gas6 | 3.4 |
| MER | — | 7.1 |

Example 29: Tumor Pharmacodynamic and Efficacy Response in Preclinical In Vivo Models Three human tumor cell lines, NCI-H441, MDA-MB-231, and SNU-5, were selected for use in tumor xenograft studies using athymic nude, NSG and CB.17 SCID mice, respectively. Pharmacodynamic modulation of MET phosphorylation was also measured in the NCI-H441 and SNU-5 xenografts. Tumor-bearing mice were orally dosed once-daily for 14 days (qd×14), and the tumors were resected and processed for MET phosphorylation analysis by Western blot. In vivo, Compound 1 potently inhibits MET phosphorylation in a dose-dependent manner. (Table 2):

TABLE 2

Summary of In Vivo Target Modulation Studies in Mice after Oral Administration of Compound 1: Decrease in Phosphorylation Levels

| Tumor Model | Dose (mg/kg) and Schedule | p-MET Inhibition % | Compound 1 Plasma Exposure[a] μM |
|---|---|---|---|
| NCI-H441 | 3, qd × 14 | 60 | 2.44 |
| | 10, qd × 14 | 82 | 9.71 |
| SNU-5 | 3, qd × 14 | 26 | 1.88 |
| | 10, qd × 14 | 67 | 7.64 |

[a]4 hours after last dose on Day 14

Compound 1 showed significant dose dependent antitumor activity in all three xenograft models tested when orally administered daily for 14 days (Table 3), suggesting that it has the potential for broad antitumor activity.

TABLE 3

Summary of Tumor Growth Inhibition (TGI) in Xenograft Models after Oral Administration of Compound 1

| Model | Dose (mg/kg) | Schedule | TGI (%) | p-value |
|---|---|---|---|---|
| NCI-H441 | 3 | qd × 14 | 63.3 | 0.0115 |
| | 10 | qd × 14 | regression | <0.0001 |
| MDA-MB-231 | 3 | qd × 14 | 73.6 | 0.0001 |
| | 10 | qd × 14 | 78.6 | <0.0001 |
| SNU-5 | 3 | qd × 14 | 54.2 | 0.0052 |
| | 10 | qd × 14 | 94.7 | <0.0001 |

TGI = [(Vc1 − Vc0) − (Vt1 − Vt0)/(Vc1 − Vc0)] × 100%

Vc1 and Vt1 are the mean volumes of control and treated groups at time of tumor extraction, while Vc0 and Vt0 are the same groups at the start of dosages. Nonparametric Mann-Whitney test was used to calculate the p-values.

Example 30: Absorption, Distribution, Metabolism and Excretion (ADME)

Plasma PK of Compound 1 was characterized in rats and beagle dogs. Toxicokinetic (TK) evaluations of oral Compound 1 were evaluated in repeat-dose studies in rats and dogs. Plasma protein binding was determined in mouse, rat, dog, monkey, and human plasma in vitro. Biotransformation and metabolite profiling of Compound 1 were investigated in vitro using mouse, rat, dog, monkey, and human liver microsomal fractions and hepatocytes and in vivo in rats and dogs. P-glycoprotein (P-gp) and breast cancer resistance protein (BCRP) transporter interaction studies, in vitro experiments evaluating cytochrome P450 (CYP) induction and inhibition by Compound 1, and CYP and glucuronosyltransferase (UGT) substrate specificity studies of Compound 1 were also performed.

Pharmacokinetics (PK) and Toxicokinetics (TK) of Compound 1 in Rats and Dogs PIB Formulation in Rats and Dogs The PK and TK of Compound 1 were assessed in rats and dogs after intravenous (IV; only single dose PK) and oral (PO) administration of Compound 1 in formulations prepared in polyethylene glycol 400 (PEG 400): ethanol (EtOH): reverse osmosis water (RO Water) (45:5:50 v/v/v).

Oral bioavailability (% F) of Compound 1 was assessed in rats (0.09-0.27 mg/kg) and dogs (0.2-0.6 mg/kg). Oral absolute bioavailability of Compound 1 was 62-77% in rats and 47-70% in dogs. After oral administration of Compound 1, the terminal phase half-life (t1/2, z) ranged from 4.5-5.3 hours in rats and 1-3 hours in dogs. After single oral doses in rats and dogs, Compound 1 exposure ($C_{max}$ [maximum plasma concentration] and $AUC_{0-inf}$ [area under the plasma concentration-time curve from time of dosing to infinity]) appeared to increase approximately dose proportionally in the dose range of 0.09-0.27 mg/kg (rats) or 0.2-0.6 mg/kg (dogs). Median time to maximum plasma concentration ($T_m$ax) occurred at approximately 2-3 hours in rats and dogs.

After a single-dose IV administration of Compound 1 (0.09-0.27 mg/kg in rats; 0.2-0.6 mg/kg in dogs), the mean plasma clearance (CL) for Compound 1 was 23.4 mL/hr/kg in rats and 380 mL/hr/kg in dogs. The mean volume of distribution at steady-state ($V_{ss}$) values was 167 mL/kg and 1975 mL/kg in rats and dogs, respectively. The mean plasma $t_{1/2,\,z}$ values were approximately 9 hours in rats and 4 hours in dogs. Interspecies scaling based on body weight to predict PK parameters in humans could not be performed because dogs (larger species) cleared Compound 1 faster than rats (smaller species). Therefore, the human PK was projected based on one species (rat). In a hepatocyte stability study, similar intrinsic clearance ($CL_{int}$) of Compound 1 was observed in rats and humans ($CL_{int}$=0.285 mL/min/g liver [rat]; $CL_{int}$=1.08 mL/min/g liver [dog]; $CL_{int}$=0.317 mL/min/g liver [human]). Assuming that human PK in vivo is similar to PK in rats (CL=23.4 mL/hr/kg and F=70%), apparent CL (CL/F) after oral administration in human is projected to be 33.4 mL/hr/kg and 2338 mL/hr for a 70-kg human. This apparent clearance value (CL/F) was used to predict steady-state exposure (AUC and average plasma concentration [$C_{avg}$]) in humans for the proposed first-in-human (FIH) starting dose for Study Compound 1-001.

In a 28-day repeat-dose toxicity study in rats dosed orally daily with Compound 1 at 1, 3 or 10 mg/kg, Compound 1 exposure ($C_{max}$ and $AUC_{0-24}$) increased with the increase in dose level from 1-10 mg/kg/day. Sex differences in Compound 1 mean $C_{max}$ and $AUC_{0-4}$ values were less than 2-fold. On both Days 1 and 28, $T_{max}$ values ranged from 2.00-8.00 hours. Half-life ($t_{1/2}$) values ranged from 3.51-3.70 hours on Day 1 and from 6.70-8.97 hours on Day 28. Compound 1 $C_{max}$ and $AUC_{0-24}$ values were similar or lower on Day 28 than on Day 1, indicating no accumulation of Compound 1 after multiple doses in rats. Accumulation ratio values ranged from 0.721-1.14 for $C_{max}$ and from 0.722-0.891 for $AUC_{0-24}$. Consistent with the single-dose PK data, exposure in rats at steady-state on Day 28 for low doses appeared to be approximately 20-fold higher than that observed in dogs.

In a 28-day repeat-dose toxicity study in dogs dosed orally daily with Compound 1 at 2, 6 and 18 mg/kg, high variability in Compound 1 exposure was generally observed for all dose levels on Days 1 and 28. Across the dose range evaluated, the mean % CV for $C_{max}$ and $AUC_{0-24}$ was 46.2-93.2% and 45.5-91%, respectively, on Day 1 and 39.3-53.9% and 36.2-51.1%, respectively, on Day 28. Sex differences in Compound 1 mean $C_{max}$ and $AUC_{0-24}$ values were less than 2-fold. After oral gavage administration, median $T_{max}$ values were 2.00 hours on Days 1 and 28. Values for $t_{1/2}$ ranged from 4.57-6.29 hours on Day 1 and from 3.96-5.23 hours on Day 28. In general, the Day 28 mean Compound 1 plasma $C_{max}$ and $AUC_{0-24}$ values were higher than those estimated on Day 1 suggesting there might be some accumulation of Compound 1 in plasma after multiple oral doses to dogs, with the exception of the 18 mg/kg/day dose level that indicated no accumulation after multiple doses. Mean accumulation ratio values ranged from 1.67 to 4.75 for $C_{max}$ and from 1.57 to 3.38 for $AUC_{0-24}$ for 2 and 6 mg/kg dose levels; mean accumulation ratio values for 18 mg/kg dose level were 0.891 for $C_{max}$ and 0.874 for $AUC_{0-24}$.

Tablet Formulation in Dogs (Non-GLP Compliant)

In a parallel design study with a total of 24 dogs (1:1 treatment allocation ratio), Group 1 received Compound 1 as a 20-mg oral tablet and Group 2 received a 20-mg reconstituted oral suspension of the PIB formulation. For each dose group, blood samples were collected from each animal at pre-dose and up to 24 hours post-dose for Compound 1 plasma concentration measurements.

After a single oral dose of 20 mg Compound 1 in dogs, the $t_{1/2,\,z}$ of Compound 1 appeared to be similar for PIB and tablet formulations (mean=4.85 hours for PIB, and 5.66 hours for tablet). The median $t_{max}$ of Compound 1 was observed at 3 hours after dosing for both formulations. Moderate inter-animal variability in Compound 1 exposure ($C_{max}$ and $AUC_{0-24}$) was observed for both formulations (% CV for $C_{max}$: 29-37; % CV for $AUC_{0-24:34.5}$-35.8). The mean $C_{max}$ and $AUC_{0-24}$ values for PIB formulation was 61% and 49% higher, respectively than the mean values observed for the tablet formulation.

In Vitro Plasma Protein Binding of Compound 1

Compound 1 (0.2 and 1 μM) showed consistently high in vitro plasma protein binding across species (>99% in mouse, rat, dog, monkey, and human plasma). Compound 1 (10 μM) was 97.2 and 97.5% protein bound in monkey and human plasma, respectively.

Evaluation of Compound 1 as a Substrate of P-gp and BCRP Transporters

Compound 1 was highly permeable in vitro in Caco-2 cells with an apparent permeability coefficient ($P_{app}$) value of 3.83 ($\times10^{-6}$ cm/s). Compound 1 was shown not to be a substrate of P-gp and BCRP transporters but was a strong inhibitor for P-gp and BCRP ($IC_{50}$ values of 0.059 and 0.189 μM, respectively).

Evaluation of Cytochrome P450 Inhibition by Compound 1

Compound 1 appeared to have a low CYP inhibition potential in vitro for CYP2D6, CYP 2B6 and CYP1A2 ($IC_{50}$ values >33 μM). However, Compound 1 appeared to have moderate to high inhibitory potential for CYP3A4 (Ki=25.2 μM), CYP2C9 (Ki=7.11 μM), CYP2C19 (Ki=1.36 μM) and CYP2C8 (Ki=1.27 μM). Compound 1 was also identified as a time-dependent inhibitor of CYP3A4 using testosterone as probe substrate.

Evaluation of Cytochrome P450 Induction by Compound 1

In vitro studies using fresh primary human hepatocytes showed that Compound 1 increased CYP3A4, CYP1A2, CYP2B6, CYP2C8, CYP2C9 and CYP2C19 mRNA levels at all concentrations tested (Compound 1 concentration range: 0.1-100 μM) with the maximal induction effect (Emax) of 24-fold for CYP3A4, 5-fold for CYP1A2, 17-fold for CYP2B6, 7-fold for CYP2C8, 5-fold for CYP2C9 and 6-fold for CY2C19. The half-maximal effective concentration ($EC_{50}$) values were also determined: 2.98 μM for CYP3A, 0.93 μM for CYP1A2, 5.41p M for CYP2B6, 2.01 μM for CYP2C8, 1.71 μM for CYP2C9 and 6.21 μM for CYP2C19.

Evaluation of Intrinsic Hepatic Microsomal and Hepatocyte Clearance of Compound 1

In vitro assays utilizing liver microsomes and hepatocytes incubations showed low to moderate Compound 1 clearance in all tested species: mouse, rat, dog, monkey, and human. In the liver microsomal stability assay, $CL_{int}$ was 0.601 mL/min/g liver in mouse, 0.563 mL/min/g liver in rat, 0.315 mL/min/g liver in dog, 0.734 mL/min/g liver in monkey, and 0.639 mL/min/g liver in human. In the hepatocyte stability assay, Compound 1 $CL_{int}$ was 0.373 mL/min/g liver in mouse, 0.285 mL/min/g liver in rat, 1.08 mL/min/g liver in dog, 0.533 mL/min/g liver in monkey, and 0.317 mL/min/g liver in human.

Evaluation of Compound 1 as a Substrate of Cytochrome P450 Isozymes and UGT Enzymes Compound 1 appeared to be a sensitive substrate for CYP3A4 and a weaker substrate for CYP2C9 as determined using in vitro incubations containing recombinant Supersomes® and specific chemical inhibitors in human liver microsomes. CYP2C8 and CYP2D6 appeared to play only a minor role in the metabolism of Compound 1. Compound 1 was shown not to be a substrate of CYP1A2, CYP2B6, CYP2C19, or UGT1A1, UGT1A9, and UGT2B7. However, UGT1A4 may play a minor role in Compound 1 metabolism.

In Vitro and In Vivo Characterization of the Metabolite Profile of Compound 1

Metabolite profiling of Compound 1 was evaluated in vitro in mouse, rat, dog, monkey, and human liver microsomes and in mouse, rat, dog, monkey, and human hepatocyte suspensions. Eleven metabolites were detected using liquid chromatography with tandem mass spectrometry (LC-MS/MS). The metabolites profiles indicated that parent compound Compound 1 underwent biotransformation pathways of oxidation, oxidative defluorination, hydrolysis, demethylation, and dehydrogenation. Most of the metabolites were present at less than 5% of the parent concentration across species except for M7 (amide demethylation), M5 (oxidation), and M2 (amide hydrolysis) which were highest in human hepatocytes (M7, 6.6%), in human liver microsomes (M5, 15.4%), and in dog hepatocytes (M2, 7.5%).

In vivo exploratory metabolite profiles of Compound 1 were evaluated in rats and dogs. A total of 11 metabolites were identified in the rat and dog plasma samples, indicating that Compound 1 underwent biotransformation pathways of oxidation, oxidative defluorination, hydrolysis, demethylation, dehydrogenation, and glucuronidation. The in vivo metabolite profiles account for less than 7% and 25% of parent Compound 1 in rat and dog plasma, respectively.

Example 31: Nonclinical Toxicology

The nonclinical toxicity of Compound 1 was characterized in dose range-finding 7-day and definitive 28-day repeat-dose studies in rats and dogs, and in in vitro bacterial and mammalian genotoxicity bioassays. Compound 1 was also evaluated in definitive neurobehavioral, respiratory and cardiovascular safety pharmacology studies.

Compound 1 toxicity in repeat-dose toxicity studies in rats and dogs was generally characterized by dose-related clinical signs (eg, hypoactivity, vomitus, and fecal changes in dogs), decreased body weight and food consumption, changes in clinical chemistry and hematology values, and histopathologic findings primarily present in bone and teeth, liver, bile duct, and ovary. Compound 1-related adverse findings appeared to be partially or completely reversible following a 14-day non-treatment recovery period.

The major Compound 1-related histomorphologic findings in rats administered Compound 1 daily for 4 weeks were associated with the process of bone formation and/or mineralization; these findings included increased physeal thickness of the femur and degeneration of the tooth dentin and enamel in animals administered >3 mg/kg/day. Following a 2-week recovery phase, increased physeal thickness and tooth degeneration persisted but were less severe. These findings are consistent with an on-target pharmacologic VEGFR inhibition by Compound 1.

Evidence of hepatobiliary injury in rats treated with Compound 1 daily for 4 weeks included adverse histologic findings of bile duct inflammation and hyperplasia, and individual hepatocyte necrosis that were generally of minimal to mild severity at the 10 mg/kg/day dose level. These microscopic lesions were fully reversible following a 14-day recovery period, and were associated with correlative reversible changes in clinical chemistry markers of hepatic function (eg, <2-fold increase in AST and <5-fold increase in ALT at 10 mg/kg/day). Increased cholesterol and triglyceride levels were noted in rats; increased cholesterol was also evident in Compound 1-treated dogs.

Compound 1 administration resulted in generally minimally-adverse effects on hematopoietic tissues reflected by microscopic findings (minimal severity decreased bone marrow cellularity in rats) and changes in hematology values (transient decreases in reticulocytes in rats and dogs). Extramedullary hematopoiesis (minimal) and increased lymphocytes (minimal-slight) were also observed in spleen tissue from Compound 1-treated rats. Finally, increased fibrinogen, globulin, neutrophil counts in Compound 1-treated rats and/or dogs may reflect possible treatment-associated inflammatory changes present in rats (bile duct inflammation, individual hepatocyte necrosis) and dogs (mixed cell inflammation in nasal turbinate mucosa).

The histologic findings in nasal turbinates were observed in both Compound 1-treated rats and dogs. In recovery cohort rats dosed at 10 mg/kg/day for 4 weeks followed by a 14-day non-treatment period, proliferation of nasal turbinate bone present in all females (minimal-moderate) and males (slight-moderate) occurred in conjunction with microscopic findings of tooth degeneration in these animals. Thus, these changes appear to represent evidence of bone regrowth in nasal turbinate tissue following discontinuation of Compound 1 treatment. In Compound 1-dose dogs, the histologic findings in nasal turbinates (ie, increased incidences and severities of mixed cell inflammation and osteolysis/osteogenesis in terminal sacrifice males administered >6 mg/kg/day) were considered to be non-adverse due to low incidence, low severity, lack of dose-relatedness, and presence in control animals, and may reflect an indirect inflammatory response associated with efflux of dose formulation into the nasal cavity postdose and thus not clinically-relevant. While histopathologic changes in nasal turbinates were present in both Compound 1-treated rats and dogs, these findings do not appear to be direct test article-related effects but rather indirect or secondary to other changes in these tissues.

Compound 1 administration resulted in histopathologic changes in female reproductive tract tissues in rats dosed at 10 mg/kg/day for 4 weeks. These findings consisted of increased size and number of regressing corpora *lutea* in ovarian tissue and a higher frequency of dilated uteri; these findings appeared to be reversible based on their absence in recovery cohort females. As comparable microscopic changes in female reproductive tract tissues have been observed in nonclinical safety studies with other inhibitors of VEGFR, these adverse effects appear to be mediated by an on-target inhibition of this pharmacologic receptor.

No adverse ophthalmic findings were observed either in rats or dogs administered Compound 1 daily for 4 weeks.

In the definitive 4-week repeat-dose toxicity studies in rats and dogs dosed orally daily with Compound 1 at 1, 3 or 10 mg/kg in rats and at 2, 6 and 18 mg/kg in dogs (all FBE doses), Compound 1 exposure ($C_{max}$ and $AUC_{0-24}$) increased with the increase in dose levels. Sex differences in Compound 1 mean $C_{max}$ and $AUC_{0-24}$ values were less than 2-fold in rats and dogs. In rats, no accumulation of Compound 1 after multiple doses was observed with accumulation ratio values ranging from 0.721-1.14 for $C_{max}$ and from 0.722-0.891 for AUC0-24. In dogs, in general, high variability in Compound 1 exposure was observed for all dose levels on both Days 1 and 28. Compound 1 plasma $C_{max}$ and $AUC_{0-24}$ values on Day 28 were higher than those estimated on Day 1 suggesting there might be some accumulation of Compound 1 in plasma after multiple oral doses to dogs, with the exception of the 18 mg/kg/day dose level that indicated no accumulation after multiple doses. Mean accumulation ratio values ranged from 1.67-4.75 for $C_{max}$ and from 1.57-3.38 for $AUC_{0-24}$ for 2 and 6 mg/kg dose levels; mean accumulation ratio values for the 18 mg/kg dose level were 0.891 for $C_{max}$ and 0.874 for AUC0-24. In the definitive 4-week toxicity studies, dose-normalized steady-state plasma exposures (AUC0-24, ss) were generally approximately 20-fold higher in rats than in dogs, consistent with the approximately 16-fold higher plasma clearance determined for Compound 1 in dogs than in rats.

Compound 1 was negative in in vitro bacterial and mammalian cell genotoxicity bioassays.

In GLP-compliant safety pharmacology studies, Compound 1 administration resulted in no adverse neurobehavioral effects or toxicologically significant respiratory system effects within 24 hours postdose in rats administered single oral doses as high as 60 mg/kg. In addition, no significant effect on cardiovascular parameters were observed in telemeterized dogs administered single oral doses of Compound 1 as high as 18 mg/kg through 18 hours postdose. Moreover, no QTc interval prolongation occurred in male telemeterized dogs at single doses as high as 18 mg/kg yielding an Compound 1 plasma $C_{max}$ (~7 μM) approximately 2-fold higher than the Compound 1 in vitro hERG channel $IC_{50}$ (~4 μM). In addition, no QTc interval prolongation occurred in male and female dogs following daily dosing for 28 days at the highest dose evaluated (18 mg/kg/day) yielding an Compound 1 plasma $C_{max}$ of ~7 μM.

The steady-state exposure of Compound 1 in humans for the proposed clinical starting dose of 10 mg daily was projected. At this dose, Compound 1 is projected to yield exposures 54-fold lower than those at the highest non-severely toxic dose (HNSTD) in rats (10 mg/kg qd), the highest dose tested in the GLP 4-week toxicity study. Per FDA guidance (FDA [S9 Nonclinical Evaluation]2010), the HNSTD is defined as the highest dose level that does not produce evidence of lethality, life-threatening toxicities, or irreversible findings. Compound 1-related findings at the 10 mg/kg/day dose included bile duct inflammation, hyperplasia and individual hepatocyte necrosis (generally minimal-mild) which were fully reversible following 14 days recovery, as were correlative <2-fold aspartate aminotransferase (AST) and <5-fold alanine aminotransferase (ALT) increases.

Nonclinical Findings of Potential Clinical Significance

Compound 1 toxicity in repeat-dose toxicity studies in rats and dogs was generally characterized by dose-related clinical signs (eg, hypoactivity, vomitus, and fecal changes in dogs), decreased body weight and food consumption, and histopathologic findings primarily present in bone (increased physeal thickness of the femur) and teeth (degeneration of the tooth dentin and enamel), liver (individual hepatocyte necrosis), bile duct (inflammation and hyperplasia), and ovary (increased size and number of regressing corpora *lutea*). Changes in clinical chemistry values (increases in AST and ALT) correlated with the histopathologic changes in liver tissue. Compound 1-related adverse findings appeared to be partially or completely reversible following a 14-day non-treatment recovery period.

Of the primary target tissues identified in repeat-dose nonclinical safety studies, the findings of potential clinical significance are the adverse effects observed in liver and female reproductive tract tissues. Subjects enrolled in Study Compound 1-001 will be routinely monitored for clinical chemistry changes suggestive of liver tissue injury. Subjects in Study Compound 1-001 will also be required to use effective contraceptive measures to avoid pregnancy based on the unknown risk of Compound 1 to the conceptus. Possible adverse effects on bone and teeth observed nonclinically would present a greater risk to a pediatric patient population than to the adult subject population that will be enrolled in Study Compound 1-001; however, subjects in this study will be monitored for any clinically-relevant treatment-emergent adverse events including possible effects on bone and teeth. Compound 1 showed no significant adverse findings in cardiovascular, neurobehavioral, or respiratory safety pharmacology studies. Compound 1 was also negative in bacterial and mammalian cell genotoxicity bioassays.

Example 32: An In Vitro Study of the Effect of Compound 1 on Macrophages

The TAM RTKs play an important role in balancing the functions of M1 and M2 macrophage subsets. Compound 1 was tested for inhibition against primary CD14+ monocytes cultured in M2 polarizing conditions. A dose dependent polarization of the monocytes to pro-inflammatory M1 macrophages across cells from all tested donors was observed (Table 4).

TABLE 4

Compound 1 Re-Polarizes Primary Human Macrophages from an M2 Anti Inflammatory to an M1 Pro-Inflammatory Phenotype

| Donor | M1/M2 Ratio, Fold Change Relative to DMSO (n = 2) | | |
|---|---|---|---|
| [Compound 1]: | 2 uM | 4 uM | 6 uM |
| Donor A * | 1.7 | 3.3 | 4.6 |
| Donor H | 1.0 ± 2.6 | 3.7 ± 1.2 | 4.5 ± 1.0 |
| Donor L | 2.2 ± 1.1 | 3.4 ± 1.4 | 4.6 ± 1.7 |

TABLE 4-continued

Compound 1 Re-Polarizes Primary Human Macrophages from an M2 Anti Inflammatory to an M1 Pro-Inflammatory Phenotype

| Donor | M1/M2 Ratio, Fold Change Relative to DMSO (n = 2) | | |
|---|---|---|---|
| [Compound 1]: | 2 uM | 4 uM | 6 uM |
| Donor D | 1.3 ± 2.6 | 3.6 ± 1.2 | 3.5 ± 1.2 |
| Donor B ** | 1.7 | 4.1 | 4.0 |

*Fold Change is from n = 1 only (performed in a singlet test).
** Fold Change is from n = 1 only.

Figure 7A:
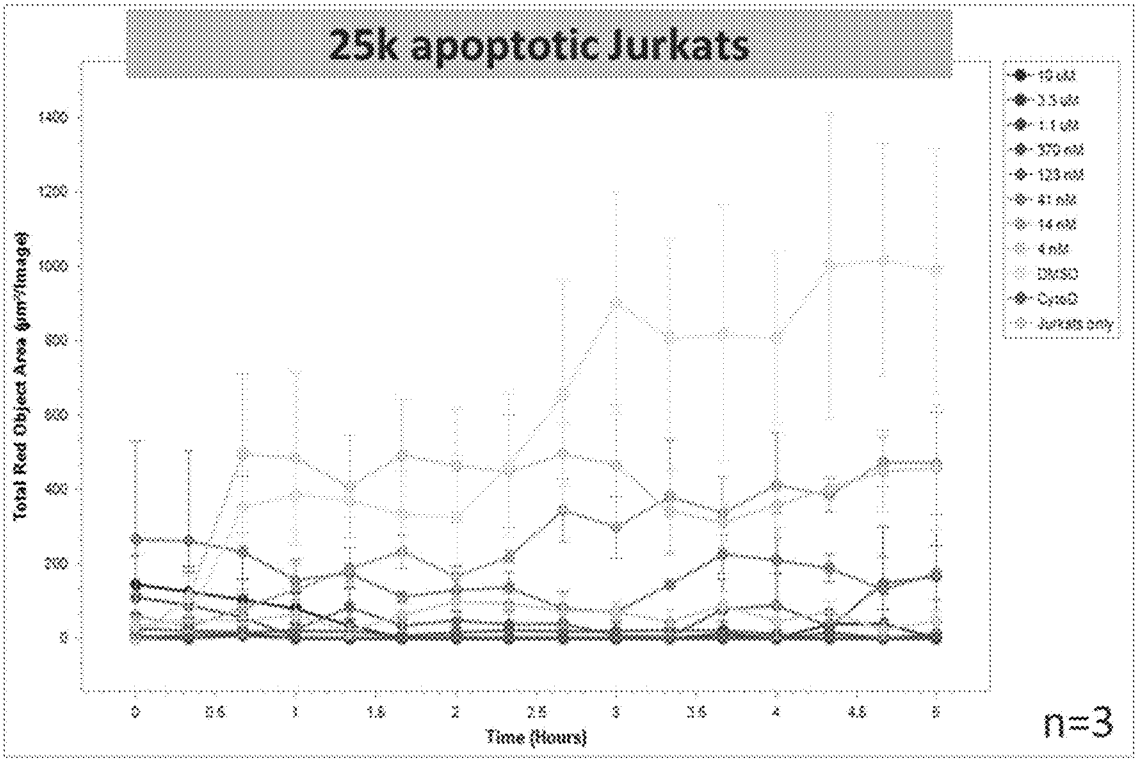
FIG. 7A shows that Compound 1 inhibited efferocytosis in a dose dependent manner using 25 k apoptotic Jurkats.
Figure 7B:
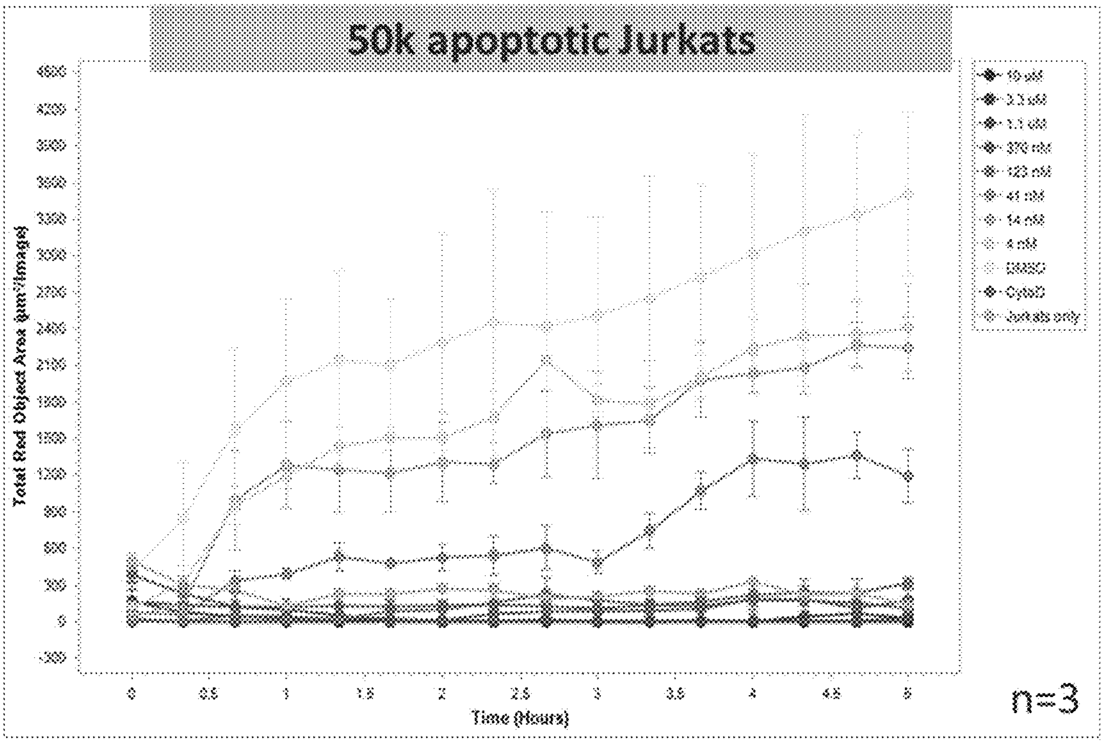
FIG. 7B shows that Compound 1 inhibited efferocytosis in a dose dependent manner using 50 k apoptotic Jurkats.

In addition, the TAM RTKs are critical in the process of efferocytosis, or the recognition and phagocytosis of apoptotic cells that maintains normal tissue homeostasis. When efferocytosis is inhibited, macrophages engage a proinflammatory activation response. When primary human macrophages are cultured with apoptotic Jurkat cells in the presence of Compound 1, their phagocytic ability was inhibited in a dose dependent manner. In Table 5, the $IC_{50}$ from 5 independent donors are listed. FIG. 7A and FIG. 7B show that Compound 1 inhibited efferocytosis in a dose dependent manner using 25 k or 50 k apoptotic Jurkats.

TABLE 5

Compound 1 Inhibits Primary Human Macrophage Efferocytosis

| Donor | Cellular $IC_{50}$ (nM) (n = 2) |
|---|---|
| Donor #1 | 42.7 ± 1.8 |
| Donor #2 | 45.1 ± 3.0 |
| Donor #3 | 44 (n = 1 only) |
| Donor #4 | 96.5 ± 1.1 |
| Donor #5 | 181.1 ± 1.1 |

IC50, concentration associated with 50% inhibition in activity.
IC50 was calculated as the geometric mean +/− the geometric standard deviation.

Example 33: A Dose-Escalation and Expansion Study of the Safety and Pharmacokinetics of Compound 1 as Single-Agent and Combination Therapy in Subjects with Inoperable Locally Advanced or Metastatic Solid Tumors

INTRODUCTION

Receptor tyrosine kinases (RTKs) play important roles in a number of cellular processes, including cellular proliferation, survival, and migration (Bhullar et al 2018). Dysregulation leading to elevated kinase expression or constitutive activation is associated with oncogenesis. In addition, several RTKs are known to contribute to the regulation of antitumor immunity (Paolino and Penninger 2016). As a result, RTK inhibition provides a strong rationale for developing new therapies for the treatment of cancer. Additionally, multi-targeted tyrosine kinase inhibitors (TKIs) and immune checkpoint inhibitors (ICIs) represent two systemic modalities that have been instrumental in the recent advancements of anticancer treatment over the past several years. Both classes of therapies have demonstrated broad clinical effects leading to new approved treatment options across multiple tumor types. The success of these therapy types as single agents with distinct mechanisms of action has naturally led to interest in evaluating combinations of TKIs with ICIs in search of further, possibly synergistic, anticancer clinical effects.

Compound 1 is a potent, orally bioavailable, small molecule inhibitor of several RTKs including MET, vascular endothelial growth factor receptor 2 (VEGFR2), and members of the TAM family (AXL and MER). Inhibition of tumor angiogenesis by blocking the VEGFR-signaling pathway is a therapeutic target for the control of growth, invasion, and metastasis of cancer. MET and AXL play important roles in the resistance to anti-angiogenic therapy. TAM family receptors are negative immune regulators and have become a particular focus as targets for cancer immunotherapy. Drugs targeting TAM family kinases are thought to promote an immune-permissive environment which may enhance response to ICIs. In a preclinical murine MC38 colon carcinoma model the combination of Compound 1 with anti-PD1 antibody showed benefit in tumor growth inhibition activity when given in combination with an ICI compared to vehicle or either single agent alone.

Atezolizumab is a humanized immunoglobulin (Ig) G1 monoclonal antibody that targets programmed death receptor 1 ligand (PD-L1) and inhibits the interaction between PD-L1 and its receptors, programmed death receptor 1 (PD-1) and B7-1 (also known as CD80), both of which function as inhibitory receptors expressed on T cells.

Atezolizumab injection for intravenous (IV) use (1200 mg once every 3 weeks [q3w]) has been approved by regulatory agencies in the US and European Union and other regions as single-agent therapy for patients with locally advanced or metastatic urothelial carcinoma, as single-agent therapy and in combination with chemotherapy for patients with metastatic non-small cell lung cancer (NSCLC), in combination with chemotherapy for extensive-stage small cell lung cancer (ES-SCLC), in combination with chemotherapy for unresectable locally advanced or metastatic triple-negative breast cancer (TNBC), and (in the US) in combination with bevacizumab for patients with advanced hepatocellular cancer (HCC). Please see TECENTRIQ® US prescribing information [US PI] and European Medicines Agency Summary of Product Characteristics [EMA SmPC]) for details.

Further, atezolizumab has demonstrated encouraging clinical activity in other tumor indications: monotherapy in advanced renal cell carcinoma (RCC) (McDermott et al 2016), metastatic castration-resistant prostate cancer (CRPC; Kim et al 2018), and advanced triple-negative breast cancer (TNBC; Schmid et al 2017); combination therapy with bevacizumab in treatment-naïve advanced RCC (Motzer et al 2018) and metastatic RCC with variant histology and/or sarcomatoid features (McGregor et al 2020); and combination therapy with cabozantinib in metastatic CRPC (Agarwal et al 2020).

Treatment with atezolizumab is generally well-tolerated but can be associated with immune-related adverse events (irAEs). Please see TECENTRIQ® US prescribing information [US PI] and European Medicines Agency Summary of Product Characteristics [EMA SmPC]) for details.

Avelumab is a human IgG1 monoclonal antibody targeting PD-L1 and selectively blocks the interaction between PD-1 and B7-H1 (PD-L1) receptors, while still allowing interaction between PD-L2 and PD-1, which allows T cell receptor activation and cell lysis. Avelumab's IgG1 Fc portion can bind Fc receptors to activate antibody-mediated cytotoxicity (ADCC) allowing to separate non-overlapping mechanism of action (Boyerinas et al 2015; Fujii et al 2016).

Avelumab as an IV injection (800 mg q2w) has been approved by regulatory agencies in the US, EU, and other regions as single-agent therapy for Merkel cell carcinoma and in combination with axitinib for first-line treatment of advanced RCC. In the US and other regions, single-agent avelumab therapy is also approved for maintenance treatment of patients with locally advanced or metastatic UC that has not progressed with first-line platinum-based chemotherapy or for UC patients with disease progression during or following platinum-based chemotherapy.

Treatment with avelumab is generally well tolerated, but can be associated with immune-related adverse events (irAEs). Please see BAVENCIO® US prescribing information [US PI] and European Medicines Agency Summary of Product Characteristics [EMA SmPC]) for details.

This first-in-human (FIH) study Compound 1-001 (NCT03845166) evaluates safety, tolerability, and preliminary antitumor activity of Compound 1 as single agent therapy and as combination therapy with ICIs in subjects with advanced solid tumors who have received life-prolonging therapies or subjects for whom such therapies do not exist. The maximum tolerated dose (MTD) and/or recommended dose (RD) of Compound 1 single-agent therapy and ICI combination therapy will be determined in a Dose-Escalation Stage. The preliminary efficacy of Compound 1 as single agent and as ICI combination therapy will be determined in a Cohort-Expansion Stage with tumor-specific expansion cohorts. As of 14 Dec. 2020, dose escalation of Compound 1 as single agent and in combination therapy with atezolizumab was ongoing: 19 subjects were enrolled in single agent cohorts across six dose levels (PIB: 10, 20 mg; Tablet: 20, 40, 80, 140 mg); three subjects were enrolled in combination therapy with atezolizumab at one dose level (Compound 1 40 mg po qd plus atezolizumab 1200 mg IV q3w). As of 14 Dec. 2020 (safety data cut-off), one DLT was observed among the completed dose-levels: one subject in Compound 1 single-agent Cohort 6 (140 mg po qd) had experienced Grade 3 uncontrolled hypertension that resulted in meeting the DLT criteria of inability to take ≥75% of the total planned Compound 1 dose for the DLT Evaluation Period. No DLTs were observed in Compound 1 combination therapy Cohort 1 (Compound 1 40 mg po qd plus atezolizumab 1200 mg IV q3w). The majority of reported adverse events (AEs) were of low-grade severity (Grade 1-2) with five subjects having experienced treatment-related Grade 3 events. There were no treatment-related Grade 4 or Grade 5 events.

Additional tumor cohorts will be introduced: evaluation of single-agent Compound 1 and Compound 1 in combination with atezolizumab in subjects with advanced colorectal cancer (CRC); evaluation of single-agent Compound 1 and Compound 1 in combination with avelumab in subjects with advanced urothelial carcinoma (UC).

Based on the target profile of Compound 1, an inhibitor of multiple RTKs involved in tumor cell proliferation, neovascularization, and immune cell regulation, as well as its demonstrated preclinical and preliminary clinical benefit, there is a clear rationale for evaluating Compound 1 as monotherapy and in combination with ICIs (eg, atezolizumab) as a potential new treatment opportunity for subjects with advanced solid tumors.

Dose-Escalation Stage (Single-Agent and Combination Therapy Cohorts)

The primary objective is:

Determine the maximum tolerated dose (MTD) and/or recommended dose (RD) for further evaluation of Compound 1 when administered alone and in combination with ICIs to subjects with advanced solid tumors The secondary objectives are:

Evaluate the safety of Compound 1 when administered alone and in combination with ICIs through the evaluation of incidence and severity of nonserious adverse events (AEs) and serious adverse events (SAEs), including immune-related adverse events (irAEs), and adverse events of special interest (AESIs)

Evaluate the plasma pharmacokinetics (PK) of Compound 1 and its potential metabolites following Compound 1 administration alone and in combination with ICI The exploratory objectives are:

ORR as assessed by the Investigator per RECIST 1.1

Figure 8:
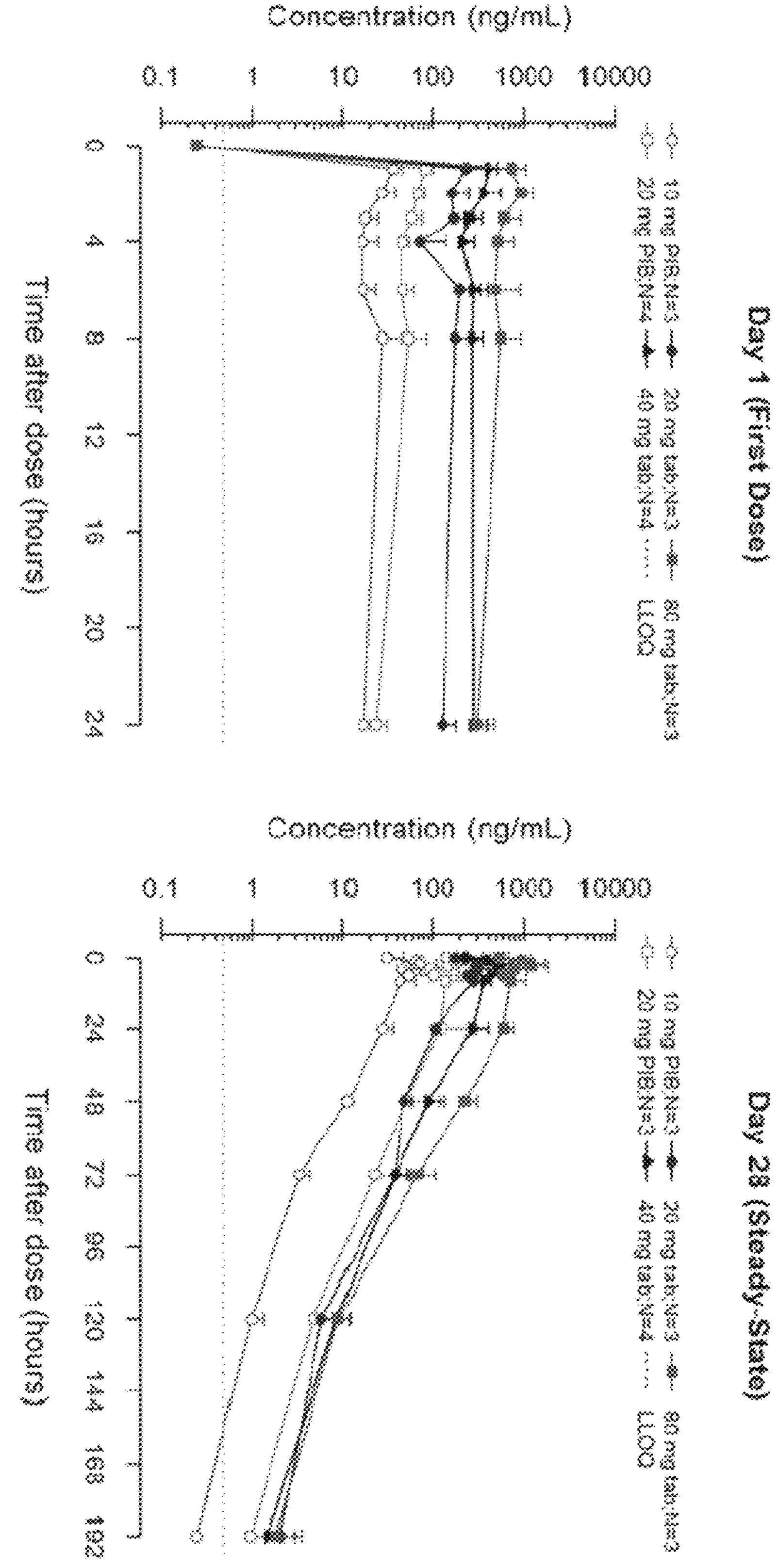
FIG. 8 shows mean (SD) Compound 1 plasma concentration-time profiles following the first dose and after 28 daily doses of compound 1 as single agent in subjects with solid tumors.

Investigate the relationship between PK and selected or exploratory biomarkers, preliminary efficacy, and safety outcomes As of 14 Dec. 2020, preliminary Compound 1 clinical PK data are available from 17 subjects in the single agent Dose-Escalation Stage of Study Compound 1-001 (n=3 for 10 mg liquid formulation [PIB]; n=4 for 20 mg liquid formulation [PIB]; n=3 for 20 mg tablet; n =4 for 40 mg tablet; n=3 for 80 mg tablet). In addition, PK of Compound 1 was evaluated when given in the combination with atezolizumab. PK data from a total of 3 subjects enrolled in the Combination Cohort 1 (40 mg Compound 1 qd+1200 mg atezolizumab q3w) are available. A summary of all available PK parameters estimated by non-compartmental approach using individual plasma concentration-time data from a single agent Compound 1 is presented in Table 1. Mean (standard deviation [SD]) plasma Compound 1 concentration-time profiles following a single agent PIB or tablet formulation are illustrated in FIG. 8.

Following the first dose administration of Compound 1 PIB on Day 1, the median $T_{max}$ was 1 hour for 10 mg and 2 hours for 20 mg Cohort. Mean exposure ($AUC_{0-24}$) increased approximately dose proportionally with increase in Compound 1 dose from 10 mg to 20 mg. At steady-state on Day 28 for both doses of liquid formulation (PIB), the median $T_{max}$ was 2 hours; mean terminal half-life ($t_{1/2}$) was approximately 20 hours and CL/F ranged from 13 to 15 L/h. Mean accumulation ratios based on the $AUC_{0-24}$ ranged from 1.92 to 3.61. For 20 mg PIB, inter-subject variability (expressed as % CV) in exposure ($AUC_{0-24}$) was 33.7% on Day 1 and 122.8% at steady-state.

Compared to PIB cohort, after a single dose of 20 mg on Day 1, a longer time was required to reach $C_{max}$ for the tablet formulation at the same dose level (median $T_{max}$, 6 hours vs 2 hours, respectively). Mean PK exposure ($C_{max}$ and $AUC_{0-24}$) for 20 mg tablet was approximately 3.7-fold higher than those of 20 mg liquid formulation (PIB) after the first dose on Day 1. At steady-state on Day 28, exposure ($AUC_{0-24}$) was approximately 50% higher for the 20-mg tablet than that for 20 mg liquid formulation (PIB). Minimal accumulation (<2-fold) at steady state was observed for the 20-mg tablet. The terminal half-life for tablet was consistent with that observed for the liquid formulation (PIB).

Following the first dose of Compound 1 tablet formulation as a single agent, Compound 1 exposure increased in approximately dose proportional manner as the dose increased from 20 to 80 mg tablets. The median $T_{max}$ was similar between Compound 1 doses and ranged from 2 to 6 hours. At steady-state, moderate to high inter-subject variability in exposure was observed (CV, 31.6 to 57.1% for $C_{max}$ and 18.5 to 50.9% for AUC). The mean $t_{1/2}$ ranged from 19-28 hours with the mean apparent CL/F of approximately 5 L/hr. Minimal accumulation (<2-fold) in exposure ($C_{max}$ and $AUC_{0-24}$) at steady-state was observed after 28 days of Compound 1 daily dosing (Table 6). At 40 mg Compound 1 dose, mean PK exposure of Compound 1 ($C_{max}$ and $AUC_{0-24}$) at steady-state in combination with atezolizumab was approximately 2-fold lower than that observed for single agent Compound 1.

TABLE 6

Preliminary Pharmacokinetic Parameter Summary of Compound 1 in Subjects with Solid Tumors after Single Agent Compound 1 Administration

| Parameter | 10 mg PIB (N = 3) | 20 mg PIB (N = 4)[a] | 20 mg Tablet (N = 3) | 40 mg Tablet (N = 4) | 80 mg Tablet (N = 3) |
|---|---|---|---|---|---|
| | | | First Dose (Day 1) | | |
| $T_{max}$ (h) | 1 (1, 1) | 2 (1, 8) | 6 (1, 8) | 5 (1, 24) | 2 (1, 2) |
| $C_{max}$ (ng/ml) | 35.7 ± 10.8 (30.3%) | 91.9 ± 13.4 (14.5%) | 342 ± 225 (65.6%) | 521 ± 202 (38.8%) | 935 ± 348 (37.2%) |
| $AUC_{0-24}$ (ng*h/mL) | 510 ± 193 (37.8%) | 1000 ± 338 (33.7%) | 3680 ± 1550 (42.3%) | 6350 ± 1540 (24.3%) | 11000 ± 6290 (57.0%) |
| | | | Steady-State (Day 28) | | |
| $T_{max}$ (h) | 2 (1, 6) | 2 (1, 8) | 1 (0, 4) | 3 (2, 4) | 3 (1, 3) |
| $C_{max}$ (ng/mL) | 95.2 ± 17.8 (18.7%) | 330 ± 409 (124.2%) | 422 ± 241 (57.1%) | 656 ± 242 (36.9%) | 1440 ± 454 (31.6%) |
| $AUC_{0-24}$ (ng*h/mL) | 971 ± 398 (41.0%) | 3270 ± 4010 (122.8%) | 5030 ± 2560 (50.9%) | 8190 ± 1560 (19.0%) | 16900 ± 3120 (18.5%) |
| AR $C_{max}$ | 2.76 ± 0.609 (22.0%) | 4.09 ± 5.40 (131.8%) | 1.30 ± 0.374 (28.9%) | 1.27 ± 0.0979 (7.7%) | 1.67 ± 0.636 (38.1%) |
| AR $AUC_{0-24}$ | 1.92 ± 0.593 (30.9%) | 3.61 ± 4.09 (113.2%) | 1.33 ± 0.136 (10.2%) | 1.46 ± 0.286 (19.6%) | 1.88 ± 0.947 (50.5%) |
| $t_{1/2}$ (h) | 19.9 ± 1.30 (6.6%) | 21.0 ± 5.70 (27.2%) | 27.8 ± 4.74 (17.0%) | 24.2 ± 5.01 (20.7%) | 19.3 ± 3.35 (17.4%) |
| CL/F | 13.1 ± 7.77 | 14.9 ± 10.8 | 4.89 ± 2.80 | 5.02 ± 1.07 | 4.86 ± 0.973 |

AR, accumulation ratio; $AUC_{0-24}$, area under the plasma concentration time curve from time 0 to 24 hours; $C_{max}$, observed maximum plasma concentration; $t_{1/2}$, terminal phase half-life; CL/F, apparent clearance at steady-state; N, number of subjects; PIB, powder in bottle; $T_{max}$, time to reach the maximum plasma concentration.

Note:

Data are reported as arithmetic mean ± SD (percent coefficient of variation, CV %) except for $T_{max}$, presented as median and range (minimum, maximum).

[a] N = 3 at steady-state (Day 28).

Expansion Stage (Single-Agent and Combination Therapy Cohorts)

The primary objectives are:

- Evaluate preliminary efficacy of Compound 1 when administered alone and in combination with ICIs by estimating the ORR as assessed by the Investigator per RECIST 1.1
- Evaluate preliminary efficacy of single-agent Compound 1 and Compound 1 in combination with ICIs for specific cohorts by estimating the percentage of subjects with PFS at 6 months (PFS rate) per RECIST 1.1 as assessed by the Investigator The secondary objective is to:

- Evaluate the safety of Compound 1 when administered alone and in combination with ICI through the evaluation of incidence and severity of nonserious AEs and SAEs, including irAEs, and AESIs The exploratory objectives of the study are:

- Duration of response (DOR) as assessed by the Investigator per RECIST 1.1
- Progression-free survival (PFS) as assessed by the Investigator per RECIST 1.1
- ORR, DOR, and PFS as assessed by a Blinded Independent Radiology Committee (BIRC) per RECIST 1.1 for selected cohorts
- Overall survival (OS)
- To further evaluate the plasma PK of daily oral administration of Compound 1 in subjects with solid tumors when given in combination with ICIs
- Assess the effects of Compound 1 on tumor and blood biomarkers when administered alone and in combination with ICIs
- Assess the immunogenicity of ICIs when administered in combination with Compound 1
- To assess drug-drug interaction between Compound 1 and combination agents
- Changes in tumor markers from baseline for selected indications Study Design Overview This is a Phase 1, first-in-human open-label, dose-escalation and expansion study, evaluating the safety, tolerability, PK, preliminary antitumor activity, and effect on biomarkers of Compound 1 administered alone, in combination with atezolizumab, and in combination with avelumab to subjects with advanced solid tumors.

This study will consist of a Dose-Escalation Stage and a Cohort-Expansion Stage for Compound 1 as single-agent therapy and in ICI combination therapy as presented below. Additionally, a limited number of subjects will be enrolled in biomarker cohorts to evaluate the pharmacodynamic effects of Compound 1 as single-agent therapy and in ICI combination therapy. During the Single Agent Dose-Escalation Stage, subjects enrolled in the first few cohorts received Compound 1 as a PIB formulation. A switch from Compound 1 PIB to Compound 1 in tablet formulation was implemented during the Compound 1 Single Agent Dose-Escalation Stage and is now being used in all subsequent Compound 1 single agent and combination therapy cohorts.

Additionally, two cohorts of subjects will be randomized to receive Compound 1 with or without an ICI. One cohort of subjects with colorectal cancer (CRC) will be randomize subjects to either Compound 1 as single agent (approx. 40 subjects) or Compound 1 in combination with atezolizumab (approx. 40 subjects). Another cohort of subjects with ICI-refractory urothelial carcinoma will be randomized to either Compound 1 as single agent (approx. 29 subjects) or Compound 1 in combination with avelumab (approx. 29 subjects).

Compound 1 Single-Agent Therapy Evaluation

Figure 9:
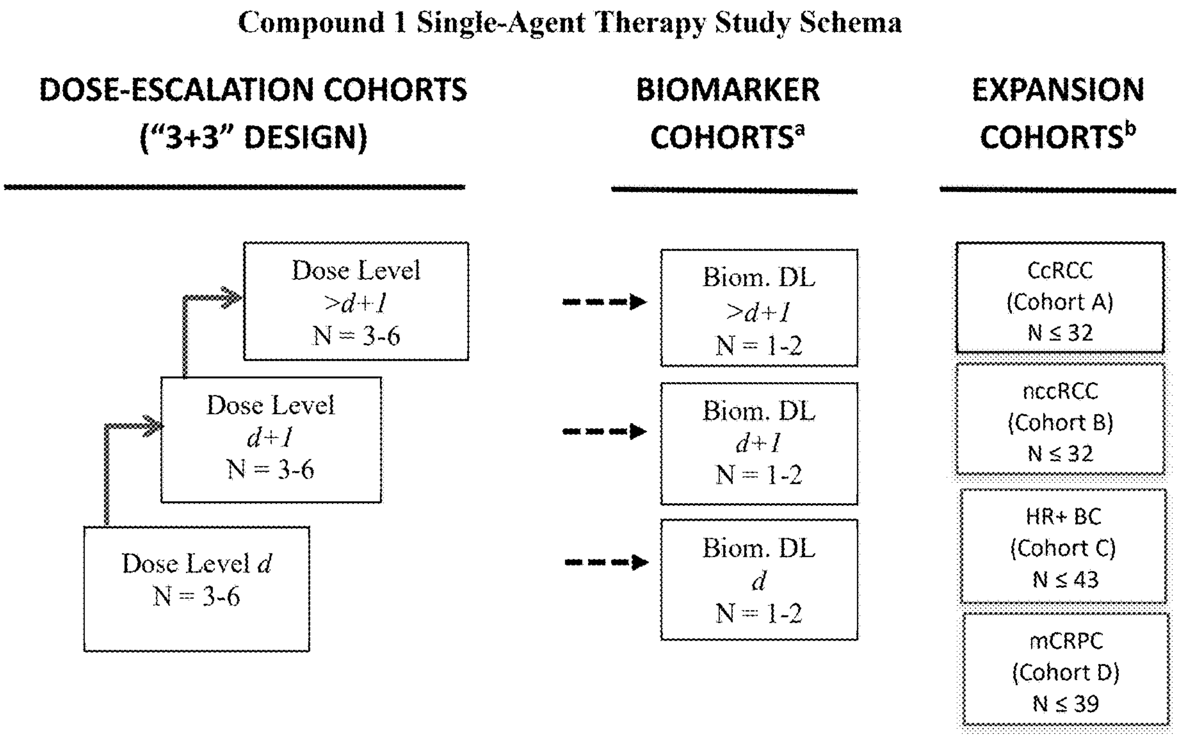

During the Dose-Escalation Stage, subjects with advanced solid tumors will be treated with Compound 1 in an estimated 8 dose escalation cohorts using a standard "3+3" design. Additionally, prior to establishing the MTD/RD, the Cohort review Committee may allow up to 12 additional subjects (18 in total) to be enrolled at any dose level if it is determined that additional safety or PK data should obtained at this dose level. After the MTD or RD has been identified, safety and efficacy of Compound 1 as single-agent therapy may be further evaluated in tumor-specific Expansion Cohorts (Expansion Stage) using a Simon's optimal two-stage design. Initially, it will include an Expansion Cohort for subjects with advanced clear cell renal cell carcinoma (ccRCC). The Sponsor may choose to initiate additional Expansion Cohorts for subjects with non-clear cell renal cell carcinoma (nccRCC), hormone receptor-positive breast cancer (HR+BC), and metastatic castration-resistant prostate cancer (mCRPC). Biomarker testing cohorts may be opened at the discretion of the Sponsor for each Compound 1 tablet dose level deemed safe per the Cohort Review Committee (CRC). FIG. 9 shows the single-agent therapy study schema of Compound 1. In addition to the dose escalation cohorts for the 3+3 design, up to 12 additional subjects (18 total) may be enrolled for further safety evaluation at any dose level in order to obtain additional safety or PK data. Subjects enrolled into biomarker cohorts will receive Compound 1 at a dose level deemed safe by the Cohort Review Committee. For the expansion cohort, subjects will be enrolled into the cohorts utilizing a Simon's optimal two-stage design.

Compound 1+Atesolizomab Combination Therapy Evaluation

During the Dose-Escalation Stage, subjects with advanced solid tumors will be treated with Compound 1 in combination with atezolizumab in an estimated four dose escalation cohorts using a "rolling six" design. Additionally, prior to establishing the MTD/RD, the Cohort review Committee may allow up to 12 additional subjects (18 in total) to be enrolled at any dose level if it is determined that additional safety or PK data should be obtained at this dose level. The Compound 1 starting dose level for the Dose-Escalation combination cohorts will be a dose that has been deemed safe for Compound 1 as single-agent therapy. For combination cohorts a standard dose level of atezolizumab will be used. After the MTD or RD has been identified for the combination therapy, safety and efficacy of Compound 1 as combination therapy with atezolizumab will be further evaluated in four tumor-specific Expansion Cohorts (Expansion Stage) using a Simon's optimal two-stage design (with the exception of the CRC Cohort H): nccRCC, HR+BC, mCRPC, and CRC.

The CRC expansion cohort will randomize (1:1) 80 subjects to receive Compound 1 in combination with atezolizumab (Cohort H, Treatment Arm H-A) or single-agent Compound 1 (Cohort H, Treatment Arm H-B). Enrollment into Cohort H will be randomized per an unstratified permuted block design following the eligibility review process by the Sponsor.

Figure 10:
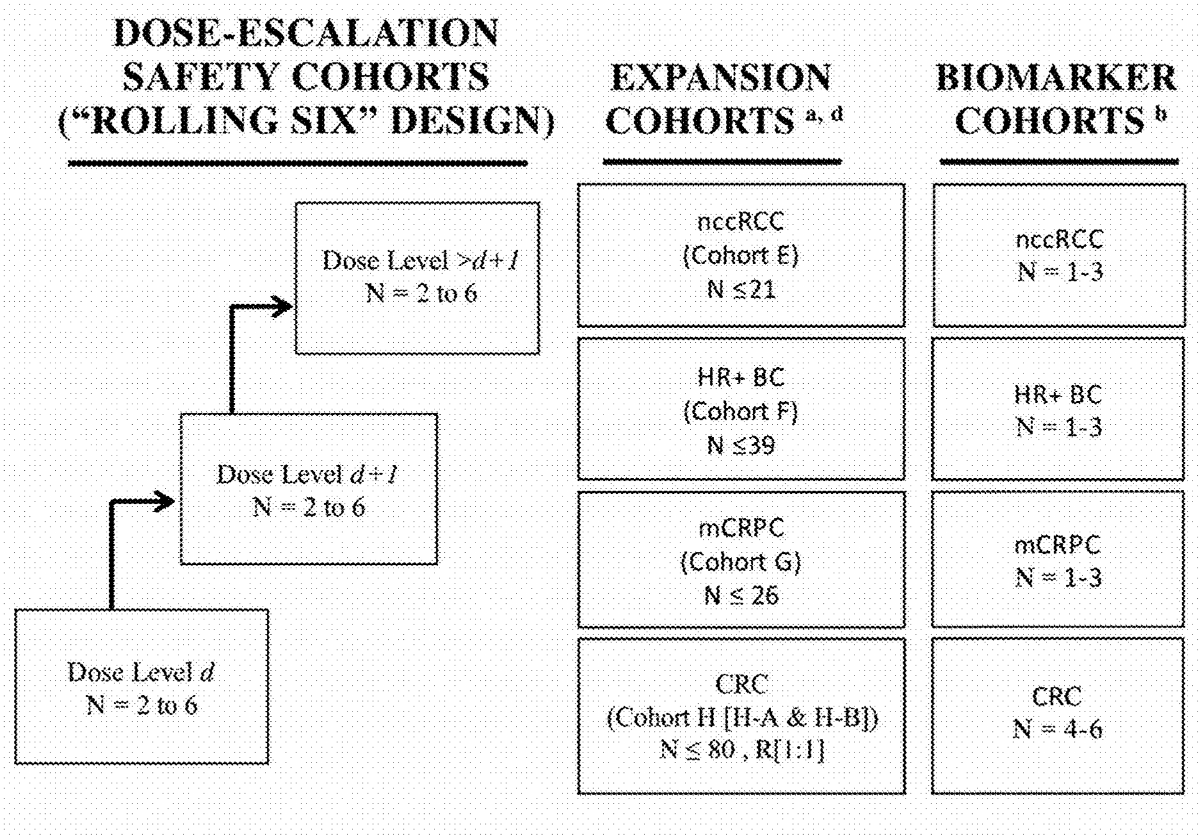

In addition, the Steering Committee (SC) of the study may decide to evaluate a tumor-specific expansion cohort at a lower dose level than the MTD or RD in order to establish a more favorable risk/benefit profile. Biomarker cohorts may be opened at the discretion of the Sponsor to enroll in parallel to the Expansion Cohorts with up to 3 subjects for each tumor indication using the same combination therapy dose level. Biomarker cohorts do not contribute to the Simon's optimal two-stage design. Fig. 10 shows the combination therapy study schema of Compound 1 and atezolizumab. In addition to the dose escalation cohorts for the rolling six design, up to 12 additional subjects (18 total) may be enrolled for further safety evaluation of a dose level if requested by the Cohort Review Committee in order to obtain additional safety or PK data. Subjects enrolled into expansion cohorts will be treated at the recommended combination therapy dose level. A lower dose level than the MTD or RD for each cohort may also be initiated for each tumor type. Expansion cohorts will utilize Simon's optimal two-stage design for enrollment. Subjects enrolled into biomarker cohort will receive Compound 1 at a dose level recommended for combination therapy by the Cohort Review Committee. Subjects will be enrolled into expansion cohorts utilizing a Simon's optimal two-stage design (with the exception of the CRC expansion Cohort H) and will be treated with the MTD or RD. Subjects with CRC enrolled into Cohort H will be randomized (1:1) to receive Compound 1 in combination with atezolizumab (Cohort H, Treatment Arm H-A) or single-agent Compound 1 (Cohort H, Treatment Arm H-B). Enrollment into Cohort H will be randomized per an unstratified permuted block design following the eligibility review process by the Sponsor. Subjects in Treatment Arm H-B may be treated at a Compound 1 dose-level lower than the single-agent Compound 1 MTD/RD if the risk/benefit profile of a lower Compound 1 dose-level proves more favorable for this population.

Compound 1+Avelumab Combination Therapy Evaluation

During the Dose-Escalation Stage, subjects with advanced solid tumors will be treated with Compound 1 in combination with avelumab in an estimated three dose escalation cohorts using a "rolling six" design.

Additionally, prior to establishing the MTD/RD, the Cohort review Committee may allow up to 12 additional subjects (18 in total) to be enrolled at any dose level if it is determined that additional safety or PK data should be obtained at this dose level.

The Compound 1 starting dose level for the Dose-Escalation combination cohort with avelumab will be a Compound 1 dose that has been deemed safe by the Cohort Review Committee during the Compound 1 single-agent therapy Dose Escalation evaluation. Additionally, the Cohort Review Committee will review available safety data from the Compound 1+atezolizumab combination therapy Dose Escalation Stage when determining the starting dose of Compound 1 to be administered in combination with avelumab.

Figure 11:
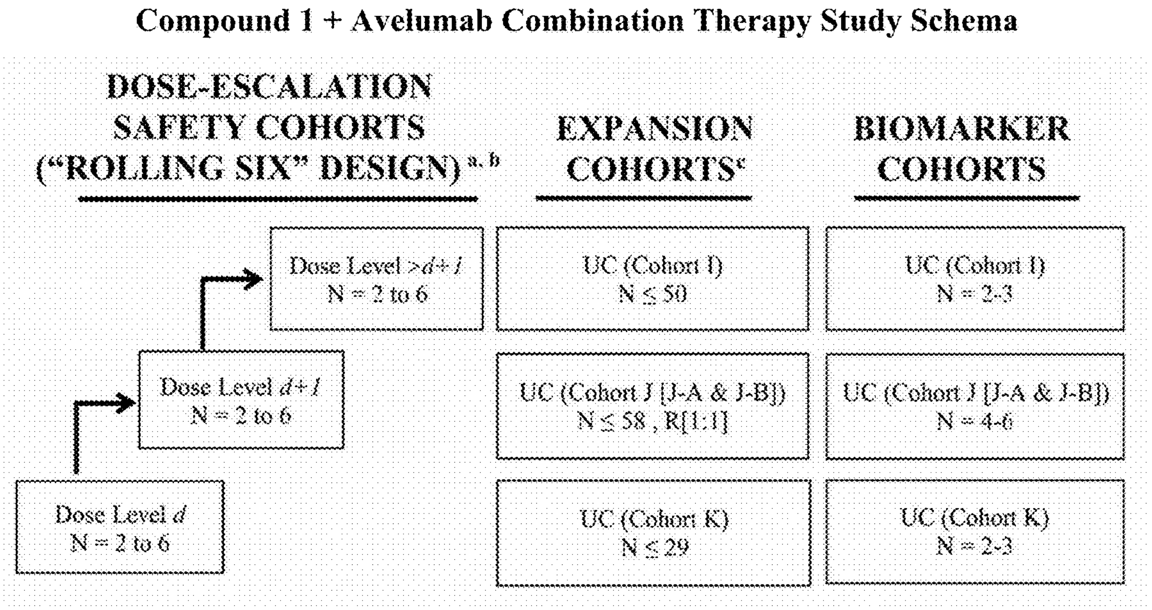

After the MTD or RD has been identified for the Compound 1 combination therapy with avelumab, safety and efficacy of the combination therapy will be further evaluated in three UC expansion cohorts (Expansion Stage): Cohort I (maintenance therapy, approx. 50 subjects, Cohort J (ICI-refractory, randomized cohort with two treatment arms each 29 subjects; J-A and J-B); and Cohort K (platinum-refractory, approx. 29 subjects). The ICI-refractory cohort will randomize subjects to either Compound 1 as single agent or in combination with avelumab (enrollment in this cohort will be randomized per an unstratified permuted block design following the eligibility review process by the Sponsor). In addition, the Steering Committee (SC) of the study may decide to evaluate specific expansion cohorts at a lower dose level than the MTD or RD in order to establish a more favorable risk/benefit profile. Biomarker cohorts may be opened at the discretion of the Sponsor to enroll in parallel to the Expansion Cohorts with 2 to 3 subjects for each Expansion Cohort using the same combination therapy dose level. Biomarker cohorts do not contribute to the Simon's optimal two-stage design. FIG. 11 shows the combination therapy study schema of Compound 1 and avelumab. In addition to the dose escalation cohorts for the rolling six design, up to 12 additional subjects (18 total) may be enrolled for further safety evaluation of a dose level if requested by the Cohort Review Committee in order to obtain additional safety or PK data. Subjects enrolled into expansion cohorts will be treated at the recommended combination therapy dose level. A lower dose level than the MTD or RD for each Compound 1+avelumab combination therapy cohort may also be initiated for each tumor type. Expansion cohorts will utilize Simon's optimal two-stage design for enrollment (with exception of Cohort J). Subjects enrolled into biomarker cohort Will receive Compound 1 at a dose level recommended for combination therapy by the Cohort Review Committee. Subjects with ICI-refractory UC enrolled into Cohort I will be randomized (1:1) to receive Compound 1 in combination with avelumab (Cohort J, Treatment Arm J-A) or single-agent Compound 1 (Cohort J, Treatment Arm J-B). Enrollment into Cohort I will be randomized per an unstratified permuted block design following the eligibility review process by the Sponsor. Subjects in Treatment Arm J-B may be treated at a Compound 1 dose-level lower than the single-agent Compound 1 MTD/RD if the risk/benefit profile of a lower Compound 1 dose-level proves more favorable for this population.

Compound 1 Single-Agent Therapy Evaluation

Dose-Escalation Stage

For the Dose-Escalation Stage with Compound 1 as a single agent, a standard "3+3" study design will be used to identify the MTD/RD and/or the maximum administered dose (MAD) of Compound 1. Subjects will accrue in escalation safety cohorts of 3 to 6 subjects.

Subjects enrolled in initial Dose-Escalation cohorts received Compound 1 utilizing a powder-in-bottle (PIB) formulation. As of Protocol Amendment 4, all subjects who were previously enrolled in PIB cohorts had either transitioned to a safe dose of Compound 1 as the tablet formulation or had discontinued Compound 1. All further cohorts will utilize a tablet formulation.

In the Compound 1 single-agent dose-escalation cohorts, study drug will be administered qd for the first 28 days, which comprises the Dose-Limiting Toxicity (DLT) Evaluation Period. At the end of the 28-day DLT period, the Cohort Review Committee will review all available safety and PK data for cohorts containing at least 3 subjects and dose escalation to the next cohort may proceed if 0 out of 3 subjects or <1 out of 6 subjects experience(s) a DLT (as defined below). Dose escalation to the next cohort will not exceed a doubling of the Compound 1 dose; however, the Cohort Review Committee may decide to institute a less-than-doubling escalation between cohorts based on evaluation of safety and PK results from the current and previous cohorts.

Dose escalation may continue until the MAD is reached (ie, ≥2 of 3 to 6 subjects in a cohort at a dose level experience a DLT in the first 28 days) or the Cohort Review Committee review of accumulating safety and PK data may indicate that dose escalation should not occur or a lower dose of Compound 1 should be evaluated. The dose escalation decision rules for single agent cohorts are provided in the table below.

Dose-Escalation Decision Rules for Single-Agent Therapy

| No. of Subjects with a DLT (Days 1~28) in Current Cohort | Dose-Escalation Decision Rule |
|---|---|
| 0 out of 3 | Enter 3 subjects at the next higher dose level. |
| 1 out of 3 | Enter 3 more subjects at the current dose level. |
| 1 out of 6 | Enter 3 subjects at the next higher dose level. |
| ≥2 out of 3 | Dose-Escalation will be stopped. This dose level will be declared the MAD.<br>Additional dose levels may be evaluated between the MAD and previous dose level to the MAD (see "2 out of 6" row below): |
| ≥2 out of 6 | This dose level will be declared the MAD.<br>If only 3 subjects have been treated at the previous dose level, an additional 3 subjects will be entered at this previous dose level (ie, one cohort lower than the MAD). If less than a third of the total number of subjects at this lower dose level has a DLT, then dose levels between this and the MAD may be explored.<br>If 6 subjects had already been treated at the previous dose level (ie, one cohort lower than the MAD) and only 0 or 1 DLT(s)have been observed, then dose levels between this and the MAD dose level may be explored.<br>If the Cohort Review Committee decides that a dose level between the previous dose level (ie, one cohort lower than the MAD) and the MAD is to be explored then the next cohort may accrue at a dose that is between this and the MAD dose level. |

DLT, dose-limiting; toxicity; MAD, maximum administered dose.

Additional 12 subjects may be added at any dose level (up to a total of 18 subjects) being evaluated if the Cohort Review Committee concludes that additional safety data should be obtained at this dose level.

Identifying the MTD and/or RD:

Once the Compound 1 MAD as single-agent therapy is identified, the cohort at the next lower dose level would be identified as the MTD unless the CRC deems that a lower dose should be expanded for evaluation. When determining the MTD, consideration will also be given to the rate, severity, and nature of cumulative toxicities, in particular end-organ toxicities (ie, cardiac, renal, hepatic, central nervous system) observed beyond the DLT Evaluation Period at all dose levels. The MTD for Compound 1 as a single-agent therapy will be based on 6 to 12 subjects in a cohort and will be defined as the highest evaluated dose level at which not more than 1 out of 6 subjects experiences a DLT during the DLT Evaluation Period. However, it is possible that the MAD and MTD may not be reached in this study based on DLTs and other safety data. If an MTD cannot be established based on these safety data, PK and biomarker data may be considered with respect to establishing a RD for subsequent use in the Cohort-Expansion Stage.

Prior to establishing the MTD/RD the CRC may allow intra-subject escalation to the highest safe Compound 1 dose level (that is, DLT evaluation has been completed for at least 3 subjects) if the subject has received 8 weeks of study treatment and has not experienced unacceptable side effects per Investigator assessment. Subjects who are allowed to dose escalate will not contribute to the DLT Evaluation at that higher dose. Once the CRC has determined the MTD/RD level, active subjects in lower dose level cohorts may be escalated to the MTD/RD level if their most current dose level is tolerated well.

Biomarker Cohorts (Single-Agent Therapy)

To understand the mechanism of action of Compound 1, separate Biomarker Cohorts will include subjects who will provide tumor and skin biopsy samples while receiving treatment with Compound 1 as a single-agent therapy. Once a dose level for single-agent therapy with the tablet formulation in the Dose-Escalation Stage has been determined to be safe by the CRC, a biomarker cohort of 1-2 subjects may be opened at the same dose level (1 dose level lower than the current enrolling dose or at the MTD dose level). Biopsy samples for analysis will be collected from at least 1-2 subjects treated with Compound 1 as a single agent at the RD level. Safety data obtained from biomarker cohorts will be included in the cumulative data review for dose escalation and MTD/RD determination by the CRC for Compound 1 single-agent therapy. Subjects in the biomarker cohorts receiving single-agent Compound 1 therapy will follow the study assessments and visit schedule as for subjects in the Dose-Escalation Stage.

Study Visits:

Subjects in the Dose-Escalation Stage will visit the clinic for study assessments during study periods as follows:

- Pre-Treatment Period (Screening): Subjects are consented and undergo screening and baseline evaluations to be qualified for the study.
- DLT Evaluation Period (Days 1-28): Dose-limiting toxicity will be determined by the CRC upon review of all available data and is defined above.
- Washout Period (Days 29-35 inclusive): There will be a washout period (no study drug administration) for subjects receiving single-agent therapy in order to determine Compound 1 half-life at steady-state (Dose-Escalation cohorts).
- Treatment Extension Period (Day 36 through up to 12 months or for an additional 12 months with the agreement of the Sponsor): Subjects will be treated and monitored for safety (including laboratory assessments) and signs of toxicity. In the absence of radiographic PD per RECIST 1.1 and unacceptable toxicity, subjects may continue to receive Compound 1 treatment for a total of up to 12 months and for an additional 12 months with the agreement of the Sponsor. Treatment with single-agent therapy may continue after radiographic progression as long as the Investigator believes that the subject is still receiving clinical benefit from study treatment and that the potential benefit of continuing study treatment outweighs potential risk.
- Post-Treatment Period:
  - Post-Treatment Follow-Up Visit (FU-1; 30+14 days after decision to discontinue study treatment): The post-treatment follow-up safety visit will occur 30 (+14) days after the date of the decision to discontinue study treatment (defined as the later of the date of the decision to permanently discontinue study treatment or the date of the last dose of study treatment) unless a related AE leading to study treatment discontinuation, related SAE or DLT (regardless of causality) is ongoing in which case the event will be followed until resolved or irreversible.
  - Extended Follow Up (Every 12 weeks (±14 days) after FU-1): After the post-treatment follow-up visit, each subject will continue to be followed for survival and receipt of nonprotocol anticancer therapy (NPACT). The investigator (or designee) will make contact with the subject every 12 weeks after the post-treatment follow-up visits until the subject expires, withdraws consent for such contacts, or the Sponsor decides to cease collecting these data for the study.

Cohort Expansion Stage

After the MTD/RD of single-agent Compound 1 therapy has been determined in the Dose-Escalation Stage, the single-agent Cohort-Expansion Stage of the study may be initiated. The Cohort-Expansion Stage will further explore safety, tolerability, and preliminary efficacy of Compound 1 as a single-agent in tumor-specific expansion cohorts. Subjects in the Cohort-Expansion groups will be treated at the MTD of Compound 1 in tablet formulation, unless accumulating safety and PK data indicate a lower dose (RD) should be evaluated. Safety and efficacy of Compound 1 single-agent therapy will be evaluated in an expansion cohort for subjects with advanced ccRCC. The Sponsor may decide to open three additional single-agent expansion cohorts for subjects with nccRCC, HR+BC, and mCRPC.

Subjects enrolled into single-agent Compound 1 expansion cohorts will follow the schedule of assessments as specified below:

| Cohort | Subjects (N) | Treatment |
|---|---|---|
| Cohort A: ccRCC | 32 | Compound 1 |
| Cohort B: nccRCC | 32 | Compound 1 |
| Cohort C: HR + BC | 43 | Compound 1 |
| Cohort D: mCRPC | 39 | Compound 1 |
| Cohort H (Treatment Arm H-B): CRC | 40 | Compound 1 |
| Cohort J (Treatment Arm J-B): UC (ICI-refractory) | 29 | Compound 1 |

Study Visits:

Each subject's course of treatment in expansion cohorts will consist of the following periods:

- Pre-Treatment Period: Subjects are consented and undergo screening and baseline evaluations to be qualified for the study.
- Treatment Period: Subjects will be treated and monitored for safety (including laboratory assessments) and signs of toxicity. In the absence of radiographic PD per RECIST 1.1 and unacceptable toxicity, subjects may continue to receive Compound 1 treatment for a total of up to 12 months and for an additional 12 months with the agreement of the Sponsor.
- Post-Treatment Period:
  - Post-Treatment Follow-Up Visit (FU-1; 30+14 days after decision to discontinue study treatment): The post-treatment follow-up safety visit will occur 30 (+14) days after the date of the decision to discontinue study treatment (defined as the later of the date of the decision to permanently discontinue study treatment or the date of the last dose of study treatment) unless a related AE leading to study treatment discontinuation, related SAE, or DLT (regardless of causality) is ongoing in which case the event will be followed until resolved or irreversible.
  - Extended Follow Up (Every 12 weeks (±14 days) after FU-1): After the post-treatment follow-up visit, each subject will continue to be followed for survival and NPACT. The investigator (or designee) will make contact with the subject every 12 weeks after the post-treatment follow-up visits until the subject expires, withdraws consent for such contacts, or the Sponsor decides to cease collecting these data for the study.

Compound 1+Atezolizumab Combination Therapy

Dose-Escalation Stage

In the Dose-Escalation Stage with evaluation of Compound 1 in combination with atezolizumab, a "rolling six" study design (Skolnik et al 2008) will be used to identify the MTD/RD for the combination therapy. Subjects will receive Compound 1 (tablet formulation) administered orally once daily (qd) in combination with atezolizumab administered intravenously (IV) once every 3 weeks (q3w), starting at Day 1. Dose escalation for combination therapy may be initiated in parallel with single-agent dose escalation prior to reaching the MTD for Compound 1 single-agent therapy, under the following conditions:

- Dose escalation for combination therapy will employ a dose of Compound 1 that has been deemed safe by the CRC for single-agent therapy with Compound 1
- A higher dose level of Compound 1 in combination therapy can only be evaluated after the current combination therapy dose level Compound 1 has been deemed safe by the CRC
- Dose escalation for combination therapy cannot exceed a doubling of the highest Compound 1 dose that has been deemed safe for combination therapy and cannot exceed the MTD/RD for Compound 1 single-agent therapy For the rolling six design, up to 6 subjects may be concurrently accrued in a cohort at the same dose level. Additionally, prior to establishing the MTD/RD, the Cohort review Committee may allow up to 12 additional subjects (18 in total) to be enrolled at any dose level if it is determined that additional safety or PK data should obtained at this dose level. For dose-level cohorts containing at least 3 subjects, a CRC will review data to determine dose escalation when subject(s) complete the 21-day DLT period. Decisions as to whether to enroll a new subject onto the current, next highest, or next lowest Compound 1 dose level are made based on available safety data at the time of new subject enrollment (See Decision Rules for Combination Therapy Dose-Escalation below). Dose de-escalation occurs if ≥2/2, ≥2/3, ≥2/4, ≥2/5, or ≥2/6 subjects experience DLTs and dose escalation to the next dose level occurs if 3/3, 4/4, 5/5, 5/6, or 6/6 subjects experience no DLT; otherwise, enroll the next subject at the same dose level, up to a total of 6 subjects. If 6 subjects have been included at the current dose level, suspend enrollment until at least 5 of those 6 subjects have completed the first cycle without DLT.

Dose escalation of Compound 1 in combination cohorts will continue until the MTD/RD level for single agent Compound 1 has been reached or dose de-escalation must occur from a dose level according to dose-escalation decision rules for combination cohorts (below). If dose de-escalation must occur the highest achieved dose level of Compound 1 in combination therapy will be considered the MAD. The CRC will also review accumulating safety and PK data in order to establish the MTD/RD for Compound 1 in combination therapy.

Decision Rules for Compound 1+Atezolizumab Combination Therapy Dose-Escalation Cohorts -continued

| | DLT Data | | | Dose Level for Next Enrolling Subject | |
|---|---|---|---|---|---|
| No. Subjects Enrolled | No. Subjects with DLTs | No. Subjects Without DLT | No. Subjects With Data Pending | MTD Not Exceeded | MTD Exceeded |
| 2 | 0, 1 | Any | Any | d | |
| 2 | 2 | 0 | 0 | d − 1 | |
| 3 | 0 | 0, 1, 2 | 3, 2, 1 | d | |
| 3 | 0 | 3 | 0 | d + 1 | |
| 3 | 1 | 0, 1 | 2, 1 | d | |
| 3 | 1 | 2 | 0 | d | |
| 3 | ≥2 | Any | Any | d − 1 | |
| 4 | 0 | 0, 1, 2 | 4, 3, 2 | d | d |
| 4 | 0 | 3 | 1 | d | d |
| 4 | 0 | 4 | 0 | d + 1 | d |
| 4 | 1 | 0, 1 | 3, 2 | d | d |
| 4 | 1 | 2 | 1 | d | d |
| 4 | 1 | 3 | 1 | d | d |
| 4 | ≥2 | Any | Any | d − 1 | d − 1 |
| 5 | 0 | 0, 1, 2 | 5, 4, 3 | d | d |
| 5 | 0 | 3, 4 | 2, 1 | d | d |
| 5 | 0 | 5 | 0 | d + 1 | d |
| 5 | 1 | 0, 1 | 4, 3 | d | d |
| 5 | 1 | 2 | 2 | d | d |
| 5 | 1 | 3, 4 | L, 0 | d | d |
| 5 | ≥2 | Any | Any | d − 1 | d − 1 |
| 6 | 0 | 0, 1, 2 | 6, 5, 4 | Suspend | Suspend |
| 6 | 0 | 3, 4 | 3, 2 | Suspend | Suspend |
| 6 | 0 | 5, 6 | 1, 0 | d + 1 | MTD |
| 6 | 1 | 0, 1 | 5, 4 | Suspend | Suspend |
| 6 | 1 | 2 | 3 | Suspend | Suspend |
| 6 | 1 | 3, 4 | 2, 1 | Suspend | Suspend |
| 6 | 1 | 5 | 0 | d + 1 | MTD |
| 6 | ≥2 | Any | Any | d − 1 | d − 1 |

d, the current dose level of subjects enrolled (d + 1, the next higher dose level; d − 1, the next lower dose level); DLT, dose-limiting toxicity; MTD, maximum tolerated dose. Suspend means enrollment is halted until no subjects have pending data.

Table is adapted from Skolnik et al 2008.

Identifying the MTD and/or RD (Compound 1 Atezolizumab Combination Therapy)

When determining the MTD of Compound 1 in combination therapy, consideration will also be given to the rate, severity, and nature of cumulative toxicities, in particular end-organ toxicities (ie, cardiac, renal, hepatic, central nervous system) observed beyond the DLT Evaluation Period at all dose levels. The MTD for Compound 1 for combination therapy will be based on 6 subjects in a cohort and will be defined as the highest evaluated dose level at which not more than 1 out of 6 subjects experiences a DLT during the DLT Evaluation Period. It is possible that the MTD/RD for single-agent Compound 1 may not be reached for the combination therapy; therefore, based on review of available data from the study, the CRC may recommend a separate MTD/RD of Compound 1 in combination with atezolizumab for the combination therapy Cohort-Expansion Stage. Once the CRC has determined the MTD/RD level for the combination therapy, active subjects at lower dose level cohorts may be escalated to the MTD/RD dose level if their most current dose level is tolerated well.

Study Visits:

Subjects in the Dose-Escalation Stage will visit the clinic for study assessments during study periods as follows:

- Pre-Treatment Period (Screening): Subjects are consented and undergo screening and baseline evaluations to be qualified for the study.
- DLT Evaluation Period (Days 1-21): Dose-limiting toxicity will be determined by the CRC upon review of all available data and is defined above.
- Treatment Extension Period (Day 22 through up to 12 months or for an additional 12 months with the agreement of the Sponsor): Subjects will be treated and monitored for safety (including laboratory assessments) and signs of toxicity. In the absence of radiographic PD per RECIST 1.1 and unacceptable toxicity, subjects may continue to receive study treatment for a total of up to 12 months and for an additional 12 months with the agreement of the Sponsor.

Treatment with combination therapy may continue after radiographic progression as long as the Investigator believes that the subject is still receiving clinical benefit from study treatment and that the potential benefit of continuing study treatment outweighs potential risk. Clinical judgment should be used for allowing treatment beyond radiographic progression. Subjects with clinically significant symptomatic deterioration at the time of radiographic progression may not be suitable for further treatment. The possibility of a delayed anti-tumor immune response should be taken into consideration: mixed responses with decreasing and increasing tumor lesion sizes at the same imaging time point or the appearance of new lesions prior to achieving a radiological response have been reported with ICI.

Post-Treatment Period:

a. First Post-Treatment Follow-Up Visit (FU-1; 30+14 days after decision to discontinue study treatment): A first post-treatment follow-up safety visit will occur 30 (+14) days after the date of the decision to discontinue study treatment (defined as the later of the date of the decision to permanently discontinue study treatment or the date of the last dose of study treatment) unless a related AE leading to study treatment discontinuation, related SAE, or DLT (regardless of causality) is ongoing in which case the event will be followed until resolved or irreversible.

b. Second Post-Treatment Follow Up Visit (FU-2; 100±14 days after decision to discontinue study treatment): A second post-treatment follow-up safety visit will occur 100 (+14) days after the date of the decision to discontinue study treatment unless a related AE leading to study treatment discontinuation, related SAE, or DLT (regardless of causality) is ongoing in which case the event will be followed until resolved or irreversible.

c. Extended Follow Up (Every 12 weeks (±14 days) after FU-2): After the post-treatment follow-up visits, each subject will continue to be followed for survival and receipt of NPACT. The investigator (or designee) will make contact with the subject every 12 weeks after the post-treatment follow-up visits until the subject expires, withdraws consent for such contacts, or the Sponsor decides to cease collecting these data for the study.

Safety assessments for subjects receiving combination therapy will be performed during Study Safety Visits (SSVs) at least every 3 weeks (ie, no more than 3 weeks apart) regardless of whether an infusion with atezolizumab is planned or not. Additional study visits may be required for imaging, PK, immunogenicity, and biomarker assessments between the SSVs.

Cohort-Expansion Stage

The Cohort-Expansion Stage will commence after the MTD or RD has been established for Compound 1 in combination with atezolizumab. This Stage will further explore safety, tolerability, and preliminary efficacy of the combination therapy in 4 tumor-specific expansion cohorts: nccRCC, HR+BC, mCRPC, and CRC. The CRC cohort will randomize subjects 1:1 to receive either Compound 1 as single agent or in combination with atezolizumab (enrollment in this cohort will be randomized per an unstratified permuted block design following the eligibility review process by the Sponsor). The Sponsor may decide to open an additional expansion cohort in each tumor indication at a lower dose level than the MTD or RD.

Subjects enrolled into the Compound 1+atezolizumab Cohort-Expansion Stage will follow the schedule of assessments as specified below:

| Cohort | Subjects (N) | Treatment |
|---|---|---|
| Cohort E: nccRCC | 21 | Compound 1 + atezolizumab |
| Cohort F: HR + BC | 39 | Compound 1 + atezolizumab |
| Cohort G: mCRPC | 26 | Compound 1 + atezolizumab |
| Cohort H (Treatment Arm H-A): CRC | 40 | Compound 1 + atezolizumab |
| Cohort H (Treatment Arm H-B): CRC | 40 | Compound 1 |

Biomarker Cohorts

For each tumor-specific expansion cohort, additional biomarker cohorts with 1 to 3 subjects will be enrolled for each tumor type. Subjects enrolled into biomarker cohorts will provide tumor and skin biopsy samples while receiving treatment with Compound 1 in combination with atezolizumab. Biomarker cohorts do not count towards the Simon's optimal two-stage design. Safety data obtained from biomarker cohorts will be included in the cumulative data review of the combination therapy. Subjects in the biomarker cohorts receiving combination therapy will follow the same study assessments and visit schedule as subjects in the Cohort-Expansion Stage.

Study Visits:

Each subject's course of treatment in expansion cohorts will consist of the following periods:

Pre-Treatment Period: Subjects are consented and undergo screening and baseline evaluations to be qualified for the study.

Treatment Period: Subjects will be treated and monitored for safety (including laboratory assessments) and signs of toxicity. In the absence of radiographic PD per RECIST 1.1 and unacceptable toxicity, subjects may continue to receive study treatment for a total of up to 12 months and for an additional 12 months with the agreement of the Sponsor. Treatment with combination therapy may continue after radiographic progression as long as the Investigator believes that the subject is still receiving clinical benefit from study treatment and that the potential benefit of continuing study treatment outweighs potential risk. Clinical judgment should be used for allowing treatment beyond radiographic progression. Subjects with clinically significant symptomatic deterioration at the time of radiographic progression may not be suitable for further treatment. The possibility of a delayed anti-tumor immune response should be taken into consideration: mixed responses with decreasing and increasing tumor lesion sizes at the same imaging time point or the appearance of new lesions prior to achieving a radiological response have been reported with ICI.

Post-Treatment Period:

First Post-Treatment Follow-Up Visit (FU-1; 30+14 days after decision to discontinue study treatment): A first post-treatment follow-up safety visit will occur 30 (+14) days after the date of the decision to discontinue study treatment (defined as the later of the date of the decision to permanently discontinue study treatment or the date of the last dose of study treatment) unless a related AE leading to study treatment discontinuation, related serious adverse event (SAE), or DLT (regardless of causality) is ongoing in which case the event will be followed until resolved or irreversible.

Second Post-Treatment Follow Up Visit (FU-2; 100±14 days after decision to discontinue study treatment): A second post-treatment follow-up safety visit will occur 100 (+14) days after the date of the decision to discontinue study treatment unless a related AE leading to study treatment discontinuation, related serious adverse event (SAE), or DLT (regardless of causality) is ongoing in which case the event will be followed until resolved or irreversible.

Extended Follow Up (Every 12 weeks (±14 days) after FU-2): After the post-treatment follow-up visits, each subject will continue to be followed for survival and receipt of NPACT. The investigator (or designee) will make contact with the subject every 12 weeks after the post-treatment follow-up visits until the subject expires, withdraws consent for such contacts, or the Sponsor decides to cease collecting these data for the study.

Safety assessments for subjects receiving combination therapy will be performed during Study Safety Visits (SSVs) least every 3 weeks (ie, no more than 3 weeks apart) regardless of whether an infusion with atezolizumab is planned or not. Additional study visits may be required for imaging, PK, immunogenicity, and biomarker assessments between the SSVs.

Compound 1+AVELUMAB COMBINATION THERAPY

Dose-Escalation Stage

During the Dose-Escalation Stage, subjects with advanced solid tumors will be treated with Compound 1 in combination with avelumab in an estimated three dose escalation cohorts using a "rolling six" design.

Additionally, prior to establishing the MTD/RD, the Cohort review Committee may allow up to 12 additional subjects (18 in total) to be enrolled at any dose level if it is determined that additional safety or PK data should obtained at this dose level The Compound 1 starting dose level for the Dose-Escalation combination cohort with avelumab will be a Compound 1 dose that has been deemed safe by the Cohort Review Committee during the Compound 1 single-agent therapy Dose Escalation evaluation. Additionally, the Cohort Review Committee will review available safety data from the Compound 1+atezolizumab combination therapy Dose Escalation Stage when determining the starting dose of Compound 1 to be administered in combination with avelumab.

After the MTD or RD has been identified for the Compound 1 combination therapy with avelumab, safety and efficacy of the combination therapy will be further evaluated in three UC expansion cohorts (Expansion Stage): Cohort I (maintenance therapy approx. 50 subjects), Cohort J (ICI-refractory, randomized cohort with two treatment arms each 29 subjects; J-A and J-B), and Cohort K (platinum-refractory, approx. 30 subjects). The ICI-refractory cohort will randomize subjects 1:1 to receive either Compound 1 as single agent or in combination with avelumab (enrollment in this cohort will be randomized per an unstratified permuted block design following the eligibility review process by the Sponsor). In addition, the Steering Committee (SC) of the study may decide to evaluate specific expansion cohorts at a lower dose level than the MTD or RD in order to establish a more favorable risk/benefit profile. Biomarker cohorts may be opened at the discretion of the Sponsor to enroll in parallel to the Expansion Cohorts with 2 to 3 subjects for each Expansion Cohort using the same combination therapy dose level. Biomarker cohorts do not contribute to the Simon's optimal two-stage design.

Dose-Escalation Decision Rules for Compound 1 + Avelumab Combination Therapy

| No. | DLT Data No. | DLT Data No. Subjects | DLT Data No. Subjects | Dose Level for Next Enrolling Subject | |
|---|---|---|---|---|---|
| Subjects Enrolled | Subjects with DLTs | Without DLT | With Data Pending | MTD Not Exceeded | MTD Exceeded |
| 2 | 0, 1 | Any | Any | d | |
| 2 | 2 | 0 | 0 | d − 1 | |
| 3 | 0 | 0, 1, 2 | 3, 2, 1 | d | |
| 3 | 0 | 3 | 0 | d + 1 | |
| 3 | 1 | 0, 1 | 2, 1 | d | |
| 3 | 1 | 2 | 0 | d | |
| 3 | ≥2 | Any | Any | d − 1 | |
| 4 | 0 | 0, 1, 2 | 4,3, 2 | d | d |
| 4 | 0 | 3 | 1 | d | d |
| 4 | 0 | 4 | 0 | d + 1 | d |
| 4 | 1 | 0.1 | 3, 2 | d | d |
| 4 | 1 | 2 | 1 | d | d |
| 4 | 1 | 3 | 1 | d | d |
| 4 | ≥2 | Any | Any | d − 1 | d − 1 |
| 5 | 0 | 0, 1, 2 | 5, 4, 3 | d | d |
| 5 | 0 | 3, 4 | 2, 1 | d | d |
| 5 | 0 | 5 | 0 | d + 1 | d |
| 5 | 1 | 0, 1 | 4, 3 | d | d |
| 5 | 1 | 2 | 2 | d | d |
| 5 | 1 | 3, 4 | 1, 0 | d | d |
| 5 | ≥2 | Any | Any | d − 1 | d − 1 |
| 6 | 0 | 0, 1, 2 | 6, 5, 4 | Suspend | Suspend |
| 6 | 0 | 3.4 | 3, 2 | Suspend | Suspend |
| 6 | 0 | 5, 6 | 1, 0 | d + 1 | MTD |
| 6 | 1 | 0, 1 | 5, 4 | Suspend | Suspend |
| 6 | 1 | 2 | 3 | Suspend | Suspend |
| 6 | 1 | 3, 4 | 2, 1 | Suspend | Suspend |
| 6 | 1 | 5 | 0 | d + 1 | MTD |
| 6 | ≥2 | Any | Any | d − 1 | d − 1 |

d, the current dose level of subjects enrolled (d + 1, the next higher dose level; d − 1, the next lower dose level); DLT, dose-limiting toxicity; MTD, maximum tolerated dose. Suspend means enrollment is halted until no subjects have pending data.

Table is adapted from Skolnik et al 2008.

Identifying the MTD and/or RD (Compound 1+Aveluamb Combination Therapy):

When determining the MTD of Compound 1 in combination therapy, consideration will also be given to the rate, severity, and nature of late occurring toxicities as well as end-organ toxicities (ie, cardiac, renal, hepatic, central nervous system) observed beyond the DLT Evaluation Period at all dose levels. The MTD for Compound 1 for combination therapy will be based on 6 to 18 subjects in a cohort and will be defined as the highest evaluated dose level at which not more than 1 out of 6 subjects experiences a DLT during the DLT Evaluation Period. It is possible that the MTD/RD for single-agent Compound 1 may not be reached for the combination therapy; therefore, based on review of available data from the study, the Cohort Review Committee may recommend a separate MTD/RD of Compound 1 in combination with avelumab for the combination therapy Cohort-Expansion Stage. Once the Cohort Review Committee has determined the MTD/RD level for the combination therapy, active subjects at lower dose level cohorts may be escalated to the MTD/RD dose level if their most current dose level is tolerated well.

Study Visits:

Subjects in the Dose-Escalation Stage will visit the clinic for study assessments during study periods as follows:

- Pre-Treatment Period (Screening): Subjects are consented and undergo screening and baseline evaluations to be qualified for the study.
- DLT Evaluation Period (Days 1-21): Dose-limiting toxicity will be determined by the Cohort Review Committee upon review of all available data and is defined above.
- Treatment Extension Period (Day 22) through up to 12 months or for an additional 12 months with the agreement of the Sponsor): Subjects will be treated and monitored for safety (including laboratory assessments) and signs of toxicity. In the absence of radiographic PD per RECIST 1.1 and unacceptable toxicity, subjects may continue to receive study treatment for a total of up to 12 months and for an additional 12 months with the agreement of the Sponsor.
- Treatment with combination therapy may continue after radiographic progression as long as the Investigator believes that the subject is still receiving clinical benefit from study treatment and that the potential benefit of continuing study treatment outweighs potential risk. Clinical judgment should be used for allowing treatment beyond radiographic progression. Subjects with clinically significant symptomatic deterioration at the time of radiographic progression may not be suitable for further treatment. The possibility of a delayed anti-tumor immune response should be taken into consideration: mixed responses with decreasing and increasing tumor lesion sizes at the same imaging time point or the appearance of new lesions prior to achieving a radiological response have been reported with ICI.
- Post-Treatment Period:
  - First Post-Treatment Follow-Up Visit (FU-1; 30+14 days after decision to discontinue study treatment): A first post-treatment follow-up safety visit will occur 30 (+14) days after the date of the decision to discontinue study treatment (defined as the later of the date of the decision to permanently discontinue study treatment or the date of the last dose of study treatment).
  - Second Post-Treatment Follow Up Phone Call (FU-2; 100+14 days after decision to discontinue study treatment): A second post-treatment follow-up phone call will occur 100 (+14) days after the date of the decision to discontinue study treatment. If a related AE leading to study treatment discontinuation, AESI, related SAE, or DLT (regardless of causality) is ongoing, the event will be followed until resolved or irreversible.
  - Extended Follow Up (Every 12 weeks (±14 days) after FU-2): After the post-treatment follow-up visits, each subject will continue to be followed for survival and receipt of NPACT. The investigator (or designee) will make contact with the subject every 12 weeks after the posttreatment follow-up visits until the subject expires, withdraws consent for such contacts, or the Sponsor decides to cease collecting these data for the study.

Safety assessments for subjects receiving combination therapy will be performed during Study Safety Visits (SSVs) at least every 2 weeks (ie, no more than 2 weeks apart) regardless of whether an infusion with avelumab is planned or not. Additional study visits may be required for imaging, PK, immunogenicity, and biomarker assessments between the SSVs.

Cohort-Expansion Stage

The Cohort-Expansion Stage will commence after the MTD or RD has been established for Compound 1 in combination with avelumab. This Stage will further explore safety, tolerability, and preliminary efficacy of the Compound 1+avelumab combination therapy in three cohorts enrolling subjects with advanced UC:

- Cohort I: Subjects will receive Compound 1 in combination with avelumab as maintenance therapy following a first line of platinum-based doublet chemotherapy. Enrollment into this cohort must occur at least 4 weeks but not more than 10 weeks after the date of administration of the last dose of first-line platinum-based doublet chemotherapy. Subjects will initiate study treatment (Day 1) within 3 days after enrollment.
- Cohort J: Subjects who have progressed after prior ICI therapy will be randomized (1:1) to receive either Compound 1 in combination with avelumab (Treatment Arm J-A) or single-agent Compound 1 (Treatment Arm J-B).
- Note: Subjects in Treatment Arm J-B may be treated at an Compound 1 dose-level lower than the single-agent Compound 1 MTD/RD if the risk/benefit profile of a lower Compound 1 dose-level proves more favorable for this population.
- Cohort K: Subjects who have progressed during or after platinum-based chemotherapy will receive Compound 1 in combination with avelumab.

The Sponsor may decide to open an additional expansion cohort in each tumor indication at a lower dose level than the MTD or RD.

Subjects enrolled into the Compound 1+avelumab Cohort-Expansion Stage will follow the schedule of assessments as specified below:

| Cohort | Subjects (N) | Treatment |
|---|---|---|
| Cohort I: UC (Maintenance Therapy) | 50 | Compound 1 + avelumab |
| Cohort J (Treatment Arm J-A): UC (ICI-refractory) | 29 | Compound 1 + avelumab |
| Cohort J (Treatment Arm J-B): UC (ICI-refractory) | 29 | Compound 1 |
| Cohort K: UC (Platinum-refractory) | 29 | Compound 1 + avelumab |

Biomarker Cohorts

For each UC expansion cohort, additional biomarker cohorts with 2 to 3 subjects will be enrolled for each of the three cohorts (Cohort I, Cohort J [Treatment Arms J-A and J-B], and Cohort K). For Cohort J, 2 to 3 subjects will be enrolled into both Treatment Arm J-A and Treatment Arm J-B. Subjects enrolled into biomarker cohorts will provide tumor and skin biopsy samples while receiving treatment with Compound 1 in combination with avelumab. Subjects in Cohort J Treatment Arm J-B (single-agent Compound 1) enrolled into a biomarker cohort will undergo the same biomarker assessments as subjects receiving Compound 1+avelumab combination therapy. Biomarker cohorts do not count towards the Simon's optimal two-stage design. Safety data obtained from biomarker cohorts will be included in the cumulative data review of the combination therapy. Subjects in the biomarker cohorts receiving combination therapy will follow the same study assessments and visit schedule as subjects in the Cohort-Expansion Stage.

Study Visits:

Each subject's course of treatment in expansion cohorts will consist of the following periods:

- Pre-Treatment Period (Screening): Subjects are consented and undergo screening and baseline evaluations to be qualified for the study.
- Treatment Period: Subjects will be treated and monitored for safety (including laboratory assessments) and signs of toxicity. In the absence of radiographic PD per RECIST 1.1 and unacceptable toxicity, subjects may continue to receive study treatment for a total of up to 12 months and for an additional 12 months with the agreement of the Sponsor. Treatment with combination therapy may continue after radiographic progression as long as the Investigator believes that the subject is still receiving clinical benefit from study treatment and that the potential benefit of continuing study treatment outweighs potential risk. Clinical judgment should be used for allowing treatment beyond radiographic progression. Subjects with clinically significant symptomatic deterioration at the time of radiographic progression may not be suitable for further treatment. The possibility of a delayed anti-tumor immune response should be taken into consideration: mixed responses with decreasing and increasing tumor lesion sizes at the same imaging time point or the appearance of new lesions prior to achieving a radiological response have been reported with ICIs.
- Post-Treatment Period:
  - First Post-Treatment Follow-Up Visit (FU-1; 30+14 days after decision to discontinue study treatment): A first post-treatment follow-up safety visit will occur 30 (+14) days after the date of the decision to discontinue study treatment (defined as the later of the date of the decision to permanently discontinue study treatment or the date of the last dose of study treatment).
  - Second Post-Treatment Follow Up Phone Call (FU-2; 100+14 days after decision to discontinue study treatment): A second post-treatment follow-up phone call will occur 100 (+14) days after the date of the decision to discontinue study treatment unless a related AE leading to study treatment discontinuation, AESI, or related SAE is ongoing, the event will be followed until resolved or irreversible.
  - Extended Follow Up (Every 12 weeks (±14 days) after FU-2): After the post-treatment follow-up visits, each subject will continue to be followed for survival and receipt of NPACT. The investigator (or designee) will make contact with the subject every 12 weeks after the post-treatment follow-up visits until the subject expires, withdraws consent for such contacts, or the Sponsor decides to cease collecting these data for the study.

Safety assessments for subjects receiving combination therapy will be performed during Study Safety Visits (SSVs) at least every 2 weeks (ie, no more than 2 weeks apart) regardless of whether an infusion with avelumab is planned or not. Additional study visits may be required for imaging, PK, immunogenicity, and biomarker assessments between the SSVs.

DLT Definition (Single-Agent and ICI Combination Cohorts)

Dose-limiting toxicity (DLT) will be determined by the Cohort Review Committee for both single-agent and combination therapy dose-escalation cohorts upon review of all available safety (adverse events [AEs], clinical laboratory tests and other relevant clinical findings as provided by the Investigator) and available PK data for each cohort.

Subjects must have received ≥75% of the total planned Compound 1 dose during the DLT Evaluation Period in order to be considered evaluable for DLTs. Subjects who fail to receive at least 75% of the total planned dose of Compound 1 during the DLT Evaluation Period for reasons other than safety (eg, withdrawal of consent, non-compliance, disease progression, logistical issues) may be replaced by Cohort Review Committee decision.

Dose escalation steps of Compound 1 will be tailored by monitoring Compound 1 safety and plasma exposure for both single agent cohorts and combination therapy cohorts. The decision to open a new cohort at a higher dose level requires that safety data from the DLT Evaluation Period are obtained and evaluated from all subjects in the current dose-level cohort. In addition, cumulative safety data from subjects enrolled in cohorts at lower dose levels (including biomarker cohorts) will be evaluated for the potential emergence of clinically significant AEs and be considered in making all dose escalation decisions. DLT criteria will be evaluated independently for single-agent therapy and combination therapy cohorts. The DLT Evaluation Period is defined as Days 1-28 for single-agent therapy and Days 1-21 for combination therapy.

Dose-limiting toxicity is defined as any of the following treatment-emergent AEs occurring during the DLT Evaluation Period for Compound 1 as single-agent therapy:

- Any treatment-emergent AE that in the opinion of the Cohort Review Committee is of potential clinical significance such that further dose escalation of Compound 1 would expose subjects to unacceptable risk
- Non-hematologic toxicity: treatment-emergent ?Grade 3 AEs
- The following hematologic toxicities that are treatment-emergent:
  - Grade 3 thrombocytopenia with clinically significant bleeding
  - Grade 4 thrombocytopenia
  - Grade 4 neutropenia of 4 days duration
  - Grade 3 neutropenia of any duration with fever (single temperature of ≥38.3° C. [101.0° F.] or sustained temperature of ≥38.0° C. [100.4° F.] for ≥1 hour) or documented infection
  - Grade 4 anemia
- Inability to take 75% of the total planned Compound 1 dose for the DLT Evaluation Period because of a treatment-emergent AE leading to a dose reduction and/or interruption
- Any AE experienced during the DLT Evaluation Period that results in permanent discontinuation of Compound 1

For subjects receiving Compound 1 as combination therapy with atezolizumab or avelumab, the above in addition to the following are defined as DLTs:

- Any related Grade 3 AE which is unexpected in severity and/or duration compared with the known safety profiles of Compound 1 and atezolizumab or avelumab when used as single agents, and that cannot be managed by dose modification (reduction or interruption) and adequate supportive care, and requires permanent discontinuation of Compound 1 and/or atezolizumab or avelumab.

Any AE experienced during the DLT Evaluation Period that results in permanent discontinuation of Compound 1 and/or atezolizumab or avelumab Note: AEs are presumed attributable to study drug. AEs that are not associated with the study treatment but definitively attributable to another cause will not be considered in the determination of DLTs.

The following AEs will not be considered DLTs:

Grade 3 fatigue or anorexia lasting <7 days; Grade 3 nausea, vomiting, dehydration, or hypertension lasting <2 days following appropriate supportive care measures Single laboratory values that are out of normal range and do not have any clinical correlate. Normal values or baseline Grade level must have been recorded on repeat testing within 1 week after the out-of-range value without direct intervention intended to correct the abnormality (eg, replacement of electrolytes for an electrolyte abnormality)

Tumor flare-related AEs (ie, localized pain, irritation at tumor sites)

Grade 3 infusion-related reaction resolving within 6 hours from the end of infusion and controlled with medical management Study Treatment Management Dose-Escalation Stage Study treatment, Compound 1 single-agent therapy or ICI combination therapy, will be withheld for subjects who experience a DLT until the toxicity resolves. Subjects who recover within 28 days will, at the investigator's discretion and with the agreement of the Sponsor, be allowed to resume Compound 1 one dose level below the dose that resulted in the DLT. Treatment with combination agents may also resume for subjects who are receiving combination therapy if the DLT does not meet other protocol-required criteria for discontinuation of combination agents. If the reduced Compound 1 dose is tolerated, the subject can continue with study treatment at this dose level.

After completing the DLT Evaluation Period, subjects who are tolerating treatment well, will be allowed to continue to receive study treatment for a total of up to 12 months and for an additional 12 months with the agreement of the Sponsor as long as the subject continues to experience clinical benefit that outweighs the risks in the opinion of the investigator.

Dose-Escalation Stage and Cohort-Expansion Stage

Study treatment must be discontinued for unacceptable toxicity or if there is a need for subsequent systemic anticancer treatment.

Permitted study drug modifications to manage AEs comprise of dose reductions or interruptions for Compound 1 and dose holds for atezolizumab or avelumab. Following Sponsor notification, subjects in combination therapy cohorts may be allowed to discontinue one component of study treatment for managing AEs but continue to receive the other if considered safe and the Investigator believes that the subject is still receiving benefit from study treatment. In single-agent therapy cohorts, treatment interruption of Compound 1 for drug-related AEs is allowed for up to 6 weeks. In combination therapy cohorts, treatment interruption for drug-related AEs of any of the combination therapy agents is allowed for up to 12 weeks. Longer treatment interruptions may be allowed for both single-agent and combination therapy cohorts, upon approval by the Sponsor, if considered safe and the Investigator believes that the subject is still receiving benefit from study treatment.

Subjects who experience disease progression during Compound 1 single-agent therapy are not allowed to receive combination therapy with atezolizumab or avelumab since the clinical benefit of this regimen has not yet been established.

End of Trial

End of trial is defined as the later of two dates: the date of the last visit or procedure for the last subject remaining or the date at which the last data point required for follow-up for the last subject is obtained.

Number of Subjects

The estimated number of subjects enrolled for Compound 1 single-agent therapy evaluation is approximately 269 subjects: 40 subjects in dose escalation cohorts, 215 subjects in expansion cohorts (MTD/RD dose level), 14 subjects in biomarker cohorts. Additionally, up to 18 subjects (total) may be enrolled to further evaluate the safety of Compound 1 single-agent therapy at any dose level in the dose-escalation cohorts.

The estimated number of subjects enrolled for Compound 1+atezolizumab combination therapy evaluation is approximately 288 subjects: 24 subjects in dose-escalation cohorts, 126 subjects in expansion cohorts (MTD/RD dose level), 12 subjects in biomarker cohorts (MTD/RD dose level). Further, up to 12 additional subjects (18 total) may be enrolled to establish the MTD/RD. Additionally, up to 126 subjects may be enrolled to further evaluate the safety and efficacy of the Compound 1+atezolizumab combination therapy at a lower dose than the MTD/RD for the expansion cohorts.

The estimated number of subjects enrolled for Compound 1+avelumab combination therapy evaluation is approximately 243 subjects: approximately 18 subjects in dose-escalation cohorts, approximately 108 subjects in expansion cohorts (MTD/RD dose level), and approximately 9 subjects in biomarker cohorts (MTD/RD dose level). Further, up to 12 additional subjects (18 total) may be enrolled to establish the MTD/RD. Additionally, up to 108 subjects may be enrolled to further evaluate the safety and efficacy of the Compound 1+avelumab combination therapy at a lower dose than the MTD/RD for the expansion cohorts.

The approximate total of 800 subjects for the study may be accrued across approximately 95 sites globally.

Note: The sample size may be increased up to an additional 25% if a review of the accumulating data suggests that the COVID-19 pandemic has caused the rate of study dropout or non-compliance to increase to a degree that the ability to adequately evaluate study endpoints may be undermined.

Enrollment Estimates for Compound 1 Single-Agent Dose Evaluation

| Cohort | Tumor Type | Compound 1 Formulation/Dose | 3 + 3 Design (n = ~40) $_d$ | Biomarker (n = ~10) |
|---|---|---|---|---|
| Dose-Escalation Stage | | | | |
| Cohort 1 | Solid tumor | PIB/10 mg $_{b, c}$ | 3 | 0 |
| Cohort 2 | Solid tumor | PIB/20 mg $_{b, c}$ | 4 | 0 |
| Cohort 3 | Solid tumor | Tablet/20 mg $_{b, c}$ | 3 | 0 |
| Cohort 4 | Solid tumor | Tablet/40 mg $_{b, c}$ | 4 | 2 |

-continued

| Enrollment Estimates for Compound 1 Single-Agent Dose Evaluation | | | | |
|---|---|---|---|---|
| Cohort 5 | Solid Tumor | Tablet/80 mg [b, c] | 3 | 2 |
| Cohort 6 | Solid Tumor | Tablet/140 mg [b, c] | Up to 6 | Up to 2 |
| Cohort 7, . . . , ~8 | Solid tumor | Tablet/TBD [c] | 3 to 6 | Up to 2 |
| Cohort-Expansion Stage | | | Expansion (n = 32 to 146) | |
| Cohort A | ccRCC | Tablet/TBD mg [e] | 32 | |
| Cohort B | nccRCC | Tablet/TBD mg [e, f] | 32 | |
| Cohort C | HR + BC | Tablet/TBD mg [e, f] | 43 | |
| Cohort D | mCRPC | Tablet/TBD mg [e, f] | 39 | |

ccRCC, clear cell renal cell carcinoma; HR + BC, hormone receptor-positive breast cancer; mCRPC, metastatic castration-resistant prostate cancer; MTD, maximum tolerated dose; n, approximate number of subjects; nccRCC, non-clear cell renal cell carcinoma; PIB, powder in bottle; TBD, to be determined.
[a] Compound 1 PIB and tablet formulation
[b] Assigned dose levels and enrollment at the time of Protocol Amendment 4
[c] Maximum dose increment of 100% for Compound 1 dose escalation
[d] Dose escalation is estimated to involve approximately 8 cohorts. In addition, up to 12 subjects (18 in total) may be enrolled to obtain additional safety or PK data at any dose level.
[e] At the MTD or recommended dose (RD) level of Compound 1 for single-agent therapy
[f] Cohorts will be initiated at the Sponsor's discretion Enrollment Estimates for Compound 1 + Atezolizumab Combination Therapy Evaluation

| Cohort | Tumor Type | Atezolizumab Dose [a] | Compound 1 Dose [b] | Rolling Six Design (n = ~24) | |
|---|---|---|---|---|---|
| | Dose-Escalation Stage | | | | |
| Cohort 1 | Solid tumor | Standard dose | 40 mg [c] | 6 | |
| Cohort 3, . . . , ~4 | Solid tumor | Standard dose | 80 mg [c] | 6 | |
| Cohort-Expansion Stage | | | | Expansion (n = ~126) | Biomarker (n = ~12) |
| Cohort E | nccRCC | Standard dose | TBD mg [d, e] | 21 | 1-3 |
| Cohort F | HR + BC | Standard dose | TBD mg [d, e] | 39 | 1-3 |
| Cohort G | mCRPC | Standard dose | TBD mg [d, e] | 26 | 1-3 |
| Cohort H [f] | CRC | Arm H-A: Standard dose<br>Arm H-B: None | TBD mg [d, e] | 40 for each treatment arm | 1-3 for each treatment arm |

CRC, colorectal cancer; HR + BC, hormone receptor-positive breast cancer; IV, intravenous; mCRPC, metastatic castration-resistant prostate cancer; MTD, maximum tolerated dose; n = approximate number of subjects; nccRCC, non-clear cell renal cell carcinoma; q3w, every 3 weeks; RD, recommended dose; TBD, to be determined.
[a] Atezolizumab 1200 mg q3w IV
[b] Compound 1 tablet formulation; maximum dose increment of 100% for Compound 1 dose escalation to establish the MTD/RD.
[d] At the MTD or RD level of Compound 1 for combination therapy
[e] In addition, the combination therapy can be explored at a lower dose level than the MTD or RD for further efficacy and safety evaluation
[f] Cohort H will be a randomized (1:1) into two treatment arms (H-A: Compound 1 + atezolizumab; H-B: Compound 1 single-agent)

Enrollment Estimates for Compound 1 + Avelumab Combination Therapy Evaluation

| Cohort | Tumor Type | Avelumab Dose[a] | Compound 1 Dose b | Rolling Six Design (n = ~18) |
|---|---|---|---|---|
| | Dose-Escalation Stage | | | |
| Cohort 1 | Solid tumor | Standard dose | TBD mg | 2 to 6 |
| Cohort 2 | Solid Tumor | Standard dose | TBD mg | 2 to 6 |
| Cohort 3, etc [d] | Solid tumor | Standard dose | TBD mg | 2 to 6 |

-continued

| Enrollment Estimates for Compound 1 + Avelumab Combination Therapy Evaluation | | | | | |
|---|---|---|---|---|---|
| Cohort-Expansion Stage | | | | Expansion (n = ~108) | Biomarker (n = ~12) |
| Cohort I | UC | Standard dose | TBD mg | 50 | 2-3 |
| Cohort J [c] | UC | Arm J-A: Standard dose Arm J-B: | TBD mg | 29 for each treatment arm | 2-3 for each treatment arm |
| Cohort K | UC | Standard dose | TBD mg | 29 | 2-3 |

TBD, to be determined
[a]Avelumab 800 mg q2w IV.
b The Compound 1 starting doses will be derived from the Compound 1 single-agent and atezolizumab combination therapy Dose-Escalation evaluation.
c Cohort J will be a randomized (1:1) into two treatment arms (J-A: Compound 1 + avelumab; J-B: Compound 1 single agent)
d Dose escalation is estimated to involve approx. 3 cohorts. Up to 12 additional subjects at any dose level may be enrolled to establish the MTD/RD.

Target Population

To be eligible for the study the subject must meet all of the inclusion and none of the exclusion criteria. The Sponsor will not grant exceptions to these eligibility criteria:

Inclusion Criteria:

1. Cytologically or histologically confirmed solid tumor that is inoperable, locally advanced, metastatic, or recurrent:

Dose-Escalation Stages (single-agent and combination therapy):

a. Subjects with a solid tumor that is unresectable or metastatic and for which life-prolonging therapies do not exist or available therapies are intolerable or no longer effective.

Cohort-Expansion Stages (single-agent and combination therapy):

The tumor cohorts for the Expansion Stages for single agent and combination therapies are as follows:

| Inclusion Criterion | Tumor Type | Treatment |
|---|---|---|
| 1b | ccRCC | Compound 1 (Cohort A) |
| 1c | nccRCC | Compound 1 (Cohort B)<br>Compound 1 + Atezolizumab (Cohort E) |
| 1d | HR + BC | Compound 1 (Cohort C)<br>Compound 1 + Atezolizumab (Cohort F) |
| 1e | CRPC | Compound 1 (Cohort D)<br>Compound 1 + Atezolizumab (Cohort G) |
| 1f | CRC | Compound 1 + Atezolizumab (Cohort H: Treatment Arm H-A) Compound 1 (Cohort H: |
| 1g | UC (maintenance) | Compound 1 + Avelumab (Cohort I) |
| 1h | UC (ICI-refractory) | Compound 1 + Avelumab (Cohort J: Treatment Arm J-A) Compound 1 (Cohort J: |
| 1i | UC (platinum-refractory) | Compound 1 + Avelumab (Cohort K) |

ccRCC, clear cell renal cell carcinoma; HR + BC, hormone receptor-positive breast cancer; CRC, colorectal cancer; mCRPC, metastatic castration-resistant prostate cancer; nccRCC, non-clear cell renal cell carcinoma; UC, urothelial carcinoma.
Note:
Subjects enrolled into Cohort H will be randomized (1:1) to receive either Compound 1 + atezolizumab combination therapy (Treatment Arm H-A) or single-agent Compound 1 (Treatment Arm H-B). Subjects enrolled into Cohort J will be randomized (1:1) to receive either Compound 1 + avelumab combination therapy (Treatment Arm J-A) or single-agent Compound 1 (Treatment Arm J-B).

Subjects in the expansion study cohorts must have received standard life-prolonging therapies or are not qualified to receive such therapies as follows:

Note: Prior investigational therapies are allowed and will count towards the maximum number of prior systemic anticancer regimens. Prior neoadjuvant/adjuvant or maintenance therapies are allowed and will not count towards the maximum allowed number of systemic anticancer regimens.

b. Cohort A (ccRCC): Subjects with previously treated advanced RCC with clear cell histology (including those with a sarcomatoid component) who have radiographically progressed following treatment with at least one prior systemic anticancer regimen for inoperable locally advanced or metastatic disease.

Allowed are a maximum of 3 prior systemic anticancer regimens for inoperable locally advanced or metastatic RCC. Examples of prior systemic therapies include VEGF-targeted therapy (eg, sunitinib, cabozantinib, axitinib, bevacizumab), immune checkpoint inhibitor (ICI) therapy (eg, pembrolizumab, nivolumab+/−ipilimumab) given either as single agents or in combination, and mTOR inhibitors (eg, everolimus).

c. Cohorts B and E (nccRCC): Subjects with previously treated advanced RCC with non-clear cell histology who have radiographically progressed following treatment with at least one prior systemic anticancer regimen for inoperable locally advanced or metastatic disease.

Allowed are a maximum of 3 prior systemic anticancer regimens for inoperable locally advanced or metastatic nccRCC. Examples of prior systemic therapies include VEGF-targeted therapy (eg, sunitinib, axitinib, bevacizumab), immune check point inhibitor (ICI) therapy for Cohort B, and mTOR inhibitors (eg, everolimus).

For Cohort E, prior immune checkpoint inhibitor (ICI) therapy is not allowed.

d. Cohorts C and F (HR+BC): Subjects with breast cancer that is hormone receptor positive (ER+ and/or PR+) and negative for human epidermal growth factor receptor 2 (HER-2) and who have radiographically progressed during or following treatment with at least one prior systemic anticancer regimen for inoperable locally advanced or metastatic disease.

Estrogen receptor (ER) and progesterone receptor (PR) positivity are defined as ≥1% of tumor cell nuclei expressing hormonal receptors via IHC analysis (ASCO/CAP Guidelines [ER and PR Testing]2020).

HER-2 negativity is defined as either of the following by local laboratory assessments (ASCO/CAP Guidelines [HER-2 Receptor Testing]2018):

In situ hybridization (ISH) non-amplified (ratio of HER-2 to CEP17<2.0 or single probe average HER-2 gene copy number <4 signals/cell), or SIIC 0 or IHC 1+(if more than one test result is available and not all results meet the inclusion criterion definition, all results should be discussed with the Sponsor to establish eligibility of the subject).

Allowed are a maximum of 3 lines of prior systemic anticancer regimens for inoperable locally advanced or metastatic disease. Examples of prior therapies include selective estrogen receptor degraders (SERDs, eg, fulvestrant), selective estrogen receptor modulators (SERMs, eg, tamoxifen), steroidal aromatase inhibitors (SAIs, eg, exemestane), non-steroidal aromatase inhibitors (NSAIs, eg, letrozole), CDK 4/6 inhibitors (eg, palbociclib), mTOR inhibitors (eg, everolimus), PI3K inhibitors (eg, alpelisib), immune checkpoint inhibitor (ICI) therapy for Cohort C, chemotherapy.

For Cohort F, prior immune checkpoint inhibitor (ICI) therapy is not allowed.

e. Cohorts D and G (mCRPC): Subjects with metastatic CRPC (adenocarcinoma of the prostate). Neuroendocrine differentiation and other features permitted if adenocarcinoma is the primary histology.

Subjects must have received the following prior therapies:

a. Prior taxane-based chemotherapy (eg, docetaxel or cabazitaxel) initiated for mCRPC (Note: Subjects are allowed to have received a taxane-based chemotherapy regimen for metastatic castration-sensitive prostate cancer [mCSPC])

b. Prior treatment with at least one novel hormone therapy (NHT; eg, abiraterone, apalutamide, darolutamide, or enzalutamide) for castration sensitive locally advanced (T3 or T4) or metastatic castration-sensitive prostate cancer (mCSPC), M0 CRPC, or mCRPC.

Allowed are a maximum of 4 prior lines of systemic anticancer regimens.

Examples of additional prior systemic therapies include sipuleucel-T, radium-223, poly ADP-ribose polymerase (PARP) inhibitor, second NHT, immune checkpoint inhibitor (ICI) therapy for Cohort D, non-taxane based chemotherapy. Other hormonal therapies, such as androgen deprivation therapy (ADT) and nonsteroidal antiandrogens (NSAA), do not count toward to the total number of prior lines. For Cohort G, prior immune checkpoint inhibitor (ICI) therapy is not allowed.

Subjects must have castration-level testosterone <50 ng/dL (≤1.73 nmol/L] following bilateral orchiectomy or by ongoing androgen-deprivation therapy (ADT) with a gonadotropin-releasing hormone (GnRH) agonist or antagonist that must be continued throughout the study.

Subjects must have progressive disease at study entry as defined by at least one of the following two criteria:

a. Prostate specific antigen (PSA) progression defined by a minimum of 2 rising PSA values from 3 or 4 consecutive assessments with an interval of at least 7 days between assessments. The most recent qualifying PSA value must be drawn within 28 days of planned enrollment. (Note: If qualifying solely by PSA progression, the screening lab PSA value must be at least 2 ng/mL [2 μg/L] but need not serve as last PSA value for determination of PSA progression; up to one PSA decrease is permitted as long as it is not the most recent value), OR b. Radiographic soft tissue disease progression in the opinion of the Investigator. Note: Bone disease progression alone does not qualify.

f. Cohort H (CRC): Subjects with histologically confirmed unresectable, locally advanced, or metastatic adenocarcinoma of the colon or rectum.

i. KRAS/NRAS wild-type, BRAF v600E wild-type ii. Subjects with known microsatellite instability-high (MSI-H) and/or mismatch repair (MMR) deficient disease are excluded.

iii. Must have radiographically progressed during or following systemic chemotherapy that contained a fluoropyrimidine (eg, 5-fluorouracil, capecitabine) in combination with oxaliplatin or irinotecan for metastatic disease iv. Received no more than two prior regimens for unresectable, locally advanced, or metastatic disease Note: Prior VEGF-targeted therapy is allowed.

g. Cohort I (UC, Maintenance Therapy): Subjects with histologically confirmed, unresectable, locally advanced or metastatic transitional cell carcinoma of the urothelium (including the renal pelvis, ureter, urinary bladder, or urethra)

i. Stage IV disease (T4b, NO, M0; any T, N1-N3, M0; any T, any N, M1) at the start date of first-line chemotherapy ii. Must have received at least 4 cycles but not more than 6 cycles of first-line chemotherapy of gemcitabine+cisplatin and/or gemcitabine+carboplatin. No other chemotherapy is allowed as first-line chemotherapy.

iii. Must have a disease status of an ongoing CR, PR, or SD per RECIST 1.1 as assessed by the investigator following completion of 4-6 cycles of first-line chemotherapy.

iv. The last dose of first-line chemotherapy must have been received no less than 4 weeks, and no more than 10 weeks before first dose of study treatment Note: Excluded are subjects with disease progression per RECIST 1.1 following first-line chemotherapy and subjects who have received prior adjuvant or neo-adjuvant systemic anticancer therapy within 12 months of first dose of study treatment.

h. Cohort J (UC, ICI-refractory): Subjects with histologically confirmed, unresectable, locally advanced or metastatic transitional cell carcinoma of the urothelium (including the renal pelvis, ureter, urinary bladder, or urethra)

i. Stage IV disease (T4b, NO, M0; any T, N1-N3, M0; any T, any N, M1)

ii. Must have progressed during or after PD-1/PD-L1 targeting ICI therapy received as the preceding line of treatment, either as monotherapy or in combination therapy.

Note: Subjects must have received a minimum of 6 weeks of prior immune checkpoint inhibitor therapy and must not have discontinued the immune checkpoint inhibitor therapy because of intolerability.

iii. Must have received no more than 2 prior lines of systemic anticancer therapies for unresectable, locally advanced or metastatic disease.

Note: Prior ICI therapy (except with avelumab) in combination with any other immunotherapy agent, chemotherapy, or VEGF-targeted therapy is allowed.

i. Cohort K (UC, platinum-refractory): Subjects with histologically confirmed, unresectable, locally advanced or metastatic transitional cell carcinoma of the urothelium (including the renal pelvis, ureter, urinary bladder, or urethra)
   i. Stage IV disease (T4b, NO, M0; any T, N1-N3, M0; any T, any N, M1)
   ii. Must have progressed during or after prior first-line platinum-based combination therapy.
   Note: Prior neoadjuvant or adjuvant platinum-containing combination therapy is allowed if disease recurred <12 months from the end of last therapy.
   iii. Must have received no more than 1 prior line of systemic anticancer therapy for unresectable locally advanced or metastatic disease.
   Note: Excluded are subjects who received prior PD-1/PD-L1 and/or VEGFR-targeted therapy for unresectable locally unresectable or metastatic disease.

2. Expansion Cohorts only: measurable disease per Response Evaluation Criteria in Solid Tumors version 1.1 (RECIST 1.1; Eisenhauer et al 2009) as determined by the investigator.
   Inclusion requirement does not apply for Cohort I (UC, Maintenance Therapy) Note: Measurable disease must be outside the radiation field if radiation therapy was administered.
3. Tumor tissue material:
   Subjects in the non-biomarker cohorts provide archival, if available, or fresh tumor tissue if it can be safely obtained.
   Subjects in the Biomarker Cohorts provide fresh tumor and skin biopsies.
4. Recovery to baseline or <Grade 1 severity (CTCAE v5) from adverse events (AEs), including immune-related adverse events (irAEs), related to any prior treatments, unless AE(s) are clinically nonsignificant and/or stable on supportive therapy (eg, physiological replacement of mineralocorticosteroid).
5. Age 18 years or older on the day of consent.
6. Eastern Cooperative Oncology Group (ECOG) Performance Status of 0-1.
7. Adequate organ and marrow function, based upon meeting all of the following laboratory criteria within 10 days before first dose of study treatment:
   a. Absolute neutrophil count (ANC) ≥1500/mm$^3$ (≥1.5 GI/L) without granulocyte colony-stimulating factor support within 2 weeks of screening laboratory sample collection.
   b. Platelets ≥100,000/mm$^3$ (≥100 GI/L) without transfusion within 2 weeks of screening laboratory sample collection.
   c. Hemoglobin ≥9 g/dL (≥90 g/L) without transfusion within 2 weeks prior to screening laboratory sample collection.
   d. International Normalized Ratio (INR)<1.5 and activated partial thromboplastin time (aPTT)<1.2×upper limit of normal (ULN).
   e. Alanine aminotransferase (ALT), aspartate aminotransferase (AST), and alkaline phosphatase (ALP) <3×ULN.

For subjects with documented bone metastasis ALP <5×ULN. For subjects with CRPC and bone metastasis ALP <10×ULN if predominantly bone-specific ALP.
   f. Total bilirubin <1.5×ULN (for subjects with Gilbert's disease <3×ULN).
   g. For subjects in the dose-escalation cohorts, serum creatinine <1.5×ULN or calculated creatinine clearance ≥60 mL/min (≥1.0 mL/sec) using the Cockcroft-Gault equation. For subjects in the Expansion Cohorts, serum creatinine <1.5×ULN or calculated creatinine clearance ≥40 mL/min (≥0.67 mL/sec).
   h. Urine protein-to-creatinine ratio (UPCR)<1 mg/mg (<113.2 mg/mmol) creatinine. For subjects with RCC: <1.5 mg/mg (<169.8 mg/mmol) creatinine; subjects with UC: <2 mg/mg (<226.4 mg/mmol) creatinine.
8. Capable of understanding and complying with the protocol requirements and must have signed the informed consent document.
9. Sexually active fertile subjects and their partners must agree to use highly effective methods of contraception during the course of the study and for 1 month after the last dose of Compound 1, for 1 month after the last dose of avelumab, or for 5 months after the last dose of atezolizumab. An additional contraceptive method, such as a barrier method (eg, condom), is required.
10. Female subjects of childbearing potential must not be pregnant at screening. Female subjects are considered to be of childbearing potential unless one of the following criteria is met: permanent sterilization (hysterectomy, bilateral salpingectomy, or bilateral oophorectomy) or documented postmenopausal status (defined as 12 months of amenorrhea in a woman >45 years-of-age in the absence of other biological or physiological causes. In addition, females <55 years-of-age must have a serum follicle stimulating hormone [FSH] level >40 mIU/mL to confirm menopause). Note: Documentation may include review of medical records, medical examination, or medical history interview by study site staff.

Exclusion Criteria:

1. Prior treatment with Compound 1 (all cohorts), prior treatment with PD-L1/PD-1 targeting immune checkpoint inhibitor (Cohorts E, F, G, H, I, and K only) or prior avelumab (Cohort J only).
2. Receipt of any type of small molecule kinase inhibitor (including investigational kinase inhibitor) within 2 weeks before first dose of study treatment.
3. Receipt of any type of anticancer antibody (including investigational antibody), systemic chemotherapy, or hormonal anticancer therapy (eg, antiandrogens for prostate cancer, aromatase inhibitors and selective estrogen receptor modulators for breast cancer) within 4 weeks before first dose of study treatment.
   Note: The antiandrogen abiraterone is permitted up to 1 week prior to first dose of study treatment. Concomitant use of megestrol acetate or leuprolide is permitted. Other types of hormonal therapies with similar use require prior Sponsor approval.
4. Radiation therapy for bone metastasis within 2 weeks, any other radiation therapy within 4 weeks before first dose of study treatment. Subjects with clinically relevant ongoing complications from prior radiation therapy are not eligible.
5. Known brain metastases or cranial epidural disease unless adequately treated with radiotherapy and/or surgery (including radiosurgery) and stable for at least 4 weeks before first dose of study treatment.

Note: Subjects with an incidental finding of an isolated brain lesion <1 cm in diameter may be eligible after Sponsor approval if the lesion is radiographically stable for 4 weeks before first dose and does not require treatment per Investigator judgement.

Note: Eligible subjects must be neurologically asymptomatic and without corticosteroid treatment at the time of first dose of study treatment.

6. Concomitant anticoagulation with oral anticoagulants (eg, warfarin, direct thrombin and Factor Xa inhibitors) and platelet inhibitors (eg, clopidogrel).

Note: Allowed anticoagulants are low-dose aspirin for cardioprotection (per local applicable guidelines) and low molecular weight heparins (LMWH). Therapeutic doses of LMWH are not permitted in subjects with known brain metastases.

Note: Subjects must have discontinued oral anticoagulants within 3 days or 5 half-lives prior to first dose of study treatment, whichever is longer.

7. Use of a strong cytochrome P450 CYP3A4 inhibitor or inducer within 5 half-lives prior to first dose of study treatment.
8. Use of a sensitive substrate of CYP3A4, CYP2C19, CYP2C9, or CYP2C8 within 5 half-lives prior to first dose of study treatment.
9. Use of a sensitive substrate of P-glycoprotein (P-gp) or breast cancer resistance protein (BCRP) transporter within 5 half-lives prior to first dose of study treatment.
10. The subject has uncontrolled, significant intercurrent or recent illness including, but not limited to, the following conditions:

a. Cardiovascular disorders:

i. Congestive heart failure New York Heart Association class 3 or 4, unstable angina pectoris, serious cardiac arrhythmias (eg, ventricular flutter, ventricular fibrillation, Torsades de pointes).

ii. Uncontrolled hypertension defined as sustained blood pressure (BP) >140 mm Hg systolic or 90 mm Hg diastolic despite optimal antihypertensive treatment.

iii. Stroke (including transient ischemic attack [TIA]), myocardial infarction, or other ischemic event or pulmonary embolism (PE) within 6 months before first dose. Upon Sponsor approval, subjects with a diagnosis of incidental, subsegmental PE or DVT within 6 months are allowed if stable, asymptomatic, and treated with anticoagulation for at least 2 weeks before first dose.

b. Gastrointestinal (GI) disorders including those associated with a high risk of perforation or fistula formation:

i. Tumors invading the GI-tract from external viscera.

ii. Active peptic ulcer disease, inflammatory bowel disease, diverticulitis, cholecystitis, symptomatic cholangitis or appendicitis, or acute pancreatitis.

iii. Acute obstruction of the bowel, gastric outlet, or pancreatic or biliary duct within 6 months unless cause of obstruction is definitively managed and subject is asymptomatic.

iv. Abdominal fistula, gastrointestinal perforation, bowel obstruction, or intra-abdominal abscess within 6 months before first dose.

Note: Complete healing of an intra-abdominal abscess must be confirmed before first dose.

v. Known gastric or esophageal varices.

c. Clinically significant hematuria, hematemesis, or hemoptysis of >0.5 teaspoon (2.5 mL) of red blood, or other history of significant bleeding (eg, pulmonary hemorrhage) within 12 weeks before first dose.

d. Cavitating pulmonary lesion(s) or known endobronchial disease manifestation.

e. Lesions invading major blood vessel including, but not limited to, inferior vena cava, pulmonary artery, or aorta.

Note: Subjects with intravascular tumor extension may be eligible following Sponsor approval.

f. Other clinically significant disorders such as:

i. Active infection requiring systemic treatment.

Note: Prophylactic antibiotic treatment is allowed.

ii. Known infection with acute or chronic hepatitis B or C, known human immunodeficiency virus (HIV) or acquired immunodeficiency syndrome (AIDS)-related illness.

iii. Known positive test for or suspected infection with SARS-CoV-2 within one month before enrollment. (Note: demonstration that the subject has fully recovered from the infection is required to be eligible for enrollment).

iv. Serious non-healing wound/ulcer/bone fracture.

Note: non-healing wounds or ulcers are permitted if due to tumor-associated skin lesions.

v. Malabsorption syndrome.

vi. Pharmacologically uncompensated, symptomatic hypothyroidism.

vii. Moderate to severe hepatic impairment (Child-Pugh B or C).

viii. Requirement for hemodialysis or peritoneal dialysis.

ix. History of solid organ or allogeneic stem cell transplant.

11. Major surgery (eg, GI surgery, removal or biopsy of brain metastasis) within 8 weeks prior to first dose. Prior laparoscopic nephrectomy within 4 weeks prior to first dose. Minor surgery (eg, simple excision, tooth extraction) within 10 days before first dose of study treatment. Complete wound healing from major or minor surgery must have occurred at least prior to first dose.

Note: Fresh tumor or skin biopsies should be performed at least 7 days before the first dose of study treatment. Subjects with clinically relevant ongoing complications from prior surgical procedures, including biopsies, are not eligible.

12. Corrected QT interval calculated by the Fridericia formula (QTcF) >460 ms within 10 days per electrocardiogram (ECG) before first dose of study treatment.

Note: Triplicate ECG evaluations will be performed and the average of these 3 consecutive results for QTcF will be used to determine eligibility. (If triplicate ECGs cannot be performed due to logistical challenges, single ECGs are permitted; however, if the single ECG read shows QTcF >460 ms, two additional ECGs must be performed to determine the average QTcF eligibility.)

13. History of psychiatric illness likely to interfere with ability to comply with protocol requirements or give informed consent.
14. Pregnant or lactating females.
15. Inability to swallow study treatment formulation.
16. Previously identified allergy or hypersensitivity to components of the study treatment formulations.

17. Any other active malignancy or diagnosis of another malignancy within 2 years before first dose of study treatment, except for superficial skin cancers, or localized, low grade tumors deemed cured and not treated with systemic therapy. Incidentally diagnosed prostate cancer is allowed if assessed as stage ≤T2N0M0 and Gleason score ≤6.

For Compound 1+Atezolizumab Combination Therapy Cohorts ONLY:

18. The subject has uncontrolled, significant intercurrent or recent illness including, but not limited to, the following conditions:
    a. Active or history of autoimmune disease or immune deficiency, including, but not limited to, myasthenia gravis, myositis, autoimmune hepatitis, systemic lupus erythematosus, rheumatoid arthritis, psoriatic arthritis, inflammatory bowel disease, antiphospholipid antibody syndrome, Wegener granulomatosis, Sjögren's syndrome, Guillain-Barre syndrome, or multiple sclerosis. Subjects with the following conditions are eligible for the study:
        i. A history of autoimmune-related hypothyroidism and on thyroid replacement hormone therapy
        ii. Controlled Type 1 diabetes mellitus and on an insulin regimen
        iii. Asthma
        iv. Eczema, psoriasis, lichen simplex chronicus, or vitiligo with dermatologic manifestations only provided all of following are true:
            Rash covers <10% of body surface area
            Disease is well controlled at baseline and requires only low-potency topical corticosteroids
            No occurrence of acute exacerbations of the underlying condition requiring psoralen plus ultraviolet A radiation, methotrexate, retinoids, biologic agents, oral calcineurin inhibitors, or high potency or oral corticosteroids within the previous 12 months
    b. Known positive test for tuberculosis infection if supported by clinical or radiographic evidence of disease.
    c. History of idiopathic pulmonary fibrosis, organizing pneumonia (eg, bronchiolitis obliterans), drug-induced pneumonitis, idiopathic pneumonitis, or evidence of active pneumonitis on screening chest computerized tomography (CT) scan. History of radiation pneumonitis in the radiation field (fibrosis) is permitted.
    d. Free thyroxine (FT4) outside the laboratory normal reference range. Asymptomatic subjects with FT4 abnormalities can be eligible after Sponsor approval.
19. Diagnosis of immunodeficiency or is receiving systemic steroid therapy (>10 mg daily prednisone equivalent) or any other form of immunosuppressive therapy within 2 weeks prior to first dose of study treatment. Inhaled, intranasal, intraarticular, and topical corticosteroids and mineralocorticoids are allowed.
    Note: Adrenal replacement steroid doses >10 mg daily prednisone equivalent are permitted in the absence of active autoimmune disease. Transient short-term use of higher doses of systemic corticosteroids for allergic conditions (eg, contrast allergy) is also allowed.
20. Administration of a live, attenuated vaccine within 30 days before first dose of study treatment.

For Compound 1+Avelumab Combination Therapy Cohorts ONLY:

21. The subject has uncontrolled, significant intercurrent or recent illness including, but not limited to, the following conditions
    i. Active autoimmune disease that might deteriorate when receiving an immunostimulatory agent.
    Note: Subjects with the following conditions are eligible for the study: Subjects with diabetes type I (controlled with an insulin regimen), vitiligo, psoriasis, hypo- or hyperthyroid disease not requiring immunosuppressive treatment. Administration of steroids through a route known to result in a minimal systemic exposure (topical, intranasal, intro-ocular, or inhalation) are acceptable.

Administration of a live, attenuated vaccine within 30 days before first dose of study treatment.

Estimated Length of Subject Participation

It is estimated that subjects with advanced solid tumors may receive study treatment for an average of approximately 6 months. The study is designed for subjects to receive study treatment for up to 24 months. Subjects will be followed until death, withdrawal of consent, or Sponsor decision to no longer collect these data.

Estimated Study Duration

It is estimated that approximately 24 to 36 months will be required to enroll and treat subjects in the study. The true study duration may be longer or shorter due to divergence from assumptions or due to the impact of the global COVID-19 pandemic on subject enrollment and other aspects of study conduct.

Investigational Regimen Dose/Route/Interval

Compound 1 was initially evaluated as a powder-in-bottle (PIB) formulation at 10-mg and 20-mg strengths. Tablet formulation of Compound 1 was introduced at 20-mg strength. As of Protocol Amendment 4, all subjects who were previously enrolled in PIB cohorts had either transitioned to a safe dose of Compound 1 as the tablet formulation or had discontinued Compound 1. The Compound 1 tablet formulation is now being used for all Compound 1 single-agent and combination therapy cohorts.

Compound 1 Tablets

Compound 1 tablet will be provided as 20-mg and 80-mg strengths. Tablets should be stored at controlled room temperature. In the initial dose escalation cohorts, subjects will take study medication orally once daily (qd).

Note: In case of lower Compound 1 dose levels than 80 mg qd, multiples of 20 mg tablets will be used; the lowest dose level in tablet formulation will be 20 mg every other day (qod; Section 6.2). In case of higher Compound 1 dose levels than 80 mg, a combination of 80 mg and 20 mg tablets will be used.

Compound 1 tablets should not be crushed or chewed. Subjects should be instructed not to eat for at least 2 hours before and at least 1 hour after taking Compound 1. The subject should take their assigned Compound 1 dose by mouth with a minimum of 8 oz (240 mL) of water. The starting Compound 1 tablet dose will be at 20 mg qd.

Atezolizumab

Atezolizumab (TECENTRIQ®) will be administered at a standard dosing regimen of 1200 mg as an IV infusion once every 3 weeks (q3w). The initial infusion of atezolizumab will be given over 60 (±15) minutes without premedication for potential infusion-related reactions or cytokine release syndrome (CRS). Subsequent IV infusions may be given over 30 (±10) minutes if the initial infusion is tolerated. Premedication for infusion-reaction is allowed after the initial infusion. No bolus or IV push of atezolizumab is allowed.

Avelumab

Avelumab (BAVENCIO®) will be administered at a standard dosing regimen of 800 mg as an IV infusion once every 2 weeks (q2w) and at least 14 days apart (−3/+1 days). Infusions of avelumab will be given over 60 (−10/+20) minutes with antihistamine and acetaminophen premedication administered 30 to 60 minutes prior to each avelumab infusion. Premedication is mandatory for the first four avelumab infusions. Premedication should be administered for subsequent avelumab doses based upon clinical judgment and presence/severity of prior infusion reaction. This regimen may be modified based on local treatment standards and guidelines as appropriate. However, the prophylactic use of systemic corticosteroids is not permitted.

Study Treatment Administration

The first doses of Compound 1, atezolizumab, and avelumab will be administered at the study site; for subjects receiving combination treatment, atezolizumab/avelumab is to be administered first. Following the first dose of Compound 1, the subject should take subsequent Compound 1 doses outside the clinic at approximately the same time every day, and should adhere to the fasting requirements described in this section.

Single-Agent Therapy Cohorts:

In the Dose-Escalation Stage, Compound 1 will be administered qd to fasted subjects on Days 1-28. Alternative dosing frequencies (eg, twice-daily dosing [bid]) may be explored in later cohorts if warranted based on emerging PK and clinical data and as permitted by the Cohort Review Committee. There will be a washout period (no study drug administration) on Days 29-35 inclusive (dose-escalation cohorts). Study drug administration will recommence on Day 36 (with no additional scheduled washout periods).

In the Cohort-Expansion Stage, Compound 1 (tablet formulation) will be administered to fasted subjects with no washout period. The other instructions above for study drug administration apply.

Compound 1+Atezolizumab Combination Therapy Cohorts:

In both the Dose Escalation and Cohort-Expansion Stages, Compound 1 drug will be administered qd to fasted subjects. Alternative dosing frequencies (eg, twice-daily dosing [bid]) may be explored in later cohorts if warranted based on emerging PK and clinical data and as permitted by the Cohort Review Committee. Subjects will also receive an IV infusion of the standard dose of atezolizumab once every 3 weeks (q3w) at the study site. Combination therapy dosing starts at day of first dose (SSV1/W1D1) with no washout period and until the subject terminates study treatment. Subjects will be monitored for at least 30 minutes in the clinic after each atezolizumab IV infusion.

Compound 1+Avelumab Combination Therapy Cohorts:

In both the Dose Escalation and Cohort-Expansion Stages, Compound 1 drug will be administered qd to fasted subjects. Alternative dosing frequencies (eg, twice-daily dosing [bid]) may be explored in later cohorts if warranted based on emerging PK and clinical data and as permitted by the Cohort Review Committee. Subjects will also receive an IV infusion of the standard dose of avelumab once every q2w at the study site. Combination therapy dosing starts at day of first dose (SSV1/W1D1) with no washout period and until the subject terminates study treatment. Subjects will be monitored for at least 30 minutes in the clinic after each avelumab IV infusion.

Biomarker Cohorts:

For all subjects enrolled in the biomarker cohorts (Dose-Escalation Stage for single-agent therapy and Cohort-Expansion Stage for combination therapy), Compound 1 dosing will be interrupted 48 hours prior to collection of the W4D7 (Day 28) biopsy, or W5D1 (Day 29) for avelumab combination cohorts, with adequate time [7 days minimum] to allow complete wound healing after the biopsy prior to resuming study treatment. If tumor biopsy is performed at screening, subjects must have complete wound healing before receiving their first Compound 1 dose. Please see Section 3.6.2 (single-agent Compound 1), Section 3.7.3 (Compound 1+atezolizumab combination therapy), and Section 3.8.3 (Compound 1+avelumab combination therapy) for further details.

Duration of Study Treatment

All subjects may continue to receive Compound 1 as a single agent or in combination for a total of up to 12 months and for an additional 12 months with the agreement of the Sponsor. Study treatment may continue after radiographic progression as long as the Investigator believes that the subject is still receiving clinical benefit from study treatment and that the potential benefit of continuing study treatment outweighs potential risk (Section 5.6.10.2).

Subject Replacement

During the Dose-Escalation Stage (Single-Agent and Combination Therapy):

If an enrolled subject in a dose-escalation cohort does not complete the DLT Evaluation Period for reasons other than safety (eg, withdrawal of consent, non-compliance, disease progression), he or she will be replaced (ie, an additional subject will be added to the cohort). The new subject will be considered for purposes of DLT evaluation; however, the subject who is replaced will not be considered for purposes of DLT evaluation but, if possible, will be followed for safety and other assessments.

During the Cohort-Expansion Stage (Single-Agent and Combination Therapy):

Subjects may be replaced only if they discontinue the study AND fail to complete any postbaseline tumor assessment for reasons known to be unrelated to safety or efficacy.

Subjects enrolled in the biomarker cohorts will not be replaced.

Study Assessments

Subjects enrolled into expansion cohorts will follow the schedule of assessments as specified below:

| Cohort | Subjects (N) | Treatment |
|---|---|---|
| Cohort A: ccRCC | 32 | Compound 1 |
| Cohort B: nccRCC | 32 | Compound 1 |
| Cohort C: HR + BC | 43 | Compound 1 |
| Cohort D: mCRPC | 39 | Compound 1 |
| Cohort E: nccRCC | 21 | Compound 1 + atezolizumab |
| Cohort F: HR + BC | 39 | Compound 1 + atezolizumab |
| Cohort G: mCRPC | 26 | Compound 1 + atezolizumab |
| Cohort H (Treatment Arm H-A): CRC | 40 | Compound 1 + atezolizumab |
| Cohort H (Treatment Arm H-B): CRC | 40 | Compound 1 |
| Cohort I: UC (Maintenance Therapy) | 50 | Compound 1 + avelumab |
| Cohort J (Treatment Arm J-A): UC (ICI-refractory) | 29 | Compound 1 + avelumab |
| Cohort J (Treatment Arm J-B): UC (ICI-refractory) | 29 | Compound 1 |
| Cohort K: UC (Platinum-refractory) | 29 | Compound 1 + avelumab |

Safety Assessments

Safety evaluations will include assessments of AEs, vital signs, electrocardiograms (ECGs), laboratory tests, and concomitant medications for all study cohorts. Adverse event seriousness, severity grade, and relationship to study treatment will be assessed by the investigator. Severity grade will be defined by the National Cancer Institute Common Terminology Criteria for Adverse Events version 5 (NCI CTCAE v5) guidelines.

Compound 1 Single-Agent Therapy

Safety for subjects receiving single-agent therapy will be assessed on a schedule starting on the date of first dose, ie, Week 1 Day 1 (WiD1).

Compound 1+Atezolizumab Combination Therapy

Safety for subjects receiving Compound 1+atezolizumab combination therapy, will be assessed on a schedule based on the date of first dose, ie, Study Safety Visit 1 (SSV1)/W1D1. An SSV is required prior to each planned infusion of atezolizumab (the SSV is allowed to occur any time within 72 hours prior to the infusion but vital signs must be assessed within 60 min prior to initiation of the infusion). SSVs will be performed at least every 3 weeks (ie, no more than 3 weeks apart) regardless of whether an infusion with atezolizumab is planned or not. Additional visits for safety and other assessments are required during the DLT Evaluation Period.

Compound 1+Avelumab Combination Therapy

Safety for subjects receiving Compound 1+avelumab combination therapy, will be assessed on a schedule based on the date of first dose, ie, Study Safety Visit 1 (SSV1)/W1D1. An SSV is required prior to each planned infusion of avelumab (the SSV is allowed to occur any time within 72 hours prior to the infusion but vital signs must be assessed within 60 min prior to initiation of the infusion). SSVs will be performed at least every 2 weeks (ie, no more than 2 weeks apart) regardless of whether an infusion with avelumab is planned or not. Additional visits for safety and other assessments are required during the DLT Subjects in Cohort J randomized to receive Compound 1 single-agent therapy (Treatment Arm J-B) will adhere to the same safety assessments as subjects receiving Compound 1+avelumab combination therapy.

Subject Daily Dosing Diary

For both the Dose-Escalation Stage and Cohort-Expansion Stage (both single agent and combination therapy cohorts), at the time of drug dispensation starting on W1D1, subjects will be provided with a daily dosing diary with instructions to record Compound 1 treatment for the first 6 months of their treatment. The diary will be returned at the subsequent drug dispensing clinic visit and a new diary issued to the subject.

Tumor Assessments

Tumors will be assessed using the RECIST 1.1 criteria. Subjects will be assessed using magnetic resonance imaging (MRI) or CT scans during screening and periodically after the date of the first dose of study treatment until radiographic PD per RECIST 1.1 as determined by the Investigator. However, study treatment may be continued after radiographic progression as long as the Investigator believes that the subject is still receiving clinical benefit from study treatment and that the potential benefit of continuing study treatment outweighs potential risk. Radiographic tumor assessments will continue on the protocol-defined schedule, regardless of whether study treatment is reduced, interrupted, delayed, or discontinued.

Chest/Abdomen/Pelvis (CAP): CT of CAP or CT chest and MRI abdomen/pelvis will be performed in all subjects at screening and at every 8 weeks (±5 days) for subjects enrolled in Compound 1 single-agent therapy, every 9 weeks (±5 days) for subjects receiving Compound 1+atezolizumab combination therapy, and every 8 weeks (±5 days) for subjects receiving Compound 1+avelumab combination therapy after initiation of study treatment throughout the first 12 months on study. Note: CT/MRI scans for subjects enrolled in Cohort J (UC), both treatment arms (J-A and J-B) will be on the same imaging schedule of every 8 weeks (±5 days) after initiation of study treatment throughout the first 12 months on study. CT/MRI scans for subjects enrolled in Cohort H (CRC), both treatment arms (H-A and H-B) will be on the same imaging schedule of every 9 weeks (±5 days) after initiation of study treatment throughout the first 12 months on study. Upon completion of 12 months on study, these assessments will be performed every 12 weeks (±7 days) for all subjects.

Technetium bone scans or PET imaging for bone metastasis (eg, 18F-NaF) are not part of study-mandated assessments but can be used per standard clinical practice to direct corroborative CT/MRI imaging per RECIST 1.1. Bone lesions, without soft tissue component, corroborated by CT/MRI must be reported as non-target or new lesions.

Brain: MRI (or CT) of the brain will be performed at screening in all subjects. Prior brain imaging performed as standard of care up to 45 days before first dose of study treatment can be used for eligibility determination. After study treatment initiation MRI (or CT) scans of the brain are only required in subjects with documented brain metastasis or if clinically indicated by signs and symptoms suggestive of new brain metastases. Assessments after the first dose of study treatment will be performed every 8 weeks (±5 days) for subjects receiving Compound 1 single-agent therapy, every 9 weeks (±5 days) for subjects receiving Compound 1+atezolizumab combination therapy, and every 8 weeks (±5 days) for subjects receiving Compound 1+avelumab combination therapy. Note: MRI (or CT) scans for subjects in Cohort J (UC), both treatment arms (J-A and J-B), will be on the same imaging schedule of every 8 weeks (±5 days) after initiation of study treatment throughout the first 12 months on study. MRI (or CT) scans for subjects enrolled in Cohort H (CRC), both treatment arms (H-A and H-B) will be on the same imaging schedule of every 9 weeks (±5 days) after initiation of study treatment throughout the first 12 months on study. Upon completion of 12 months on study, these assessments will be performed every 12 weeks (±7 days) for all subjects. MRI is the preferred imaging method for brain. If CT of the brain is performed instead of MRI, ambiguous results must be confirmed by MRI. Subjects without documented brain metastasis during the screening assessment are not required to undergo brain imaging after initiating study treatment unless clinically indicated. In order to meet the eligibility requirements of the study, brain metastasis must have been treated and stable for at least 4 weeks before first dose.

For the purpose of determining radiographic study endpoints, radiographic response and PD will be determined using RECIST 1.1 (by Investigator and BIRC [as applicable]) for selected cohorts. Investigators are encouraged to continue study treatment and imaging until the subject is no longer clinically benefitting.

Overall Survival Follow-Up Assessments

All subjects will be contacted approximately every 12 weeks (±14 days) after their last post-treatment follow-up visit to assess survival status and to document receipt of systemic NPACT unless consent to participate in non-interventional study assessments is withdrawn, or the Sponsor deems sufficient efficacy data have been collected for the study.

Pharmacokinetic Assessments

Blood samples will be obtained to assess the PK of Compound 1 and its potential metabolites for single agent and combination therapies. Blood samples for atezolizumab or avelumab PK will also be collected for combination therapy cohorts.

Single-Agent Therapy Cohorts For Dose-Escalation Stage:
- Blood samples to assess the PK of Compound 1 and its potential metabolites will be obtained during the DLT Evaluation Period:
  - On the date of first dose of study treatment (prior to study treatment administration) at hourly intervals up to 8 hours postdose on W1D1 and W4D7 (Day 28)
  - Predose on W1D2
  - Predose and 2 hours postdose on W2D1, W3D1, and W4D1
  - During the Washout Period on W5D1, W5D2, W5D3, and W5D5 (W5D2, W5D3, and W5D5 PK samples are not required for biomarker cohorts.)
- Blood samples for PK analysis will be obtained after the DLT Evaluation and Washout Periods
  - Predose and 2 hours postdose on W6D1, W9D1, and W13D1.
- For Cohort-Expansion Stage:
- Blood samples will be obtained to assess the PK of Compound 1 and its potential metabolites. PK samples will be obtained predose and 2-hour postdose on W1D1, W3D1, W5D1, W9D1, and W13D1 (Days 1, 15, 29, 57, and 85 respectively).

Compound 1+Atezolizumab Combination Therapy Cohorts For the Dose-Escalation Stage:
- Blood samples will be obtained to assess the PK of Compound 1 and its potential metabolites:
  - During the DLT Evaluation Period, predose and at hourly intervals up to 8 hours postdose on SSV1 (W1D1) and W3D7 (Day 21); predose on W1D2; predose and 2 hours postdose on W2D1, W3D1, and W4D1 (SSV2)
  - After the DLT Evaluation, predose and 2 hours postdose on SSV3, SSV4, and SSV5
- Blood samples will be obtained for serum atezolizumab concentration measurement:
  - Predose and at the end of infusion on SSV1 (W1D1), SSV2, SSV3, SSV4, SSV5, SSV9, and at the Post-Treatment Follow-up visit For the Cohort-Expansion Stage:
- Blood samples will be obtained for Compound 1 and its potential metabolites at predose and 2 hours postdose at SSV1 (W1D1), SSV2, SSV3, SSV4, and SSV5.
- Blood samples will be collected for serum atezolizumab concentration measurement predose and at the end of infusion on SSV1 (W1D1), SSV2, and predose at SSV3, SSV4, SSV5, and SSV9, and at the Post-Treatment Follow-up visit.

Compound 1+Avelumab Combination Therapy Cohorts For the Dose-Escalation Stage:
- Blood samples will be obtained to assess the PK of Compound 1 and its potential metabolites:
  - During the DLT Evaluation Period, predose and at hourly intervals up to 6 hours postdose on SSV1 (W1D1) and W3D7 (Day 21); predose on W1D2; predose and 2 hours postdose on W2D1, W3D1 (SSV2), and W3D7.
  - After the DLT Evaluation, predose and 2 hours postdose on W4D1, SSV3, SSV4, SSV5, and SSV7.
- Blood samples will be obtained for serum avelumab concentration measurement:
  - Predose and at the end of infusion on SSV1 (W1D1), SSV2 (W3D1), SSV3, SSV5, SSV9, SSV13, and at the Post-Treatment Follow-up visit.
- For the Cohort-Expansion Stage:
- Blood samples will be obtained for Compound 1 and its potential metabolites at predose and 2 hours postdose at SSV1 (W1D1), SSV2 (W3D1), SSV3, SSV4, SSV5, and SSV7.
- Blood samples will be collected for serum avelumab concentration measurement predose and at the end of infusion on SSV1 (W1D1), SSV2 (W3D1), and predose at SSV3, SSV5, SSV9, SSV13, and at the Post-Treatment Follow-up visit.

Immunogenicity Assessments

Blood samples will be obtained from all subjects in the Compound 1+atezolizumab combination therapy cohorts during the Dose-Escalation Stage and the Cohort-Expansion Stage for immunogenicity assessment predose on SSV1 (W1D1), SSV3, SSV5, SSV9, and at the Post-Treatment Follow-up visits.

Blood samples will be obtained from all subjects in the Compound 1+avelumab combination therapy cohorts during the Dose-Escalation Stage and the Cohort-Expansion Stage for immunogenicity assessment predose on SSV1 (W1D1), SSV3, SSV5, SSV9 and SSV13 and at the Post-Treatment Follow-up visit.

Immunogenicity assessments are not required for subjects receiving Compound 1 single-agent therapy.

Biomarker Assessments

Peripheral blood samples will be obtained for either single-agent or combination therapy cohorts.

For all subjects except those in the biomarker cohorts, tumor tissue (most recent archival tissue) will be obtained prior to first dose of study treatment. If archival tissue is not available then a fresh tumor biopsy will be taken if it can be safely acquired.

For subjects in the biomarker cohorts fresh tumor and skin biopsies will be obtained prior to first dose of study treatment and approximately 4 weeks after first dose. If subjects require a tumor biopsy at screening, this screening biopsy must be completed at least 7 days prior to study treatment initiation and subjects must have complete wound healing before receiving their first dose of Compound 1. Compound 1 dosing will be interrupted 48 hours prior to collection of the Day 28 biopsy (Day 29 biopsy for avelumab combination cohorts) with adequate time [7 days minimum] to allow complete wound healing after the on-treatment biopsy prior to resuming study treatment.

Exploratory analyses may include the following:
- Genomic and expression analyses (eg, mutation alterations, tumor mutational burden [TMB], mismatch repair/microsatellite instability [MMR/MSI], etc)
  - Baseline expression of relevant targets
  - If tumor biopsies are consented and obtained, exploratory analyses may include but not be limited to changes in relevant biomarkers Pharmacogenetic analyses Plasma biomarker analysis Immune cell profiling (eg, T cells, monocytes, other relevant cell types)

Other analyses relevant for specific indications (eg, metabolomics, circulating tumor cells [CTCs], circulating tumor DNA [ctDNA])

Samples may also be used for assay development to facilitate identification of new biomarkers. Collection of biomarker samples may be halted early or sampling frequency may be modified at the discretion of the Sponsor.

Statistical Methods

The number of subjects per single-agent Dose-Escalation cohort has been chosen based on a well-established Phase 1 dose-escalation "3+3" trial design. Subjects are accrued into cohorts in a "3+3" manner with each cohort consisting initially of 3 subjects and potentially expanding to 6 subjects based upon the number of DLTs observed. In addition, the Cohort Review Committee may decide that an additional 6 subjects at any dose level including the MTD/RD (total of up to 18 subjects) should be enrolled in order to obtain additional safety or PK data.

The Dose-Escalation Stage for Compound 1 in combination with atezolizumab or in combination with avelumab will use a "rolling six" study design to determine the MTD/RD and/or the MAD for Compound 1. The design will allow for concurrent accrual of 6 subjects in a safety cohort. Up to 6 additional subjects may be enrolled to establish the MTD/RD for combination therapy.

Summaries will focus on AEs and tumor response by cohort. Adverse events will be tabulated by Medical Dictionary for Regulatory Activities (MedDRA) system organ class (SOC) and preferred term (PT). Selected laboratory parameters will be summarized.

Each of the cohorts in the Cohort-Expansion Stages for single-agent Compound 1 and for the combination therapy, except Cohort H and Cohort I, will utilize Simon's optimal two-stage design (Simon 1989) assuming a power of 80% and one-sided a of 5%.

For Cohort H and Cohort I, the sample size calculations are based on a precision approach with respect to the Kaplan-Meier estimate of the six month PFS. The goal of this method is to estimate this parameter with a specified level of precision. For Cohort H, the rationale for this approach is based on the fact that objective tumor responses using a VEGFR TKI are not expected in this population. For Cohort I, the rationale is based on the fact that avelumab has demonstrated improvement of PFS in this patient population.

Single-Agent Therapy Expansion Cohorts

Single-agent Cohort A and B: For the evaluation of single-agent Compound 1 therapy in each of the ccRCC and nccRCC expansion cohorts A and B, the maximum objective response rate (ORR) of a definitely ineffective drug (p0) is assumed to be 1% under the null hypothesis and the minimum clinically meaningful response rate of an effective drug (p 1) is assumed to be 12% under the alternative hypothesis. Fourteen subjects will be enrolled in Stage 1 of each of these cohorts. A cohort will be stopped for futility if there are no responders out of these 14 subjects. In a given cohort, if there is at least one responder in Stage 1 then an additional 18 subjects will be enrolled in Stage 2. A cohort will be deemed successful if there are at least two responders out of a total of 32 subjects in that cohort. The probability of stopping early after Stage 1 under the null hypothesis, ie, for an ineffective drug, is nearly 87%.

Single-agent Cohort C: For the evaluation of single-agent Compound 1 therapy in the HR+BC expansion cohort C, the maximum ORR of a definitely ineffective drug (p0) is assumed to be 1% under the null hypothesis and the minimum clinically meaningful response rate of an effective drug (p1) to be 9% under the alternative hypothesis. Nineteen subjects will be enrolled in Stage 1 of this cohort. The cohort will be stopped for futility if there are no responders out of these 19 subjects. If there is at least one responder in Stage 1, then an additional 24 subjects will be enrolled in Stage 2. The cohort will be deemed successful if there are at least two responders out of a total of 43 subjects in the cohort. The probability of stopping early after Stage 1 under the null hypothesis, ie, for an ineffective drug, is nearly 83%.

Single-agent Cohort D: For the evaluation of single-agent Compound 1 therapy in the mCRPC expansion cohort D, the maximum ORR of a definitely ineffective drug (p0) is assumed to be 1% under the null hypothesis and the minimum clinically meaningful response rate of an effective drug (p1) to be 10% under the alternative hypothesis. Seventeen subjects will be enrolled in Stage 1 of this cohort. The cohort will be stopped for futility if there are no responders out of these 17 subjects. If there is at least one responder in Stage 1, then an additional 22 subjects will be enrolled in Stage 2. The cohort will be deemed successful if there are at least two responders out of a total of 39 subjects in the cohort. The probability of stopping early after Stage 1 under the null hypothesis, ie, for an ineffective drug, is nearly 85%.

Single-agent Cohort H-B: Subjects enrolled in Cohort H will be randomized between Cohort H-A (Compound 1+atezolizumab) and Cohort H-B (single-agent Compound 1). The cohort size calculation is based on estimation of the expected PFS rate at 6 months using a hybrid Kaplan-Meier estimator with an exponential tail. A sample size of 40 subjects for each cohort (80 in total) was selected that results in an acceptable average difference between the Kaplan Meier Product Limit PFS rate at 6 months and the lower one-sided 90% confidence limit for this same timepoint. The average difference between the Kaplan Meier Product Limit PFS rate at 6 months and the lower one-sided 90% confidence limit was calculated via a simulation study. In the simulation study, a total of 2500 simulations were performed. An accrual rate of 5 subjects per month and a minimum follow up after the last subject enrolled of 6 months was used for the sample size calculation. Moreover, the overall median PFS is assumed to be 3 months (corresponding to a 25% 6-month PFS rate). Based on these assumptions the average one-sided 90% CI half-width is 7.2% for data generated under an exponential distribution.

Single-agent Cohort J-B: For the evaluation of the Compound 1 single agent combination therapy in the mUC expansion cohort J (ICI-refractory) the maximum ORR of a definitely ineffective drug (p0) to be 5% under the null hypothesis and the minimum clinically meaningful response rate of an effective drug (p1) to be 20% under the alternative hypothesis. Ten (10) subjects will be enrolled in Stage 1 of each cohort (JA and J-B). The cohort will be stopped for futility if there are no responders out of these 10 subjects. If there is at least one responder in Stage 1, then an additional 19 subjects will be enrolled in Stage 2. The cohort will be deemed successful if there are at least 4 responders out of a total of 29 subjects in the cohort. The probability of stopping early after Stage 1 under the null hypothesis, ie, for an ineffective drug, is nearly 60%.

Compound 1+Atezolizumab Combination Therapy Expansion Cohorts

Combination Cohort E: For the evaluation of Compound 1+atezolizumab combination therapy in the nccRCC expansion cohort E, the maximum objective response rate (ORR) of a definitely ineffective drug (p0) is assumed to be 1% under the null hypothesis and the minimum clinically meaningful response rate of an effective drug (p1) is assumed to be 18% under the alternative hypothesis. Nine subjects will be enrolled in Stage 1 of each of these cohorts. A cohort will be stopped for futility if there are no responders out of these 9 subjects. In a given cohort, if there is at least one responder in Stage 1 then an additional 12 subjects will be enrolled in Stage 2. A cohort will be deemed successful if there are at least two responders out of a total of 21 subjects in that cohort. The probability of stopping early after Stage 1 under the null hypothesis, ie, for an ineffective drug, is around 91%.

Combination Cohort F: For the evaluation of Compound 1+atezolizumab combination therapy in the HR+BC expansion cohort F, the maximum ORR of a definitely ineffective drug (p0) is assumed to be 1% under the null hypothesis and the minimum clinically meaningful response rate of an effective drug (p1) to be 10% under the alternative hypothesis. Seventeen subjects will be enrolled in Stage 1 of this cohort. The cohort will be stopped for futility if there are no responders out of these 17 subjects. If there is at least one responder in Stage 1, then an additional 22 subjects will be enrolled in Stage 2. The cohort will be deemed successful if there are at least two responders out of a total of 39 subjects in the cohort. The probability of stopping early after Stage 1 under the null hypothesis, ie, for an ineffective drug, is nearly 85%.

Combination Cohort G: For the evaluation of the Compound 1+atezolizumab combination therapy in the mCRPC expansion cohort G, the maximum ORR of a definitely ineffective drug (p0) is assumed to be 1% under the null hypothesis and the minimum clinically meaningful response rate of an effective drug (p1) to be 15% under the alternative hypothesis. Eleven subjects will be enrolled in Stage 1 of this cohort. The cohort will be stopped for futility if there are no responders out of these 11 subjects. If there is at least one responder in Stage 1, then an additional 15 subjects will be enrolled in Stage 2. The cohort will be deemed successful if there are at least two responders out of a total of 26 subjects in the cohort. The probability of stopping early after Stage 1 under the null hypothesis, ie, for an ineffective drug, is around 89%.

Combination Cohort H-A: Subjects enrolled in Cohort H will be randomized between Cohort H-A (Compound 1+atezolizumab) and Cohort H-B (single-agent Compound 1). The cohort size calculation is based on estimation of the expected PFS rate at 6 months using a hybrid Kaplan-Meier estimator with an exponential tail. A sample size of 40 subjects for each cohort (80 in total) was selected that results in an acceptable average difference between the Kaplan Meier Product Limit PFS rate at 6 months and the lower one-sided 90% confidence limit for this same timepoint. The average difference between the Kaplan Meier Product Limit PFS rate at 6 months and the lower one-sided 90% confidence limit was calculated via a simulation study. In the simulation study, a total of 2500 simulations were performed. An accrual rate of 5 subjects per month and a minimum follow up after the last subject enrolled of 6 months was used for the sample size calculation. Moreover, the overall median PFS is assumed to be 3 months (corresponding to a 25% 6-month PFS rate). Based on these assumptions the average one-sided 90% CI half-width is 7.2% for data generated under an exponential distribution.

Compound 1+Avelumab Combination Therapy Expansion Cohorts

Combination Cohort I: For the evaluation Compound 1+avelumab combination therapy in the UC maintenance therapy Cohort I, the cohort size calculation is based on estimation of the expected PFS rate at 6 months using a hybrid Kaplan-Meier estimator with an exponential tail. A cohort size of 50 subjects was selected that results in an acceptable average difference between the Kaplan Meier Product Limit PFS rate at 6 months and the lower one-sided 90% confidence limit for this same timepoint. The average difference between the Kaplan Meier Product Limit PFS rate at 6 months and the lower one-sided 90% confidence limit was calculated via a simulation study. In the simulation study, a total of 2500 simulations were performed. An accrual rate of 5 subjects per month and a minimum follow up after the last subject enrolled of 6 months was used for the sample size calculation. Moreover, the overall median PFS is assumed to be 6 months (corresponding to a 50% 6-month PFS rate). Based on these assumptions the average 90% one-sided CI half-width is 8.2% for data generated under an exponential distribution.

Combination Cohort J-A: Subjects enrolled in Cohort J will be randomized between Cohort J-A (Compound 1+avelumab) and Cohort J-B (single-agent Compound 1). For the evaluation of mUC expansion cohort J (ICI-refractory) the maximum ORR of a definitely ineffective drug (p0) to be 5% under the null hypothesis and the minimum clinically meaningful response rate of an effective drug (p1) to be 20% under the alternative hypothesis. Ten (10) subjects will be enrolled in Stage 1 of each cohort. Either cohort will be stopped for futility if there are no responders out of these 10 subjects. If there is at least one responder in Stage 1, then an additional 19 subjects will be enrolled in Stage 2. The cohort will be deemed successful if there are at least 4 responders out of 29 subjects (58 in total) in the cohort. The probability of stopping early after Stage 1 under the null hypothesis, ie, for an ineffective drug, is nearly 60%.

Combination Cohort K: For the evaluation of the Compound 1+avelumab combination therapy in the mUC expansion cohort K (platinum-refractory), the maximum ORR of a definitely ineffective drug (p0) to be 10% under the null hypothesis and the minimum clinically meaningful response rate of an effective drug (p1) to be 30% under the alternative hypothesis. Ten (10) subjects will be enrolled in Stage 1 of this cohort. The cohort will be stopped for futility if there are not 2 responders out of these 10 subjects. If there are at least 2 responders in Stage 1, then an additional 19 subjects will be enrolled in Stage 2. The cohort will be deemed successful if there are at least 6 responders out of a total of 29 subjects in the cohort. The probability of stopping early after Stage 1 under the null hypothesis, ie, for an ineffective drug, is around 74%.

Methodology

Descriptive statistics will be provided for ORR, duration of response, and progression-free survival (PFS) estimates for the Cohort-Expansion Stage. The ORR will also be estimated for each of the cohorts in the Dose-Escalation Stage.

All subjects will be followed for overall survival (OS) and OS estimates will be provided for the Dose-Escalation and Cohort-Expansion Stage cohorts.

The sample size may be increased up to an additional 25% if a review of the accumulating data suggests that the COVID-19 pandemic has caused the rate of study dropout or non-compliance to increase to a degree that the ability to adequately evaluate study endpoints may be undermined.

Example 34: A Safety and Pharmacokinetics Study of Compound 1 and Avelumab as a Combination Therapy in Subjects with Advanced Urothelial Carcinoma This first-in-human (FIH) study evaluates safety, tolerability, and preliminary antitumor activity of Compound 1 in combination with avelumab.

Avelumab is a humanized immunoglobulin G1 (IgG1) monoclonal antibody that targets programmed death ligand 1 (PD-L1) and inhibits the interaction between PD-L1 and its receptors, programmed death receptor 1 (PD-1).

Avelumab infusion has been approved by regulatory agencies in the US and European Union and other regions as single-agent therapy for patients with Merkel-cell carcinoma, in combination with chemotherapy for extensive-stage small cell lung cancer (ES-SCLC), in combination with axitinib for the first-line treatment of people with advanced renal cell carcinoma.

Based on the target profile of Compound 1, an inhibitor of multiple RTKs involved in tumor cell proliferation, neovascularization, and immune cell regulation, as well as its demonstrated preclinical and preliminary clinical benefit, there is a clear rationale for evaluating Compound 1 in combination with avelumab as a potential new treatment opportunity for subjects with advanced urothelial carcinoma.

Expansion Cohort 1

This Phase 1 study will include subjects with advanced urothelial carcinoma who has received first-line platinum-based doublet chemotherapy. This is a non-randomized single arm cohort of Compound 1+Avelumab as maintenance therapy. The number of subjects is about 30-40.

The objectives of the study are the determination of the safety and tolerability of Compound 1+Avelumab combination and the determination of the preliminary efficacy of the combination.

Disease specific inclusion criteria:

- Histologically confirmed, unresectable locally advanced or metastatic transitional cell carcinoma of the urothelium (including renal pelvis, ureter, urinary bladder, urethra)
- Stage IV disease per AJCC TNM staging criteria ($8^{th}$ edition, 1 Jan. 2018) at the start date of first-line platinum-based chemotherapy
- Archival tumor tissue or freshly obtained tumor tissue by core needle biopsy or excision for PD-L1 expression status testing
- Measurable disease prior to start of first-line chemotherapy by RECIST 1.1
  - Must have received prior first-line platinum-based doublet chemotherapy (gemcitabine+cisplatin and/or gemcitabine+carboplatin) of at least 4 cycles but not more than 6 cycles. No other chemotherapy regimen is allowed as the first-line chemotherapy.
  - The last dose of first-line chemotherapy must have been received no less than 4 weeks, and no more than 10 weeks, prior to first dose of study treatment.
  - Must have radiographically documented CR, PR or SD by RECIST 1.1 per investigator assessment following completion of 4-6 cycles of platinum-based doublet chemotherapy.
- Estimated creatinine clearance ≥40 mL/min as calculated using the Cockcroft-Gault equation or by 24-hour urine collection for creatinine clearance.
- AST/ALT <3×ULN (for subjects with liver metastasis AST/ALT <5×ULN); Total bilirubin <1.5×ULN.

Disease specific exclusion criteria:

- Subjects with progressive disease by RECIST 1.1 following first-line platinum-based doublet chemotherapy for urothelial carcinoma.
- Prior adjuvant or neoadjuvant systemic anticancer therapy within 12 months of first dose of study treatment.
- Prior immunotherapy with IL-2, IFN-α or any anti-PD-1, anti-PD-L1, anti-PD-L2, anti-CD137, or CTLA-4 antibody (including ipilimumab), or any other antibody or drug specifically targeting T-cell co-stimulation or immune checkpoint.

Enrollment process:

Enrollment in study must occur at least 4 weeks but not more than 10 weeks after the date of administration of the last dose of first-line platinum-based doublet chemotherapy. Subjects will initiate study treatment (Cycle 1 Day 1) within 3 days after enrollment.

Post-chemotherapy confirmatory scans for study eligibility must be performed within 28 days prior to planned enrollment in the study to assess response status following first-line platinum-based doublet chemotherapy.

Figure 12:
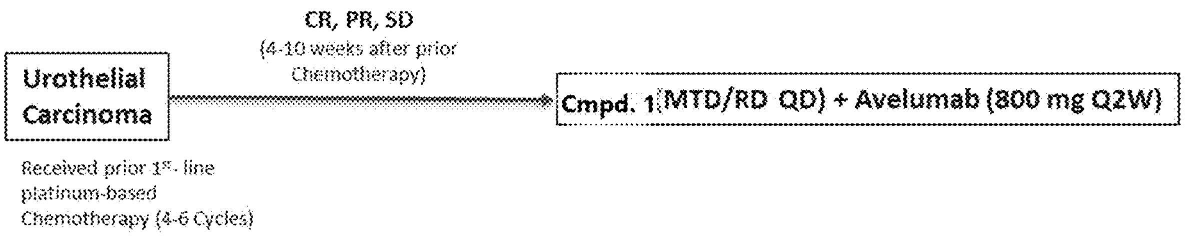

FIG. 12 shows the design of this study.

Expansion Cohort 2

This study evaluates the combination of Compound 1+Avelumab as Second or Third-Line therapy following platinum-based doublet chemotherapy in subjects with advanced Urothelial Carcinoma. This is a randomized two-arm cohort of Compound 1+Avelumab versus Compound 1+BSC. The number of subjects for each arm is about 30-40.

The objectives of the study are the determination of the safety and tolerability of Compound 1+Avelumab combination versus Compound 1 alone, and the determination of the preliminary efficacy of the combination versus Compound 1 alone.

Disease specific inclusion criteria:

- Histologically confirmed, unresectable locally advanced or metastatic transitional cell carcinoma of the urothelium (including renal pelvis, ureter, urinary bladder, urethra)
- Stage IV disease per AJCC TNM staging criteria ($8^{th}$ edition, 1 Jan. 2018)
- Archival tumor tissue or freshly obtained tumor tissue by core needle biopsy or excision for PD-L1 expression status testing
- Measurable disease by RECIST 1.1
- Must have progressed after prior first-line platinum-based doublet chemotherapy (gemcitabine+cisplatin and/or gemcitabine+carboplatin).
  - Subjects may have received prior neoadjuvant or adjuvant platinum-containing therapy if disease recurred <12 months from the end of last therapy.
  - Must have received no more than 3 prior regimens for advanced urothelial carcinoma. Note prior therapy with antibody-drug conjugate agents is allowed.
- Estimated creatinine clearance ≥40 mL/min as calculated using the Cockcroft-Gault equation or by 24-hour urine collection for creatinine clearance
- AST/ALT≤3×ULN, Total bilirubin≤1.5×ULN Disease specific exclusion criteria:

- Prior therapy with Compound 1 or cabozantinib
- Prior immunotherapy with IL-2, IFN-α or any anti-PD-1, anti-PD-L1, anti-PD-L2, anti-CD137, or CTLA-4 antibody (including ipilimumab), or any other antibody or drug specifically targeting T-cell co-stimulation or immune checkpoint pathways.

Figure 13:
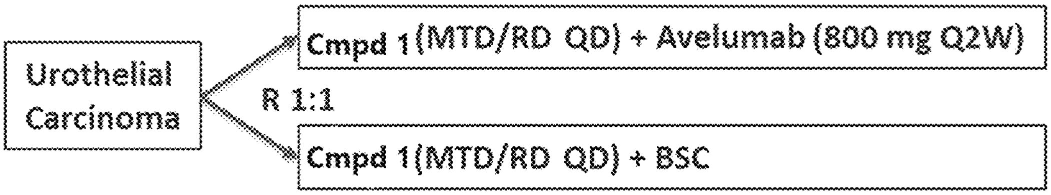

FIG. 13 shows the design of this study.

Dose-Escalation Stage

If necessary, dose escalation stage will be implemented. This stage is to determine the safety, tolerability, and MTD/RD of Compound 1+Avelumab combination. The number of subjects is about 18. There will be two dose escalation steps using a "3+3" trial design:

Dose Level 1 (DL1): Safe dose of Compound 1 below MTD/RD from ongoing Phase 1 study of Compound 1.

DL2: MTD/RD from ongoing Phase 1 study of Compound 1.

Figure 14:
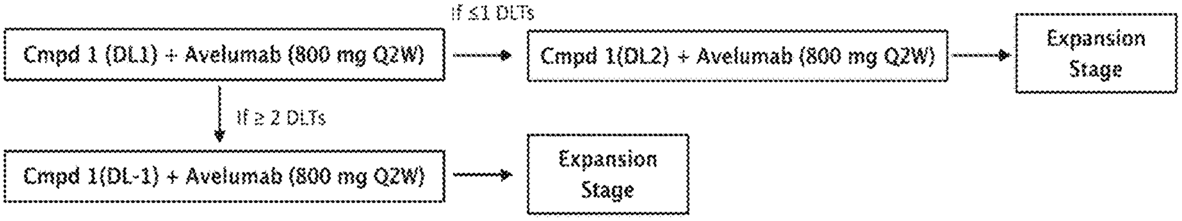

FIG. 14 shows the design of this study.

Example 35: Dose-Escalation and Expansion Study of the Safety and Efficacy of Compound 1 in Combination with Immuno-Oncology Agents in Subjects with Unresectable Advanced or Metastatic Solid Tumors Receptor tyrosine kinases (RTKs) play important roles in a number of cellular processes, including cellular proliferation, survival, and migration (Bhullar et al 2018). Dysregulation leading to elevated kinase expression or constitutive activation is associated with oncogenesis. In addition, several RTKs are known to contribute to the regulation of anti-tumor immune response (Paolino and Penninger 2016). As a result, RTK inhibition provides a strong rationale for developing new therapies for the treatment of cancer. Furthermore, antibodies targeting the T-cell inhibitory checkpoint proteins PD(L)1 or CTLA-4 have shown potent antitumor activities as single agents or in combination therapy and are approved for the treatment of a variety of tumors including genitourinary cancers such as renal cell carcinoma (RCC) and urothelial carcinoma (UC). Despite the broad applicability of PD(L)1 and CTLA-4 targeting agents, there is a significant variability in treatment outcome with the approved checkpoint inhibitors, and only a subset of patients with advanced disease stage experience long lasting responses and potential for cure from their cancers. Cytokines, which act on T cells to promote survival, proliferation, and memory immune responses, are thought to contribute to long-lasting antitumor activity. Bempegaldesleukin (BEMPEG) is a pegylated form of the cytokine IL-2, which has been shown to induce proliferation and activation of cytotoxic T cells and natural killer cells in the blood and tumor microenvironment, including increased expression of PD-1. BEMPEG is currently being evaluated for the treatment of multiple tumor types and, when combined with the approved PD-1 targeting agent nivolumab, appears to increase tumor response rates with a non-overlapping safety profile. Despite the advances in immunotherapy, a heterogenous tumor microenvironment, low tumor immunogenicity, as well as lack and exhaustion of T cells are barriers for robust antitumor immunity. New combination therapies with different types of immunomodulating agents such as receptor tyrosine kinase inhibitors, PD(L)1 or CTLA-4 immune checkpoint inhibitors, and immune cell stimulating cytokines such as BEMPEG show promising clinical results and are a focus for the development of new anticancer combination therapies for patients with advanced malignancies.

Compound 1 is a novel, potent, orally bioavailable, small molecule inhibitor of several RTKs including MET, vascular endothelial growth factor receptor 2 (VEGFR2), AXL, and MER (members of the TAM family). Inhibition of tumor angiogenesis by blocking the VEGFR-signaling pathway is a therapeutic target for the control of growth, invasion, and metastasis of cancer. MET and AXL play important roles in the resistance to anti-angiogenic therapy. TAM family receptors are negative immune regulators and have become a focus as targets for cancer immunotherapy. TAM receptors inhibit various types of immune cells including macrophages, dendritic cells, natural killer (NK) cells, NKT cells, and indirectly T cells. Therefore, inhibition of TAM signaling may promote antitumor activity at different levels of immunity. Drugs targeting VEGFR/TAM family kinases are thought to promote an immune-permissive environment, which may enhance response to immune checkpoint inhibitors. In a preclinical murine syngeneic colon carcinoma model (MC38), the combination of Compound 1 with an anti-PD-1 antibody showed benefit in tumor growth inhibition activity when compared with vehicle or either single agent alone. The ongoing first-in-human (FIH) Phase 1 clinical study Compound 1-001 (NCT03845166) is currently evaluating the safety and preliminary clinical activity of Compound 1 as monotherapy and in combination therapy with the PD-L1 ICI atezolizumab. As of April 2021, dose escalation of Compound 1 as single-agent and in combination therapy with atezolizumab is ongoing: 20 subjects were enrolled in Compound 1 single-agent cohorts across seven dose levels (Compound 1 PIB: 10, 20 mg po qd; Tablet: 20, 40, 80, 100, 140 mg po qd); 9 subjects were enrolled in Compound 1+atezolizumab combination therapy cohorts across two dose levels (Compound 1 40 mg and 80 mg po qd+atezolizumab 1200 mg q3w). One DLT was observed among the completed dose-levels: one subject in the Compound 1 single-agent dose escalation cohort at 140 mg po qd experienced Grade 3 uncontrolled hypertension that resulted in the inability to take ≥75% of the total planned Compound 1 dose for the DLT Evaluation Period. In the ongoing Compound 1+atezolizumab combination dose escalation cohorts, no DLTs have been observed with 80 mg Compound 1 being the highest dose so far evaluated. The adverse events thus far reported indicate that Compound 1 is well tolerated as single agent and in combination with ICI therapy. Pharmacokinetic (PK) results of the FIH Phase 1 study show that Compound 1 administered as a tablet has a short terminal half-life at steady state with approximately 24-28 hours which is favorable for adverse event (AE) management as monotherapy and in combination therapy. Compound 1 has also demonstrated encouraging clinical activity as a monotherapy and in combination with ICI therapy in the ongoing FIH Phase 1 study.

This Phase 1b clinical study Compound 1-002 evaluates safety, tolerability, PK, pharmacodynamics, and preliminary antitumor activity of Compound 1 alone, in combination with nivolumab (doublet), and as a triplet with either ipilimumab or BEMPEG. Antibodies targeting the T-cell inhibitory checkpoint proteins PD-(L)1 or cytotoxic T-lymphocyte associated protein 4 (CTLA-4) have been shown to enhance the immune response against tumor cells and are part of standard of care for a variety of cancers. Nivolumab is a fully human immunoglobulin G4 (IgG4) monoclonal antibody (mAb) that binds to the PD-1 cell surface membrane receptor, a negative regulatory molecule expressed transiently following T-cell activation and on chronically stimulated T cells characterized by an "exhausted" phenotype. Through the inhibition of the interaction of PD-1 with its ligands (PD-L1 and PD-L2), nivolumab has demonstrated the ability to generate increased antitumor immune responses and improvements in survival of cancer patients. Nivolumab has been approved as a single agent therapy and in combination with ipilimumab for the treatment of multiple cancer types including RCC (Opdivo US PI).

Ipilimumab is a fully human monoclonal IgG1 kappa antibody that binds to the cytotoxic T-lymphocyte associated protein 4 (CTLA-4) antigen expressed on a subset of human T cells. The proposed mechanism of action for ipilimumab is interference of the interaction of CTLA-4 with B7 molecules on antigen presenting cells with subsequent blockade of the inhibitory modulation of T-cell activation promoted by the CTLA4/B7 interaction. Ipilimumab has been approved as single-agent therapy in melanoma and in combination with nivolumab for the treatment of other solid tumors including RCC (Yervoy® US PI).

Despite the clinical success of PD-(L)1 and CTLA-4 targeting agents as novel anticancer therapies, most patients with advanced stage of cancer still do not achieve long-term benefit. Proinflammatory cytokines such as interleukins (IL) can contribute to cancer immunotherapy by improving antigen priming and by increasing the number of effector immune cells and enhancing their cytolytic activity. Therefore, these cytokines are thought to contribute to long-lasting antitumor activity. IL-2 plays a major role in the activation and expansion of T lymphocytes and natural killer (NK) cells. Systemic administration of recombinant IL-2 at an effective dose for cancer immunotherapy has been challenging because of its toxicity profile.

Bempegaldesleukin (BEMPEG, NKTR-214) is an investigational CD122-preferential IL-2 pathway agonist that leverages the clinically validated IL-2 pathway to stimulate an antitumor immune response (Bentebibel 2019). BEMPEG consists of recombinant human IL-2 conjugated with an average of six releasable chains of polyethylene glycol (PEG) (Charych 2016, Charych 2017). Progressive release of PEG chains in the body yields a series of increasingly active IL-2 conjugates to achieve a sustained concentration of active drug and stable activity (Charych 2016, Charych 2017). Compared with native IL-2, the location of the PEG chains directs bempegaldesleukin to preferentially bind the heterodimeric IL-2 receptor beta gamma complex (IL-2Rβγ; CD122/CD132) over the heterotrimeric IL-2Rαβγ complex (Charych 2016, Charych 2017). Upon intravenous (IV) administration, the PEG chains slowly release to generate the active bempegaldesleukin-related species (mainly 2-PEG-IL-2 and 1-PEG-IL-2) that have a peak plasma concentration of 24 to 48 hours after infusion. The slow generation of the 2-PEG-IL-2 and 1-PEG-IL-2 significantly mitigates the rapid-onset, systemic cytokine-related toxicities associated with high dose IL-2.

In preclinical studies, BEMPEG showed therapeutic synergy with anti-PD-1 and anti-CTLA-4 directed therapy evidenced by a significant increase of systemic and intratumoral CD8+ T-cells. In addition, treatment with BEMPEG significantly reduced the number of intratumoral regulatory T cells (Sharma et al 2020). In a Phase 1 study the combination of BEMPEG with nivolumab was well tolerated without dose-limiting toxicity (Diab et al 2020). The combination of nivolumab with BEMPEG showed encouraging preliminary activity in multiple solid tumor types and did not appear to increase the incidence of immune-related adverse events (AEs) associated with nivolumab. Nivolumab in combination with BEMPEG is currently being evaluated in multiple different tumor types including RCC (NCT03729245), UC (NCT03785925, NCT04209114) and melanoma (NCT03635983).

Based on the target profile of Compound 1, an inhibitor of multiple RTKs involved in tumor cell proliferation, neovascularization, and immune cell regulation, as well as its demonstrated preclinical and preliminary clinical benefit, there is a clear rationale for evaluating Compound 1 as monotherapy and in combination therapy with different immunomodulating agents (nivolumab, ipilimumab, BEMPEG) as a potential new treatment opportunity for subjects with advanced solid tumors including genitourinary tumors.

In this Phase 1b study, Compound 1 as monotherapy and in combination therapy with the immunomodulating agents nivolumab, ipilimumab, and BEMPEG will be evaluated as potential new anticancer therapy for subjects with advanced solid tumors. Combination therapies of VEGFR-TKIs and nivolumab with or without ipilimumab is clinically well precedented with manageable safety profiles observed for both doublet and triplet regimens. Encouraging preliminary clinical data for the combination of nivolumab with BEMPEG was accompanied by a combined safety profile not significantly different from either of the agents alone, suggesting that the addition of a VEGFR-TKI to this combination therapy may lead to further improvements in clinical activity while maintaining tolerability. The short half-life of Compound 1 has the potential to facilitate rapid AE management for improved tolerability when combined with other immunomodulating agents in doublets and triplets.

Rationale For Tumor Indication Selection For Cohort-Expansion Stage

1. Compound 1 Combination Therapies in Renal Cell Carcinoma (Clear-Cell and Non-Clear Cell)

In the US, approximately 65,000 new cases of RCC are diagnosed each year; it is the seventh most common cancer worldwide (Noone et al 2018, Muglia and Prando 2015). The most common variant of RCC is clear-cell RCC (ccRCC), which makes up 75% of all RCC. Non-clear cell RCC (nccRCC) is composed of a variety of histological subtypes, the most common of which include papillary (10%) and chromophobe RCC (5%). While the number of patients who die each year from RCC has gradually declined over the past 20 years, the 5-year survival rate remains a dismal 11% for patients diagnosed with metastatic disease (Noone et al 2018). Despite the recent treatment advances, tumor resistance and limited life-prolonging therapies indicate that additional therapeutic options are needed to improve the outcome of patients with advanced RCC.

Clear Cell RCC (ccRCC)

For patients with advanced or metastatic ccRCC, the treatment paradigm has evolved rapidly over the past few years (NCCN [Kidney Cancer v2.2021]2021). RCC is a highly vascularized tumor, and genetic alterations affecting the von Hippel-Lindau tumor suppressor gene in some RCC types lead to increased expression of VEGF and hypoxia inducible factor 1 (HIF-1), which provides the scientific rationale of using VEGF-targeting agents in this indication. Several clinical trials with VEGF-targeting agents have shown clinical benefit in subjects with advanced RCC either as a first-line therapy or as salvage therapy following progression on first-line or second-line therapy (Sutent® USPI, Cabometyx® USPI, Inlyta® USPI). Resistance to VEGFR-targeting agents includes the activation of alternative angiogenic pathways, such as the MET signaling pathway (Shojaei et al 2010) and the acquisition of the epithelial-mesenchymal transition (EMT) phenotype of cancer cells (Landolt et al 2017, Bielecka et al 2014, Zhou et al 2016, Hammers et al 2010). EMT allows epithelial cells to escape from their typical biological structure, lose cell-cell adherence and, as a result, enhance tumor cell metastasis. In addition, changes in the tumor immune microenvironment may contribute to resistance of VEGFR-targeting TKIs (eg, by an increase of tumor infiltrating of immune suppressive regulatory T cells [Treg] and PD-L1 expression [Liu et al 2015]). TAM receptors (eg, AXL and MER) play an important role in tumor cell proliferation, migration, EMT, and immunosuppression (Schoumacher and Burbridge 2017). Expression of AXL has been associated with a worse prognosis for ccRCC patients (Zucca et al 2018) and was found to increase following sunitinib therapy (Zhou et al 2016).

Agents targeting immune checkpoints such as PD-1 or CTLA-4 have also demonstrated clinical benefits in patients with advanced ccRCC by activation of the antitumor immune system. Nivolumab (anti-PD-1 mAb) as monotherapy or in combination with ipilimumab (anti-CTLA-4 mAb) are standard-of-care therapies for patients with advanced ccRCC (Opdivo® USPI, Yervoy® USPI). In addition, combination therapies of VEGFR-TKIs with anti-PD-1/PD-L1 targeting agents have demonstrated significant benefit over monotherapies targeting either of those pathways alone (Cabometyx® and Opdivo® USPIs, Inlyta® and Keytruda® USPIs; Bavencio® and Keytruda® USPIs). In addition, the IL-2 cytokine agent BEMPEG has shown very encouraging clinical activity in a Phase 1 study in combination with nivolumab administered to subjects with ccRCC as first-line therapy or second-line therapy with ORR rates of 71% and 29%, respectively (Diab et al 2020).

Non-Clear Cell RCC (nccRCC)

For patients with non-clear cell RCC (nccRCC), a standard-of-care therapy has not yet been established as it comprises biologically unique subtypes (Zhang et al 2017). Treatment recommendations include VEGFR-targeting TKIs as monotherapy or in combination with anti-PD-1/PD-L1 mAbs, or anti-PD-1/PD-L1 mAbs in combination with anti-CTLA-4 mAbs. However, the clinical data to support these combination therapies are limited due to lack of prospective evaluation of these regimens in nccRCC (NCCN [Kidney Cancer v2.2021]2021). Furthermore, the response rates in certain types of nccRCC are lower than for ccRCC (Tannir et al 2016). Therefore, patients with advanced nccRCC are in need of new treatment options, potentially including combination therapies of VEGFR-targeting agents with PD-1/PD-L1 targeting agents and other immune-stimulating cytokines such as BEMPEG.

In summary, based on its mechanism of action by targeting major signaling pathways involved in RCC (VEGFR, MET) and providing an immune permissive microenvironment by targeting TAM family kinases (AXL, MER) involved in immune response regulation to tumors, Compound 1 with its short half-life is an ideal agent for evaluation as a potential new therapeutic option in combination with nivolumab with or without ipilimumab or BEMPEG for the treatment of patients with advanced RCC.

2. Compound 1 Combination Therapies in Castration-Resistant Prostate Cancer (CRPC)

Prostate cancer is the fourth most diagnosed malignancy worldwide behind cancers of the lung, breast, and colorectum (Bray et al 2018). It is the most common cancer among men worldwide and the second leading cause of cancer deaths in the US (Bashir 2015, US Cancer Statistics Working Group 2018). Adenocarcinoma is the most common histological subtype and is typically associated with elevation in serum PSA. De novo metastatic disease (metastatic castration-sensitive prostate cancer [CSPC]) accounts for 3-7% of new cases of prostate cancer in developed nations and its incidence in the US may be rising due to declines in population-based PSA surveillance (Dall'Era et al 2018). Approximately two-thirds of men with radiographically localized disease are cured with surgery (radical prostatectomy) or radiotherapy. The remainder will experience recurrence heralded by a rising PSA, local radiographic recurrence, and/or metastatic disease.

Androgen-deprivation therapy (ADT) is the mainstay of treatment for advanced or metastatic prostate cancer due to the androgen dependency of this disease. Castration-resistant prostate cancer (CRPC) is defined as either a rise in PSA or radiographic progression during or following ADT. Treatment alternatives for patients with metastatic CRPC include chemotherapy, immunotherapy, androgen signaling pathway receptor inhibitors, and radionuclide therapy. Chemotherapy with docetaxel plus prednisone demonstrated improved OS compared with mitoxantrone plus prednisone in men with advanced, hormone-refractory (castration-resistant) disease (Tannock et al 2004). Cabazitaxel, a tubulin-binding taxane has also shown improved OS relative to mitoxantrone in men with metastatic CRPC previously treated with docetaxel (de Bono et al 2010). More recently, cabazitaxel demonstrated superiority over androgen-signaling targeted therapy (abiraterone or enzalutamide) in patients with mCRPC who had been previously treated with docetaxel and abiraterone or docetaxel and enzalutamide (de Witt et al 2019).

Studies of the novel hormonal therapies (NHTs) abiraterone, enzalutamide, apalutamide, and darolutamide which target the androgen receptor (AR) signaling pathway have shown efficacy in metastatic CRPC (NCCN [Prostate Cancer v1.2021]2021). Abiraterone has been approved in combination with prednisone for the treatment of metastatic CRPC, both after and before treatment with docetaxel. In the post-docetaxel metastatic CRPC setting, abiraterone/prednisone improved median OS compared with placebo/prednisone as well as median radiographic PFS (de Bono et al 2011). Similarly, in the pre-docetaxel metastatic CRPC setting, abiraterone/prednisone improved median OS and median radiographic PFS compared with placebo/prednisone (Ryan et al 2015, Ryan et al 2013). In the post-docetaxel setting, enzalutamide improved median and median radiographic PFS compared with placebo (Scher et al 2012). In the pre-docetaxel setting, enzalutamide improved median OS and median radiographic PFS over placebo (Beer et al [Eur Urol]2017, Beer et al 2014).

Prominent expression of MET has been observed in primary and metastatic prostate carcinomas (Pisters et al 1995, Humphrey et al 1995) with evidence for higher levels of expression in bone metastases compared to lymph node metastases or primary tumors (Knudsen et al 2002, Zhang et al 2010). Overexpression of HGF, the ligand for MET, has also been observed in prostate carcinoma (Zhu and Humphrey 2000), and increased plasma levels of HGF in CRPC are associated with decreased OS (Humphrey et al 2006).

Data from preclinical studies suggest that both HGF and MET are regulated by the androgen signaling pathway in prostatic tissue. Both proteins are expressed at low levels in xenograft models of androgen-sensitive prostate cancer but are upregulated in CRPC models (Humphrey et al 1995, Verras et al 2007). MET expression increases substantially in androgen-sensitive tumor cells after androgen withdrawal (Humphrey et al 1995; Verras et al 2007). Administration of a MET kinase inhibitor after castration reduced tumor cell proliferation in a preclinical model of CRPC (Tu et al 2010). These observations indicate that upregulation of MET signaling may be associated with and contribute to the emergence of resistance to androgen suppression in prostate cancer. Further, elevated VEGF in either plasma or urine is associated with shorter OS (Bok et al 2001, George et al 2001). VEGF may play a role in activating the MET pathway in tumor cells by binding to neuropilin-1, which is frequently upregulated in prostate cancer and appears to activate MET in a co-receptor complex (Zhang et al 2010). In addition, agents targeting the VEGF signaling pathway have demonstrated activity in subjects with CRPC (Michaelson et al 2014, Aragon-Ching et al 2009).

Immune checkpoint inhibitor monotherapies targeting either CTLA-4 (Kwon et al 2014, Beer et al [J Clin Oncol] 2017) or the PD-1/PD-L1 pathway have as of yet not been successful in improving clinical outcomes of patients with advanced mCRPC (Kim et al 2018). However, studies evaluating the immunological impact of CTLA-4 inhibitor ipilimumab in prostate cancer noted the upregulation of the PD-1/PD-L1 pathway as a compensatory mechanism for tumor immunological evasion (Gao et al 2017), suggesting that combination treatment with CTLA-4 and PD-1/PD-L1 inhibitors had potential for clinical benefit. Toward these ends, the combination of nivolumab and ipilimumab was evaluated in patients with mCRPC in the Phase 2 CheckMate 650 trial providing encouraging results (Sharma et al 2020). The study subjects were enrolled and evaluated in pre- and post-chemotherapy cohorts (n=45 each) leading to respective ORRs of 25% and 10% with 2 CRs (6.3%) reported in each cohort. The median OS in the two cohorts was 19.0 and 15.2 months, respectively.

In summary, Compound 1 is a multi-targeted TKI that not only targets VEGFR2 and MET but also other kinases relevant to solid tumors including prostate cancer. As Compound 1 may have the ability to target multiple pathways of TKI resistance found in metastatic CRPC patients, it may offer an alternative therapeutic approach for this patient population.

3. Compound 1 Combination Therapies in Urothelial Carcinoma

Urothelial carcinoma (bladder cancer) is the sixth most common cancer in the United States and the tenth most common worldwide. In 2018, approximately 594,000 new cases and 200,000 deaths from bladder cancer were reported globally (Bray et al 2018). Platinum-containing combination chemotherapy (eg, cisplatin/gemcitabine or carboplatin/gemcitabine or methotrexate/vinblastine/doxorubicin/cisplatin [MVAC]) are standard first-line therapies for patients with advanced or metastatic urothelial carcinoma (Bellmunt et al 2011; NCCN [Bladder Cancer]2021). For subjects who achieve a radiographic response or stable disease after first-line platinum containing chemotherapy, maintenance therapy with the PD-L1 ICI avelumab is indicated (BAVENCIO® USPI). For subjects who are not able to tolerate platinum-containing chemotherapy and highly express PD-L1 on tumor tissue, single-agent ICI (pembrolizumab [KEYTRUDA® USPI] or atezolizumab [TECENTRIQ® USPI]) is a first-line treatment alternative. For patients who progress following platinum-containing chemotherapy, second-line therapies include single agent ICI therapy with nivolumab (OPDIVO® USPI), pembrolizumab (KEYTRUDA® USPI), or avelumab (BAVENCIO® USPI); or chemotherapy (NCCN [Bladder Cancer]2021). Enfortumab, a nectin-4-directed antibody and microtubule-inhibitor conjugate (ADC) has received accelerated approval by the FDA based on tumor response rate for adult patients with locally advanced or metastatic UC who have previously received a PD-1/PD-L1 ICI, and a platinum-containing chemotherapy in the neoadjuvant/adjuvant, locally advanced or metastatic setting (PADCEV™ USPI). Erdafitinib a small molecule kinase inhibitor received accelerated approval by the FDA based on tumor response for the treatment of patients with advanced UC who have FGFR3 or FGFR2 genetic alterations and have progressed during or following at least one line of prior platinum-containing chemotherapy including within 12 months of neoadjuvant or adjuvant platinum-containing chemotherapy (BALVERSA™ USPI).

Nivolumab has also been evaluated in subjects with platinum pre-treated locally advanced or metastatic UC in combination with ipilimumab in the CheckMate 032 study (Sharma et al 2019). Two different combination dosing regimens were administered: NIVO3+IPI1 (nivolumab 3 mg/kg+ipilimumab 1 mg/kg every 3 weeks for four doses followed by nivolumab monotherapy maintenance; n=104) or NIVO1+IPI3 (nivolumab 1 mg/kg plus ipilimumab 3 mg/kg every 3 weeks for four doses followed by nivolumab monotherapy maintenance; n=92). The respective response rates for the NIVO3+IPI1 and NIVO1+IPI3 treatment arms were 26.9% (7.7% CR) and 38.0% (6.5% CR), and median PFS was 2.6 and 4.9 months, respectively. Median OS in the NIVO3+IPI1 arm was 7.4 months and was 15.3 months in the NIVO1+IPI3 arm. Treatment-related Grade 3 or 4 AEs were numerically lower in the NIVO3+IPI1 arm compared with the NIVO1+IP3 arm (30.8% vs 39.1%, respectively) as were treatment-related SAEs (25.0% vs 27.2%, respectively).

Small molecule kinase inhibitors targeting the VEGFR and MET signaling pathway as well as TAM kinases similar to Compound 1 have shown clinical benefits with an acceptable safety profile as single agent therapy and in combination with ICIs in patients with locally advanced or metastatic UC as a salvage therapy following progression on platinum-based chemotherapy (Apolo et al [Lancet Oncol]2020, Apolo [J Clin Oncol] et al 2020).

The IL-2 cytokine agent BEMPEG in combination with nivolumab has been evaluated in a Phase 1/2 clinical study enrolling 34 subjects with cisplatin-ineligible disease or refused such chemotherapy (PIVOT-02, NCT02983045; Siefer-Radtke et al 2019). At an interim analysis of the study, among 23 evaluable subjects the overall ORR was 48% (44% in the cisplatin-ineligible population, 55% in subjects who refused first-line standard of care therapy), and the CR rate was 19%. Tumor shrinkage was observed in 78% of subjects and responses were observed regardless of PD-L1 expression status. These preliminary encouraging results led to the initiation of an ongoing Phase 2 study evaluating the combination of BEMPEG in combination with nivolumab in 1L cisplatin-ineligible UC subjects whose tumors have low expression of PD-L1 (PIVOT-10, NCT03785925).

The observed clinical activity of a VEGFR-targeting TKI in combination with nivolumab as well as nivolumab in combination with BEMPEG warrants the evaluation of a triplet combination of Compound 1 with nivolumab and BEMPEG in subjects with UC who are ICI naïve as well as ICI experienced.

Rationale For Study Treatment Doses

Efforts to identify an MTD/RD of Compound 1 as a single-agent and in combination with the PD-L1 inhibitor atezolizumab are currently ongoing in the Phase 1 FI Compound 1-001 study. The highest dose level for single-agent Compound 1 evaluated as of April 2021 is 140 mg daily (qd), and the highest dose of Compound 1 in combination with atezolizumab is 80 mg qd. Encouraging preliminary clinical activity has been observed with prolonged disease stabilization and tumor regressions in subjects enrolled in single agent therapy and atezolizumab combination therapy cohorts.

Nivolumab and ipilimumab are approved therapies for the treatment of multiple oncological indications both as single agents and in combination therapies. Similarly, BEMPEG at a dose of 0.006 mg/kg IV q3w was evaluated in combination treatment with nivolumab, and no overlapping toxicities were observed between the two agents. That dose will be administered for combination treatment regimens including BEMPEG in this study.

Rationale For Dose Holds Before Bone Scans In Mcrpc Subjects With Bone Metastases Bone metastases are a very common manifestation of advanced prostate cancer and are associated with poorer disease prognosis. As such, new therapies for mCRPC patients with extensive bone disease represent an unmet medical need. However, the evaluation of anti-angiogenic agents for the treatment of patients with a preponderance of osteoblastic bone lesions has been found to be potentially confounded by interference on 99-Tc uptake in osteoblasts when performing bone scans (Saylor et al 2012). An evaluation of men who had received the VEGFR-TKI sunitinib revealed a discordance between improvements identified by bone scan response and other measures of disease progression (ie, PSA and CT). In an effort to circumvent potential interfering effects by Compound 1 on 99-Tc uptake for bone scans in this study, mCRPC subjects in the Cohort-Expansion Stage (Cohort 3) with metastatic bone lesions will be required to hold Compound 1 for at least 7 days before undergoing regular bone scan examinations. The intent of this dose hold is to allow Compound 1 to be washed out thereby mitigating its impact on bone scans and allowing for a more accurate evaluation of treatment effects on bone lesions in subjects with mCRPC.

Objectives and Endpoints

The objective of this study is to evaluate the safety, tolerability, PK, pharmacodynamics, and efficacy of Compound 1 in combination with the immuno-oncology agents nivolumab (doublet), nivolumab/ipilimumab (triplet), and nivolumab/bempegaldesleukin (triplet) in subjects with advanced genitourinary cancers.

Dose-Escalation Stage (Compound 1 Combination Therapy):

The primary objective is:

- Determine the safety and maximum tolerated dose (MTD) and/or recommended dose (RD) of the combination therapies.

The secondary objectives are:

- Evaluate the safety of the combination therapies as measured by incidence and severity of adverse events (AEs) and serious adverse events (SAEs), including immune-related adverse events (irAEs).
- Evaluate the plasma pharmacokinetics (PK) of daily oral administration of Compound 1 and its potential metabolites when given in combination therapy.

The exploratory objectives are:

- Determine the objective response rate (ORR) as assessed by the Investigator per RECIST 1.1.
- Determine the duration of response (DOR) as assessed by the Investigator per RECIST 1.1.
- Determine the progression-free survival (PFS) as assessed by the Investigator per RECIST 1.1.
- To assess drug-drug interactions between Compound 1 and combination agents.
- Evaluate the PK of nivolumab, ipilimumab, and BEMPEG when given in combination therapy with Compound 1.
- Evaluate the relationship between PK of Compound 1 and selected biomarkers with respect to preliminary safety and efficacy outcomes.
- Assess the immunogenicity of nivolumab, ipilimumab, and BEMPEG when administered in combination with Compound 1

Cohort-Expansion Stage (Compound 1 Monotherapy and Combination Therapy):

The primary objective is:

- Evaluate the preliminary efficacy by estimating the ORR in subjects with measurable disease treated with single-agent Compound 1 or combination therapy as assessed by the Investigator per RECIST 1.1.
- For Cohort 3 (mCRPC): Determine duration of radiographic PFS as determined per Prostate Working Group 3 (PCWG3) criteria (Scher et al 2016) by BIRC.

The secondary objectives are:

- Determine the contribution of components via descriptive comparison of the primary endpoints for the treatment arms within an Expansion Cohort
- Evaluate safety through the evaluation of incidence and severity of nonserious AEs and SAEs, including irAEs The exploratory objectives are:

- Determine duration of response (DOR) as assessed by the Investigator per RECIST 1.1
- Determine progression-free survival (PFS) for subjects with measurable disease as assessed by the Investigator assessed by the Investigator per RECIST 1.1
- For Cohort 3 (mCRPC): Determine duration of radiographic PFS as determined per Prostate Working Group 3 (PCWG3) criteria (Scher et al 2016) by Investigator
- For Cohort 3 (mCRPC): Determine proportion of subjects achieving a >50% decrease in PSA from baseline confirmed by a second consecutive PSA assessment at least 3 weeks later
- Determine ORR, DOR, and PFS for subjects with measurable disease as assessed by a Blinded Independent Radiology Committee (BIRC) per RECIST 1.1 for selected cohorts as determined by the Sponsor
- Determine overall survival (OS)
- Further evaluate the plasma PK of daily oral administration of Compound 1 as a single agent or in combination therapy
- Assess the effects on tumor and blood biomarkers when administered alone and in combination therapies
- For Cohort 3 (mCRPC): Assess the effects on bone biomarkers
- Assess the immunogenicity of nivolumab, ipilimumab, and BEMPEG when administered in combination therapy
- Assess drug-drug interactions between Compound 1 and combination agents Study Design This Phase 1b Study Compound 1-002 will evaluate the safety, PK, pharmacodynamics, and preliminary antitumor activity of Compound 1 in combination with the immuno-oncology agents nivolumab (doublet), nivolumab+ipilimumab (triplet), and nivolumab/BEMPEG (triplet) in two stages.

During the Dose-Escalation Stage the MTD/RD for each of the Compound 1 combination therapies (doublet and triplets) will be determined in subjects with advanced solid tumors for whom life-prolonging therapies do not exist or available therapies are intolerable or no longer effective.

Figure 15:
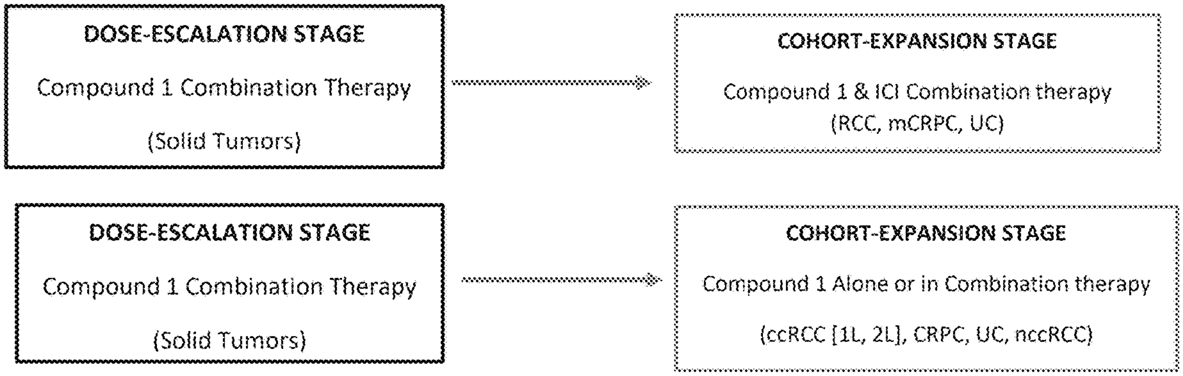

During the Cohort-Expansion Stage subjects with genitourinary cancers will be enrolled in tumor-specific expansion cohorts. For each expansion cohort, subjects will be randomized to multiple treatment arms. Depending on treatment assignment, subjects in the Cohort-Expansion Stage will receive the MTD/RD of single-agent Compound 1 determined in the Phase 1 FIH Compound 1-001 study, the MTD/RD of the combination regimens from the Dose-Escalation Stage of this study, or previously established combination regimens of nivolumab plus either ipilimumab or BEMPEG without concomitant Compound 1. Nivolumab and BEMPEG will be provided for a maximum of 2 years based on the time snice the first dose of study treatment. Ipilimumab will be administered for a maximum of 4 doses. FIG. 15 provides the diagrams from the dose-escalation stage to the cohort-expansion stage.

All enrolled subjects may receive study treatment, even after radiographic progression, until they are no longer clinically benefitting from study treatment in the opinion of the Investigator, unless they 1) need subsequent systemic anticancer treatment or other urgent tumor-directed medical intervention to prevent life-threatening complications, 2) experience unacceptable toxicity, or 3) have any other reason for treatment discontinuation as listed in the protocol. Note: The maximum allowed treatment period with nivolumab and BEMPEG is 2 years and with ipilimumab 4 doses.

Continued treatment after radiographic progression per RECIST 1.1 as assessed by the investigator may occur in subjects who meet all the following criteria:

Clinical benefit per Investigator medical judgment

Karnofsky performance status of ≥70%

Absence of unmanageable treatment-related AEs

Subject provides written informed consent prior to receiving additional treatment with the study drug regimen. All other elements of the main consent including description of reasonably foreseeable risks or discomforts, or other alternative treatment options will still apply.

The assessment of clinical benefit should be balanced by clinical judgment as to whether the subject is clinically deteriorating and unlikely to receive any benefit from continued study drug treatment.

Dose-Escalation Stage

The Dose-Escalation Stage will enroll subjects with advanced solid tumors and follow a standard 3+3 study design with a 21-day Dose-Limiting Toxicity (DLT) Evaluation Period. Two different Dose Escalation combination therapies will be evaluated in parallel.

Cohort A: Compound 1+nivolumab (doublet)

Cohort B: Compound 1+nivolumab+ipilimumab (triplet)

Each combination therapy will enroll approximately 12 subjects (total n=~24). The Compound 1 starting dose (Dose level 1 [DL1]) in the Dose-Escalation Stage will be a safe dose level (ie, one dose level below the MTD or RD) derived from the ongoing first in human Phase 1 study Compound 1-001. DL2 will be one dose level higher and DL-1 will be one dose level lower compared with DL1. Dose levels above the established MTD/RD for single-agent Compound 1 will not be evaluated.

Once the Compound 1 MTD/RD is determined for Cohort A (Compound 1+nivolumab), a third treatment combination therapy will be evaluated.

Cohort C: Compound 1 (MTD/RD Cohort A)+nivolumab+BEMPEG

This combination therapy will enroll approximately 6 subjects. Due to the known lack of overlapping toxicities for the combination therapy of nivolumab and BEMPEG, the Compound 1 starting dose (DL1) will be the MTD/RD as determined for the combination therapy Compound 1+nivolumab (Dose Escalation Cohort A). If ≤1 of 6 subjects experiences a DLT at the starting dose level, then that dose level will be deemed the MTD/RD for the Compound 1+nivolumab+BEMPEG combination therapy. If two or more subjects experience DLTs during the DLT Evaluation Period, lower dose levels of Compound 1 in combination with nivolumab and BEMPEG will be evaluated.

Dose Escalation Cohorts:

Cohort A: Compound 1+Nivolumab (Doublet)

Figure 16:
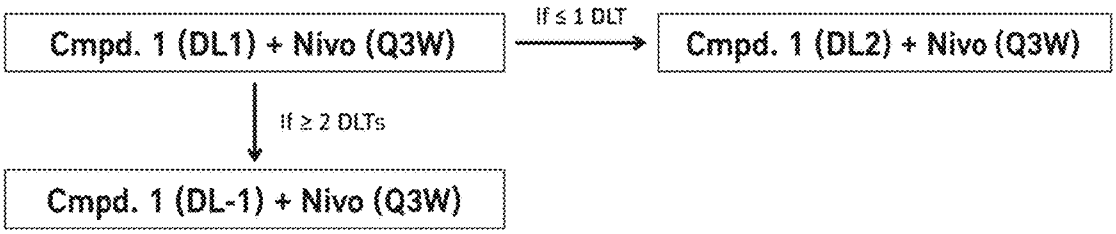

Compound 1 orally once daily (PO qd) will be evaluated in combination with a flat dose of nivolumab administered intravenously every three weeks (360 mg; IV q3w). FIG. 16 provides the diagram for this study.

Cohort B: Compound 1+Nivolumab+Ipilimumab (Triplet)

Figure 17:
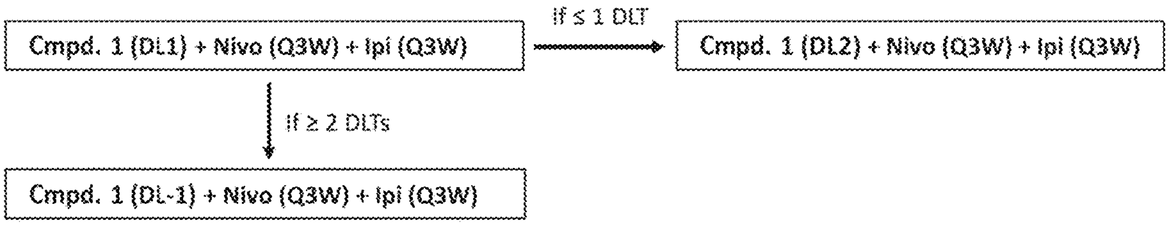

Compound 1 (PO qd) will be evaluated in combination with nivolumab (3 mg/kg q3w) and ipilimumab (1 mg/kg IV q3w×4 Doses). After subjects have completed 4 doses of nivolumab on the q3w schedule, nivolumab dosing will continue at a flat dose of 480 mg IV q4w. FIG. 17 provides the diagram for this study.

Cohort C: Compound 1+Nivolumab+BEMPEG (Triplet)

Figure 18:
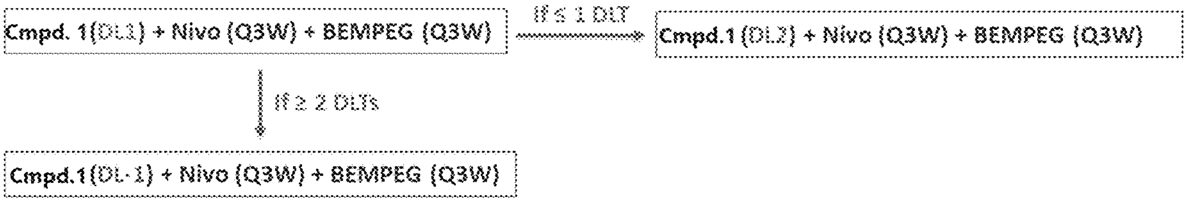

Compound 1 (PO qd) will be evaluated in combination with a flat dose of nivolumab (360 mg IV q3w) and BEMPEG (0.006 mg/kg IV q3w). FIG. 18 provides the diagram for this study.

3+3 Dose-Escalation Study Design:

Subjects with advanced solid tumor will accrue in Dose Escalation Cohorts A and B using a standard “3+3” study design. This design will be used to identify the MTD/RD and the maximum administered dose (MAD) of Compound 1 when given in combination with nivolumab (Cohort A) and nivolumab+ipilimumab (Cohort B). Dose escalation in Cohorts A and B may be initiated in parallel. The starting dose of Compound 1 for these two cohorts will be a safe dose (ie, at least one dose level below the MTD/RD derived from the ongoing FI Phase 1 study Compound 1-001 as determined by that study’s Cohort Review Committee). Dose escalation to the next cohort may proceed if 0 out of 3 subjects or 1 out of 6 subjects experience a DLT (as defined below).

Six subjects will be enrolled in Cohort C after the MTD/RD in Cohort A of Compound 1 in combination with nivolumab has been determined. The Compound 1 starting dose will be the MTD/RD for Cohort A. If no DLTs occur in these 6 subjects, the evaluated dose level of Compound 1 will be the MTD/RD for Cohort C. De-escalation of the Compound 1 dose in Cohort C may occur if more than 1 of 6 subjects in this combination therapy cohort experience a DLT. Enrollment at lower doses of Compound 1 in Cohort C will follow a 3+3 design until the MTD/RD has been identified.

The Compound 1-002 Cohort Review Committee will review all available safety and PK data at the end of the 21-day Dose Limiting Toxicity Evaluation Period (DLT period) for cohorts containing at least 3 subjects. The dose levels evaluated for Compound 1 in combination with nivolumab (Cohort A) or nivolumab+ipilimumab (Cohort B) will not exceed the MTD/RD for single-agent Compound 1. The dose levels evaluated for Compound 1 in combination with nivolumab+BEMPEG (Cohort C) will not exceed the MTD/RD for Cohort A. The dose escalation decision rules are provided in the table below.

Decision Rules for Compound 1 Combination Therapy Dose-Escalation Cohorts

| No. of Subjects with a DLT (Days 1-21) in Current Cohort | Dose-Escalation Decision Rule |
|---|---|
| 0 out of 3 | Enter 3 subjects at the next higher dose level. |
| 1 out of 3 | Enter 3 more subjects at the current dose level. |
| 1 out of 6 | Enter 3 subjects at the next higher dose level. |
| ≥2 out of 3 | Dose-Escalation will be stopped. This dose level will be declared the MAD.<br>Additional dose levels may be evaluated between the MAD and previous dose level to the MAD (see "" out of 6" row below): |
| ≥2 out of 6 | This dose level will be declared the MAD.<br>If only 3 subjects have been treated at the previous dose level, an additional 3 subjects will be entered at this previous dose level (ie, one cohort lower than the MAD). If less than a third of the total number of subjects at this lower dose level has a DLT, then dose levels between this and the MAD may be explored.<br>If 6 subjects had already been treated at the previous dose level (ie, one cohort lower than the MAD) and only 0 or 1 DLT(s)have been observed, then dose levels between this and the MAD dose level may be explored.<br>If the Cohort Review Committee decides that a dose level between the previous dose level (ie, one cohort lower than the MAD) and the MAD is to be explored then the next cohort may accrue at a dose that is between this and the MAD dose level. |

DLT, dose-limiting toxicity; MAD, maximum administered dose.

Additional subjects may be added at any dose level (up to a total of 12 subjects) being evaluated if the Cohort Review Committee concludes that additional safety data should be obtained at this dose level.

DLT Definition

Dose-limiting toxicity (DLT) will be determined by the Cohort Review Committee for the dose-escalation cohorts upon review of all available safety (AEs), clinical laboratory tests and other relevant clinical findings as provided by the Investigator, and available COMPOUND 1 PK data for each cohort. The decision to open a new cohort at a higher or lower dose level requires that safety data from the DLT Evaluation Period are obtained and evaluated from all subjects in the current dose-level cohort. The DLT Evaluation Period is defined as Days 1-21.

DLTs will be defined as:

Any treatment-emergent AE that in the opinion of the Cohort Review Committee is of potential clinical significance such that further dose escalation of COMPOUND 1 would expose subjects to unacceptable risk Any related ≥Grade 3 AE which is unexpected in severity and/or duration compared with the known safety profiles of COMPOUND 1, nivolumab, ipilimumab, and BEMPEG when used as single agents or in combination therapy, and that cannot be managed by dose modification (reduction or hold/delay) and adequate supportive care, and requires permanent discontinuation of COMPOUND 1 and/or the combination therapy agents.

Inability to take ≥75% of the planned COMPOUND 1 dose during the DLT Evaluation Period because of a treatment-related AE Note: Subjects who fail to receive at least 75% of the total planned dose of Compound 1 during the DLT Evaluation Period for reasons other than safety (eg, withdrawal of consent, non-compliance, disease progression, logistical issues) may be replaced by Cohort Review Committee decision.

The following AEs will not be DLTs:

Transient infusion-related AEs which can be controlled with medical management (eg, flu-like symptoms, fever).

Tumor flare-related AEs (eg, localized pain, irritation at tumor sites).

Any Grade 3 AE (regardless of relationship to study treatment) which the Cohort Review Committee determines is unlikely to compromise the subject's safety and resolves to ≤Grade 1 or is controlled with adequate supportive care including short dose delays or dose reductions. Examples could include manageable events that are expected to occur with single-agent therapy with COMPOUND 1 or the combination therapy agents (eg, hypertension, hypotension, skin toxicity, headache, nausea, fatigue, emesis, diarrhea).

Single laboratory values that are out of normal range and unlikely to be related to study treatment and do not have any clinical correlate.

As a note, AEs are presumed attributable to study drug. AEs that are not associated with the study treatment but definitively attributable to another cause will not be considered in the determination of DLTs.

Identifying the Maximum Tolerated Dose or Recommended Dose

When determining the MTD/RD of COMPOUND 1 in combination therapy, consideration will also be given to the rate, severity, and nature of late occurring toxicities and end-organ toxicities (ie, cardiac, renal, hepatic, central nervous system) observed beyond the DLT Evaluation Period at all dose levels. The MTD for COMPOUND 1 for combination therapy will be based on a standard 3+3 dose-escalation design and will be defined as the highest evaluated dose level at which not more than 1 out of 6 subjects experiences a DLT during the DLT Evaluation Period. Once the Cohort Review Committee has determined the MTD/RD level for each combination therapy regimen, active subjects in lower dose level cohorts may be escalated to the MTD/RD dose level if their most current dose level is tolerated well.

Study Treatment Management

Combination study treatment will be withheld for subjects who experience a DLT until the toxicity resolves. Subjects who recover will, at the Investigator's discretion and with the agreement of the Sponsor, be allowed to resume Compound 1 at one dose level below the dose that resulted in the DLT if the DLT does not meet other protocol-defined criteria for treatment discontinuation. If the reduced Compound 1 dose is tolerated, the subject can continue with combination therapy at this dose level.

Permitted study treatment modifications to manage AEs comprise dose reductions or holds for Compound 1, dose reductions or delays for BEMPEG, and dose delays for nivolumab and ipilimumab. Following Sponsor notification, subjects in combination therapy cohorts may be allowed to discontinue components of study treatment for managing AEs and continue to receive the other component(s) if considered safe and the Investigator believes that the subject is still receiving benefit from study treatment. Treatment holds or delays for drug-related AEs are allowed for up to 8 weeks. Longer treatment holds and delays may be allowed for both single-agent and combination therapy treated subjects, upon approval by the Sponsor, if considered safe and the Investigator believes that the subject is still receiving benefit from study treatment. Tumor assessments should continue as per protocol even if study treatment is held or delayed.

Subjects are allowed to continue to receive nivolumab and BEMPEG for up to 2 years (based on the time since the first dose of study treatment) and ipilimumab for up to 4 doses if the subject continues to experience clinical benefit that outweighs the risks in the opinion of the investigator.

Study Visits

Subjects in the Dose-Escalation Stage will visit the clinic for study assessments during study periods as follows:

- Pre-Treatment Period (Screening): Subjects will be consented and undergo screening and baseline evaluations to be qualified for the study.
- DLT Evaluation Period (Days 1-21): Subjects will receive study treatment, and dose-limiting toxicity will be determined by the Cohort Review Committee upon review of all available data and is defined above.
- Treatment Extension Period: Subjects will continue treatment and will be monitored for safety (including laboratory assessments) and signs of toxicity. In the absence of radiographic PD per RECIST 1.1 and unacceptable toxicity, subjects may continue to receive Compound 1 treatment. Nivolumab and BEMPEG treatment is limited to a maximum duration of 2 years (based on the time since the first dose of study treatment), and ipilimumab treatment is limited to a maximum of 4 doses.

Treatment may continue after radiographic progression if the Investigator believes that the subject is still receiving clinical benefit from study treatment and that the potential benefit of continuing study treatment outweighs potential risk (see the criteria for treatment beyond progression above). Clinical judgment should be used for allowing treatment beyond radiographic progression. Subjects with clinically significant symptomatic deterioration at the time of radiographic progression may not be suitable for further treatment. The possibility of a delayed antitumor immune response should be taken into consideration: mixed responses with decreasing and increasing tumor lesion sizes at the same imaging time point or the appearance of new lesions prior to achieving a radiological response have been reported with immunomodulating therapies.

- Post-Treatment Period:
  - Post-Treatment Follow-Up Visit: Two post-treatment follow-up safety visits will occur 30 (+14) days [FU-1] and 100 (+14) days [FU-2] after the date of the decision to discontinue study treatment. If a related AE leading to study treatment discontinuation or related SAE is ongoing at the 100-day follow-up visit, it is to be followed until considered resolved or irreversible. Both follow-up visits should be conducted in person.
  - Extended Follow Up (Every 12 weeks (±14 days) after FU-2): After the post-treatment follow-up visits, each subject will continue to be followed for survival and receipt of non-protocol anticancer therapy (NPACT). The Investigator (or designee) will contact the subject every 12 weeks after the second post-treatment follow-up visit (FU-2) until the subject expires, withdraws consent for such contacts, or the Sponsor decides to cease collecting these data for the study. Survival visits may be conducted in person or by telephone.

Safety assessments for subjects receiving combination therapy will be performed during Study Safety Visits (SSVs) at least every 3 weeks (ie, no more than 3 weeks apart) regardless of whether an immunotherapy infusion is planned or not. For subjects assigned to receive Compound 1+nivolumab+ipilimumab, the SSV interval will change to at least every 4 weeks (ie, no more than 4 weeks apart) after they have completed their ipilimumab treatment. Additional study visits may be required for imaging, PK, immunogenicity, and biomarker assessments between the SSVs.

Cohort-Expansion Stage

The Cohort-Expansion Stage will be initiated once the MTD/RD of each Compound 1 combination therapy of the Dose-Escalation Stage (Cohorts A, B and C) has been established. The Cohort-Expansion Stage will further characterize the safety, tolerability, and preliminary efficacy of Compound 1 in combination therapy with nivolumab, nivolumab+ipilimumab, and nivolumab+BEMPEG. Subjects with genitourinary cancers will enroll in tumor-specific expansion cohorts of the following types: clear cell renal cell carcinoma (ccRCC, first- and second line for locally advanced or metastatic disease), metastatic castration-resistant prostate cancer (mCRPC, second-line post-NHT), urothelial carcinoma (UC, ICI naïve and ICI experienced), and non-clear cell renal cell carcinoma (nccRCC, first-line for advanced or metastatic disease). Each expansion cohort will have multiple treatment arms to which subjects will be randomized. In order to better understand the individual contribution of agents of the Compound 1 combination therapies, treatment arms of the expansion cohorts may also include combination therapies of nivolumab+ipilimumab, nivolumab+BEMPEG, and Compound 1 alone. Treatment arms within a tumor-specific expansion cohort will be evaluated in parallel. Randomization within a tumor type will be used to minimize potential imbalances between the treatment arms.

All enrolled subjects may receive study treatment until radiographic progression per RECIST 1.1 per investigator assessment or unacceptable toxicity, and a subject may be allowed to continue to receive study treatment beyond radiographic progression if the Investigator believes that the subject is still benefitting from treatment and that the benefits of continued treatment outweigh the risks (specific criteria for treatment beyond progression are described above). Compound 1, Nivolumab, and BEMPEG will be provided for a maximum of 2 years based on the time since the first dose of study treatment. Ipilimumab will be administered for a maximum of 4 doses.

Overview Of The Cohort-Expansion Stage

Figure 19:
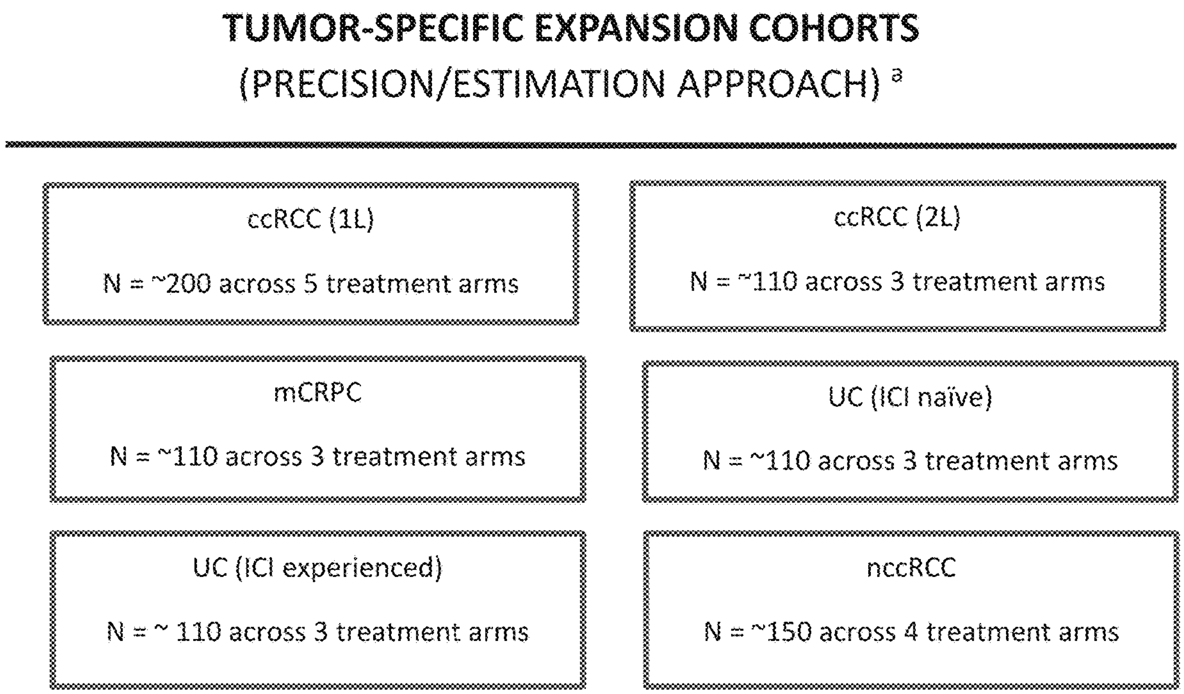

FIG. 19 provides an overview of the tumor-specific expansion cohorts. Cohort-Expansion cohorts will have 3 to 5 separate treatment arms which will be evaluated in parallel. Subjects will be evenly allocated by randomization to the open treatment arms within a tumor-specific expansion cohort. Enrollment of an individual treatment arm may be paused or closed (eg, when the treatment arm meets its planned enrollment), while the remaining treatment arms in the cohort continue enrollment.

Enrollment of an individual treatment arm may be paused or closed (eg, when the treatment arm meets its planned enrollment), while the remaining treatment anns in the cohort continue enrollment.

Expansion Stage with Tumor Cohorts and Treatment Arms

Expansion Stage with Tumor Cohorts and Treatment Arms

| Cohort # | Tumor type | Randomization [a] (Enrollment Ratio) [b] | Treatment Arms |
|---|---|---|---|
| 1 | ccRCC 1L | 1:1:1:1:1 (40:40:40:40:40) | Arm 1: Compound 1 + nivolumab<br>Arm 2: nivolumab + ipilimumab |

-continued

Expansion Stage with Tumor Cohorts and Treatment Arms

| Cohort # | Tumor type | Randomization [a] (Enrollment Ratio) [b] | Treatment Arms |
|---|---|---|---|
| | | | Arm 3: Compound 1 + nivolumab + ipilimumab<br>Arm 4: nivolumab + BEMPEG<br>Arm 5: Compound 1 + nivolumab + BEMPEG |
| 2 | ccRCC 2L | 1:1:1 (30:40:40) | Arm 1: Compound 1<br>Arm 2: Compound 1 + nivolumab<br>Arm 3: Compound 1 + nivolumab + BEMPEG |
| 3 | mCRPC | 1:1:1 (30:40:40) | Arm 1: Compound 1<br>Arm 2: Compound 1 + nivolumab<br>Arm 3: Compound 1 + nivolumab + ipilimumab |
| 4 | UC (ICI naïve) | 1:1:1 (30:40:40) | Arm 1: Compound 1<br>Arm 2: Compound 1 + nivolumab<br>Arm 3: Compound 1 + nivolumab + BEMPEG |
| 5 | UC (ICI experienced) | 1:1:1 (30:40:40) | Arm 1: Compound 1<br>Arm 2: Compound 1 + nivolumab<br>Arm 3: Compound 1 + nivolumab + BEMPEG |
| 6 | nccRCC 1L | 1:1:1:1 (30:40:40:40) | Arm 1: Compound 1<br>Arm 2: Compound 1 + nivolumab<br>Arm 3: Compound 1 + nivolumab + ipilimumab<br>Arm 4: Compound 1 + nivolumab + BEMPEG |

1L, first line; 2L, second line; BEMPEG, bempegaldesleukin; ccRCC, clear-cell renal cell carcinoma; CRPC, castration-resistant prostate cancer; ICI, immune checkpoint inhibitor; nccRCC, non-clear cell renal cell carcinoma; UC, urothelial carcinoma.

[a] Subjects will be evenly randomly assigned across the open treatment arms in the respective cohort. Treatment arms may be paused due to safety concerns or for futility analyses or may be closed because total enrollment in the arm has been reached.

[b] The enrollment ratio represents the planned enrollment for each treatment arm in the cohort.

[c] Cohort 1 has no single agent Compound 1 treatment arm since approved effective therapies are available for this tumor type and treatment line.

Cohort-Expansion Stage Study Design

The multi-treatment arm tumor-specific expansion cohorts will enroll subjects until the target sample size is reached. A tumor-specific expansion cohort or treatment arm may be opened or closed to enrollment at any time at the Sponsor's discretion. Subjects will be evenly randomly assigned across the open treatment arms in the respective cohort.

Study Treatment Management

Study treatment must be discontinued for unacceptable toxicity or if there is a need for subsequent systemic anti-cancer treatment.

Permitted study treatment modifications to manage AEs comprise dose reductions or holds for Compound 1, dose reductions or delays for BEMPEG, and dose delays for nivolumab and ipilimumab. Following Sponsor notification, subjects in combination therapy cohorts may be allowed to discontinue components of study treatment for managing AEs and continue to receive the other component(s) if considered safe and the Investigator believes that the subject is still receiving benefit from study treatment. Treatment holds or delays for drug-related AEs are allowed for up to 8 weeks. Longer treatment holds and delays may be allowed for both single-agent and combination therapy treated subjects, upon approval by the Sponsor, if considered safe and the Investigator believes that the subject is still receiving benefit from study treatment.

Subjects are allowed to continue to receive nivolumab and BEMPEG for up to 2 years (based on the time since the first dose of study treatment) and ipilimumab for up to 4 doses if the subject continues to experience clinical benefit that outweighs the risks in the opinion of the investigator. There is no maximum treatment duration for Compound 1 if the subject has not experienced a loss of clinical benefit or met a discontinuation criterion.

Study Visits

Each subject's course of treatment in expansion cohorts will consist of the following periods:

Pre-Treatment Period: Subjects will be consented and undergo screening and baseline evaluations to be qualified for the study.

Treatment Period: Subjects will be treated and monitored for safety (including laboratory assessments) and signs of toxicity. In the absence of radiographic PD per RECIST 1.1 and unacceptable toxicity, subjects may continue to receive Compound 1 treatment. Nivolumab and BEMPEG treatment is limited to a maximum duration of 2 years (based on the time since the first dose of study treatment), and ipilimumab treatment is limited to a maximum of 4 doses.

Treatment after radiographic progression if the Investigator believes that the subject is still receiving clinical benefit from study treatment and that the potential benefit of continuing study treatment outweighs potential risk (see the criteria for treatment beyond progression above). Clinical judgment should be used for allowing treatment beyond radiographic progression. Subjects with clinically significant symptomatic deterioration at the time of radiographic progression may not be suitable for further treatment. The possibility of a delayed antitumor immune response should be taken into consideration: mixed responses with decreasing and increasing tumor lesion sizes at the same imaging time point or the appearance of new lesions prior to achieving a radiological response have been reported with immunomodulating therapies.

Post-Treatment Period:

Post-Treatment Follow-Up Visit: Two post-treatment follow-up safety visits will occur 30 (+14) days [FU-1] and 100 (+14) days [FU-2] after the date of the decision to discontinue study treatment. If a related AE leading to study treatment discontinuation or related SAE is ongoing at the 100-day follow-up visit, it is to be followed until considered resolved or irreversible. Both follow-up visits should be conducted in person.

Extended Follow Up (Every 12 weeks (±14 days) after FU-2): After the post-treatment follow-up visits, each subject will continue to be followed for survival and receipt of NPACT. The Investigator (or designee) will make contact with the subject every 12 weeks after the second post-treatment follow-up visit (FU-2) until the subject expires, withdraws consent for such contacts, or the Sponsor decides to cease collecting these data for the study. Survival visits may be conducted in person or by telephone.

Safety assessments for subjects receiving combination therapy will be performed during Study Safety Visits (SSVs) at least every 3 weeks (ie, no more than 3 weeks apart) regardless of whether an immunotherapy infusion is planned or not. For subjects assigned to receive a combination regimen including ipilimumab, the SSV interval will change to at least every 4 weeks (ie, no more than 4 weeks apart) after they have completed the first 4 nivolumab doses.

Additional study visits may be required for imaging, PK, immunogenicity, and biomarker assessments between the SSVs.

Study Committees

The Sponsor will engage the following committees to review safety, PK and efficacy data for this study:

A Cohort Review Committee will review data for dose escalation. During the Dose-Escalation Stage, the Cohort Review Committee will review safety data for each cohort in conjunction with all available safety and PK data for all subjects to determine DLTs and make dose escalation recommendations. The Cohort Review Committee will also review all available safety and PK data to determine the MTD/RD for each treatment regimen. The Cohort Review Committee will include the Sponsor's medical monitor and/or Drug Safety physician, chief medical officer and/or head of Clinical Development, and participating principal investigators in the Dose-Escalation Stage.

A Study Oversight Committee (SOC) will periodically monitor the safety and antitumor activity for subjects in the Cohort-Expansion Stage. This committee will consist of Sponsor medical, safety, and biostatistical personnel and selected investigators who are experts in the treatment of the enrolled tumor types. The SOC membership may include members of the Cohort Review Committee.

The Sponsor's Executive Safety Committee (ESC) will provide oversight for potential safety signals identified. The results of safety reviews will guide potential amendments to the protocol entry criteria and assessments.

A Blinded Independent Radiology Committee (BIRC) may be established to evaluate tumor scans and prior radiation history data of trial subjects in a central, blinded, and independent fashion.

Number of Subjects

Approximately 30 subjects will be enrolled during the Dose-Escalation Stage with approximately 12 subjects enrolled into each of the three combination therapies (Cohorts A-C).

Approximately 790 subjects will be enrolled during the Cohort-Expansion Stage: ~200 subjects for Cohort 1 (ccRCC, 1L, 5 treatment arms), and ~110 subjects each for Cohorts 2-5 (RCC 2L, mCRPC, UC ICI naïve and ICI experienced; 3 treatment arms each), and ~150 subjects for Cohort 6 (nccRCC; 4 treatment arms).

For the Dose-Escalation Stage approximately 9 sites will be participating, and for the Cohort-Expansion Stage approximately 140 sites globally.

| Enrollment Estimates and Dosing Information | | | | | | |
|---|---|---|---|---|---|---|
| Dose-Escalation Stage (3+3 Design) | | | | | | |
| Cohort | Tumor Type | Cmpd 1 (PO qd) | Nivolumab (IV q3w) | Ipilimumab IV (IV q3w) | BEMPEG (IV q3w) | Enrollment N ~ 36 |
| A | Solid Tumor | TBD mg | 360 mg | — | — | 6-12 |
| B | Solid Tumor | TBD mg | 3 mg/kg[a] | 1 mg/kg (4 doses) | — | 6-12 |
| C | Solid Tumor | TBD mg | 360 mg | — | 0.006 mg/kg | ~6 |
| Cohort Expansion Stage (Precision/Estimation Approach) | | | | | | |
| Cohort (Tumor) | Randomization | Cmpd 1 (PO qd) | Nivolumab (IV q3w) | Ipilimumab (IV q3w) | BEMPEG (IV q3w) | Enrollment N ~790 |
| 1 | Arm 1 | TBD mg | 360 mg | — | — | up to 40 for |
| (ccRCC IL) | Arm 2 | — | 360 mg | 1 mg/kg (4 doses) | — | each arm |
| | Arm 3 | TBD mg | 3 mg/kg[a] | 1 mg/kg (4 doses) | — | |
| | Arm 4 | — | 360 mg | — | 0.006 mg/kg | |
| | Arm 5 | TBD mg | 360 mg | — | 0.006 mg/kg | |
| 2 | Arm 1 | TBD mg | — | — | — | up to 30 |
| (ccRCC 2L) | Arm 2 | TBD mg | 360 mg | — | — | up to 40 for |
| | Arm 3 | TBD mg | 360 mg | — | 0.006 mg/kg | each arm |
| 3 | Arm 1 | TBD mg | — | — | — | up to 30 |
| (mCRPC) | Arm 2 | TBD mg | 360 mg | — | — | up to 40 for |
| | Arm 3 | TBD mg | 3 mg/kg[a] | 1 mg/kg (4 doses) | — | each arm |
| 4 | Arm 1 | TBD mg | — | — | — | up to 30 |
| (UC ICI-naive) | Arm 2 | TBD mg | 360 mg | — | — | up to 40 for |
| | Arm 3 | TBD mg | 360 mg | — | 0.006 mg/kg | each arm |
| 5 | Arm 1 | TBD mg | — | — | — | up to 30 |
| (UC | Arm 2 | TBD mg | 360 mg | — | — | up to 40 for |
| ICI-experienced) | Arm 3 | TBD mg | 360 mg | — | 0.006 mg/kg | each arm |
| 6 | Arm 1 | TBD mg | — | — | — | up to 30 |
| (nccRCC 1L) | Arm 2 | TBD mg | 360 mg | — | — | up to 40 for |
| | Arm 3 | TBD mg | 3 mg/kg[a] | 1 mg/kg (4 doses) | — | each arm |
| | Arm 4 | TBD mg | 360 mg | — | 0.006 mg/kg | |

IL, first line; 2L, second line; BEMPEG, bempegaldesleukin; ccRCC, clear-cell renal cell carcinoma; mCRPC, metastatic castration-resistant prostate cancer; ICI, immune checkpoint inhibitor; IV, intravenous; nccRCC, non-clear cell renal cell carcinoma; PO, administered orally; q3w, once every 3 weeks; qd, once daily; TBD, to be determined; UC, urothelial carcinoma.

[a]Subjects receiving combination therapies containing both nivolumab and ipilimumab will have their nivolumab treatment administered at 3 mg/kg q3w weight-based dosing for the first 4 doses, after which nivolumab dosing will change to a flat dose of 480 mg q4w.

Target Population

To be eligible for the study, the subject must meet all the inclusion and none of the exclusion criteria. The Sponsor will not grant exceptions to these eligibility criteria:

Inclusion Criteria

Cytologically or histologically confirmed solid tumor that is unresectable, locally advanced or metastatic:

Dose-Escalation Stage:

Subjects with a solid tumor that is unresectable or metastatic and for which life-prolonging therapies do not exist or available therapies are intolerable or no longer effective.

Cohort-Expansion Stage:

The tumor cohorts for the Expansion Stage are as follows:

| Inclusion Criterion | Expansion Cohort |
|---|---|
| 1b | Cohort 1: ccRCC (1L) |
| 1c | Cohort 2: ccRCC (2L) |
| 1d | Cohort 3: mCRPC |
| 1e | Cohort 4: UC ICI naïve |
| 1f | Cohort 5: UC ICI experienced |
| 1g | Cohort 6: nccRCC (1L) |

Cohort 1 (ccRCC, 1L): Subjects with unresectable advanced or metastatic renal cell carcinoma with a clear-cell component, including subjects who also have a sarcomatoid feature.

All risk groups as defined by International Metastatic RCC Database Consortium (IMDC) criteria No prior systemic anticancer therapy for RCC with the following exception: One prior adjuvant or neoadjuvant therapy if such therapy did not include an agent that targets vascular endothelial growth factor (VEGF) or VEGF receptors and if disease recurrence occurred at least 6 months after the last dose of the adjuvant or neoadjuvant therapy Cohort 2 (ccRCC, 2L): Subjects with unresectable advanced or metastatic renal cell carcinoma with a clear-cell component, including subjects who also have a sarcomatoid feature.

All risk groups as defined by IMDC criteria

Must have radiographically progressed during or after treatment with an immune checkpoint inhibitor combination therapy consisting of a PD-1/PD-L1 targeting mAb with a VEGFR-TKI or a PD-1 targeting mAb with a CTLA-4 mAb as the preceding line of therapy before study treatment. Subjects who have been previously treated with a triplet therapy including a VEGFR-TKI, a PD-1 targeting mAb, and a CTLA-4 mAb are not eligible.

Must have received no more than one prior systemic anticancer therapy for unresectable advanced or metastatic renal cell carcinoma Cohort 3 (mCRPC): Men with metastatic adenocarcinoma of the prostate (neuroendocrine differentiation and other histological features are allowed if adenocarcinoma is the primary histology).

Must have progressed during or after one, and only one, NHT (eg, abiraterone, apalutamide, darolutamide, or enzalutamide) given for castration-sensitive locally advanced (T3 or T4) or metastatic castration-sensitive prostate cancer, M0 CRPC, or mCRPC.

Note: Subjects may have previously received taxane-based chemotherapy for metastatic castration-sensitive prostate cancer but no other approved or experimental nonhormonal systemic therapies for mCRPC.

Bilateral orchiectomy or ongoing androgen deprivation therapy with a gonadotropin-releasing hormone (GnRH) agonist/antagonist (surgical or medical castration), with serum testosterone <50 ng/dL (<1.73 nmol/L) at screening Progressive disease at study entry as defined by at least one of the following two criteria:

a) Prostate specific antigen (PSA) progression defined by a minimum of 2 rising PSA values from 3 or 4 consecutive assessments with an interval of at least 7 days between assessments. Note: If qualifying solely by PSA progression, the screening PSA value must be at least 2 ng/mL (2 ug/L), and the oldest qualifying value must have been based on a blood sample drawn no longer than one year prior to signing of the informed consent form (ICF) with no change in systemic regimen for the treatment of prostate cancer; up to one PSA decrease is permitted as long as it is not the most recent value. If the study lab is the local lab at which the subject's previous PSA blood samples were drawn, then the screening local lab PSA must be the highest, OR b) Radiographic progression (PD) in soft tissue and/or bone by Investigator assessment Note: Subjects with bone-only disease are allowed if they meet all eligibility criteria Cohort 4 (UC, ICI naïve): Subjects with histologically confirmed, unresectable, locally advanced or metastatic transitional cell carcinoma of the urothelium (including the renal pelvis, ureter, urinary bladder, or urethra)

Stage IV disease (T4b, NO, M0; any T, N1-N3, M0; any T, any N, M1)

Must have progressed during or after prior first-line platinum-based combination therapy.

Must have received no more than 1 prior line of systemic anticancer therapy for unresectable, locally advanced or metastatic disease.

Note: Subjects who have had recurrence within the 6 months of completing adjuvant anti-PD-(L)1 treatment are not eligible Cohorts 5 (UC, ICI experienced): Subjects with histologically confirmed, unresectable, locally advanced or metastatic transitional cell carcinoma of the urothelium (including the renal pelvis, ureter, urinary bladder, or urethra)

Stage IV disease (T4b, NO, M0; any T, N1-N3, M0; any T, any N, M1)

Must have progressed during or after prior PD-1/PD-L1 targeting immune checkpoint inhibitor therapy given as monotherapy, combination therapy, or maintenance therapy Must have received no more than 2 prior lines of systemic anticancer therapy for unresectable advanced or metastatic disease.

Cohort 6 (nccRCC): Subjects with unresectable advanced or metastatic non-clear cell renal cell carcinoma of the following subtypes: Papillary RCC (any type), unclassified RCC, sarcomatoid RCC (≥50% of the tumor has sarcomatoid features).

All risk groups as defined by IMDC criteria

No prior systemic anticancer therapy for RCC is allowed with the following exception: One prior adjuvant or neoadjuvant therapy is allowed if disease recurrence occurred at least 6 months after the last dose of the adjuvant or neoadjuvant therapy.

Expansion Cohorts 1, 2, 4, 5, 6: Measurable disease per Response Evaluation Criteria in Solid Tumors version 1.1 (RECIST 1.1; Eisenhauer et al 2009) as determined by the Investigator.

Note: Measurable disease must be outside the radiation field if radiation therapy was administered. Expansion cohort 3 (mCRPC) does not require measurable disease for study eligibility Archival tumor tissue material, if available, or fresh tumor tissue if it can be safely obtained. Specific requirements for tumor tissue samples will be described in the Pharmacodynamic/Biomarker Laboratory Manual.

Recovery to baseline or <Grade 1 CTCAE v5 from adverse events related to any prior treatments unless AE(s) are clinically nonsignificant and/or stable on supportive therapy. Examples of exceptions are Grade 2 neuropathy, alopecia, physiological hormone replacement therapy.

Age 18 years or older on the day of consent.

Karnofsky Performance Status (KPS) ≥70%.

Adequate organ and marrow function, based upon meeting all of the following laboratory criteria within 14 days before first dose of study treatment:

- Absolute neutrophil count (ANC) ≥1500/μL (≥1.5 109/L) without granulocyte colony-stimulating factor support within 2 weeks of screening laboratory sample collection.
- Platelets ≥100,000/$mm^3$ (≥100 GI/L) without transfusion within 2 weeks of screening laboratory sample collection.
- Hemoglobin ≥9 g/dL (≥90 g/L) without transfusion within 2 weeks prior to screening laboratory sample collection.
- International Normalized Ratio (INR)<1.5 and activated partial thromboplastin time (aPTT)<1.2× upper limit of normal (ULN).
- Alanine aminotransferase (ALT), aspartate aminotransferase (AST), and alkaline phosphatase (ALP)<3× ULN.
  - For all subjects with documented bone metastases: ALP <5×ULN. (For mCRPC subjects ALP <10× ULN if it can be demonstrated that the increase is predominantly bone-specific ALP).
- Total bilirubin <1.5×ULN (for subjects with Gilbert's disease <3×ULN).
- Serum creatinine <1.5×ULN or calculated creatinine clearance ≥40 mL/min (≥0.67 mL/sec).
- Urine protein-to-creatinine ratio (UPCR)<1 mg/mg (<113.2 mg/mmol) creatinine or 24-hour urine protein <1 g. For subjects with UC: <2.0 mg/mg (<226.4 mg/mmol) creatinine or 24-hour urine protein <2 g.
- Negative hepatitis B surface antigen (HBsAg) test
- Negative hepatitis C virus (HCV) antibody test, or positive HCV antibody test followed by a negative HCV RNA test and no ongoing anti-HCV therapy. Note: The HCV RNA test will be performed only for patients who have a positive HCV antibody test.

Capable of understanding and complying with the protocol requirements and must have signed the informed consent document.

Sexually active fertile subjects and their partners must agree to use highly effective methods of contraception during the course of the study and (a) for 1 month after the last dose of Compound 1 and (b) for 5 months for women after the last dose of nivolumab, ipilimumab, or BEMPEG. An additional contraceptive method, such as a barrier method (eg, condom), is also required. In addition, men must agree not to donate sperm during these same periods.

Female subjects of childbearing potential must not be pregnant at screening. Female subjects are considered to be of childbearing potential unless one of the following criteria is met: permanent sterilization (hysterectomy, bilateral salpingectomy, or bilateral oophorectomy) or documented postmenopausal status (defined as 12 months of amenorrhea in a woman >45 years-of-age in the absence of other biological or physiological causes. In addition, females <55 years-of-age must have a serum follicle stimulating hormone [FSH] level >40 mIU/mL to confirm menopause). Note: Documentation may include review of medical records, medical examination, or medical history interview by study site staff Exclusion Criteria

- Prior treatment with Compound 1, nivolumab, ipilimumab, or agents targeting the IL-2 pathway. Note: Prior PD-1/PD-L1 and CTLA-4 targeting therapy for locally advanced or metastatic disease is allowed for Cohorts 2 (ccRCC 2L) and 5 (UC [ICI experienced]).
- For Cohorts 2 (ccRCC 2L), 3 (mCRPC), 4 and 5 (UC): Receipt of any type of small molecule kinase inhibitor (including investigational kinase inhibitor) within 2 weeks before first dose of study treatment.
- For Cohort 3 (mCRPC): Receipt of abiraterone within 1 week; cyproterone within 10 days; or receipt of flutamide, nilutamide, bicalutamide, enzalutamide, or other androgen-receptor inhibitors within 2 weeks before first dose of study treatment.
- For Cohorts 2 (ccRCC 2L), 3 (mCRPC), 4 and 5 (UC): Receipt of any type of anticancer antibody or systemic chemotherapy within 4 weeks before first dose of study treatment.
- Any complementary medications (e.g. herbal supplements or traditional Chinese medicines) to treat the disease under study within 2 weeks before first dose of study treatment.
- Prior radiation therapy within 2 weeks prior to first study treatment. Subjects must have recovered (ie, Grade <1 or at baseline) from radiation-related toxicities (eg, radiation associated esophagitis) prior to first study treatment.
- Known brain metastases or cranial epidural disease unless adequately treated with radiotherapy and/or surgery (including radiosurgery) and stable for at least 4 weeks before first dose of study treatment.
- Note: Subjects with an incidental finding of an isolated brain lesion <1 cm in diameter may be eligible after Sponsor approval if the lesion is radiographically stable for 4 weeks before first dose and does not require treatment per Investigator judgement.
- Note: Eligible subjects must be neurologically asymptomatic and without corticosteroid treatment at the time of first dose of study treatment. A stable dose of anticonvulsants is allowed.
- Concomitant anticoagulation with oral anticoagulants (eg, warfarin, direct thrombin and Factor Xa inhibitors) and platelet inhibitors (eg, clopidogrel).
- Allowed Anticoagulants are
  - i. Low-dose aspirin for cardioprotection (per local applicable guidelines) and low-dose low molecular weight heparins (LAMfWH).

ii. Therapeutic doses of LMvWH in subjects without known brain metastases.

Note: Subjects must have discontinued oral anticoagulants within 3 days or 5 half-lives prior to first dose of study treatment, whichever is longer.

Administration of a live, attenuated vaccine within 30 days prior to randomization. Note: If feasible, vaccines for SARS-CoV-2 should be administered at least 2 weeks before initiating study treatment.

The subject has uncontrolled, significant intercurrent or recent illness including, but not limited to, the following conditions:

Unstable or deteriorating cardiovascular disease including but not limited to the following:

Congestive heart failure New York Heart Association class 3 or 4, unstable angina pectoris, serious cardiac arrhythmias (eg, ventricular flutter, ventricular fibrillation, Torsades de pointes), or ejection fraction <45% on screening echocardiogram or multigated acquisition scan (MUGA).

Uncontrolled hypertension defined as sustained blood pressure (BP) >150 mm Hg systolic or >90 mm Hg diastolic despite optimal antihypertensive treatment. Note: Subjects with hypertension must be on a stable anti-hypertensive regimen for the 7 days before first dose.

Stroke (including transient ischemic attack [TIA]), myocardial infarction, or other ischemic event or pulmonary embolism (PE) within 12 months before first dose.

Pulmonary embolism (PE) or deep vein thrombosis (DVT) or prior clinically significant venous or non-CVA/TIA arterial thromboembolic events within 3 months prior to first dose unless stable, asymptomatic, and treated with low molecular weight heparin (LMWH) or oral anticoagulants for at least 3 weeks before first dose. Note: Subjects who don't require prior anticoagulation therapy may be eligible but must be discussed and approved by the study Medical Monitor.

Gastrointestinal (GI) disorders including those associated with a high risk of perforation or fistula formation:

Tumors invading the GI-tract from external viscera.

Active peptic ulcer disease, inflammatory bowel disease, diverticulitis, cholecystitis, symptomatic cholangitis or appendicitis, or acute pancreatitis.

Acute obstruction of the bowel, gastric outlet, or pancreatic or biliary duct within 6 months unless cause of obstruction is definitively managed and subject is asymptomatic.

Abdominal fistula, gastrointestinal perforation, bowel obstruction, or intra-abdominal abscess within 6 months before first dose.

Note: Complete healing of an intra-abdominal abscess must be confirmed before first dose.

Clinically significant hematuria, hematemesis, or hemoptysis of >0.5 teaspoon (2.5 mL) of red blood, or other history of significant bleeding (eg, pulmonary hemorrhage) within 12 weeks before first dose.

Cavitating pulmonary lesion(s) or known endobronchial disease manifestation.

Lesions invading major blood vessel including, but not limited to, inferior vena cava, pulmonary artery, or aorta. Note: Subjects with intravascular tumor extension may be eligible following Sponsor approval.

History of life-threatening toxicity related to prior immune therapy (eg. anti-CTLA-4 or anti-PD-1/PD-L1 treatment or any other antibody or drug specifically targeting T-cell co-stimulation or immune checkpoint pathways except those that are unlikely to re-occur with standard countermeasures (eg. hypothyroidism)

Other clinically significant disorders such as:

Any active, known or suspected autoimmune disease.

Note: Subjects with type I diabetes mellitus, hypothyroidism only requiring hormone replacement, skin disorders (such as vitiligo, psoriasis, or alopecia) not requiring systemic treatment, or conditions not expected to recur in the absence of an external trigger are permitted to enroll.

Any condition requiring systemic treatment with either corticosteroids (>10 mg daily prednisone equivalent) or other immunosuppressive medications within 14 days of randomization. Note: Inhaled, intranasal, intra-articular, or topical steroids are permitted. Adrenal replacement steroid doses >10 mg daily prednisone equivalent are permitted in the absence of active autoimmune disease. Transient short-term use of systemic corticosteroids for allergic conditions (eg, contrast allergy) is also allowed.

Active infection requiring systemic antimicrobial treatment (antibiotics, antimycotic, antiviral). Note: Prophylactic antibiotic treatment is allowed.

Known infection with the human immunodeficiency virus (HIV) or acquired immunodeficiency syndrome (AIDS)-related illness.

History of idiopathic pulmonary fibrosis, organizing pneumonia, drug-induced pneumonitis, idiopathic pneumonitis, or evidence of active pneumonitis on screening chest CT scan Known or suspected infection with SARS-CoV-2 within one month before enrollment. Note: demonstration that the subject has recovered from the infection is required to be eligible for enrollment.

Serious non-healing wound/ulcer/bone fracture.

Note: non-healing wounds or ulcers are permitted if due to tumor-associated skin lesions.

Malabsorption syndrome.

Pharmacologically uncompensated, symptomatic hypothyroidism.

Moderate to severe hepatic impairment (Child-Pugh B or C).

Requirement for hemodialysis or peritoneal dialysis.

History of solid organ or allogeneic stem cell transplant.

History of life-threatening toxicity related to prior immune therapy (eg, anti-CTLA-4 or anti-PD-1/PD-L1 treatment or any other antibody or drug specifically targeting T-cell co-stimulation or immune checkpoint pathways) except those that are unlikely to recur and manageable by standard of care treatment (eg, hypothyroidism)

1. Complete wound healing from major surgery must have occurred at least 2 weeks before first dose and 1 week from minor surgery (Note: Tumor biopsies should be performed ≥7 days before first dose). Subjects with clinically relevant ongoing complications from prior surgery are not eligible.

2. Corrected QT interval calculated by the Fridericia formula (QTcF) >480 ms per electrocardiogram (ECG) within 14 days before first dose of study treatment.
   Note: If a single ECG shows a QTcF with an absolute value >480 ms, two additional ECGs at intervals of approximately 3 min must be performed within 30 min after the initial ECG, and the average of these three consecutive results for QTcF will be used to determine eligibility
3. History of psychiatric illness likely to interfere with ability to comply with protocol requirements or give informed consent.
4. Pregnant or lactating females.
5. Inability to swallow study treatment formulation.
6. Previously identified allergy or hypersensitivity to components of the study treatment formulations history of severe infusion-related reactions to monoclonal antibodies.
7. Any other active malignancy within 2 years before first dose of study treatment, except for except for locally curable cancers that have been apparently cured such as basal or squamous cell skin cancer, superficial bladder cancer, or carcinoma in situ of the prostate, cervix, or breast.

Estimated Length of Subject Participation

It is estimated that subjects with advanced solid tumors may receive study treatment for an average of approximately 6-14 months depending on the tumor type and line of therapy. The study is designed for subjects to receive ipilimumab for up to 4 doses, nivolumab and BEMPEG for up to 2 years based on the date of first dose of study treatment, and Compound 1 as long as the subject has not experienced a loss of clinical benefit or met a discontinuation criterion. Subjects will be followed until death, withdrawal of consent, or Sponsor decision to no longer collect these data.

Estimated Study Duration

It is estimated that approximately 24 to 36 months will be required to enroll and treat subjects in the study. After sufficient data have been collected to adequately evaluate all study endpoints, including OS, and upon site notification by the Sponsor, the study will be considered complete at sites and in countries that no longer have active subjects. The true study duration may be longer or shorter due to divergence from assumptions or due to the impact of the global COVID-19 pandemic on subject enrollment and other aspects of study conduct.

End of Trial

End of trial is defined as the later of two dates: the date of the last visit or procedure for the last subject remaining or the date at which the last data point required for follow-up for the last subject is obtained.

Investigational Regimen Dose/Route/Interval

Compound 1 Tablets

Compound 1 tablets will be provided at 20-mg and 80-mg strengths. Tablets should be stored at controlled room temperature. Subjects will take study medication orally once daily (qd).

Note: In case of lower Compound 1 dose levels than 80 mg qd, multiples of 20 mg tablets will be used. In case of higher Compound 1 dose levels than 80 mg, a combination of 80 mg and 20 mg tablets will be used.

Compound 1 tablets should not be crushed or chewed. Subjects should be instructed not to eat for at least 2 hours before and at least 1 hour after taking Compound 1. The subject should take their assigned Compound 1 dose by mouth with a minimum of 8 oz (240 mL) of water.

Nivolumab

Nivolumab will be administered at the clinic as an IV infusion over approximately 30 minutes.

Nivolumab will be given in one of two dosing regimens:

360 mg once every 3 weeks (q3w) when given in combination with Compound 1 and/or BEMPEG 3 mg/kg once every 3 weeks (q3w) for the first four doses when given in combination with ipilimumab (with or without Compound 1). After the first four doses are completed and no further ipilimumab will be given, nivolumab will be administered at a flat dose of 480 mg as an IV infusion over 30 min every 4 weeks (q4w).

The initial infusion of nivolumab will be given without premedication for potential infusion-related reactions. Premedication for infusion-reaction is allowed after the initial infusion. No bolus or IV push of nivolumab is allowed.

Ipilimumab

Ipilimumab will be administered in the clinic at a dose of 1 mg/kg as an IV infusion over approximately 30 minutes once every 3 weeks (q3w) for a maximum of 4 doses. The initial infusion will be given without premedication for potential infusion-related reactions. Premedication for infusion-reaction is allowed after the initial infusion. No bolus or IV push of ipilimumab is allowed.

BEMPEG

BEMPEG will be administered in the clinic at 0.006 mg/kg as an IV infusion q3w.

Subjects should be carefully monitored for infusion reactions during bempegaldesleukin administration. If the subject experiences a Grade ≥2 infusion-related reaction or hypotension during the days after bempegaldesleukin dosing, the subject may be monitored overnight or for longer periods at the discretion of the Investigator.

Due to the potential risk of development of hypotension after BEMPEG administration, consideration should be given to withholding antihypertensive medications including diuretics, as well as other drugs with hypotensive properties (eg, alpha blockers for benign prostatic hyperplasia), particularly when therapy involves multiple antihypertensive drugs and classes other than thiazide diuretics. Study subjects who are on medications with antihypertensive effects for the treatment of coronary artery disease (eg, beta-blockers, calcium channel blockers, nitrates, etc.) should be able to withhold these drugs. If withholding antihypertensive medications, withhold no less than 12 hours and no more than 48 hours prior to each dose of BEMPEG. Antihypertensive medications may be reinstituted between doses of BEMPEG at any time as clinically indicated (eg, based on blood pressure monitoring result).

Study Treatment Administration

The first doses of Compound 1 and all doses of IV study treatment will be administered at the study site. Following the first dose of Compound 1, the subject should take subsequent Compound 1 doses outside the clinic at approximately the same time every day and should adhere to the fasting requirements described in this section. NOTE: For subjects enrolled in Cohort-Expansion Stage Cohort 3 (mCRPC), Compound 1 treatment must be held for ≥7 days prior to any scheduled bone scan.

Compound 1+Nivolumab Combination Therapy:

In both the Dose-Escalation and Cohort-Expansion Stages, Compound 1 drug will be administered qd to fasted subjects. Subjects will also receive an IV infusion of nivolumab (360 mg q3w) over approximately 30 minutes at the study site. On days when both agents are administered, Compound 1 should be given first. Combination therapy dosing starts at day of first dose (SSV1/Day 1) and continues until the subject terminates study treatment. Subjects will be monitored for at least 30 minutes in the clinic after each nivolumab IV infusion.

Compound 1+Nivolumab+Ipilimumab Combination Therapy:

In both the Dose-Escalation and Cohort-Expansion Stages, Compound 1 drug will be administered qd to fasted subjects. Subjects will also receive IV infusions of nivolumab (3 mg/kg q3w×4 then 480 mg q4w) and ipilimumab (1 mg/kg q3w×4) at the study site. On days when all agents are administered, Compound 1 should be given first followed by nivolumab and then ipilimumab. On days when both IV agents are administered, nivolumab should be given first followed by ipilimumab. Nivolumab infusion (approximately 30 minutes) must be promptly followed by a flush of diluent to clear the line of nivolumab before starting the ipilimumab infusion. The second infusion will always be the ipilimumab study drug (approximately 30 minutes infusion) and will start after the infusion line has been flushed, filters changed, and subject has been observed to ensure no infusion reaction has occurred. The time in between infusions is expected to be at least 30 minutes (from the end of the nivolumab infusion to the start of the ipilimumab infusion). Combination therapy dosing starts at day of first dose (SSV1/Day 1) and continues until the subject terminates study treatment. Subjects will be monitored for at least 30 minutes in the clinic after all IV infusions are complete.

Compound 1+Nivolumab+BEMPEG Combination Therapy:

In both the Dose-Escalation and Cohort-Expansion Stages, Compound 1 drug will be administered qd to fasted subjects. Subjects will also receive IV infusions of nivolumab (360 mg q3w) and BEMPEG (0.006 mg/kg q3w) at the study site. On days when all agents are administered, Compound 1 should be given first followed by BEMPEG and then nivolumab. BEMPEG infusion must be promptly followed by a flush of diluent to clear the line, and administration time should include the time required for flushing. Nivolumab administration should start at least 30 minutes from the end of the BEMPEG administration. Combination therapy dosing starts at day of first dose (SSV1/Day 1) and continues until the subject terminates study treatment. Subjects will be monitored for at least 30 minutes in the clinic after all IV infusions are complete.

Single-Agent Compound 1 Therapy (Cohort-Expansion Stage only):

Compound 1 will be administered qd to fasted subjects.

Nivolumab+Ipilimumab Combination Therapy (Cohort-Expansion Stage only):

Subjects will receive IV infusions of nivolumab (3 mg/kg q3w×4 then 480 mg q4w) and ipilimumab (1 mg/kg q3w×4) at the study site. On days when both agents are administered, nivolumab should be given first followed by ipilimumab. Nivolumab infusion (approximately 30 minutes) must be promptly followed by a flush of diluent to clear the line of nivolumab before starting the ipilimumab infusion. The second infusion will always be the ipilimumab study drug (approximately 30 minutes infusion) and will start after the infusion line has been flushed, filters changed, and subject has been observed to ensure no infusion reaction has occurred. The time in between infusions is expected to be at least 30 minutes (from the end of the nivolumab infusion to the start of the ipilimumab infusion). Combination therapy dosing starts at day of first dose (SSV1/Day 1) and continues until the subject terminates study treatment. Subjects will be monitored for at least 30 minutes in the clinic after all IV infusions are complete.

Nivolumab+BEMPEG Combination Therapy (Cohort-Expansion Stage only):

Subjects will receive IV infusions of nivolumab (360 mg) and BEMPEG (0.006 mg/kg) q3w at the study site. On days when both agents are administered, BEMPEG should be given first followed by nivolumab. BEMPEG infusion must be promptly followed by a flush of diluent to clear the line, and administration time should include the time required for flushing. Nivolumab administration should start at least 30 minutes from the end of the BEMPEG administration. Combination therapy dosing starts at day of first dose (SSV1/Day 1) and continues until the subject terminates study treatment. Subjects will be monitored for at least 30 minutes in the clinic after all IV infusions are complete.

Safety Assessments

Safety evaluations will include assessments of AEs, vital signs, electrocardiograms (ECGs), laboratory tests, and concomitant medications for all study cohorts. Adverse event seriousness, severity grade, and relationship to study treatment will be assessed by the investigator. Severity grade will be defined by the National Cancer Institute Common Terminology Criteria for Adverse Events version 5 (NCI CTCAE v5) guidelines.

Safety for subjects receiving combination therapy, will be assessed on a schedule based on the date of first dose, ie, Study Safety Visit 1 (SSV1)/Day 1. An SSV is required prior to each planned study treatment infusion (the SSV can occur any time within 72 hours prior to the infusion but vital signs must be assessed within 60 min prior to initiation of the infusion). SSVs will be performed at least every 3 weeks (ie, no more than 3 weeks apart) regardless of whether an immunotherapy infusion is planned or not. For subjects assigned to receive Compound 1+nivolumab+ipilimumab, the SSV interval will change to at least every 4 weeks (ie, no more than 4 weeks apart) after they have completed their ipilimumab treatment. Additional visits for safety and other assessments are required during the DLT Evaluation Period.

Tumor Assessments

Tumors will be assessed using the RECIST 1.1 criteria. Subjects will be assessed using magnetic resonance imaging (MRI) or CT scans during screening and periodically after the date of the first dose of study treatment until radiographic PD per RECIST 1.1 as determined by the Investigator. Radiographic tumor assessments will continue according to the protocol-defined schedule, regardless of whether study treatment is reduced, held, delayed, or discontinued.

Chest/Abdomen/Pelvis (CAP): CT of CAP or CT chest and MRI abdomen/pelvis will be performed in all subjects at screening and at every 9 weeks (±5 days) throughout the first 12 months on study. Upon completion of 52 weeks on study, these assessments will be performed every 12 weeks (±7 days).

Brain: MRI (or CT) of the brain will be performed at screening in all subjects. Prior brain imaging performed as standard of care up to 45 days before first dose of study treatment can be used for eligibility determination. After study treatment initiation MRI (or CT) scans of the brain are only required in subjects with documented brain metastasis or if clinically indicated by signs and symptoms suggestive of new brain metastases. Assessments after the first dose of study treatment will be performed every 9 weeks (±5 days)

throughout the first 12 months on study. Upon completion of 52 weeks on study, these assessments will be performed every 12 weeks (±7 days). MRI is the preferred imaging method for brain. If CT of the brain is performed instead of MRI, ambiguous results must be confirmed by MRI. Subjects without documented brain metastasis during the screening assessment are not required to undergo brain imaging after initiating study treatment unless clinically indicated.

Bone scans: Technetium bone scans (TBS) will be performed at screening in all subjects with mCRPC and for subjects with other tumor indications who have a history or clinical symptoms (ie, bone pain) of bone metastases. After study treatment initiation, bone scans are required in all subjects in Cohort-Expansion Stage Cohort 3 (mCRPC) and any other subjects with documented bone lesions or if clinically indicated by signs and symptoms suggestive of new bone metastases. Assessments for subjects with mCRPC will done every 9 weeks (±5 days) after the first dose for the first 12 months and every 12 weeks (±14 days) thereafter; for subjects with other tumor types, bones scans will be performed every 12 weeks (±7 days) throughout the first 12 months and every 24 weeks (±14 days) thereafter.

NOTE: For subjects enrolled in Cohort-Expansion Stage Cohort 3 (mCRPC), Compound 1 treatment must be held for ≥7 days prior to any scheduled bone scan. Except for mCRPC subjects, bone scan findings alone cannot be used for the determination of progression or response in this study and need to be corroborated by CT/MRI. Bone lesions corroborated by CT/MRI must be reported as non-target or new lesions. PET scan or plain films are not considered adequate imaging techniques to measure bone lesions. Bone scan evaluations will end on the date of last CT/MRI scan. If the bone scan schedule does not coincide with the last CT/MRI scan, no additional bone scan is needed after the last CT/MRI has been performed.

Independent Central Review:

To determine radiographic study endpoints for selected cohorts, central review of radiographic images may be conducted by a BIRC. All protocol-required radiographic tumor assessments for these selected cohorts will be sent to the BIRC, which also will review prior radiation history data and prior local therapy information for the purpose of selection of target lesions. Details are provided in the Imaging Manual.

Tumor Marker Assessment

For subjects with mCRPC in the Cohort-Expansion Stage, tumor marker samples (PSA) will be collected at screening and while on study until the earlier of initiation of subsequent systemic anticancer therapy or permanent loss to radiographic follow-up (including hospice admission). The tumor marker assessments will not be used to determine progressive disease or to make study treatment decisions in this study.

Overall Survival Follow-Up Assessments

All subjects will be contacted approximately every 12 weeks (±14 days) after their last post-treatment follow-up visit (ie, FU-2) to assess survival status and to document receipt of systemic NPACT unless the subject expires, consent to participate in non-interventional study assessments is withdrawn, or the Sponsor deems sufficient efficacy data have been collected for the study.

Pharmacokinetic Assessments

Blood samples will be obtained to assess the PK of Compound 1 and its potential metabolites for single agent and combination therapies. Blood samples for nivolumab, ipilimumab, and/or BEMPEG PK will also be collected for combination therapy cohorts.

For the Dose-Escalation Stage:

- Blood samples will be obtained to assess the PK of Compound 1 and its potential metabolites:
  - On the date of first dose of study treatment (SSV1[Day 1]): prior to any study treatment administration and at 2 h, 4 h, and 6-8 h after Compound 1 Compound 1 dosing.
  - On Day 10: pre-dose and 2 h after Compound 1 dosing.
  - On Day 21: prior to any study treatment administration and at 2 h, 4 h, and 6-8 h after Compound 1 dosing.
  - On SSV2 (Day 22), SSV3, SSV4, SSV5, SSV7, and SSV10: pre-dose and at 2 h after Compound 1 dosing.
- Blood samples will be obtained for nivolumab (serum) and ipilimumab (serum) concentration measurement:
  - Predose and at the end of each infusion on SSV1 (Day 1), SSV2, SSV4, SSV7, SSV10, and at the Post-Treatment Follow-Up visits (FU-1 and FU-2)
- Blood samples will be obtained for BEMPEG (plasma) concentration measurement:
  - Predose, at the end of BEMPEG infusion, and at 4 h post-dose on SSV1 (Day 1), and on Days 5 (±2 days) and 10 (±2 days) post-Day 1 infusion.
  - Predose and at the end of infusion at SSV2, SSV7, and SSV10

For the Cohort-Expansion Stage:

- Blood samples will be obtained for Compound 1 Compound 1 and its potential metabolites at the following times:
  - Predose and at 2 h after Compound 1 Compound 1 dosing at SSV1 (Day 1), SSV2 (Day 22), SSV3, SSV4, SSV5, SSV7, and SSV10.
  - For subjects with mCRPC (Cohort 3): PK samples will be collected at time of bone scan for the first two bone scans after treatment initiation (ie, approximately Days 85 and 169).
- Blood samples will be collected for nivolumab (serum) and ipilimumab (serum) concentration measurement in combination treatment arms:
  - Predose and at the end of each infusion on SSV1 (Day 1), SSV2, SSV4, SSV7, SSV10, and at the Post-Treatment Follow-up visits (FU-1 and FU-2)
- Blood samples will be collected for BEMPEG (plasma) concentration measurement in combination treatment arms:
  - Predose and at the end of each infusion on SSV1 (Day 1), SSV2, SSV4, SSV7, and SSV10

Immunogenicity Assessments

Blood samples will be obtained from all subjects in the combination therapy cohorts during the Dose-Escalation Stage and the Cohort-Expansion Stage for immunogenicity assessment predose on SSV1 (Day 1), SSV2, SSV4, SSV7, SSV10, and at the last Post-Treatment Follow-up visits (FU-2). Immunogenicity assessments are not required for Compound 1 Compound 1 single-agent therapy treatment arms.

Biomarker Assessments

Peripheral blood samples will be obtained for either single-agent or combination therapy cohorts. If possible, blood samples for immune-cell profiling should also be collected for subjects who experience CRS.

For all subjects, tumor tissue (most recent archival tissue, <2 years from collection) will be obtained prior to first dose of study treatment. If archival material is not available, subjects should undergo a fresh tumor biopsy if it can be safely accessible as assessed by local interventional radiology (IR) and the Investigator (eg, skin lesions, subcutaneous lymph node lesions, lesions with a low risk if accessed by image-guided biopsy). Refer to the Pharmacodynamic/Biomarker Laboratory Manual and contact the Sponsor Translational Medicine representatives with queries and for specific instructions.

If subjects undergo a tumor biopsy at screening, this biopsy must be completed at least 7 days prior to study treatment initiation, and subjects must have complete wound healing before receiving their first study treatment dose. If applicable, Compound 1 dosing will be held starting 48 hours prior to collection of optional on-treatment biopsies with adequate time (7 days minimum) to allow complete wound healing after the biopsy prior to resuming study treatment. If the subject is not receiving Compound 1 as part of the assigned treatment regimen, no study treatment delay or wound healing period is required.

For mCRPC subjects in Cohort 3 of the Cohort-Expansion Stage, plasma and/or serum bone biomarker samples will be collected in conjunction with bone scans.

Exploratory analyses may include the following:

- Genomic and expression analyses (eg, mutation alterations, tumor mutational burden [TMB], etc)
  - Baseline expression of relevant targets
  - Changes of biomarkers from baseline where applicable
- Plasma/serum biomarker analysis (eg, cytokines, chemokines, bone biomarkers for relevant indications etc)
- Immune cell profiling (eg, T cells, monocytes, other relevant cell types)
- Other analyses relevant for specific indications (eg, metabolomics, circulating tumor cells [CTCs], circulating tumor DNA [ctDNA])

Samples may also be used for assay development to facilitate identification of new biomarkers. Collection of biomarker samples may be halted early, or sampling frequency may be modified at the discretion of the Sponsor.

Statistical Methods

Dose-Escalation Stage

The number of subjects per Dose-Escalation cohort has been estimated based on the well-established Phase 1 dose-escalation "3+3" trial design. Subjects are accrued into cohorts evaluating a combination treatment regimen in a "3+3" manner with each cohort consisting initially of 3 subjects at an Compound 1 Compound 1 dose level and potentially expanding to 6 subjects based upon the number of DLTs observed. Additional subjects may be added at any Compound 1 Compound 1 dose level for a combination treatment regimen (up to a total of 12 subjects) being evaluated if the Cohort Review Committee concludes that additional safety data should be obtained at this dose level.

Summaries will focus on AEs and tumor response by cohort. Adverse events will be tabulated by Medical Dictionary for Regulatory Activities (MedDRA) system organ class (SOC) and preferred term (PT). Selected laboratory parameters will be summarized.

Cohort-Expansion Stage:

The multi-treatment arm tumor-specific expansion cohorts will enroll subjects until the target sample size for each treatment arm is reached. A tumor-specific expansion cohort or treatment arm may be open and closed to enrollment at any time at the Sponsor's discretion. The enrollment design for the Compound 1 single-agent treatment arms includes a futility assessment due to the limited available clinical evidence for benefit in the planned patient populations. No futility assessment is necessary for the combination treatment arms as the IV agents planned have clinical precedent for clinical activity.

Combination Therapy Arms

The objective for the Cohort-Expansion Stage combination-therapy arms is to estimate ORR of each treatment arm. Thus, 2-sided 80% and 60% Blaker Confidence intervals (CIs) will be constructed for ORR, providing 90% and 80%, respectively, 1-sided confidence when interpreting the lower bound. The sample size of 40 subjects for each combination-therapy arm was chosen to ensure the lower bound of the 2-sided 80% CI extended no more than approximately 10 percentage points from the point estimate.

Example Blaker Confidence Intervals for ORR for the Expansion Cohorts with 1-Sided Interpretations of the Lower Bound

| | | 80% 2-Sided CI | | | 60% 2-Sided CI | | |
|---|---|---|---|---|---|---|---|
| Observed Responses (Total N = 40) | Observed ORR | LCL | UCL | True ORR[b] (90% Confidence) | LCL | UCL | True ORRI (80% Confidence) |
| 20 | 0.500 | 0.399 | 0.601 | ≥ 0.399 | 0.425 | 0.575 | >0.425 |
| 15 | 0.375 | 0.274 | 0.487 | ≥ 0.274 | 0.313 | 0.450 | ≥ 0.313 |
| 14 | 0.350 | 0.251 | 0.462 | >0.251 | 0.288 | 0.425 | >0.288 |
| 13 | 0.325 | 0.237 | 0.437 | >0.237 | 0.263 | 0.400 | >0.263 |
| 12 | 0.300 | 0.212 | 0.404 | ≥ 0.212 | 0.239 | 0.375 | ≥ 0.239 |
| 11 | 0.275 | 0.186 | 0.375 | ≥0.186 | 0.213 | 0.350 | ≥0.213 |
| 10 | 0.250 | 0.168 | 0.350 | ≥0.168 | 0.188 | 0.319 | >0.188 |

CI, confidence interval; LCL, lower confidence limit; ORR, objective response rate; UCL, upper confidence limit

[b]1-sided interpretation of the lower bound

Single-Agent Therapy Arms

A Gehan design will be used for the Cohort-Expansion Stage single-agent Compound 1 arms with the intent to ensure that Compound 1 shows clinical activity in at least 20% of subjects of a tumor cohort. Initially 14 subjects will be enrolled in the Compound 1 single-agent treatment arm of the tumor cohort and followed for 6 months. If none of the initially enrolled subjects experience a tumor response per RECIST 1.1, then the treatment arm will be closed, and the true response rate will be declared to be less than 20%. If 1 or more subjects experience a tumor response per RECIST 1.1, an additional 16 subjects will be enrolled. At the end of the study response rates will be estimated and the corresponding 90% CIs will be calculated.

OTHER EMBODIMENTS

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive.

The scope of the invention should, therefore, be determined not with reference to the above description, but should instead be determined with reference to the following appended claims, along with the full scope of equivalents to which such claims are entitled.

The invention claimed is:

1. A method for treating colorectal cancer in a subject, the method comprising administering to the subject in need of such treatment a dosage of from 5 mg to 100 mg of Compound 1:

(1)

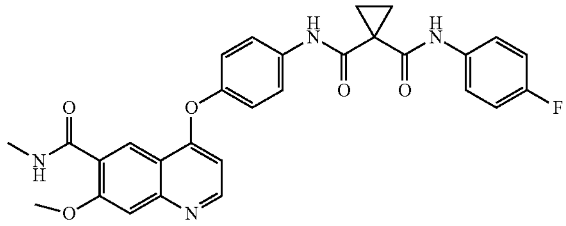

or a pharmaceutically acceptable salt thereof, or a pharmaceutical composition comprising Compound 1 or the pharmaceutically acceptable salt thereof, and a pharmaceutically acceptable carrier or excipient, in combination with a therapeutically effective amount of a checkpoint inhibitor or a pharmaceutical composition comprising the checkpoint inhibitor, wherein the checkpoint inhibitor is atezolizumab.

2. The method of claim 1, wherein Compound 1 or a pharmaceutically acceptable salt thereof is administered orally once per day (qd) or twice per day (bid).

3. The method of claim 2, wherein the dosage of Compound 1 or a pharmaceutically acceptable salt thereof is from 5 mg to 80 mg.

4. The method of claim 3, wherein the dosage of Compound 1 or a pharmaceutically acceptable salt thereof, is selected from 10 mg, 20 mg, 40 mg, 60 mg, and 80 mg.

5. The method of claim 1, wherein atezolizumab is administered intravenously (IV) to the subject.

6. The method of claim 1, wherein atezolizumab is administered once every two weeks, once every three weeks, or once every four weeks for the duration of the treatment period.

7. The method of claim 6, wherein atezolizumab is administered in an amount from 800 mg to 1700 mg.

8. The method of claim 1, wherein a dosage of atezolizumab is 840 mg administered once every two weeks, 1200 mg administered once every three weeks, or 1680 mg administered once every four weeks.

9. The method of claim 8, wherein atezolizumab is administered to a subject in an IV unit dosage form, wherein the dosage form comprises 840 mg, 1200 mg, or 1680 mg of atezolizumab, water, glacial acetic acid, L-histidine, polysorbate 20, and sucrose.

10. The method of claim 1, wherein Compound 1 is administered as a pharmaceutical composition comprising:

a. 25 to 35 percent by weight of Compound 1 or a pharmaceutically acceptable salt thereof;
b. 37 to 43 percent by weight of microcrystalline cellulose;
c. 18 to 22 percent by weight of anhydrous lactose;
d. 2 to 6 percent by weight of hydroxypropyl cellulose;
e. 5 to 7 percent by weight of croscarmellose sodium;
f. 0.2 to 0.4 percent by weight of colloidal silicon dioxide;
g. 0.5 to 3.5 percent by weight magnesium stearate; and optionally
h. a film coating.

11. The method of claim 1, wherein Compound 1 is administered as a pharmaceutical composition comprising:

a. 25 to 35 percent by weight of Compound 1 or a pharmaceutically acceptable salt thereof;
b. 35 to 40 percent by weight of microcrystalline cellulose;
c. 16 to 22 percent by weight of anhydrous lactose;
d. 3 to 7 percent by weight of hydroxypropyl cellulose;
e. 3 to 7 percent by weight of croscarmellose sodium
f. 0.1 to 0.5 percent by weight of colloidal silicon dioxide;
g. 0.5 to 3.5 percent by weight stearic acid; and optionally
h. a film coating.

12. The method of claim 1, wherein the colorectal cancer is a solid tumor that is inoperable, locally advanced, metastatic, or recurrent.

13. The method of claim 12, wherein the solid tumor is an unresectable or metastatic solid tumor for which no life-prolonging therapies exist, or for which available therapies are intolerable or no longer effective.

14. The method of claim 1, wherein the colorectal cancer is right-sided colorectal cancer (RCRC) or left-sided colorectal cancer (LCRC).

15. The method of claim 1, wherein the subject has received a prior anticancer therapy.

16. The method of claim 15, wherein the prior anticancer therapy is chemotherapy, platinum-based combination therapy, PD-1 immune checkpoint inhibitor monotherapy, PD-1 immune checkpoint inhibitor combination therapy, PD-L1 immune checkpoint inhibitor monotherapy, PD-L1 immune checkpoint inhibitor combination therapy, CTLA-4 checkpoint inhibitor therapy or a combination thereof.

17. The method of claim 1, wherein the method further comprises assessing treatment with said combination therapy by determining one or more of: inhibition of disease progression, inhibition of tumor growth, reduction of primary tumor, relief of tumor-related symptoms, inhibition of tumor secreted factors, delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased overall response rate, increased Overall Survival (OS) or increased Duration of Response (DOR), changes in tumor markers from baseline.

18. The method of claim 15, wherein the prior anticancer therapy comprises a fluoropyrimidine in combination with oxaliplatin or irinotecan.

* * * * *